(12) United States Patent
Horseman

(10) Patent No.: US 10,307,104 B2
(45) Date of Patent: *Jun. 4, 2019

(54) CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES

(71) Applicant: Saudi Arabian Oil Company, Dhahran (SA)

(72) Inventor: Samantha J. Horseman, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

This patent is subject to a terminal disclaimer.

(21) Appl. No.: 16/202,533

(22) Filed: Nov. 28, 2018

(65) Prior Publication Data

US 2019/0090816 A1    Mar. 28, 2019

Related U.S. Application Data

(60) Continuation of application No. 14/180,529, filed on Feb. 14, 2014, which is a division of application No.
(Continued)

(51) Int. Cl.
*A61B 5/00* (2006.01)
*A61B 5/11* (2006.01)
(Continued)

(52) U.S. Cl.
CPC ............ *A61B 5/6891* (2013.01); *A61B 5/002* (2013.01); *A61B 5/0008* (2013.01);
(Continued)

(58) Field of Classification Search
None
See application file for complete search history.

(56) References Cited

U.S. PATENT DOCUMENTS

| | | | |
|---|---|---|---|
| 4,951,963 A | 8/1990 | Behr et al. | |
| 4,998,534 A | 3/1991 | Claxton, III et al. | |

(Continued)

FOREIGN PATENT DOCUMENTS

| | | |
|---|---|---|
| AU | 167533 B2 | 11/2003 |
| CN | 101065752 A | 10/2007 |

(Continued)

OTHER PUBLICATIONS

"40 Best Companies for Leaders—2014" Chief Executive, available as of Dec. 13, 2015 at the website: http://chiefexecutive.net/40-best-companies-for-leaders-2014/; pp. 1-3.
(Continued)

*Primary Examiner* — Carl H Layno
*Assistant Examiner* — Manolis Pahakis
(74) *Attorney, Agent, or Firm* — Bracewell LLP; Constance G. Rhebergen; Christopher L. Drymalla

(57) ABSTRACT

Provided are embodiments of systems, computer medium and computer-implemented methods for sensing health characteristics of a user using a chair pad including a set of health sensors integrated therewith and including temperature sensors, body position sensors, and body fat sensors. A method for sensing health characteristics of a user including receiving, from the temperature sensors, temperature data corresponding to a sensed body temperature of the user, receiving, from the body position sensors, body position data corresponding to a sensed body position of the user, receiving, from the body fat sensors, body fat data corresponding to a sensed body fat of the user, and transmitting, to a computer workstation, health data corresponding to the
(Continued)

temperature data, the body position data, and the body fat data for use in determining the body temperature, the body position, and the body fat of the user.

19 Claims, 44 Drawing Sheets

Related U.S. Application Data

13/540,095, filed on Jul. 2, 2012, now Pat. No. 9,492,120.

(60) Provisional application No. 61/504,368, filed on Jul. 5, 2011, provisional application No. 61/659,831, filed on Jun. 14, 2012, provisional application No. 61/659,824, filed on Jun. 14, 2012, provisional application No. 61/659,818, filed on Jun. 14, 2012, provisional application No. 61/659,810, filed on Jun. 14, 2012, provisional application No. 61/659,807, filed on Jun. 14, 2012, provisional application No. 61/659,800, filed on Jun. 14, 2012, provisional application No. 61/659,796, filed on Jun. 14, 2012, provisional application No. 61/659,790, filed on Jun. 14, 2012.

(51) Int. Cl.
| | | |
|---|---|---|
| *A61B 5/0205* | (2006.01) | |
| *G06F 19/00* | (2018.01) | |
| *G16H 50/20* | (2018.01) | |
| *A61B 5/01* | (2006.01) | |
| *A61B 5/053* | (2006.01) | |
| *G16H 15/00* | (2018.01) | |
| *G16H 40/67* | (2018.01) | |

(52) U.S. Cl.
CPC ............. *A61B 5/0015* (2013.01); *A61B 5/01* (2013.01); *A61B 5/0537* (2013.01); *A61B 5/11* (2013.01); *A61B 5/1114* (2013.01); *A61B 5/4866* (2013.01); *A61B 5/4872* (2013.01); *A61B 5/7275* (2013.01); *A61B 5/7282* (2013.01); *A61B 5/743* (2013.01); *A61B 5/744* (2013.01); *G06F 19/00* (2013.01); *G16H 15/00* (2018.01); *G16H 40/67* (2018.01); *G16H 50/20* (2018.01); *A61B 5/4842* (2013.01); *F04C 2270/041* (2013.01)

(56) References Cited

U.S. PATENT DOCUMENTS

| | | | |
|---|---|---|---|
| 5,000,188 | A | 3/1991 | Kojima |
| 5,111,539 | A | 5/1992 | Hiruta et al. |
| 5,253,656 | A | 10/1993 | Rincoe et al. |
| 5,304,112 | A | 4/1994 | Mrklas et al. |
| 5,305,238 | A | 4/1994 | Starr, III |
| 5,323,650 | A | 6/1994 | Fullen et al. |
| 5,331,549 | A | 7/1994 | Crawford, Jr. |
| 5,343,869 | A | 9/1994 | Pross et al. |
| 5,410,471 | A | 4/1995 | Alyfuku et al. |
| 5,435,315 | A * | 7/1995 | McPhee ............... A61B 5/222 600/483 |
| 5,441,047 | A | 8/1995 | David et al. |
| 5,542,420 | A | 8/1996 | Goldman et al. |
| 5,570,301 | A | 10/1996 | Barrus |
| 5,573,269 | A | 11/1996 | Gentry et al. |
| 5,626,145 | A | 5/1997 | Clapp et al. |
| 5,673,691 | A | 10/1997 | Abrams et al. |
| 5,792,047 | A | 8/1998 | Coggins |
| 5,813,993 | A | 9/1998 | Kaplan et al. |
| 5,926,806 | A | 7/1999 | Marshall et al. |
| 5,937,387 | A | 8/1999 | Summerell et al. |
| 6,033,344 | A | 3/2000 | Trulaske et al. |
| 6,049,281 | A | 4/2000 | Osterweil |
| 6,080,106 | A | 6/2000 | Lloyd et al. |
| 6,083,156 | A | 7/2000 | Lisiecki |
| 6,104,296 | A | 8/2000 | Yasuchi et al. |
| 6,148,280 | A | 11/2000 | Kramer |
| 6,149,586 | A | 11/2000 | Elkind |
| 6,190,314 | B1 | 2/2001 | Ark et al. |
| 6,198,394 | B1 | 3/2001 | Jacobsen et al. |
| 6,203,495 | B1 | 3/2001 | Bardy |
| 6,269,339 | B1 | 7/2001 | Silver |
| 6,281,594 | B1 | 8/2001 | Sarich |
| 6,291,900 | B1 | 9/2001 | Tiemann et al. |
| 6,293,771 | B1 | 9/2001 | Haney et al. |
| 6,307,476 | B1 | 10/2001 | Smith et al. |
| 6,309,342 | B1 | 10/2001 | Blazey et al. |
| 6,334,837 | B1 | 1/2002 | Hein et al. |
| 6,345,839 | B1 | 2/2002 | Kuboki et al. |
| 6,353,764 | B1 | 3/2002 | Imagawa et al. |
| 6,369,337 | B1 | 4/2002 | Machiyama |
| 6,381,577 | B1 | 4/2002 | Brown |
| 6,383,136 | B1 | 5/2002 | Jordan |
| 6,408,263 | B1 | 6/2002 | Summers |
| 6,425,862 | B1 | 7/2002 | Brown |
| 6,450,530 | B1 | 9/2002 | Frasher et al. |
| 6,452,862 | B1 | 9/2002 | Tomotani |
| 6,546,286 | B2 | 4/2003 | Olson |
| 6,572,558 | B2 | 6/2003 | Masakov et al. |
| 6,585,645 | B2 | 7/2003 | Hutchinson |
| 6,594,607 | B2 | 7/2003 | Lavery |
| 6,646,556 | B1 | 11/2003 | Smith et al. |
| 6,648,820 | B1 | 11/2003 | Sarel |
| 6,658,572 | B1 | 12/2003 | Craig |
| 6,669,286 | B2 | 12/2003 | Iusim |
| 6,673,027 | B2 | 1/2004 | Fischer |
| 6,675,130 | B2 | 1/2004 | Kanevsky et al. |
| 6,692,258 | B1 | 2/2004 | Kurzweil |
| 6,705,990 | B1 | 3/2004 | Gallant et al. |
| 6,736,642 | B2 | 5/2004 | Bajer |
| 6,767,330 | B2 | 7/2004 | Lavery et al. |
| 6,768,246 | B2 | 7/2004 | Pelrine et al. |
| 6,781,067 | B2 | 8/2004 | Montagnino et al. |
| 6,828,908 | B2 | 12/2004 | Clark |
| 6,832,987 | B2 | 12/2004 | David et al. |
| 6,850,798 | B2 | 2/2005 | Morgan |
| 6,918,769 | B2 | 7/2005 | Rink |
| 6,931,359 | B2 | 8/2005 | Tamada |
| 6,982,497 | B2 | 1/2006 | Rome |
| 7,005,757 | B2 | 2/2006 | Pandian |
| 7,027,621 | B1 | 4/2006 | Prokoski |
| 7,063,665 | B2 | 6/2006 | Hasegawa et al. |
| 7,074,198 | B2 | 7/2006 | Krullaards |
| 7,104,965 | B1 | 9/2006 | Jiang et al. |
| 7,109,872 | B2 | 9/2006 | Balaban et al. |
| 7,128,577 | B2 | 10/2006 | Renaud |
| 7,152,024 | B2 | 12/2006 | Marschner |
| 7,155,158 | B1 | 12/2006 | Iuppa |
| 7,163,489 | B1 | 1/2007 | Nelson |
| 7,188,151 | B2 | 3/2007 | Kumar et al. |
| 7,233,312 | B2 | 6/2007 | Stern et al. |
| 7,273,453 | B2 | 9/2007 | Shallenberger |
| 7,304,580 | B2 | 12/2007 | Sullivan et al. |
| 7,315,249 | B2 | 1/2008 | Littell |
| 7,351,206 | B2 | 4/2008 | Suzuki |
| 7,399,276 | B1 | 7/2008 | Brown et al. |
| 7,407,484 | B2 | 8/2008 | Korman |
| 7,481,779 | B2 | 1/2009 | Large |
| 7,598,881 | B2 | 10/2009 | Morgan |
| 7,624,037 | B2 | 11/2009 | Bost |
| 7,652,582 | B2 | 1/2010 | Littell |
| 7,689,271 | B1 | 3/2010 | Sullivan |
| 7,717,866 | B2 | 5/2010 | Damen |
| 7,771,318 | B2 | 8/2010 | Narayanaswami |
| 7,830,249 | B2 | 11/2010 | Dorneich et al. |
| 7,844,347 | B2 | 11/2010 | Brabec |
| 7,849,115 | B2 | 12/2010 | Reiner |
| 7,901,324 | B2 | 3/2011 | Kodama |
| 7,958,002 | B2 | 6/2011 | Bost |

(56) References Cited

U.S. PATENT DOCUMENTS

| | | |
|---|---|---|
| 7,972,266 B2 | 7/2011 | Gobeyn et al. |
| 7,988,627 B2 | 8/2011 | Bagan |
| 8,015,022 B2 | 9/2011 | Gore |
| 8,018,346 B2 | 9/2011 | Gottlieb et al. |
| 8,019,121 B2 | 9/2011 | Marks |
| 8,021,298 B2 | 9/2011 | Baird |
| 8,024,202 B2 | 9/2011 | Carroll |
| 8,030,786 B2 | 10/2011 | Jackson et al. |
| 8,038,615 B2 | 10/2011 | Gobeyn |
| 8,081,083 B2 | 12/2011 | Hinterlong |
| 8,083,676 B2 | 12/2011 | Halliday |
| 8,092,226 B2 | 1/2012 | Findlay |
| 8,095,641 B2 | 1/2012 | Aggarwal et al. |
| 8,103,333 B2 | 1/2012 | Tran |
| 8,179,269 B2 | 5/2012 | Yanagi et al. |
| 8,180,457 B2 | 5/2012 | Matos |
| 8,200,323 B2 | 6/2012 | Dibenedetto et al. |
| 8,203,454 B2 | 6/2012 | Knight et al. |
| 8,219,184 B2 | 7/2012 | Stelzer et al. |
| 8,235,895 B2 | 8/2012 | David |
| 8,308,562 B2 | 11/2012 | Patton |
| 8,359,231 B2 | 1/2013 | Fitzpatrick et al. |
| 8,428,962 B1 | 4/2013 | Brinkley et al. |
| 8,477,039 B2 | 7/2013 | Gleckler et al. |
| 8,487,456 B2 | 7/2013 | Donelan et al. |
| 8,597,121 B2 | 12/2013 | Andres Del Valle |
| 8,597,142 B2 | 12/2013 | Mayles et al. |
| 8,612,247 B2 | 12/2013 | Sawano |
| 8,636,670 B2 | 1/2014 | Ferren et al. |
| 8,704,110 B2 | 4/2014 | Forshaw et al. |
| 8,738,129 B2 | 5/2014 | Packer |
| 8,775,196 B2 | 7/2014 | Simpson et al. |
| 8,956,292 B2 | 2/2015 | Wekell et al. |
| 9,043,217 B2 | 5/2015 | Cashman et al. |
| 9,044,172 B2 | 6/2015 | Baxi et al. |
| 9,364,714 B2 | 6/2016 | Koduri et al. |
| 2001/0039372 A1 | 11/2001 | Yasushi et al. |
| 2001/0040591 A1 | 11/2001 | Abbott et al. |
| 2001/0041845 A1 | 11/2001 | Kim |
| 2001/0042004 A1 | 11/2001 | Taub |
| 2002/0008625 A1 | 1/2002 | Adams et al. |
| 2002/0050924 A1 | 5/2002 | Mahbub |
| 2002/0062069 A1 | 5/2002 | Mault |
| 2002/0077534 A1 | 6/2002 | Durousseau |
| 2002/0087093 A1 | 7/2002 | Chai |
| 2002/0095099 A1 | 7/2002 | Quyen et al. |
| 2002/0108576 A1 | 8/2002 | Lely et al. |
| 2002/0132092 A1 | 9/2002 | Wagner |
| 2002/0156351 A1 | 10/2002 | Sagel |
| 2002/0167486 A1 | 11/2002 | Tan et al. |
| 2002/0183644 A1 | 12/2002 | Levendowski et al. |
| 2002/0193707 A1 | 12/2002 | Atlas et al. |
| 2002/0197591 A1 | 12/2002 | Ebersole et al. |
| 2003/0010345 A1 | 1/2003 | Koblasz et al. |
| 2003/0058111 A1 | 3/2003 | Lee et al. |
| 2003/0060957 A1 | 3/2003 | Okamura et al. |
| 2003/0073552 A1 | 4/2003 | Knight |
| 2003/0109322 A1 | 6/2003 | Funk et al. |
| 2003/0113698 A1 | 6/2003 | Von Der Geest |
| 2003/0149379 A1 | 8/2003 | Krullaards |
| 2003/0154107 A1 | 8/2003 | Medvedeff |
| 2003/0163351 A1 | 8/2003 | Brown et al. |
| 2003/0173120 A1 | 9/2003 | Desrochers et al. |
| 2003/0181830 A1 | 9/2003 | Guimond et al. |
| 2003/0201978 A1 | 10/2003 | Lee et al. |
| 2003/0204130 A1 | 10/2003 | Colston, Jr. et al. |
| 2003/0209113 A1 | 11/2003 | Brooks et al. |
| 2003/0212579 A1 | 11/2003 | Brown et al. |
| 2003/0214408 A1 | 11/2003 | Grajales et al. |
| 2003/0222440 A1 | 12/2003 | Basir |
| 2003/0226695 A1 | 12/2003 | Mault |
| 2004/0002634 A1 | 1/2004 | Nihtila |
| 2004/0015191 A1 | 1/2004 | Otman |
| 2004/0095378 A1 | 5/2004 | Vigue |
| 2004/0100283 A1 | 5/2004 | Meyer et al. |
| 2004/0148140 A1 | 7/2004 | Tarassenko et al. |
| 2004/0152956 A1 | 8/2004 | Korman |
| 2004/0162466 A1 | 8/2004 | Quy |
| 2004/0167381 A1 | 8/2004 | Lichter et al. |
| 2004/0193068 A1 | 9/2004 | Burton et al. |
| 2004/0195876 A1 | 10/2004 | Huiban |
| 2004/0214148 A1 | 10/2004 | Salvino et al. |
| 2004/0222892 A1 | 11/2004 | Balaban |
| 2004/0242976 A1 | 12/2004 | Abreu |
| 2004/0260156 A1 | 12/2004 | David |
| 2004/0263633 A1 | 12/2004 | Shinohara et al. |
| 2005/0060217 A1 | 3/2005 | Douglas et al. |
| 2005/0075542 A1 | 4/2005 | Goldreich |
| 2005/0101845 A1 | 5/2005 | Nihtila |
| 2005/0108086 A1 | 5/2005 | Kosman |
| 2005/0113650 A1 | 5/2005 | Pacione et al. |
| 2005/0124864 A1 | 6/2005 | Mack et al. |
| 2005/0164833 A1 | 7/2005 | Florio |
| 2005/0165284 A1 | 7/2005 | Gefen |
| 2005/0181347 A1* | 8/2005 | Barnes .................. G09B 5/00 434/350 |
| 2005/0237385 A1 | 10/2005 | Kosaka et al. |
| 2005/0250996 A1 | 11/2005 | Shirai et al. |
| 2005/0260548 A1 | 11/2005 | Nava |
| 2005/0268401 A1 | 12/2005 | Dixon et al. |
| 2005/0270163 A1 | 12/2005 | Littell |
| 2005/0273890 A1 | 12/2005 | Flaherty et al. |
| 2006/0001545 A1 | 1/2006 | Wolf |
| 2006/0026036 A1 | 2/2006 | Mahmood |
| 2006/0030783 A1 | 2/2006 | Tsai et al. |
| 2006/0047188 A1 | 3/2006 | Bohan |
| 2006/0074708 A1 | 4/2006 | Woods |
| 2006/0090135 A1 | 4/2006 | Fukuda |
| 2006/0122863 A1 | 6/2006 | Gottesman et al. |
| 2006/0135857 A1 | 6/2006 | Ho et al. |
| 2006/0155175 A1 | 7/2006 | Ogino et al. |
| 2006/0183980 A1 | 8/2006 | Yang |
| 2006/0203991 A1 | 9/2006 | Kramer et al. |
| 2006/0240395 A1 | 10/2006 | Faist et al. |
| 2006/0241977 A1 | 10/2006 | Fitzgerald et al. |
| 2006/0253303 A1 | 11/2006 | Brown |
| 2006/0267747 A1 | 11/2006 | Kondo |
| 2006/0287883 A1 | 12/2006 | Turgiss et al. |
| 2007/0004969 A1 | 1/2007 | Kong et al. |
| 2007/0011273 A1 | 1/2007 | Greenstein et al. |
| 2007/0016449 A1 | 1/2007 | Cohen et al. |
| 2007/0017531 A1 | 1/2007 | Large |
| 2007/0038153 A1 | 2/2007 | Basson et al. |
| 2007/0050715 A1 | 3/2007 | Behar |
| 2007/0055185 A1 | 3/2007 | Trandafir et al. |
| 2007/0055549 A1 | 3/2007 | Moore et al. |
| 2007/0083384 A1 | 4/2007 | Geslak et al. |
| 2007/0118398 A1 | 5/2007 | Perls |
| 2007/0136093 A1 | 6/2007 | Rankin |
| 2007/0139362 A1 | 6/2007 | Colton et al. |
| 2007/0146131 A1 | 6/2007 | Boverie |
| 2007/0149360 A1 | 6/2007 | Narayanaswami |
| 2007/0169364 A1 | 7/2007 | Townsend et al. |
| 2007/0179360 A1 | 8/2007 | Mikat |
| 2007/0191727 A1 | 8/2007 | Fadem |
| 2007/0193811 A1 | 8/2007 | Breed et al. |
| 2007/0219419 A1 | 9/2007 | Kenknight et al. |
| 2007/0225118 A1 | 9/2007 | Giorno |
| 2007/0225585 A1 | 9/2007 | Washbon et al. |
| 2007/0232937 A1 | 10/2007 | Lam et al. |
| 2007/0244724 A1 | 10/2007 | Pendergast et al. |
| 2007/0256494 A1 | 11/2007 | Nakamura et al. |
| 2007/0270909 A1 | 11/2007 | Saketkhou |
| 2007/0276202 A1 | 11/2007 | Raisanen et al. |
| 2007/0282177 A1 | 12/2007 | Pilz |
| 2007/0296556 A1 | 12/2007 | Wang et al. |
| 2007/0299325 A1 | 12/2007 | Farrell et al. |
| 2008/0001735 A1 | 1/2008 | Tran |
| 2008/0001736 A1 | 1/2008 | Steadman et al. |
| 2008/0052837 A1 | 3/2008 | Blumberg |
| 2008/0077620 A1 | 3/2008 | Gilley et al. |
| 2008/0081963 A1 | 4/2008 | Naghavi et al. |
| 2008/0083416 A1 | 4/2008 | Xia et al. |
| 2008/0015422 A1 | 6/2008 | Wessel |

(56) References Cited

U.S. PATENT DOCUMENTS

| | | |
|---|---|---|
| 2008/0140140 A1 | 6/2008 | Grimley |
| 2008/0146892 A1 | 6/2008 | Leboeuf et al. |
| 2008/0150889 A1 | 6/2008 | Stern |
| 2008/0161654 A1 | 7/2008 | Teller et al. |
| 2008/0171914 A1 | 7/2008 | Ouwerkerk et al. |
| 2008/0177158 A1 | 7/2008 | Teller et al. |
| 2008/0177341 A1 | 7/2008 | Bowers |
| 2008/0177614 A1 | 7/2008 | An et al. |
| 2008/0177836 A1 | 7/2008 | Bennett |
| 2008/0188777 A1 | 8/2008 | Bedziouk |
| 2008/0193905 A1 | 8/2008 | Leung |
| 2008/0194995 A1 | 8/2008 | Grady-Van Den Nieuwboer |
| 2008/0200774 A1 | 8/2008 | Luo |
| 2008/0218331 A1 | 9/2008 | Baillot |
| 2008/0228046 A1 | 9/2008 | Futatsuyama et al. |
| 2008/0242521 A1 | 10/2008 | Einav |
| 2008/0242951 A1 | 10/2008 | Jung et al. |
| 2008/0242952 A1 | 10/2008 | Jung et al. |
| 2008/0258921 A1 | 10/2008 | Woo et al. |
| 2008/0292151 A1 | 11/2008 | Kurtz et al. |
| 2008/0294018 A1 | 11/2008 | Kurtz et al. |
| 2008/0304712 A1 | 12/2008 | Rowe et al. |
| 2008/0306357 A1 | 12/2008 | Korman |
| 2008/0306762 A1 | 12/2008 | James |
| 2009/0002178 A1 | 1/2009 | Guday et al. |
| 2009/0030290 A1 | 1/2009 | Kozuch et al. |
| 2009/0030767 A1 | 1/2009 | Morris et al. |
| 2009/0040196 A1 | 2/2009 | Duckstein |
| 2009/0047644 A1 | 2/2009 | Mensah |
| 2009/0047645 A1 | 2/2009 | Dibenedetto et al. |
| 2009/0055204 A1 | 2/2009 | Pennington et al. |
| 2009/0058661 A1 | 3/2009 | Glecker et al. |
| 2009/0137882 A1 | 5/2009 | Baudino et al. |
| 2009/0149721 A1* | 6/2009 | Yang ............... A61B 5/0002 600/301 |
| 2009/0149799 A1 | 6/2009 | Dacey, Jr. et al. |
| 2009/0156888 A1 | 6/2009 | Su et al. |
| 2009/0160640 A1 | 6/2009 | Leung et al. |
| 2009/0173549 A1 | 7/2009 | Lev |
| 2009/0177688 A1 | 7/2009 | Karlsen et al. |
| 2009/0178858 A1 | 7/2009 | Daniels et al. |
| 2009/0198521 A1 | 8/2009 | Barker |
| 2009/0209829 A1 | 8/2009 | Yanagidaira et al. |
| 2009/0216558 A1 | 8/2009 | Reisman et al. |
| 2009/0231145 A1 | 9/2009 | Wada et al. |
| 2009/0241177 A1 | 9/2009 | Bluth |
| 2009/0287101 A1 | 11/2009 | Ferren et al. |
| 2009/0287191 A1 | 11/2009 | Ferren et al. |
| 2009/0298025 A1 | 12/2009 | Raber |
| 2009/0300616 A1 | 12/2009 | Sicurello et al. |
| 2009/0307025 A1 | 12/2009 | Menon |
| 2009/0319297 A1 | 12/2009 | Hernandez et al. |
| 2009/0324024 A1 | 12/2009 | Worthington |
| 2010/0010365 A1 | 1/2010 | Terao et al. |
| 2010/0014711 A1 | 1/2010 | Camhi et al. |
| 2010/0049004 A1 | 2/2010 | Edman et al. |
| 2010/0049541 A1 | 2/2010 | Pollard et al. |
| 2010/0063837 A1 | 3/2010 | Bellante et al. |
| 2010/0130808 A1 | 5/2010 | Hattori |
| 2010/0131283 A1 | 5/2010 | Linthicum et al. |
| 2010/0169118 A1 | 7/2010 | Rottsolk et al. |
| 2010/0169219 A1 | 7/2010 | Sellers et al. |
| 2010/0205541 A1* | 8/2010 | Rapaport ............... G06Q 10/10 715/753 |
| 2010/0225489 A1 | 9/2010 | Hinterlong |
| 2010/0240458 A1 | 9/2010 | Gaiba et al. |
| 2010/0259043 A1 | 10/2010 | Balsamo |
| 2010/0261978 A1 | 10/2010 | Lithgow |
| 2010/0283265 A1 | 11/2010 | Rastegar et al. |
| 2010/0286567 A1 | 11/2010 | Wolfe et al. |
| 2010/0292545 A1 | 11/2010 | Berka et al. |
| 2010/0293267 A1* | 11/2010 | Ribak ............... G06F 11/3438 709/224 |
| 2010/0298656 A1 | 11/2010 | McCombie et al. |
| 2010/0299257 A1 | 11/2010 | Turk |
| 2010/0305480 A1 | 12/2010 | Fu et al. |
| 2010/0312606 A1 | 12/2010 | Gala |
| 2010/0332250 A1 | 12/2010 | Simpson |
| 2011/0033830 A1 | 2/2011 | Cherian |
| 2011/0035231 A1 | 2/2011 | Firminger et al. |
| 2011/0046688 A1 | 2/2011 | Schwibner |
| 2011/0055720 A1 | 3/2011 | Potter et al. |
| 2011/0060252 A1 | 3/2011 | Simonsen et al. |
| 2011/0080290 A1 | 4/2011 | Baxi et al. |
| 2011/0098056 A1 | 4/2011 | Rhoads et al. |
| 2011/0119075 A1 | 5/2011 | Dhoble |
| 2011/0125662 A1 | 5/2011 | Perry et al. |
| 2011/0137211 A1 | 6/2011 | Weisberg |
| 2011/0137669 A1 | 6/2011 | Bennett |
| 2011/0152635 A1 | 6/2011 | Morris et al. |
| 2011/0152696 A1 | 6/2011 | Ryan |
| 2011/0161100 A1 | 6/2011 | Peak et al. |
| 2011/0172744 A1 | 7/2011 | Davis et al. |
| 2011/0183305 A1 | 7/2011 | Orbach |
| 2011/0196212 A1 | 8/2011 | Peters et al. |
| 2011/0201960 A1 | 8/2011 | Price |
| 2011/0213664 A1 | 9/2011 | Osterhout et al. |
| 2011/0238591 A1 | 9/2011 | Kerr et al. |
| 2011/0257537 A1 | 10/2011 | Alatriste |
| 2011/0269601 A1* | 11/2011 | Nelson ............... A47C 7/021 482/8 |
| 2011/0275939 A1 | 11/2011 | Walsh et al. |
| 2011/0285146 A1 | 11/2011 | Kozinsky et al. |
| 2011/0295466 A1 | 12/2011 | Ostu et al. |
| 2011/0295656 A1 | 12/2011 | Venkatasubramanian et al. |
| 2012/0007367 A1 | 1/2012 | Chang |
| 2012/0010488 A1 | 1/2012 | Henry et al. |
| 2012/0035433 A1 | 2/2012 | Chance |
| 2012/0040799 A1 | 2/2012 | Jaquish et al. |
| 2012/0052971 A1 | 3/2012 | Bentley |
| 2012/0071731 A1 | 3/2012 | Gottesman |
| 2012/0075483 A1 | 3/2012 | Paoletti |
| 2012/0086249 A1 | 4/2012 | Rotary et al. |
| 2012/0117020 A1 | 5/2012 | Davis et al. |
| 2012/0122430 A1 | 5/2012 | Hutchings et al. |
| 2012/0127157 A1 | 5/2012 | Adler |
| 2012/0130196 A1 | 5/2012 | Jain et al. |
| 2012/0139731 A1 | 6/2012 | Razoumov et al. |
| 2012/0143031 A1 | 6/2012 | Belalcazar et al. |
| 2012/0143374 A1 | 6/2012 | Mistry et al. |
| 2012/0146795 A1 | 6/2012 | Margon et al. |
| 2012/0154277 A1 | 6/2012 | Bar-Zeev et al. |
| 2012/0203465 A1 | 8/2012 | Callewaert et al. |
| 2012/0203491 A1 | 8/2012 | Sun et al. |
| 2012/0209563 A1 | 8/2012 | Takeda et al. |
| 2012/0215076 A1 | 8/2012 | Yang et al. |
| 2012/0215976 A1 | 8/2012 | Inoue |
| 2012/0253484 A1 | 10/2012 | Burich et al. |
| 2012/0271121 A1 | 10/2012 | Della Torre et al. |
| 2012/0271143 A1 | 10/2012 | Aragones et al. |
| 2012/0283929 A1 | 11/2012 | Wakita et al. |
| 2012/0289793 A1 | 11/2012 | Jain et al. |
| 2012/0290215 A1 | 11/2012 | Adler |
| 2012/0302910 A1 | 11/2012 | Freeman et al. |
| 2012/0323590 A1 | 12/2012 | Udani |
| 2013/0009761 A1 | 1/2013 | Horseman |
| 2013/0009993 A1 | 1/2013 | Horseman |
| 2013/0011819 A1 | 1/2013 | Horseman |
| 2013/0012786 A1 | 1/2013 | Horseman |
| 2013/0012787 A1 | 1/2013 | Horseman |
| 2013/0012788 A1 | 1/2013 | Horseman |
| 2013/0012789 A1 | 1/2013 | Horseman |
| 2013/0012790 A1 | 1/2013 | Horseman |
| 2013/0012802 A1 | 1/2013 | Horseman |
| 2013/0013327 A1 | 1/2013 | Horseman |
| 2013/0013331 A1 | 1/2013 | Horseman |
| 2013/0056981 A1 | 3/2013 | Mullins et al. |
| 2013/0097093 A1 | 4/2013 | Kolber et al. |
| 2013/0158423 A1 | 6/2013 | Kapoor |
| 2013/0178960 A1 | 7/2013 | Sheehan et al. |
| 2013/0226413 A1 | 8/2013 | Cuddihy et al. |
| 2013/0234826 A1* | 9/2013 | Sekiguchi ............ H04N 21/42201 340/5.53 |
| 2013/0243208 A1 | 9/2013 | Fawer |

(56) References Cited

U.S. PATENT DOCUMENTS

| | | | |
|---|---|---|---|
| 2013/0281798 A1 | 10/2013 | Rau et al. | |
| 2013/0289889 A1 | 10/2013 | Yuen et al. | |
| 2013/0297219 A1* | 11/2013 | Bangera | G16H 50/30 702/19 |
| 2013/0297344 A1 | 11/2013 | Cosentino et al. | |
| 2013/0308099 A1 | 11/2013 | Stack | |
| 2013/0331993 A1 | 12/2013 | Detsch et al. | |
| 2013/0334851 A1 | 12/2013 | Hoell et al. | |
| 2014/0067001 A1 | 3/2014 | Schwibner et al. | |
| 2014/0100464 A1 | 4/2014 | Kaleal et al. | |
| 2014/0107718 A1 | 4/2014 | Foote | |
| 2014/0129401 A1 | 5/2014 | Kruz et al. | |
| 2014/0156259 A1 | 6/2014 | Dolan et al. | |
| 2014/0172461 A1 | 6/2014 | Rogers | |
| 2014/0222095 A1 | 8/2014 | Einy | |
| 2014/0317914 A1 | 10/2014 | Shaker | |
| 2015/0025928 A1 | 1/2015 | Kang et al. | |
| 2015/0050623 A1 | 2/2015 | Falash et al. | |
| 2015/0199494 A1 | 7/2015 | Koduri et al. | |
| 2015/0222096 A1 | 8/2015 | Nakayama | |
| 2015/0338265 A1 | 11/2015 | Carreel et al. | |
| 2015/0375028 A1 | 12/2015 | Oteman et al. | |
| 2017/0270481 A1 | 9/2017 | Morgenthau et al. | |

FOREIGN PATENT DOCUMENTS

| | | |
|---|---|---|
| CN | 101115438 A | 1/2008 |
| CN | 201127606 Y | 10/2008 |
| CN | 101454050 A | 6/2009 |
| CN | 101930125 A | 12/2010 |
| DE | 102005048496 A1 | 4/2007 |
| EP | 1407713 BI | 9/2008 |
| EP | 2151355 A1 | 2/2010 |
| EP | 2248461 A2 | 11/2010 |
| EP | 2924674 A1 | 9/2015 |
| JP | 05-049603 A | 3/1993 |
| JP | H07204168 A | 8/1995 |
| JP | H10283150 A | 10/1998 |
| JP | H10312241 A | 11/1998 |
| JP | H11328593 A | 11/1999 |
| JP | 2000037357 A | 2/2000 |
| JP | 2000342537 A | 12/2000 |
| JP | 2001187030 A | 7/2001 |
| JP | 2001209717 A | 8/2001 |
| JP | 2001236141 A | 8/2001 |
| JP | 2001356849 A | 12/2001 |
| JP | 2002065630 A | 3/2002 |
| JP | 2002109061 A | 4/2002 |
| JP | 2002159052 A | 5/2002 |
| JP | 2002183647 A | 6/2002 |
| JP | 2002215880 A | 8/2002 |
| JP | 2002259120 A | 9/2002 |
| JP | 2002291952 A | 10/2002 |
| JP | 2003070774 A | 3/2003 |
| JP | 2003091598 A | 3/2003 |
| JP | 2003521972 A | 7/2003 |
| JP | 2003235813 A | 8/2003 |
| JP | 2003247991 A | 9/2003 |
| JP | 2003256578 A | 9/2003 |
| JP | 2003525676 A | 9/2003 |
| JP | 2003310580 A | 11/2003 |
| JP | 2004113581 A | 4/2004 |
| JP | 2004135829 A | 5/2004 |
| JP | 3109753 U | 6/2005 |
| JP | 2005287688 A | 10/2005 |
| JP | 2005321869 A | 11/2005 |
| JP | 2006085262 A | 3/2006 |
| JP | 2006106952 A | 4/2006 |
| JP | 2006178805 A | 7/2006 |
| JP | 2006239157 A | 9/2006 |
| JP | 2008099834 A | 1/2008 |
| JP | 2008110032 A | 5/2008 |
| JP | 2008178546 A | 8/2008 |
| JP | 2008230366 A | 10/2008 |
| JP | 2008264188 A | 11/2008 |
| JP | 2008304978 A | 12/2008 |
| JP | 2009171544 A | 7/2009 |
| JP | 2009532072 A | 9/2009 |
| JP | 2009301360 A | 12/2009 |
| JP | 2010003070 A | 1/2010 |
| JP | 2010181324 A | 8/2010 |
| JP | 2010267267 A | 11/2010 |
| JP | 2010538701 A | 12/2010 |
| JP | 2011067708 A | 4/2011 |
| JP | 2011120787 A | 6/2011 |
| JP | 2011123579 A | 6/2011 |
| WO | 9601585 A1 | 1/1996 |
| WO | 2001028416 A1 | 4/2001 |
| WO | 2001086403 A2 | 11/2001 |
| WO | 03077110 A2 | 9/2003 |
| WO | 2005064447 A2 | 7/2005 |
| WO | 2006022465 A2 | 3/2006 |
| WO | 2007016056 A2 | 2/2007 |
| WO | 2007130591 A2 | 11/2007 |
| WO | 2008044325 A1 | 4/2008 |
| WO | 2010048145 A1 | 4/2010 |
| WO | 2010051037 A1 | 5/2010 |
| WO | 2010067275 A1 | 6/2010 |
| WO | 2011020299 A1 | 2/2011 |
| WO | 2013006627 A1 | 1/2013 |
| WO | 2013006642 A2 | 1/2013 |
| WO | 2013006644 A1 | 1/2013 |
| WO | 2014023422 A1 | 2/2014 |

OTHER PUBLICATIONS

"Augmented Reality", retrieved from <http://en.wikipedia.org/wiki/Augmented_reality>, May 30, 2012. (pp. 1-18).

"Biofeedback—MayoClinic.com", retrieved from <http://www.mayoclinic.com/health/biofeedback/MY01072>, May 7, 2012. (pp. 1-2).

"Cardinus Risk Management | Ergonomic & DSE Risk Assessments", retrieved from <http://www.cardinus.com/>, Sep. 12, 2012. (pp. 1-2).

"Chronic diseases and health promotion" Centers for Disease Control and Prevention, 2011, <http://www.cdc.gov/chronicdisease/overview> [Accessed Feb. 2, 2011].

"Clever toilet checks on your health", retrieved from <http://articles.cnn.com/2005-06-28/tech/spark.toilet_1_toilet-toto-bathroom?_s=PM:TECH>, Jun. 28, 2005. (pp. 1-2).

"Electroencephalography (EEG)", retieved from <http://www.emedicinehealth.com/script/main/art.asp?articlekey-59319&pf=3&page=1>, Jun. 11, 2012. (pp. 1-4).

"Emotiv|EEG System|Electroencephalography", retrieved from <www.emotiv.com/index.asp>, Jun. 11, 2012. (pp. 1-2).

"EmotivEPOC Software Devlopment Kit", retrieved from <www.emotiv.com/store/hardware/epoc-bci-eeg/developer-neuro-headset/>, Jun. 11, 2012. (pp. 1-2).

"Kinect—Xbox.com", retrieved from <http://www.xbox.com/en-US/kinect>, Jun. 11, 2012. (pp. 1-3).

"MomToBe: The Pregnancy Assistant 3.0", retreved from <http://3d2f.com/programs/4-230-momtobe-the-pregnancy-assistant-download.shtml>, Jun. 11, 2012. (pp. 1-2).

"Murray Hill, WellMed Team to Offer Next Generation Online Preventive Health Services" ProQuest, PR Newswire, New York, Nov. 3, 1999, 3 pages.

"National Health Expenditure Data", Centers for Medicare & Medicaid Services, available at: <https://www.cms.gov/Research-Statistics-Data-and-Systems/Statistics-Trends-and-Reports/NationalHealthExpendData/index.html>, accessed Nov. 18, 2013, pp. 1-2.

"Office Athlete Software Prevents Common Repetitive Stress Injuries", retrieved from <http://www.officeathlete.com/>, Sep. 14, 2012. (pp. 1-2).

"OSHA Ergonomic Solutions: Computer Workstations eTool—Checklists", retrieved from <www.osha.gov/SLTC/etools/computerworkstations/checklist.html>, Jun. 11, 2012. (pp. 1-5).

(56) References Cited

OTHER PUBLICATIONS

"OSHA Ergonomic Solutions: Computer Workstations eTool—Good Working Positions", retrieved from <www.osha.gov/SLTC/etools/computerworkstations/positions.html>, Jun. 11, 2012. (pp. 1-2).
"OSHA Ergonomic Solutions: Computer Workstations eTool—Work Process and Recognition", retrieved from <www.osha.gov/SLTC/etools/computerworkstations/workprocess.html>, Jun. 11, 2012. (pp. 1-2).
"OSHA Ergonomic Solutions: Computer Workstations eTool—Workstation Environment", retrieved from <www.osha.gov/SLTC/etools/computerworkstations/wkstation_enviro.html>, Jun. 11, 2012. (pp. 1-3).
"OSHA Ergonomic Solutions: Computer Workstations eTool—Workstations eTool", retrieved from <www.osha.gov/SLTC/etools/computerworkstations/index.html>, Jun. 11, 2012. (p. 1).
"Philips Research—Download Pictures", retrieved from <http://www.research.philips.com/downloads/pictures/healthcare-personal.html>, May 7, 2012. (pp. 1-2).
"Philips Research Technology Backgrounder—MyHeart project", retrieved from <http://www.research.philips.com/technologies/heartcycle/myheart-gen.html>, May 7, 2012. (pp. 1-3).
"Piezo Electric Energy Harvester", Mide Technology Corporation, retrieved Nov. 18, 2013, pp. 1-2.
"RJL Systems, Products", retrieved from <http://www.rjlsystems.com/products.shtml>, May 7, 2012. (p. 1).
"Signal Conditioning Piezoelectric Sensors", (PDF) Texas Instruments, Application Report SLOA033A, Sep. 2000, pp. 1-6.
"SmartHeart SE102 Heart Rate Monitor", retrieved from <http://us.oregonscientific.com/cat-Sports-and-Health-sub-Heart-Rate-Monitors-prod-SmartHeart-SE102-Heart-Rate-Monitor.html>, May 7, 2012. (pp. 1-4).
"Speedy Assessment Chiropractic Assessment and Patient Education", retrieved from <http://speedyassessment.com/>, May 7, 2012. (pp. 1-3).
"Stress Thermometer", retrieved from <http://www.biof.com/onlinestore/stressthermometer.asp?redirect=yes>, May 7, 2012. (pp. 1-4).
"The Wellness Imperative, Creating More Effective Organizations", World Economic Forum, 2010. (pp. 1-20).
"Wireless measurement devices—Philips", retreved from <http://www.healthcare.philips.com/us_en/products/telehealth/Products/devices.wpd>, May 7, 2012. (pp. 1-2).
"WorkPace : RSI Injury Prevention Software, Stretch Break Exercise Reminder Software", retrieved from <http://www.workpace.com/>, Sep. 14, 2012. (p. 1).
"Workrave", retrieved from <http://www.workrave.org/>, Sep. 14, 2012. (p. 1).
"www.mydailyhealth.com" retrieved from Internet Archive Wayback Machine, 1999, 20 pages.
"Footrests—Adjustable Footrest Solutions for the Office", Ergo in Demand, Aug. 20, 2009, pp. 1-4, Ergo in Demand Inc., www.ergoindemand.com/footrest.html.
"Pulse Oximetry" SparkFun Electronics, Oct. 7, 2005 (p. 1).
"Statement in accordance with the Notice from the European Patent Office dated Oct. 1, 2007 concerning business methods" Nov. 1, 2007, XP002456414, 1 page.
Abstract for "Psychosocial job factors and symptoms from the locomotor system—a multicausal analysis", retrieved from <http://www.ncbi.nlm.nih.gov/pubmed/1962160>, May 7, 2012. (p. 1).
Abstract for "Signal Characteristics of EMG at Different Levels of Muscle Tension", retrieved from <http://onlinelibrary.wiley.com/doi/10.1111/j.1748-1716.1976.tb10195.x/abstract>, May 7, 2012. (p. 1).
Agarabi, Mina, et al., "A sEMG-based Method for Assessing the Design of Computer Mice" 26th Annual International Conference of the IEEE EMBS, Sep. 1-5, 2004; pp. 2450-2453.
Aldana, S. et al.; "Financial impact of a comprehensive multi-site worksite health promotion program", Preventive Medicine, 40, Jul. 2004, pp. 131-137.

Aldana, S., "Financial Impact of health promotion programs: a comprehensive review of the literature", American Journal of Health Promotion,155, 2001, pp. 296-320.
Amato, Neil, "Top 20 companies for leadership development" CGMA Magazine, Sep. 23, 2013; available as of Dec. 13, 2015 at the website: http://www.cgma.org/magazine/news/pp./20138765.aspx?TestCookiesEnabled=redirect; pp. 1-5.
Anonymous: "Automated analyser" —Wikipedia, Jan. 16 2015; https: ex.php?title=Automated_analyser&oldid=642687889 retrieved on Feb. 8, 2017; XP055343828 (pp. 1-4).
Asplund, Christopher L., et al. "A central role for the lateral prefrontal cortex in goal-directed and stimulus-driven attention." Nature neuroscience 13.4 (2010): pp. 507-512.
Asplund, Christopher L., et al. "The attentional blink reveals the probabilistic nature of discrete conscious perception." Psychological science 25.3 (2014): 824-831.
Baicker, K. et al.; "Worksite wellness programs can generate savings", Health Affairs 29(2), Jan. 2010, pp. 1-8.
Bed-Check Co., Bed-Check Monitoring Systems, 2006; pp. 1-8.
Berger et al. 'Investing in Healthy Human Capital' —J Occup Environ Med. (JOEM) vol. 45, No. 12, dated Dec. 2003; pp. 1213-1225.
Berry, Leonard et al., "What's the Hard Return on Employee Wellness Programs?", Harvard Business Review, Dec. 2010. (pp. 1-10).
Borah, J. "Conceptual modeling-The missing link of simulation development." Proceedings of the 2002 Spring Simulation Conference. 2002. AEgis Technologies Group; pp. 1-7.
Brown et al, "Prowess Proactive Wellness Environment Support System", Dec. 10, 2009, pp. 1-19, www.hsi.gatech.edu/onsitecenter/index.php/PROWESS.
International Search Report and Written Opinion for International Application No. PCT/US2012/045410 dated Jan. 31, 2013. (pp. 1-13).
International Search Report and Written Opinion for International Application No. PCT/US2012/045414 dated Mar. 25, 2013. (pp. 1-13).
International Search Report and Written Opinion for International Application No. PCT/US2012/045419 dated Dec. 6, 2012. (pp. 1-16).
International Search Report and Written Opinion for International Application No. PCT/US2012/045427 dated Dec. 3, 2012. (pp. 1-14).
International Search Report and Written Opinion for International Application No. PCT/US2012/045435 dated Jan. 25, 2013. (pp. 1-14).
International Search Report and Written Opinion for International Application No. PCT/US2012/045447 dated Jan. 18, 2013. (pp. 1-12).
International Search Report and Written Opinion for International Application No. PCT/US2012/045452 dated Dec. 3, 2012. (pp. 1-14).
International Search Report and Written Opinion for International Application No. PCT/US2016/064518 dated Feb. 17, 2017. (pp. 1-16).
International Search Report and Written Opinion for International Application No. PCT/US2016/065042 dated Mar. 17, 2017. (pp. 1-15).
International Search Report and Written Opinion for International PCT application PCT/US2016/064520 dated Mar. 27, 2017. (pp. 1-10).
International Search Report and Written Opinion for International PCT application PCT/US2016/064521 dated Mar. 20, 2017. (pp. 1-17).
International Search Report and Written Opinion for International PCT application PCT/US2014/056427 dated Apr. 22, 2015.
International Search Report and Written Opinion for International PCT application PCT/US2014/069498 dated Apr. 1, 2015.
Ivanoff, Jason et al.; "fMRI evidence for a dual process account of the speed-accuracy tradeoff in decision-making." PLoS one 3.7 (2008): e2635. pp. 1-14.

(56) References Cited

OTHER PUBLICATIONS

Jamison, Dean T., et al.; "The World Health Report 1999" World Health Organization, WHO Library Cataloguing in Publication Data, 1999; pp. 1-136.

Johns, G., "Presenteeism in the Workplace: A review and research agenda", Journal of Organizational Behavior, Jul. 31, 2009, pp. 519-542.

Kelly et al. The Novartis Health Index: A Method for Valuing the Economic Impact of Risk Reduction in a Workforce' —J Occup Environ Med. (JOEM) vol. 52, No. 5, dated May 2010; pp. 528-535.

Knikou, Maria. "The H-reflex as a probe: pathways and pitfalls." Journal of neuroscience methods 171.1 (2008): 1-12.

Kuriyama, Shigeru "Visualization model for a human action based on a visual perception" Measurement and Control, Japan, Journal of the Society of Instrument and Control Engineers, Dec. 10, 2006, vol. 45, No. 12, pp. 1024-1029.

Kymissis et al. "Parasitic Power Harvesting in Shoes" Digest of Papers, Second International Symposium on Wearable Computers, Pittsburgh, PA, Oct. 19-20, 1998, pp. 132-139, XP032385438.

Lamkin, Paul; "The best VR headsets: Oculust Rift, PlayStation VR, Gear VR, HTC Vive . . . virtual reality is back baby"10 Sep. 16, 2015; available as of Oct. 21, 2015 at the website: http://www.wearable.com/headgear/the-best-ar-and-vrheadsets;pp. 1-1.

Marois, René et al.; "Capacity limits of information processing in the brain." Trends in cognitive sciences 9.6 (2005): 296-305.

Moreno, Roxana et al.; "Cognitive load and learning effects of having students organize pictures and words in multimedia environments: The role of student interactivity and feedback." Educational Technology Research and Development 53.3 (2005): 35-45.

Moreno, Roxana et al.; "Interactive multimodal learning environments." Educational Psychology Review 19.3 (2007):309-326.

Moreno, Roxana. "Learning in high-tech and multimedia environments." Current directions in psychological science 15.2 (2006): 63-67.

Myatt, Mike, "The #1 Reason Leadership Development Fails" Forbes, Dec. 19, 2012; available as of Dec. 13, 2015 at the website: http://www.forbes.com/sites/mikemyatt/2012/12/19/the-1-reason-leadership-development-fails/#7e53fcd834ce; pp. 1-4.

Nintendo of America Inc., Wii Balance Board Operations Manual, 2008, pp. 1-10.

Nintendo of America Inc., Wii Fit Instruction Booklet, 2008, pp. 1-28.

Nintendo Wii Fit, https://www.youtube.com/watch?v=-Taruqvk30E, May 11, 2008.

Ovans, Andrea; "What Resilience Means, and Why it Matters" Harvard Business Review Jan. 5, 2015; pp. 1-6.

Priya, S., "Advances in Energy Harvesting Using Low Profile Piezoelectric Transducers", Materials Science & Engineering, Springer, Mar. 2007, pp. 165-182.

Prochaska et al. 'The Well-Being Assessment for Productivity' —J Occup Environ Med. (JOEM) vol. 53, No. 7, dated Jul. 2011; pp. 735-768.

Qlik Technology Partners available as of Oct. 21, 2015 at the website: http://www.glik.com/us/partners/technologypartners;pp. 1-21.

Quick, James Campbell, et al. "Executive health: Building strength, managing risks" Academy of Management Executive, May 2000, vol. 14, No. 2, pp. 33-45.

Rao, Leena; "Backed by Google Ventures and Eric Schmidt, Urban Engines Wants to Solve Urban Congestion Using Data Intelligence" available as of Oct. 2, 2015 at the website: http://www.techcrunch.com/2014/05/15/backed-by-google-entures-and-eric-schmidt-urban-engines; pp. 1-7.

Raybourn, Elaine M., et al. "Adaptive thinking & leadership simulation game training for special forces officers." ITSEC 2005 Proceedings, Interservice/Industry Training, Simulation and Education Conference Proceedings, Nov. 2005; pp. 1-9.

Ready, Douglas A., et al.; "Are You a High Potential?" Harvard Business Review Jun. 2010; pp. 1-13.

Reidel, J.E., Baase, C., "The effect of disease prevention & health promotion on worksite productivity: a literature review", American Journal of Health Promotion, 15:3, Jan./Feb. 2001, pp. 167-191, 243.

Rimor, Rikki et al.; "Complexity of social interactions in collaborative learning: The case of online database environment." Interdisciplinary Journal of E-Learning and Learning Objects 6.1 (2010): 355-365.

Robertini, Nadia, et al., "Capture of Arm-Muscle Deformations using a Depth-Camera" 10 European Conference on Visual Media Production, London, UK, Nov. 6-7, 2013; pp. 1-10.

Roberts, R.O. et al.; "Comparison of Self Reported and Medical Record Health Care Utilization Measures", Journal of Clinical Epidemiology, 49:9, Feb. 1996, pp. 989-995.

Rosen, Yigal. "The effects of an animation-based on-line learning environment on transfer of knowledge and on motivation for science and technology learning." Journal of Educational Computing Research 40.4 (2009): 451-467.

Seligman, Martin E.P., "Building Resilience" Harvard Business Review from the Apr. 2011 issue; available as of Dec. 13, 2015 at the website: https://hbr.org/2011/04/building-resilience; pp. 1-15.

Simmonds, Bethany, et al. "Objectively assessed physical activity and subsequent health service use of UK adults aged 70 and over: A four to five year follow up study." PloS one 9.5 (2014): e97676.

Slater et al., "Taking Steps: the Influence of a Walking Technique on Presence in Virtual Reality", ACM Transactions on Computer-Human Interaction, Sep. 1995, pp. 201-219, vol. 2 No. 3.

Spisak, Brian R., et al., "A face for all seasons: Searching for context-specific leadership traits and discovering a general preference for perceived health" Frontiers in Human Neuroscience; Nov. 5, 2014; available as of Dec. 13, 2015 at the website www.frontiersin.org; pp. 1-9.

Stephens: "I am 38. My heart is only 33, but my lungs are aged 52. Why?" Mail Online; http://www.dailymail.co.uk/health/article-1249009/I-38-My-heart-only33-lungs-aged-52-Why.html; retrieved on Feb. 3, 2017; XP055342045 (pp. 1-7).

Sullivan 'Making the Business Case for Health and Productivity Management' —J Occup Environ Med. (JOEM) vol. 46, No. 6 suppl, dated Jun. 2004; pp. S56-S61.

The American Heritage Dictionary of the English Language, definition of planar, 2000.

The constitution of the World Health Organization, World Health Organization, WHO Chronicle, 1947, pp. 1-202.

Vazquez Carazo; "Novel Piezoelectric Transducers for High Voltage Measurements", Jan. 2000, pp. 1-277.

Veeva Systems and Zinc Ahead Join Forces available as of Oct. 2, 2015 at the website: http://www.veeva.com; pp. 1-6.

Wang, Xiaoning. "An Empirical Study of Optimizing Cognitive Load in Multimedia Integrated English Teaching." Studies in Literature and Language 9.3 (2014): 70.

Withings, The Internet connected Body Scale, retrieved with the Wayback Machine using link at www.withings.com, Jan. 11, 2010. (pp. 1-5).

World Economic Forum 'The Workplace Wellness Alliance-Making the Right Investment: Employee Health and the Power of Metrics' dated Jan. 2013; pp. 1-35.

Burkus, David, "For Leaders, Looking Healthy Matters More than Looking Smart" Harvard Business Review, Jan. 2, 2015; pp. 1-5.

Business Wire Health/Medical Writers eHealthcareWorld 2000. (May 1). MyDailyHealth.com (pp. 1-3).

Campbell et al., "The Rise of People-Centric Sensing", IEEE Computer Society, 2008, pp. 12-21, IEEE.

Chapman, L., "Expert opinions on 'best practice' in worksite health promotion (WHP)", Jul./Aug. 2004, pp. 1-13.

Chapman, L.. "Meta-evaluation of worksite health promotion economic return studies: 2012 Update", Mar./Apr. 2012, pp. 1-13.

Chapman, Larry S. MPH, "Meta-evaluation of Worksite Health Promotion Economic Return Studies: 2005 Update", Jul./Aug. 2005. (pp. 1-11).

Collins English Dictionary, definition of mat, 2008, retrieved at www.collinsdictionary.com; pp. 1-8.

Duke, Sean, "A 'smartphone' based defibrillator" Science Spin, Jan. 11, 2011: pp. 1-2.

(56) References Cited

OTHER PUBLICATIONS

Dux, Paul E. et al.; "The attentional blink: A review of data and theory." Attention, Perception, & Psychophysics 71.8(2009): pp. 1683-1700.
Dux, Paul E. et al.; "Training improves multitasking performance by increasing the speed of information processing in human prefrontal cortex." Neuron 631 (2009): pp. 127-138.
Edington, D. W., "Emerging research: a view from one research centre", American Journal of Health Promotion, 15(5), May/Jun. 2001, pp. 341-349.
Edington, M. et al.; "The UAW-GM Health Promotion Program: Successful Outcomes", American Association of Occupational Health Nursing Journal.50, Jan. 2002, pp. 26-31.
Electric double-layer capacitor Wikipedia; available at the website: http://en.wikipedia.org/wiki/electric_double-layer_capacitor as of Dec. 5, 2014; pp. 1-8.
Elliott, Stephen N., et al. "Cognitive load theory: Instruction-based research with applications for designing tests." Proceedings of the National Association of School Psychologists' Annual Convention, Boston, MA, Feb. vol. 24. 2009.
EPO: "Notice from the European Patent Office dated Oct. 1, 2007 concerning business methods" Official Journal EPO, vol. 30, No. 11, Nov. 1, 2007, XP007905525, pp. 592-593.
Fadel, Charles, et al. "Multimodal Learning Through Media: What the Research Says" Cisco Systems, Inc. (2008) pp. 1-24.
Fadjo, Cameron L., et al. "Pedagogy and Curriculum for Video Game Programming Using Scratch." Institute for Learning Technologies, Teachers College, Columbia University, New York, NY, presented at the Scratch Conference, Aug. 13, 2010; pp. 1-2.
Filmer, Hannah L., et al. "Disrupting prefrontal cortex prevents performance gains from sensory-motor training." The Journal of Neuroscience 33.47 (2013): pp. 18654-18660.
Fougnie, Daryl, et al.; "What limits working memory capacity? Evidence for modality-specific sources to the simultaneous storage of visual and auditory arrays." Journal of Experimental Psychology: Learning, Memory, and Cognition 37.6 (2011): 132.
Georgia Tech, "Prowess Proactive Wellness Environment Support System", Dec. 12, 2009, pp. 1-27, www.hsi.gatech.edu/onsitecenter/index.php/PROWESS.
Goetzel et al.; "Estimating the Return-on-Investment From Changes in Employee Health Risks on The Dow Chemical Company's Health Care Costs" J Occup Environ Med. (JOEM) vol. 47, No. 8, Aug. 2005; pp. 759-776.
Goetzel et al.; "Health, Absence, Disability, and Presenteeism Cost Estimates of Certain Physical and Mental Health Conditions Affecting U.S. Employers" J Occup Environ Med. (JOEM) vol. 46, No. 4, Apr. 2004; pp. 398-412.
Goetzel et al.; "Second-Year Results of an Obesity Prevention Program at TheDow Chemical Company" J Occup Environ Med. (JOEM) vol. 52, No. 3, Mar. 2010; pp. 291-302.
Goetzel et al.; "The Health and Productivity Cost Burden of the "Top 10" Physical and Mental HealthConditions Affecting Six Large U.S. Employers in 1999" J Occup Environ Med. (JOEM) vol. 45, No. 1, Jan. 2003; pp. 5-14.
Goetzel et al.; "The Long-Term Impact of Johnson & Johnson's Health & Wellness Program onEmployee Health Risks" J Occup Environ Med. (JOEM) vol. 44, No. 5, May 2002; pp. 417-424.
Goetzel et al.; "The Predictive Validity of the Hero Scorecard in Determining Future Health Care Cost and Risk Trends" J Occup Environ Med. (JOEM) vol. 56, No. 2, Feb. 2014; pp. 136-144.
Goetzel et al.; "The Relationship Between Modifiable Health Risks and Health Care Expenditures: An Analysis of the Multi-Employer HERO Health Risk and Cost Database" Journal of Occupational Environmental Medicine, vol. 40, No. 10, Oct. 1998, 30 pages.
Goetzel et al.; "The Workforce Wellness Index" J Occup Environ Med. (JOEM) vol. 55, No. 3, Mar. 2013; pp. 272-279.
Hacker, et al. "Representation and visualization of variability in a 3D anatomical atlas using the kidney as an example." Medical Imaging. International Society for Optics and Photonics, 2006. XP055342027 (pp. 1-7).
Hemp, P.; "Presenteeism: At Work—But Out of It", Harvard Business Review, Oct. 2004, pp. 49-58.
Hill, Jr., Randall W.; "How Virtual Humans Can Build Better Leaders" Harvard Business Review Jul. 25, 2014; pp. 1-4.
Horseman, S. et al.; "Gamefication of Health, Safety and the Environment (HSE): An Avatarial Solution" American Society of Safety Engineers 11th Professional Development Conference & Exhibition, Bahrain, Mar. 2014; pp. 1-10.
Horseman, S.; "ErgoWELL : An Integrative Strategy", SPE 152629. Society of Petroleum Engineers, MEFISSE. Paper and Workshop, Abu Dhabi, 2012, pp. 1-17.
Horseman, S.; "Healthy Human Capital as a Business Strategy: The Saudi Aramco Wellness Program (SAWP)", American Society of Safety Engineers (ME Chapter), (9) Conference Proceedings. Bahrain. Feb. 2010, pp. 178-185.
Index for "Micro-NanoMechatronics and Human Science (MHS), 2010 International Symposium Nov. 2010", retrieved from <http://ieeexplore.ieee.org/xpl/mostRecentIssue.jsp?punumber=5658189> Ma 7, 2012. (pp. 1-5).
International Preliminary Report on Patentability for International Application No. PCT/US2012/045395 dated Jan. 7, 2014. (pp. 1-12).
International Preliminary Report on Patentability for International Application No. PCT/US2012/045401 dated Jan. 7, 2014. (pp. 1-9).
International Preliminary Report on Patentability for International Application No. PCT/US2012/045407 dated Jan. 7, 2014. (pp. 1-8).
International Preliminary Report on Patentability for International Application No. PCT/US2012/045410 dated Jan. 7, 2014. (pp. 1-8).
International Preliminary Report on Patentability for International Application No. PCT/US2012/045414 dated Jan. 7, 2014. (pp. 1-8).
International Preliminary Report on Patentability for International Application No. PCT/US2012/045419 dated Jan. 7, 2014. (pp. 1-11).
International Preliminary Report on Patentability for International Application No. PCT/US2012/045427 dated Jan. 7, 2014. (pp. 1-10).
International Preliminary Report on Patentability for International Application No. PCT/US2012/045435 dated Jan. 7, 2014. (pp. 1-10).
International Preliminary Report on Patentability for International Application No. PCT/US2012/045442 dated Jan. 7, 2014. (pp. 1-10).
International Preliminary Report on Patentability for International Application No. PCT/US2012/045447 dated Jan. 7, 2014. (pp. 1-8).
International Preliminary Report on Patentability for International Application No. PCT/US2012/045452 dated Jan. 7, 2014. (pp. 1-9).
International Search Report and Written Opinion for International Application No. PCT/US2004/045442 dated Nov. 7, 2012. (pp. 1-14).
International Search Report and Written Opinion for International Application No. PCT/US2012/045395 dated Dec. 3, 2012. (pp. 1-16).
International Search Report and Written Opinion for International Application No. PCT/US2012/045401 dated Feb. 5, 2013. (pp. 1-13).
International Search Report and Written Opinion for International Application No. PCT/US2012/045407 dated Jan. 23, 2013. (pp. 1-15).
International Search Report and Written Opinion for related PCT application PCT/US2018/064161 (SA5721) dated Feb. 28, 2019; pp. 1-13.

* cited by examiner

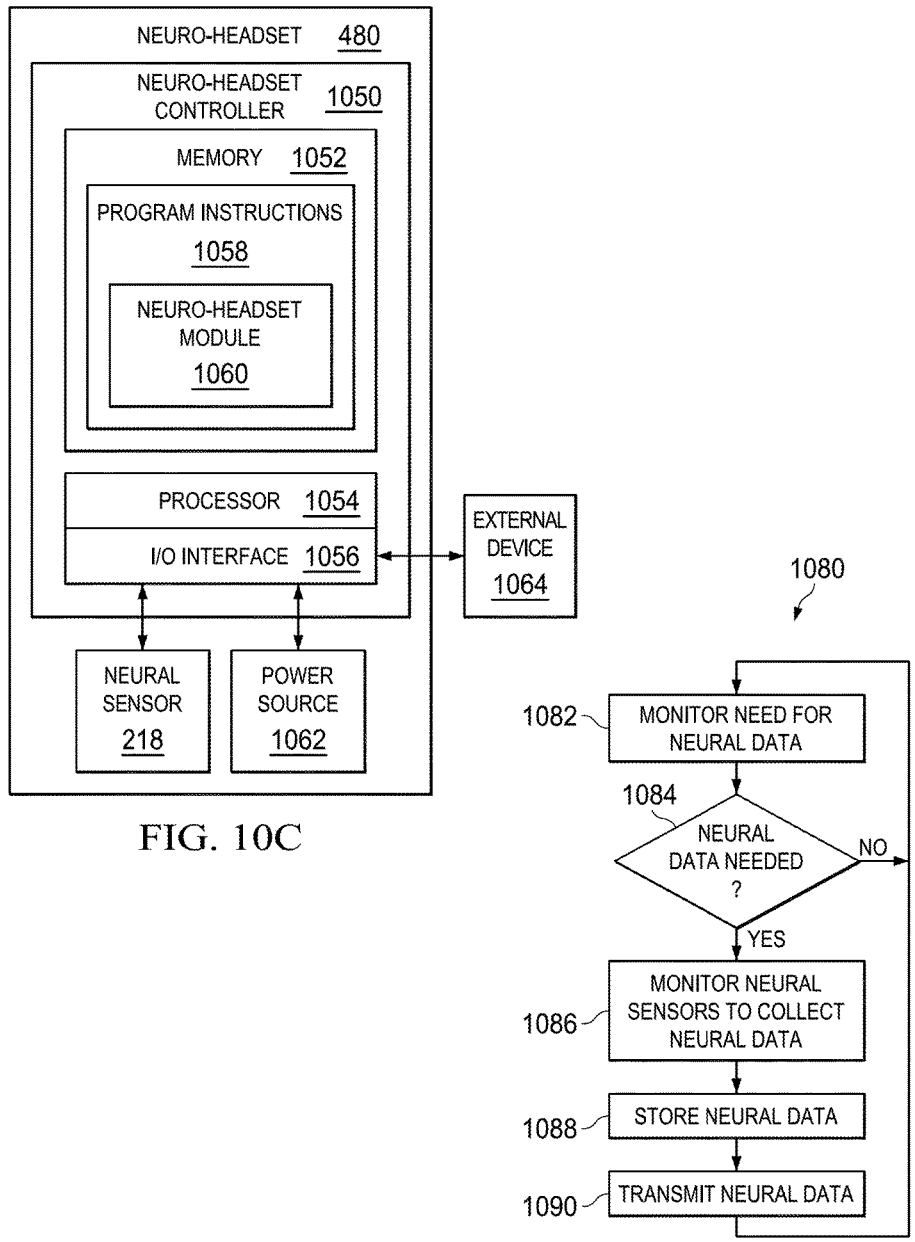

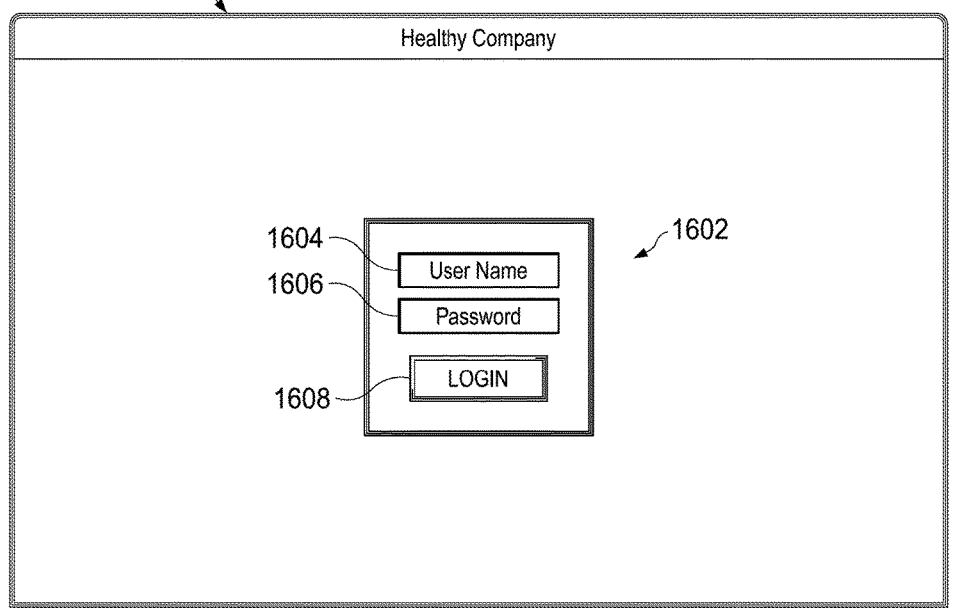
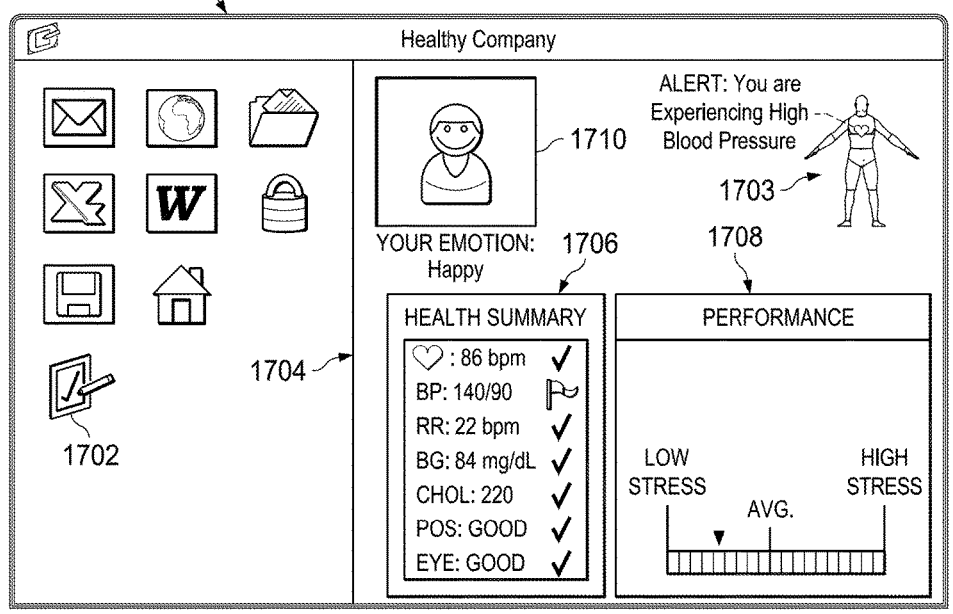

Edit Profile    1802

Name _____
Age _____          Submit
Height _____
Weight _____       Exit
Sex _____
                                    1806
Goal
    Lower Blood Pressure _____
    Lose Weight _____
    Body Fat _____
    Blood Sugar Control _____
    Resting Heart Rate _____

1804

CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES

RELATED APPLICATIONS

This application is a continuation of U.S. patent application Ser. No. 14/180,529 filed on Feb. 14, 2014 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", which is a divisional of U.S. patent application Ser. No. 13/540,095 filed on Jul. 2, 2012 (now U.S. Pat. No. 9,492,120) which claims the benefit of and priority to U.S. Provisional Patent Application No. 61/504,638 filed on Jul. 5, 2011 and titled "SYSTEM, COMPUTER PROGRAM PRODUCT AND COMPUTER-IMPLEMENTED METHOD FOR IMPROVING AND MONITORING THE HEALTH AND PRODUCTIVITY OF EMPLOYEES", U.S. Provisional Patent Application No. 61/659,831 filed on Jun. 14, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,790 filed on Jun. 14, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. Provisional Patent Application No. 61/659,796 filed on Jun. 14, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,800 filed on Jun. 14, 2012 and #5824809.1 titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,807 filed on Jun. 14, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,810 filed on Jun. 14, 2012 and titled "SYSTEMS, COMPUTER MEDIUM AND COMPUTER-IMPLEMENTED METHODS FOR MONITORING AND IMPROVING BIOMETRIC HEALTH OF EMPLOYEES", U.S. Provisional Patent Application No. 61/659,818 filed on Jun. 14, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", and U.S. Provisional Patent Application No. 61/659,824 filed on Jun. 14, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", the disclosures of which are each hereby incorporated by reference in their entireties.

FIELD OF INVENTION

The present invention relates generally to health monitoring in the work place and more particularly to chair pad systems, machines and associated non-transitory computer medium having computer program instructions stored thereon, and computer-implemented methods for monitoring the health of employees.

BACKGROUND OF THE INVENTION

A major concern among employers is the issue of presenteeism, or the phenomena that, while employees may be at work, health problems such as, lower back pain, fatigue, high blood pressure and obesity, keep them from working optimally, and cause a rapid rise in employee healthcare costs. Many human resource ("HR") executives consider presenteeism a problem in their companies, estimating an annual cost to companies of over $180 billion/year, and a per employee cost between $22 and $157 annually. Moreover, presenteeism appears to be a problem at over 50% of workplaces. In 2006, 56% of HR executives viewed it as a problem, while only 39% of HR managers found it to be a problem in 2004. Because such health problems may be caused by a combination of employee lifestyle and work practices, workplace health programs have been employed to make employees aware of sound health and ergonomic practices in an effort to promote employee health and help lower employer costs.

Unfortunately, even if employees are made aware of sound health and ergonomic practices, employees often slip back into poor health and ergonomic practices while engrossed in their day-to-day work activities. The current state of the art solution to address these issues includes health programs that rely on periodic tests to assess employee health and ergonomics. Such tests typically require employees to expend a great deal of effort to participate in the programs. For example, health programs may monitor the employee's health via test conducted in test facilities at discrete testing times (e.g., quarterly or annual health tests). Unfortunately, the presence of traditional health testing equipment and personnel may be overly burdensome in the user's work environment. For example, health testing personnel located in the employee's office to monitor a set of sensors may be distracting. Moreover, the ability to monitor a plurality of employees throughout their workday may be difficult or impossible due to constraints on the number of health personnel available. Thus, existing health programs may require the employee to take time out of their day to attend a health test, existing health programs may not assess the employee in their day-to-day work environment, and existing health programs may not provide continuous feedback that can be used to dynamically adjust the employee's day-to-day activities and/or may not be able to rapidly identify and predict health issues based on changes in the employee's health.

SUMMARY OF THE INVENTION

Applicant has recognized the need for a health monitoring system that provides for assessment of employees in their day-to-day work environment, that reduce the effort required to take part in a health program, that continuously monitors the employees' health in their day-to-day work environments, that rapidly identifies and predicts health issues for the employees, and that provides frequent (e.g. real-time) feedback that can be used dynamically adjust the employee's day-to-day activities to improve the employees' health and/or to help prevent the predicted health issues from escalating into an actual health conditions. Applicant has recognized that, although existing health programs provide some level of health monitoring, the complexities associated with employees having to proactively take part in health tests may reduce employee involvement in the health programs. For example, employees may decide to forgo a health program in view of the time and effort required to engage in health tests at a testing facility. Moreover, the infrequent nature of the health tests may inhibit the ability of existing health programs to promptly identify and predict health issues (e.g., health risks such as injury or disease). For example, semi-annual test may not be able to identify changes in the employee's health that can occur within days or weeks, such as sickness, short term injuries, and diseases that manifest themselves over a short period. Thus, existing health programs fail to provide a framework for continuously acquiring health data that can be used to rapidly identify changes in the employee's health over relatively short periods of time. Applicant has recognized that such shortcomings have failed to be addressed by others, and has recognized that such shortcomings may be addressed by a system that can continuously collect employee health data while employees are situated in their day-to-day work environment (e.g., at the employees' offices), that can process the health data to assess the employees' current health and predict potential health issues, and that can provide feedback indicative of the employees' current health and predict potential health issues such that the employees can take proactive measures to address their current health conditions and prevent the predict potential health issues. In view of the foregoing, various embodiments of the present invention advantageously provide systems, machines, non-transitory computer medium having computer program instructions stored thereon, and computer-implemented methods for monitoring the health of employees in their work environment using various sensors disposed about their work environment, for determining employee health profiles (e.g., including existing or predicted health conditions/risks and health plans to guide the employee with regard to a healthy lifestyle) based on the health data, and for providing feedback to communicate the determined health profile and associated information.

In some embodiments, provide is a system for monitoring an employee's health while the employee is working at a including a workstation surface located above and parallel to a floor, a computer workstation and a chair located on the floor adjacent to the workstation surface. The chair having a seat portion and a back portion. The system including a chair pad in communication with the computer workstation and including a seat-pad configured to be disposed in the seat portion of the chair and a back-pad portion configured to be disposed on the back portion of the chair. At least one of the seat-pad and the back-pad of the chair pad including a set of health sensors integrated therewith for detecting biometric and biomechanical characteristics of the employee's health. The set of health sensors including one or more temperature sensors, one or more position sensors, and one or more body fat sensors The set of health sensors configured to output health sensor data including of temperature data output by one or more of the temperature sensors that is indicative of a body temperature of the employee, position data output by one or more of the position sensors that is indicative of the body position of the employee, and body fat data output by one or more of the body fat sensors that is indicative of a body fat of the employee. The system including a database in communication with a communications network and storing health information associated with one or more employees, and a computer server in communication with the communication network. The computer server configured to serve, to the computer workstation for display to the employee, health profile information for the employee. The computer server including a non-transitory computer readable storage medium, an input/output (I/O) device interface and a processor. The I/O device interface connecting the computer server to the communications network and the non-transitory computer readable storage medium having a set of computer readable instructions stored thereon that are executable by the processor to cause the computer server to perform the steps of collecting, via the communications network, the health sensor data output by the set of health sensors of the chair pad, and determining an updated health profile for the employee using the health sensor data collected. The updated health profile including health characteristics for the employee including one or more of a body temperature, a body weight, a body fat, and a body position for the employee determined using the health sensor data collected, and a health plan for the employee based on one or more of the health characteristics determined using the health sensor data collected. The computer readable instructions executable by the processor to cause the computer server to perform the steps updating the health information stored in the database to reflect the updated health profile for the employee, and serving, for display to the employee via the computer workstation, the updated health profile for the employee.

The step of collecting, via the communications network, the health sensor data output by the set of health sensors of the chair pad includes, in some embodiments, identifying a need to initiate a health test using a predetermined test schedule that specifies times at which the health sensor data needs to be collected from the health sensors, in response to identifying a need to initiate a health test using a predetermined test schedule that specifies times at which the health sensor data needs to be collected from the health sensors, querying the computer workstation for the health sensor data corresponding to the health test where the computer workstation is configured to collect the health sensor data from the set of health sensors of the chair pad, and receiving, from the computer workstation and via the communications network, the health sensor data corresponding to the health test.

In some embodiments, the chair pad includes a chair pad controller configured to receive the temperature data output by one or more of the temperature sensors, the body position data output by one or more of the body position sensors, and the body fat data output by one or more of the body fat sensors, and transmit, to the computer workstation, health data corresponding to the received temperature data, body position data, and body fat data received, wherein the computer workstation is configured to transmit health data corresponding to the health data received to the computer server.

In certain embodiments, the chair pad controller is wirelessly connected to the computer workstation, and the health data corresponding to the received temperature data, body position data, and body fat data received is transmitted from the chair pad controller to the computer workstation via the wireless connection.

In some embodiments, the one or more temperature sensors include one or more temperature transducers located in at least one of a right portion of the seat-pad, a left portion of the seat-pad, a right portion of the back-pad, and a left portion of the back-pad such that a temperature of at least one of the employee's right buttocks/upper-leg, left buttocks/upper-leg, right back, or left back is sensed while the employee is seated in the chair.

In some embodiments, the one or more position sensors include one or more forces transducers located in at least one of a right portion of the seat-pad, a left portion of the seat-pad, a right portion of the back-pad, and a left portion of the back-pad such that a force of at least one of the employee's right buttocks/upper-leg, left buttocks/upper-leg, right back, or left back is sensed while the employee is seated in the chair.

In certain embodiments, the one or more body fat sensors include one or more conductive contacts located in at least one of a right portion of the seat-pad, a left portion of the seat-pad, a right portion of the back-pad, and a left portion of the back-pad such that body fat across at least one of the employee's right buttocks/upper-leg and left buttocks/upper-leg, right back and left back, right buttocks/upper-leg and right back, and left buttocks/upper-leg and left back is sensed while the employee is seated in the chair.

In some embodiments, the seat-pad of the chair pad is integrated into an upper seating surface of the chair seat portion and the back-pad of the chair pad is integrated into a front surface of the chair back portion.

In some embodiments, provided is a chair pad for sensing health characteristics of a user. The chair pad including a chair pad controller, a seat-pad configured to be disposed on a seat portion of a chair; a back-pad configured to be disposed on a back portion of the chair, and a set of health sensors integrated within at least one of the seat-pad and the back-pad. The set of health sensors including one or more temperature sensors configured to sense a body temperature of the user. The chair pad controller being configured to transmit temperature data corresponding to the sensed body temperature to a computer workstation for use in determining the body temperature of the user. The set of health sensors including one or more body position sensors configured to sense a body position of the user. The chair pad controller being configured to transmit body position data corresponding to the sensed body position to the computer workstation for use in determining the body position of the user. The set of health sensors including one or more body fat sensors configured to sense body fat of the user. The chair pad controller configured to transmit body fat data corresponding to the sensed body fat to the computer workstation for use in determining the body fat of the user.

In some embodiments, the one or more temperature sensors include one or more temperature transducers located in at least one of a right portion of the seat-pad, a left portion of the seat-pad, a right portion of the back-pad, and a left portion of the back-pad such that a temperature of at least one of the user's right buttocks/upper-leg, left buttocks/upper-leg, right back, or left back is sensed while the user is seated in the chair.

In certain embodiments, the one or more position sensors include one or more forces transducers located in at least one of a right portion of the seat-pad, a left portion of the seat-pad, a right portion of the back-pad, and a left portion of the back-pad such that a force of at least one of the user's right buttocks/upper-leg, left buttocks/upper-leg, right back, or left back is sensed while the user is seated in the chair.

In some embodiments, the one or more body fat sensors include one or more conductive contacts located in at least one of a right portion of the seat-pad, a left portion of the seat-pad, a right portion of the back-pad, and a left portion of the back-pad such that body fat across at least one of the user's right buttocks/upper-leg and left buttocks/upper-leg, right back and left back, right buttocks/upper-leg and right back, and left buttocks/upper-leg and left back is sensed while the user is seated in the chair.

The chair pad controller being configured to, in some embodiments, receive a request for health data from the computer workstation, and, in response to receiving a request for health data from the computer workstation collect the temperature data from the one or more temperature sensors, the body position data from the one or more body position sensors, and the body fat data from the one or more body fat sensors, and transmit, to the computer workstation, health data corresponding to the temperature data, the body position data, and the body fat data for use in determining the body temperature, the body position, and the body fat of the user.

In some embodiments, provided is a non-transitory computer readable storage medium including program instructions for use in monitoring an employee's health while the employee is working at a workstation including one or more of a workstation surface located above and parallel to a floor, a computer workstation and a chair located on the floor adjacent to the workstation surface. The chair having a seat portion and a back portion. The computer program instructions being executable by a computer processor to cause the steps of activating set of health sensors integrated with a chair pad connected to a communications network via the computer workstation. The chair pad including a seat-pad configured to be disposed in the seat portion of the chair and a back-pad configured to be disposed on the back portion of the chair, with at least one of the seat-pad and the back-pad of the chair pad including the set of health sensors integrated therewith for detecting biometric and biomechanical characteristics of the employee's health. The set of health sensors including one or more temperature sensors, one or more position sensors, and one or more body fat sensors. The set of health sensors configured to output health sensor data including of temperature data output by one or more of the temperature sensors that is indicative of a body temperature of the employee, position data output by one or more of the position sensors that is indicative of the body position of the employee, and body fat data output by one or more of the body fat sensors that is indicative of a body fat of the employee. The computer program instructions being executable by a computer processor to cause the steps of collecting, via the communications network, the health sensor data output by the set of health sensors of the chair pad, and determining an updated health profile for the employee using the health sensor data collected. The updated health profile including health characteristics for the employee including one or more of a body temperature, a body weight, a body fat, and a body position for the employee determined using the health sensor data collected, and a health plan for the employee based on one or more of the health characteristics determined using the health sensor data collected. The computer program instructions being executable by a computer processor to cause the steps of updating the health information stored in the database to reflect the updated health profile for the employee, and serving, for display to the employee via the computer workstation, the updated health profile for the employee.

In some embodiments, provided is a computer-implemented method for sensing health characteristics of a user using a chair pad including a seat-pad configured to be disposed on a seat portion of a chair, a back-pad configured to be disposed on a back portion of the chair, and a set of health sensors integrated within at least one of the seat-pad and the back-pad. The set of health sensors including one or more temperature sensors configured to sense a body temperature of the user, one or more body position sensors configured to sense a body position of the user, and one or more body fat sensors configured to sense body fat of the user. The computer-implemented method including receiving, from the one or more temperature sensors, temperature data corresponding to a sensed body temperature of the user, receiving, from the one or more body position sensors, body position data corresponding to a sensed body position of the user, receiving, from the one or more body fat sensors, body fat data corresponding to a sensed body fat of the user, and transmitting, to a computer workstation, health data corresponding to the temperature data, the body position data, and the body fat data for use in determining the body temperature, the body position, and the body fat of the user.

Accordingly, as will be described herein below, embodiments of the system, computer program instructions and associated computer-implemented methods allow for monitoring of the employee's health.

BRIEF DESCRIPTION OF THE DRAWINGS

So that the manner in which the features and advantages of the invention, as well as others, which will become apparent, may be understood in more detail, a more particular description of the invention briefly summarized above may be had by reference to the embodiments thereof, which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 10C is a block diagram that illustrates components of the neuro-headset in accordance with one or more embodiments of the present invention.

FIG. 10D is a flowchart that illustrates a method of operating the neuro-headset in accordance with one or more embodiments of the present invention.

FIG. 16 is a screen-shot that illustrates a login screen in accordance with one or more embodiments of the present invention.

FIG. 17 is a screen-shot that illustrates a home page screen in accordance with one or more embodiments of the present invention.

FIG. 18 is a screen-shot that illustrates an edit profile dialog in accordance with one or more embodiments of the present invention.

DETAILED DESCRIPTION

Figure 1:
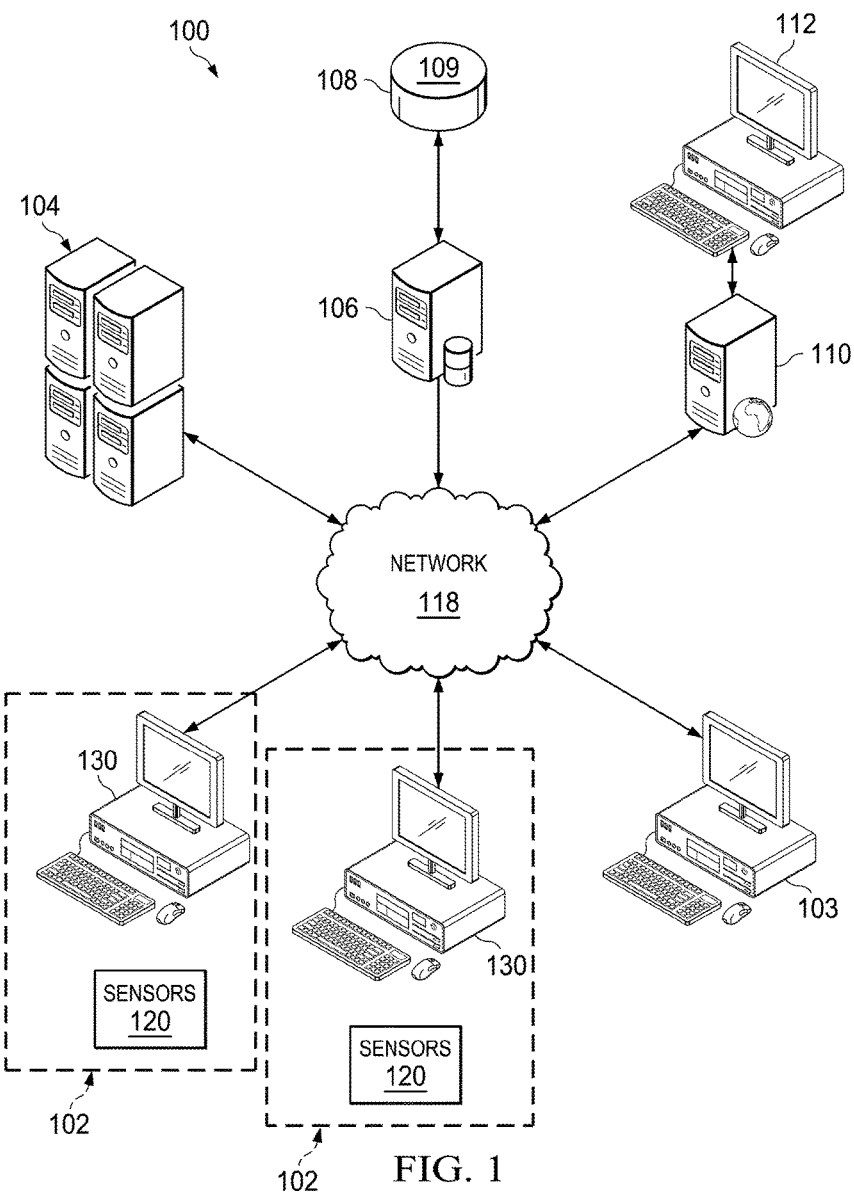
FIG. 1 is a block diagram that illustrates an employee heath monitoring system in accordance with one more embodiments of the present invention.

The present invention will now be described more fully hereinafter with reference to the accompanying drawings in which embodiments of the invention are shown. This invention may, however, be embodied in many different forms and should not be construed as limited to the illustrated embodiments set forth herein, rather, these embodiments are provided so that this disclosure will be thorough and complete, and will fully convey the scope of the invention to those skilled in the art.

In view of the Applicant's recognition of the issues associated with presenteeism, the Applicant engaged in investigations to assess the impact of "wellness programs" on the health of employees. One internal study conduct indicated that certain wellness programs improved productivity, improved work factors, and reduced employee's risks for disease. The study involved tracking a population of 1,157 employees from 2005-2011. The results of the study indicate a shift of employees from higher risk categories (e.g., a high risk category for employee's diagnosed as being at risk for three or more conditions, such as risks for chronic disease such as high blood pressure (BP), inactive, high body mass index (BMI), high fat percentage, or the like) to lower risk categories (e.g., a low risk category for employee's diagnosed as being at risk for one or no conditions). More specifically, the results of the study indicated a reduction of the number of employees in a high risk category (e.g., for employee's diagnosed as being at risk for three or more conditions) by 49.6%, a reduction of the number of employees in a medium risk category (e.g., for employee's diagnosed as being at risk for two or more conditions) by 0.4%, and an increase in the number of employees in a low risk category (e.g., for employee's diagnosed as being at risk for one or no conditions) by 12.6%. The results of the internal study also estimated a 6.4% reduction in medical claims cost (e.g., a cost savings of approximately $3.4 M for the study population of 1,157 employees) that can be attributable to the wellness program and associated reduction in risks.

Related internal studies have also indicated that such wellness programs have a positive impact on employee work factors, including stress management, job satisfaction, work engagement and productivity. For example, results of the study indicate that 60% to 75% of the employees agree with the position that the wellness programs provided improvements in each of stress management, job satisfaction, work engagement and productivity, with only about 7% to 12% of the employees disagreeing with the position that the wellness programs provided improvements in each of the areas.

The Applicant has recognized that such study results demonstrate the potential effectiveness of wellness programs in reducing health risks, improving employee's work factors, and reducing health costs to employers. Based at least in part on the recognition of the benefits of employee health programs as well as the limitations of existing health programs, the Applicant has recognized the need for improved employee health programs that can provide increased health and economic benefits to employees and employers, and has developed a specially adapted health monitoring system and related methods that further assist in monitoring the employee's health and solving limitations of traditional health monitoring programs.

In some embodiments, provided is an employee health monitoring system that provides for monitoring of an employee's health, that provides feedback to the employee regarding the current status of their health, that provides the employee with information to guide the employee in a healthy lifestyle, and that provides the employee with reinforcing information to encourage the employee to continue to engage in the healthy lifestyle.

In certain embodiments, monitoring of the employee's health includes monitoring the employee while they are engaged in their day-to-day work activities within their work environment. In some embodiments, various monitoring devices (e.g., health sensors) are placed in the employee's work environment to collect health data that can be used to assess various biometric and biomechanical characteristics (e.g., characteristics, conditions and risks) of the employee, such as the employee's body weight, body temperature, body fat percentage, heart rate, blood pressure, blood glucose level, blood oxygenation level, body position/posture, eye fatigue, neural activity, emotions, thoughts, facial movements/expressions, motor skills, and the like. In certain embodiments, the monitoring devices are integrated with the employee's workstation (e.g., in and around the employee's desk and computer workstation) such that the employee's health can be monitored without requiring the employee to leave their workstation to take part in a health test/exam. In some embodiments, for example, health sensors are integrated with a chair, a floor, a computer mouse, or the like located in and around the employee's workstation. In certain embodiments, the health sensors provide multiple points of contact with the employee for collecting health data (e.g., at least five points of contact, including a first point of contact with the head/eyes, a second point of contact with arms/hands, a third point of contact with torso/back/legs, a fourth point of contact with feet of the employee, and a fifth point of contact with the head/brain of the employee).

In some embodiments, the health data collected and/or the health characteristics/conditions identified can be used to identify/predict health risks for the employee, such as risks for obesity, injury, diabetes, infection, circulation problems, cardiovascular disease, cardiovascular accidents (e.g., stroke or heart attack), back injury, eye disease, depression, fatigue, and/or the like. In certain embodiments, health risks are determined via predictive analytics that use employee's current and/or historical health characteristics/conditions. For example, where the recent health data for an employee indicates a trend of increasing body weight for an employee, it may be predicted that the employee is at risk for becoming obese within a given time period. In some embodiments, an alert may be provided to the employee to make them aware of the predictions/risks. For example, the employee may be presented with a listing of risks that correspond to predicted health issues. Such predictions and corresponding alerts may enable the employee to proactively improve their health before the associated risks escalate to a critical level. For example, as a result of a prediction and alert that communicates to the employee that they are at risk for becoming obese, the employee may have the motivation needed to change their eating and exercise habits to avoid actually becoming obese. Thus, the system may provide an environment for proactively predicting and responding to health risks before they escalate into actual health conditions.

In some embodiments, the health data, characteristics, conditions and/or risks are used to generate health plans for the employee. In certain embodiments, the health plans include preventative health plans that provide guidance to reduce health risks and/or promote a healthy lifestyle. In some embodiments, the health plans provide a suggested nutrition plan and/or a suggested exercise regime. In certain embodiments, the employee health monitoring system provides coaching (e.g., suggestions) to help the employee follow through with the health plan. In some embodiments, the health data, characteristics, conditions and/or plans may be logged over time to generate a health profile for the employee.

In some embodiments, the employee health monitoring system provides for automated health testing based on a predetermined schedule. In certain embodiments, for example, automated health test are executed continuously (e.g., constantly from 8am to 5 pm) or at regular intervals (e.g., hourly from 8am to 5 pm). Such embodiments may enable the employee's health to be monitored passively, with little to no effort from the employee. In some embodiments, the employee health monitoring system provides for manually initiated health testing. In certain embodiments, for example, an employee may select to initiate a health test. Such embodiments may enable employees to take a more active role in the monitoring of their health.

In some embodiments, the results of the health tests are provided to the employee for review. In certain embodiments, for example, the health monitoring system provides a health report including the employee's health profile information (e.g., the health data collected, the health characteristics/conditions, and/or the health risks for the employee). In some embodiments, the health report is accessible by the employee at their work computer (e.g., via a desktop widget, an interactive dashboard, and/or the like) such that the employee can view the results at their convenience throughout the workday. Such embodiments may enable the employee to receive real-time feedback regarding their health and immediately make corresponding adjustments throughout the workday. In some embodiments, the results of the health tests are provided to the employer or other interested parties (e.g., a physician) for review. Such embodiments may enable the employer to monitor the health of some or all of their employees such that they can readily identify health concerns/trends and take action to alleviate those concerns/trends, thereby improving the work environment for the employees.

In some embodiments, the health monitoring system monitors the health profile information to identify whether the employee is experiencing a health crisis (e.g., a stroke or heart attack) and, in the instance the employee is experiencing a health crisis, transmits corresponding alerts. In certain embodiments, for example, upon determining that the employee is having a heart attack based on the results of a health test, the health monitoring system may forward an alert to emergency response personnel (e.g., police, fire, emergency medical technicians ("EMT's") or the like). Such embodiments may help to ensure that the employee receives prompt medical treatment in the event of a medical emergency at the workplace.

Embodiments of the health monitoring system may provide a work environment that promotes employee involvement in monitoring their health via a non-intrusive health testing environment that enables the employee's health to be monitored from the convenience of their workstation. Moreover, embodiments of the health monitoring system may provide feedback that informs the employee of their current health, that identifies/predicts health risks and goals based on the employee's health and provides guidance to reduce the employee's health risks and attain the identified health goals. Although some of the embodiments are described with regard to health data collected via a workstation (e.g., via sensors disposed about an employee's office), similar embodiments may be employed using health data collected from any variety of sources. For example, the health data may be collected from an employee workstation, from a mobile device that is capable of collecting health data from the employee while they are working remotely (e.g., at a jobsite), at the workstation and/or traveling there between, and any variety of other sources of health data. In such embodiments, the health report and the resulting reports, interactive dashboard displays and/or the like may be generated based on health data collected from any variety of sources (e.g., the workstation, mobile device and/or the like) such that the employee's health is monitored while they are located in a variety of locations and conditions. Such embodiments may provide a thorough representation and analysis of the employee's health when they are located at a workstation and/or away from the workstation.

FIG. 1 is a block diagram that illustrates an employee heath monitoring system ("system") 100 in accordance with one more embodiments of the present invention. As depicted, system 100 may include one or more employee workstations 102, one or more employer workstations (e.g., employer computers) 103, a server 104, a file server 106 coupled to a datastore 108, and a web server 110 connected to remote workstation 112 (e.g., remote computers). In some embodiments, the entities of the system 100 are communicatively coupled via a network 118. Datastore 108 may store health information 109 (e.g., personal profile information, health profile information, and/or the like) for one or more employees.

In some embodiments, the network 118 includes an element or system that facilitates communications between entities of system 100. For example, the network 118 may include an electronic communications network, such as the Internet, a local area network ("LAN"), a wide area ("WAN"), a wireless local area network ("WLAN") a cellular communications network or the like. In some embodiments, the network 118 includes a single network or combination of networks. For example, the employee workstations 102, the employer workstation 103, the server 104, the file server 106, and/or the web server 110, may be networked using a private/LAN, with the remote computers 112 (e.g., employee home computers, emergency personnel computer devices, or the like) connected to the web server 104 via a WAN.

As described in more detail below, the employee workstations 102 may include health sensors ("sensors") 120 and/or an employee computer workstation ("employee computer") 130 for collecting employee health data that may be employed by the server 104 for use in monitoring an employee's health. In some embodiments, the employee workstations 102 are located in or include traditional employee work environments (e.g., an employee's office employee's office, cubicle, assigned station on an assembly/manufacturing line, or the like) such that the sensors 120 may collect health data from the employee while the employee is working in their work environment.

In some embodiments, the health data may include measurements that can be used to assess various biometric aspects of the employee's health, such as one or more of body temperature, body weight, body fat, heart rate, respiratory rate, blood pressure, blood oxygen saturation (e.g., blood oxygenation), blood glucose level, neural/brain activity, and/or the like. In some embodiments, the health data may include measurements that can be used to assess various biomechanical aspects of the employee's health, such as one or more of body position, posture, muscle tension, eye fatigue, facial expression, motor skills, and/or the like. Sensors that are used to acquire measurements for use in assessing various biometric aspects of the employee's health may be referred to as "biometric sensors". Sensors that are used to acquire measurements for use in assessing various biomechanical aspects of the employee's health may be referred to as "biomechanical sensors". Sensors that are used to acquire measurements that are indicative of both biometric and biomechanical aspects of the employee's health may be referred to as "biometric" and/or "biomechanical" sensors.

As discussed in more detail below, in some embodiments, the employee computer 130 may provide for collecting health data from the various sensors 120 and/or forwarding corresponding health data to the server 104 for use in monitoring an employee's health. For example, in response to determining that employee health data needs to be collected (e.g., based on a request from the server 104, based on a request from the employee, a predetermined test schedule, or the like), the employee computer 130 may monitor sensors 120 to collect health data (e.g., measurements) from the sensors 120, and forward the health data to server 104 for use in monitoring the health of the employee. Although certain embodiments are described herein with regard to the employee computer 130 forwarding health data to the server 104, it will be appreciated that in other embodiments, some or all of the health data is provided directly to the server 104 (i.e., without having to pass the data through the employee computer 130). For example, the sensors 120 may be communicatively coupled to the server 104 via the network 118 (e.g., via a WLAN) such that they can transmit heath data directly to the server 104.

Figure 2:
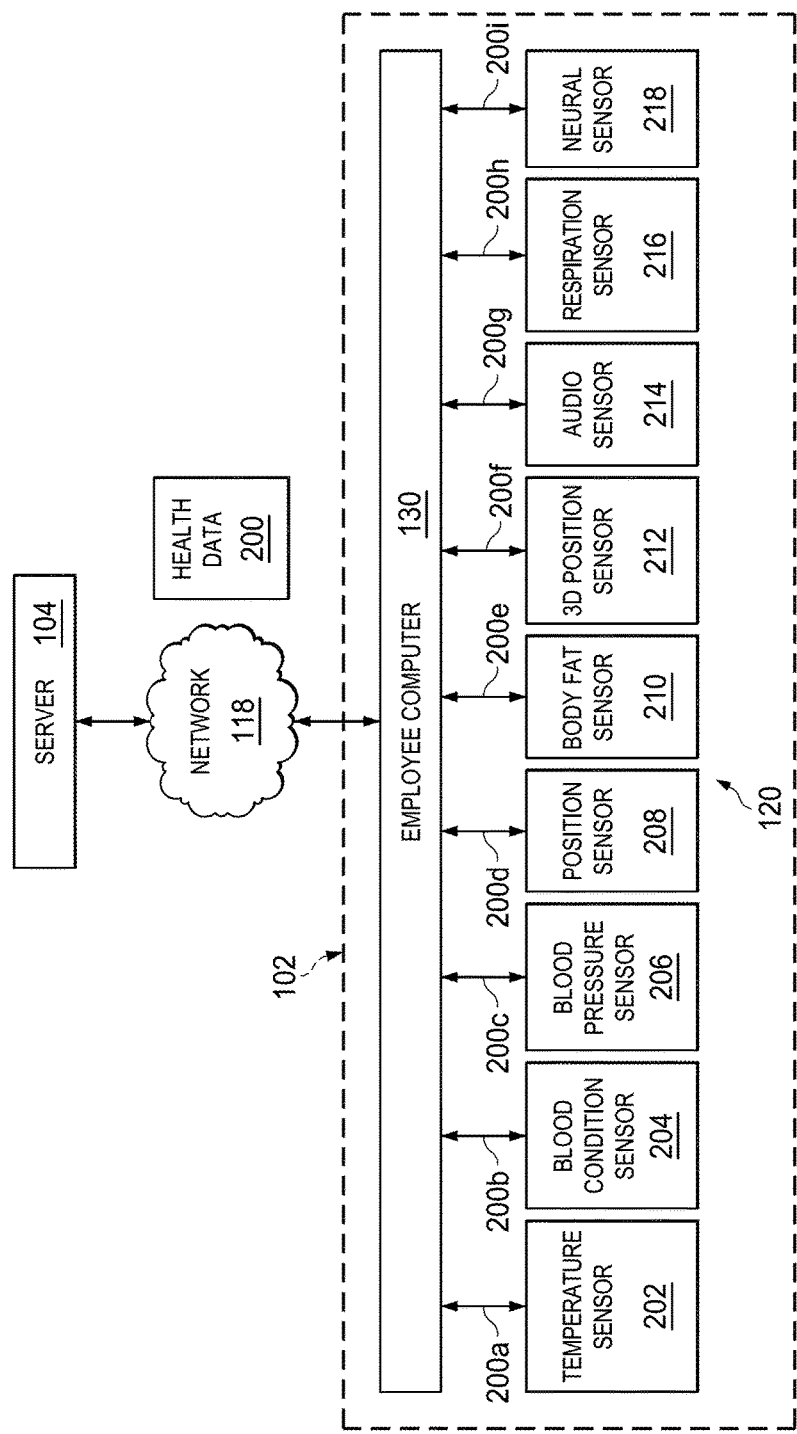
FIG. 2 is a block diagram that illustrates an employee workstation connected to a server in accordance with one or more embodiments of the present invention.

FIG. 2 is a block diagram that illustrates an employee workstation 102 connected to the server 104 in accordance with one or more embodiments of the present invention. In some embodiments the employee workstation 102 includes an employee computer 130 communicatively coupled to one or more of the sensors 120 for collecting employee health data 200. For example, employee the computer 130 may be communicatively coupled to one or more temperature sensors (e.g., thermocouples, IR sensors, etc.) 202, one or more blood condition sensors (e.g., pule oximeters) 204, one or more blood pressure sensors (e.g., blood pressure cuffs) 206, one or more position sensors (e.g., force transducers) 208, one or more body fat sensors (e.g., conductive contacts) 210, one or more three-dimensional ("3D") position sensors (e.g., 3D image/video sensors) 212, one or more audio sensors (e.g., microphone) 214, one or more respiration sensors 216, one or more neural sensors 218, and/or the like for collecting corresponding health data 200 (e.g., measurements) therefrom. In some embodiments, the health data 200 includes temperature data 200a, blood condition data 200b, blood pressure data 200c, position data 200d, body fat data 200e, 3D position data 200f, audio data 200g, respiration data 200h and/or neural data 200i collected from corresponding one of the sensors 120. The health data 200 may be provided to the server 104 for use in monitoring the employee's health.

In some embodiments, the employee computer 130 is communicatively coupled to the sensors 120 via a wired connection. For example, some or all of the sensors 120 may include a communication cable extending between the respective sensor 120 and the employee computer 130. In some embodiments, employee computer 130 is communicatively coupled to the sensors 120 via a wireless connection. For example, some or all of the sensors 120 may communicate with the employee computer 130 via a wireless connection (e.g., a Bluetooth connection, a wireless connection to a WLAN of network 118, and/or the like). In some embodiments, the heath data 200 is transmitted from the sensors 120 to the employee computer 130 via the wired or wireless connection (e.g., a Bluetooth connection, a WLAN of network 118, and/or the like). In some embodiments, the health data 200 is transferred between devices of the system 100 via a physical memory medium such as a universal serial bus ("USB") memory stick (e.g., a flash drive). For example, the health data 200 acquired from the sensors 120 may be downloaded from the sensors 120 and/or the employee computer 130 to a USB memory stick and may be uploaded from the USB memory stick to another device of the system 100, such as the employee computer 130, the employer computer 103, and/or the sever 104.

Figure 3:
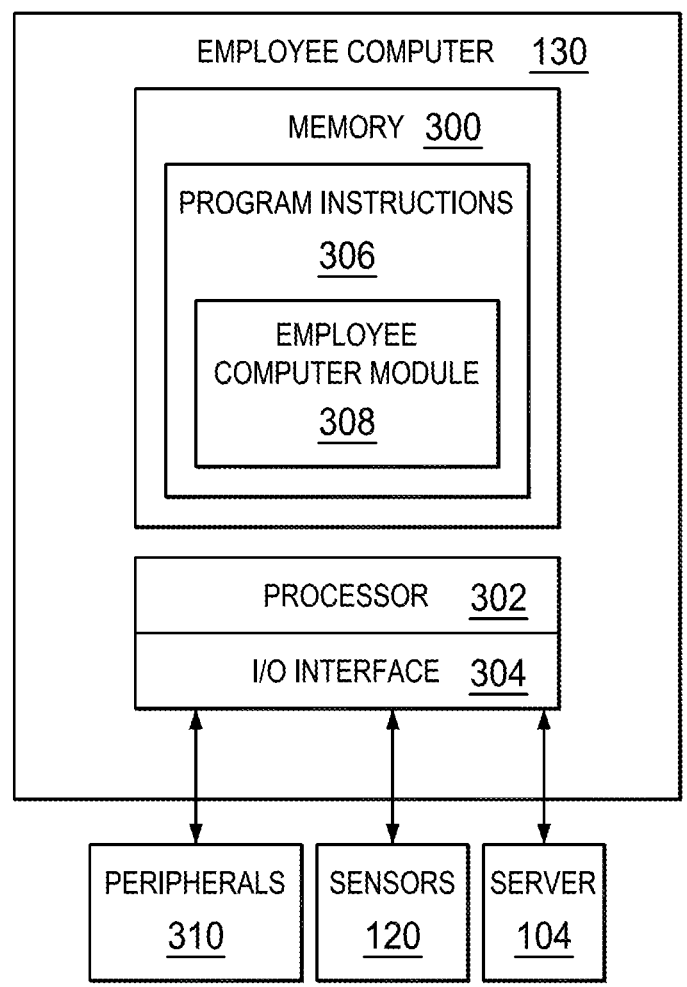
FIG. 3 is a block diagram that illustrates components of an employee computer in accordance with one or more embodiments of the present invention.

FIG. 3 is a block diagram that illustrates components of the employee computer 130 in accordance with one or more embodiments of the present invention. In some embodiments, the employee computer 130 includes a memory 300, a processor 302 and an input/output (I/O) interface 304.

The memory 300 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 300 may include a non-transitory computer readable storage medium having program instructions 306 stored thereon that are executable by a computer processor (e.g., the processor 302) to cause the functional operations (e.g., methods/routines/processes) described herein with regard to the employee computer 130. The program instructions 306 may include an employee computer module 308 including program instructions that are executable by the processor 302 to provide some or all of the functionality described herein with regard to the employee computer 130.

The processor 302 may be any suitable processor capable of executing/performing program instructions. The processor 302 may include a central processing unit (CPU) that carries out program instructions (e.g., program instruction of the employee computer module 308) to perform arithmetical, logical, and input/output operations of the employee computer 130, including those described herein.

The I/O interface 304 may provide an interface for connection of one or more I/O devices to the employee computer 130. I/O devices may include peripherals 310, sensors 120, the server 104, and/or the like. The peripherals 310 may include, for example, graphical user interface displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, and/or the like. The I/O devices (e.g., the peripherals 310, the sensors 120, and the server 104) may be connected to the I/O interface 304 via a wired or wireless connection.

The employee computer 130 may be employed to collect health data 200 from the various sensors 120 and/or forward corresponding health data 200 to the server 104 for use in monitoring the employee's health. For example, in response to determining that health data 200 (e.g., temperature data 200$a$, blood condition data 200$b$, blood pressure data 200$c$, position data 200$d$, body fat data 200$e$, 3D position data 200$f$, audio data 200$g$, respiration data 200$h$, and/or neural data 200$i$) needs to be collected, the employee computer 130 may employ one or more of the sensors 120 capable of sensing/acquiring the needed health data 200 to acquire the needed health data 200, the employee computer 130 may collect/store the acquired health data 200 (e.g., store/queue the acquired health data 200 in the memory 300), and the employee computer 130 may forward the acquired health data 200 to the server 104 for use in monitoring the employee's health.

In some embodiments, the employee computer 130 processes the raw/acquired health data 200 to generate the corresponding processed health data 200. For example, where the employee computer 130 receives raw health data (e.g., temperature data 200$a$ including a voltage indicative of a sensed temperature), the employee computer 130 may process the raw health data 200 to generate a corresponding value (e.g., using a look-up table, equation or the like to identify a temperature value corresponding to the voltage) that may be included in the health data 200 transmitted to the server 104. Accordingly, in some embodiments, the health data 200 may include the raw/acquired health data (e.g., a voltage value) and/or the processed health data corresponding thereto (e.g., the temperature value corresponding to the voltage value). Similar processing may be provided for other type of data measurements.

In some embodiments, the employee computer 130 forwards the health data 200 as the corresponding health data 200 is received. For example, the employee computer 130 may receive health data 200 from the sensors 120 and immediately forward the health data with little to no delay such that continuous stream of health data is provided to the server 104 for use in monitoring the employee's health. In some embodiments, the employee computer 130 stores (e.g., queues or buffers) the health data 200 for transmission at a later time. For example, where a test routine requires that the employee computer 130 transmits a batch of the health data 200 at the end of a test cycle, transmits a batch of the health data 200 on a regular interval (e.g., every ten minutes), or the like, the health data 200 received may be stored in memory 300 of the employee computer 130 and may be queued or buffered in the memory 300 for transmission as a batch of health data 200 to server 104 at the end of the test cycle, at the regular interval, or the like.

In some embodiments, the temperature sensor 202 includes thermocouples, IR sensors, or the like. During use, the temperature sensor 202 may transmit health data 200 indicative of a temperature sensed by the temperature sensor 202 (e.g., a temperature measurement). For example, where a temperature sensor 202 is positioned to acquire the employee's body temperature at a given location (e.g., at their, hand, back, or the like), the employee computer 130 may receive, from the temperature sensor 202, temperature data 200$a$ indicative of the temperature (e.g., 37° C. (98.6° F.) at the given location.

In some embodiments, a blood condition sensor 204 includes pulse oximeters, blood glucose testing devices and/or the like. The Blood condition sensor 204 may include, for example, the OctiveTech™ 3001H Pulse Oximeter manufactured by Nellcor™ or the BCI™ 3301 Hand Held Pulse Oximeter manufactured by Smiths Medical™. During use, the employee computer 130 may receive health data 200 indicative of blood characteristics sensed by the blood condition sensor 204. For example, where a pulse oximeter is positioned about the employee's fingertip, the employee computer 130 may receive, from the pule oximeter, blood condition data 200$b$ indicative of various aspects of the employee's blood, such as the oxygenation (e.g., 95% oxygenation) at the employee's fingertip.

In some embodiments, a blood pressure sensor 206 includes blood pressure cuffs and/or the like. The Blood pressure sensor 206 may include, for example, the UA-789PC Extra Large Cuff sold by LifeSource™ and the CMS-08A Professional Upper Arm Blood Pressure Monitor manufactured by CMS™. During use, the employee computer 130 may receive health data 200 indicative of the employee's blood pressure sensed by the blood pressure sensor 206. For example, where a blood pressure cuff is positioned about the employee's wrist/arm, the employee computer 130 may receive, from the blood pressure cuff, blood pressure data 200$c$ indicative of the employee's blood pressure (e.g., 90/60 mmHg).

In some embodiments, a position sensor 208 includes force transducers, such as strain gauges, load cells and/or the like. During use, employee computer 130 may receive health data 200 indicative of the force sensed by the position sensor 208. For example, where a load cell is positioned in the employee's chair and the employee is seated in the chair, the employee computer 130 may receive, from the load cell, position data 200*d* indicative of the force sensed by the load cell that can be used to determine the weight of the employee (e.g., 56.5 kg (124.6 lbs.)).

In some embodiments, a body fat sensor 210 includes conductive contacts that can be used to sense resistivity in the employee's body tissue and/or the like. During use, the employee computer 130 may receive health data 200 indicative of the employee's body fat sensed by the body fat sensor 210. For example, where conductive contacts are positioned in the seat of the employee's chair and the employee is seated in the chair, the employee computer 130 may receive, from the conductive contacts, body fat data 200*e* including a resistance measurement across the conductive contacts that is indicative of the body fat of the employee.

In some embodiments, a 3D position sensor 212 includes 3D cameras or the like that can be used to sense the employee's body position. During use, the employee computer 130 may receive health data 200 indicative of the physical position of the employee as sensed by the 3D position sensor 212. For example, where a 3D position sensor 212 includes a video camera positioned such that the employee is within the camera's field of view, the employee computer 130 may receive, from the 3D camera, 3D position data 200*f* (e.g., a three-dimensional image/video) indicative of the position (e.g., head, arm, hand, torso, leg, and feet position and/or posture) of the employee.

In some embodiments, an audio sensor 214 includes a microphone or the like for acquiring audio data (e.g., words spoken by the employee). During use, the employee computer 130 may receive health data 200 indicative of the audio data sensed by the audio sensor 214. For example, where the audio sensor 214 includes a microphone, the employee computer 130 may receive, from the audio sensor 214, audio data 200*g* (e.g., an audio feed) indicative of words spoken by the employee.

In some embodiments, respiration sensor 216 includes a device for sensing the employee's respiration rate (e.g., number of breaths taken within a set amount of time, typically sixty seconds. During use, the employee computer 130 may receive health data 200 indicative of the respiration rate ("RR") of the employee sensed by the respiration sensor 216. For example, the employee computer 130 may receive, from the respiration sensor 216, respiration data 200*h* indicative of number of breaths taken by the employee over sixty seconds (e.g., 15 breaths per minute).

In some embodiments, the neural sensor 218 includes a device (e.g., an electrode) for sensing brain activity (e.g., neural activity) of the employee. In some embodiments, the neural sensors 218 may employ electroencephalography ("EEG") to measure neuro-signal voltage fluctuations resulting from ionic current flows within the neurons of the brain. EEG may refer to recording of the brain's spontaneous electrical activity over a short period of time (e.g., twenty-forty minutes) from a plurality of the neural sensors 218 disposed on the employee's scalp. For example, a plurality of the neural sensor 218 (e.g., sixteen neural sensors/channels) may be disposed about the employee's scalp to detect neuro-signals (e.g., including alpha, beta, gamma, and delta waves) that can be used to determine the employee's brain state, including, for example, their emotional state (e.g., happy, sad, excited, etc.), thoughts (e.g., cognitive thoughts, subconscious thoughts, intent, etc.), facial movements (e.g., facial expressions), motor functions and/or the like. During use, the employee computer 130 may receive health data 200 indicative of the employee's neural activity sensed by the plurality of neural sensors 218. For example, the employee computer 130 may receive, from the neural sensors 218, neural data 200*i* indicative of the sensed neuro-signals. In some embodiments, neural sensors 218 may include dry electrodes that can be used to sense neuro signals. Such dry electrodes may require minimal or no skin preparation for disposing the contact on the employee's scalp. As described herein, neural sensor 218 maybe provided via a headset and/or in various surfaces that contact/support the employee's head, such as a headrest of a chair/seat.

In some embodiments, some or all of the sensors 120 may be located throughout the employee's workstation 102 and surrounding workstation environment. For example, various ones of the sensors 120 may be located at or near the employee's desk, chair, computer, or the like.

Figure 4:
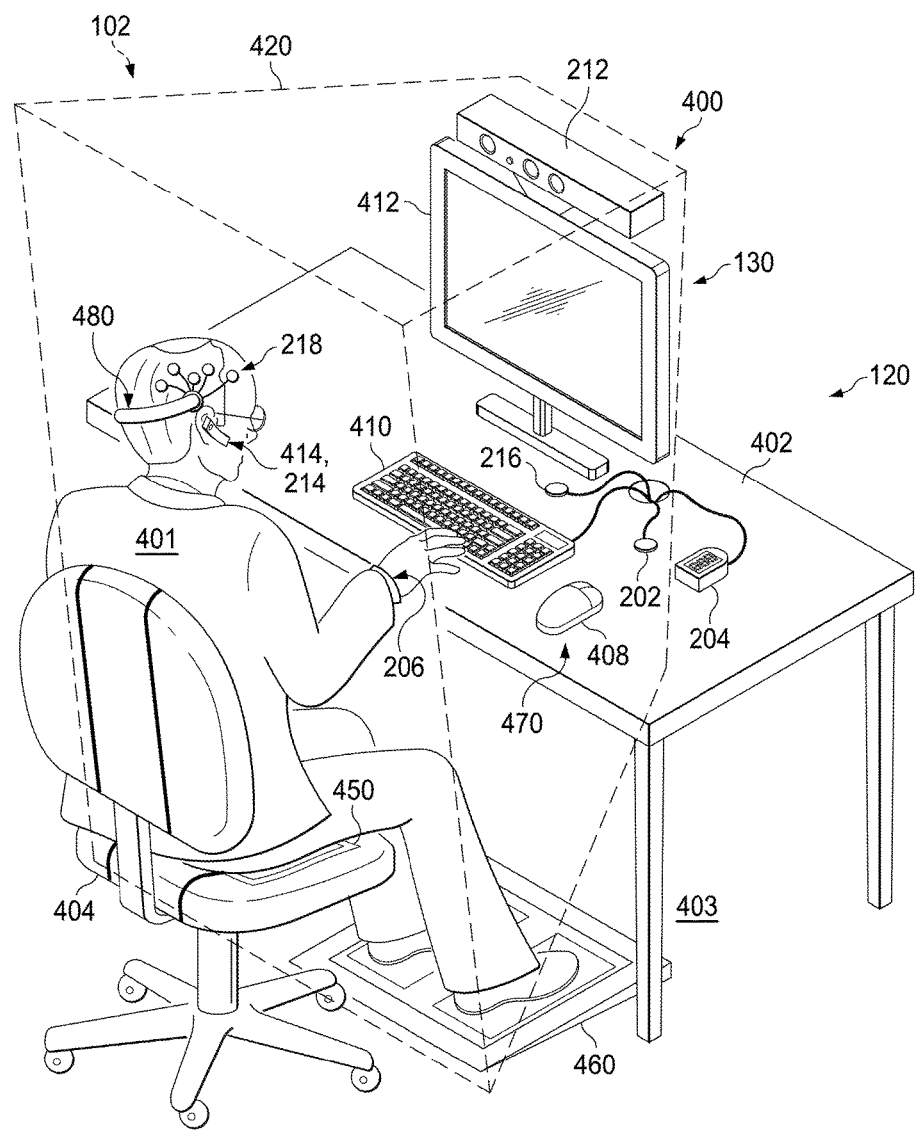
FIG. 4 is a diagram that illustrates an exemplary workstation environment in accordance with one or more embodiments of the present invention.

FIG. 4 is a diagram that illustrates an exemplary workstation environment 400 in accordance with one or more embodiments of the present invention. In some embodiments, the workstation environment 400 includes a location at which the employee 401 spends some or all of their work day (e.g., eight hours or more). For example, the workstation environment 400 may include the employee's office, the employee's cubicle, the employee's assigned station on an assembly/manufacturing line, or the like. In some embodiments, the workstation environment 400 includes an employee workstation 102. The workstation 102 may include devices, furniture and the like that facilitate the employee in accomplishing their work duties. For example, the workstation 102 may include a workstation surface 402 (e.g., a desk), floor 403, a chair 404, and the employee computer 130. In some embodiments, the employee computer 130 may include various peripherals, such as a computer mouse ("mouse") 408, a computer keyboard 410, a computer display (e.g., computer monitor) 412, an audio headset 414 (e.g., a Bluetooth headset including a speaker and/or a microphone), or the like.

In some embodiments, the area around the workstation 102 may define a workstation zone 420. In some embodiments, the workstation zone 420 includes an area (e.g., a three-dimensional region) in which the employee typically resides during some or all of their workday. For example, as depicted by the dashed lines of FIG. 4, the workstation zone 420 may include the region immediately in front of the computer display 412 and including the location of the employee's chair 404. As the employee 401 may be expected to spend a great deal of time within the zone 420, the zone 420 may be a region in which it is desirable to gather information (e.g., health data) relating to the employee's actions and general health while located therein.

The workstation 102 may include one or more of the sensors 120 for acquiring health data relating to the employee's actions and general health while located in or near zone 420. In some embodiments, the sensors 120 include one or more biometric and/or biomechanical sensors. For example, the sensors 120 may include one or more temperature sensors (e.g., thermocouples, IR sensors, etc.) 202, one or more blood condition sensors (e.g., pule oximeters) 204, one or more blood pressure sensors (e.g., cuff) 206, one or more position sensors (e.g., force transducers) 208, one or more body fat sensors (e.g., conductive contacts) 210, one or more 3D position sensors (e.g., video sensors) 212, one or more audio sensors (e.g., microphones) 214, one or more respiration sensors 216, one or more neural sensors (e.g., electrodes) 218 and/or the like for sensing health data 200 indicative of the employee's biometric health (e.g., the employee's body temperature, body weight, body fat, heart rate, respiratory rate, blood pressure, blood oxygenation, blood glucose level, neural activity, and/or the like) and/or biomechanical health (e.g., the employee's body position, posture, muscle tension, eye fatigue, facial expression, motor skills, and/or the like).

In some embodiments, various sensors 120 are integrated with areas/components of the workstation 102. For example, one or more temperature sensors 202, body fat sensors 210, position sensors 208, and/or the like may be integrated with the chair 404 (e.g., via a chair pad system ("chair pad") 450 disposed on or integrated with the employee's chair 404). As another example, one or more temperature sensors 202, body fat sensors 210, position sensors 208, and/or the like may be integrated with the floor 403 underfoot of the employee (e.g., via a floor mat system ("floor pad") 460 disposed on or integrated with the floor 403 of the workstation environment 400). As yet another example, one or more temperature sensors 202, blood condition sensors 204, blood pressure sensors 206 and/or the like may be integrated with the mouse 408 or other peripheral devices of the employee computer 130 (e.g., via a mouse system 470). As another example, one or more neural sensors 218 may be integrated into a neuro-headset system ("neuro-headset") 480 worn on the head of the employee.

Figure 5:
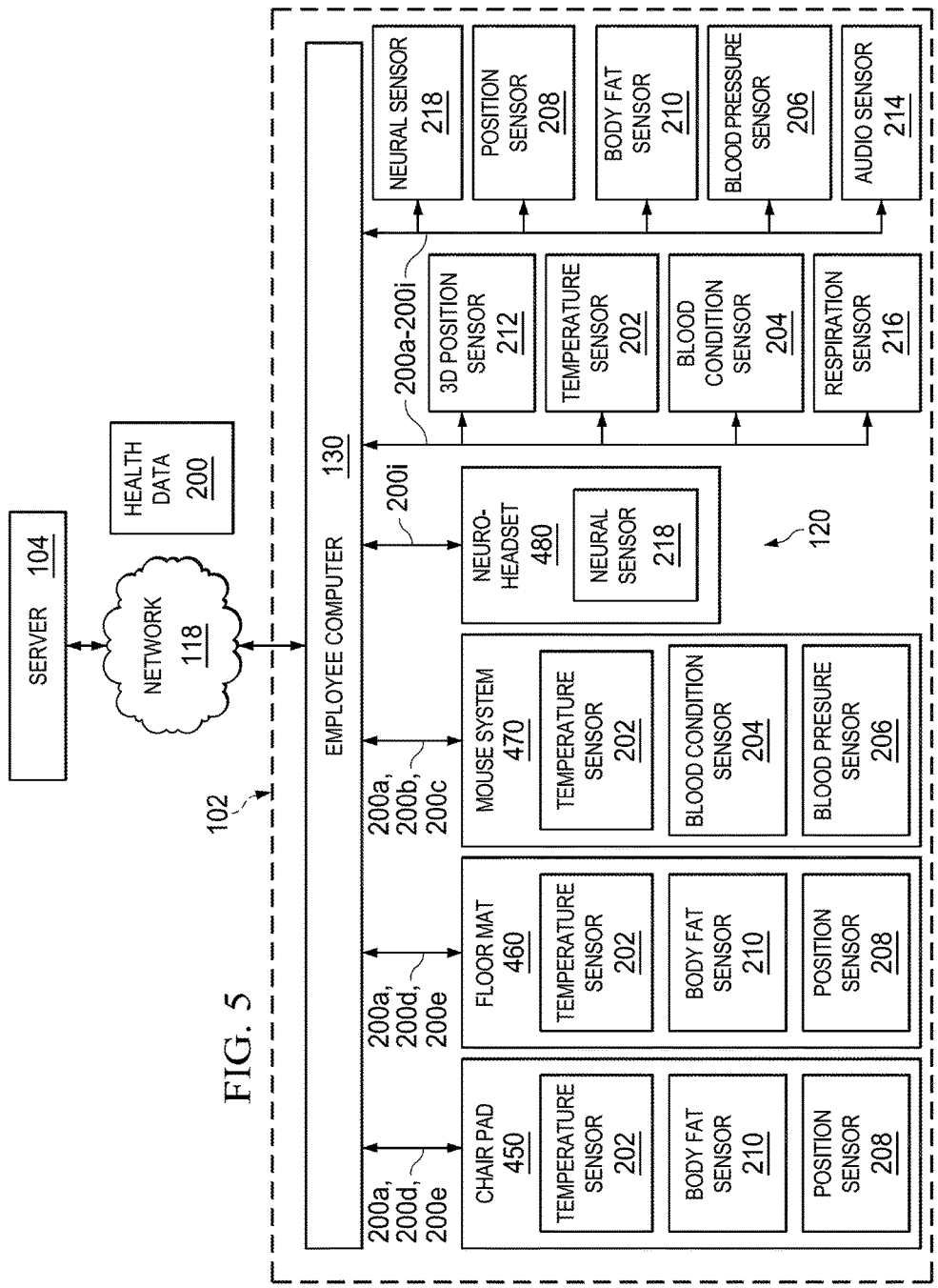
FIG. 5 is a block diagram that illustrates a workstation including integrated sensors in accordance with one or more embodiments of the present invention.

FIG. 5 is a is a block diagram that illustrates a workstation 102 including integrated sensors 120 in accordance with one or more embodiments of the present invention. Such an integration of the sensors 120 within the workstation environment may help to reduce the physical profile of the sensors 120, reduce distractions to the employee 401 that may otherwise be caused by the presence of the sensors 120 and/or enhance the ease of use to the employee 401 by allowing the health data 200 to be acquired while the employee is engaging in their day-to-day work duties. For example, the sensors 120 may be able to passively acquire health data 200 without requiring the employee to take special efforts to engage in a health test.

Figure 6A:
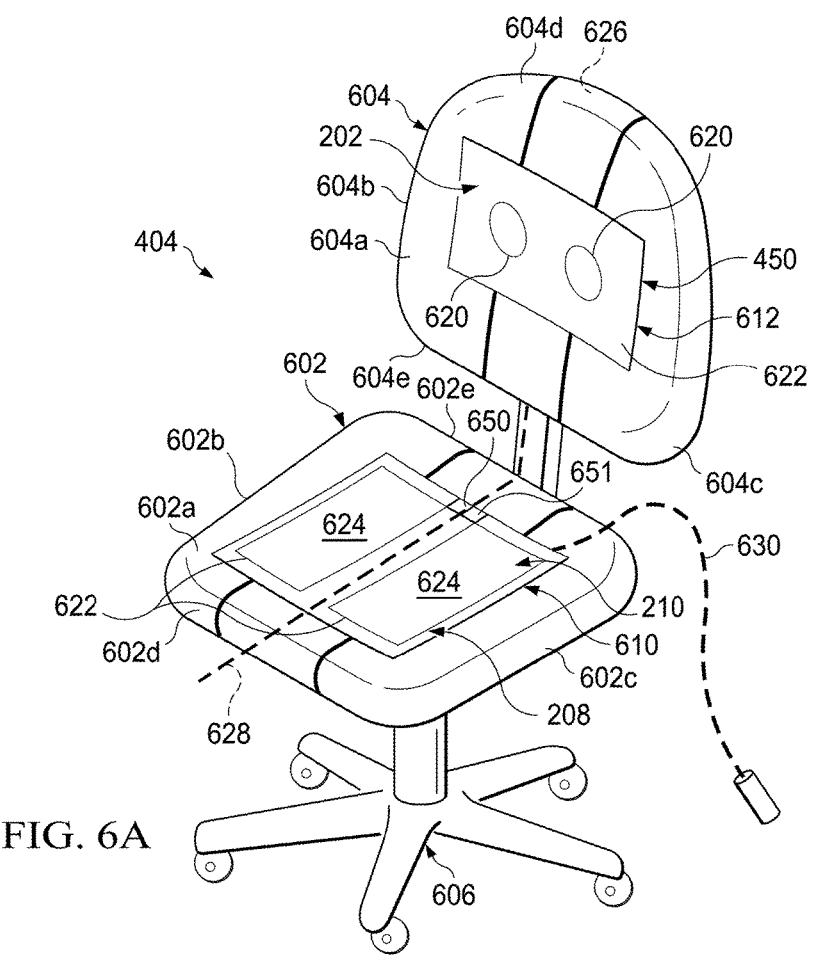
FIGS. 6A-6C are perspective views of various embodiments of a chair and a chair pad specially adapted to include sensors for use in monitoring an employee's health in accordance with one or more embodiments of the present invention.
Figure 6B:
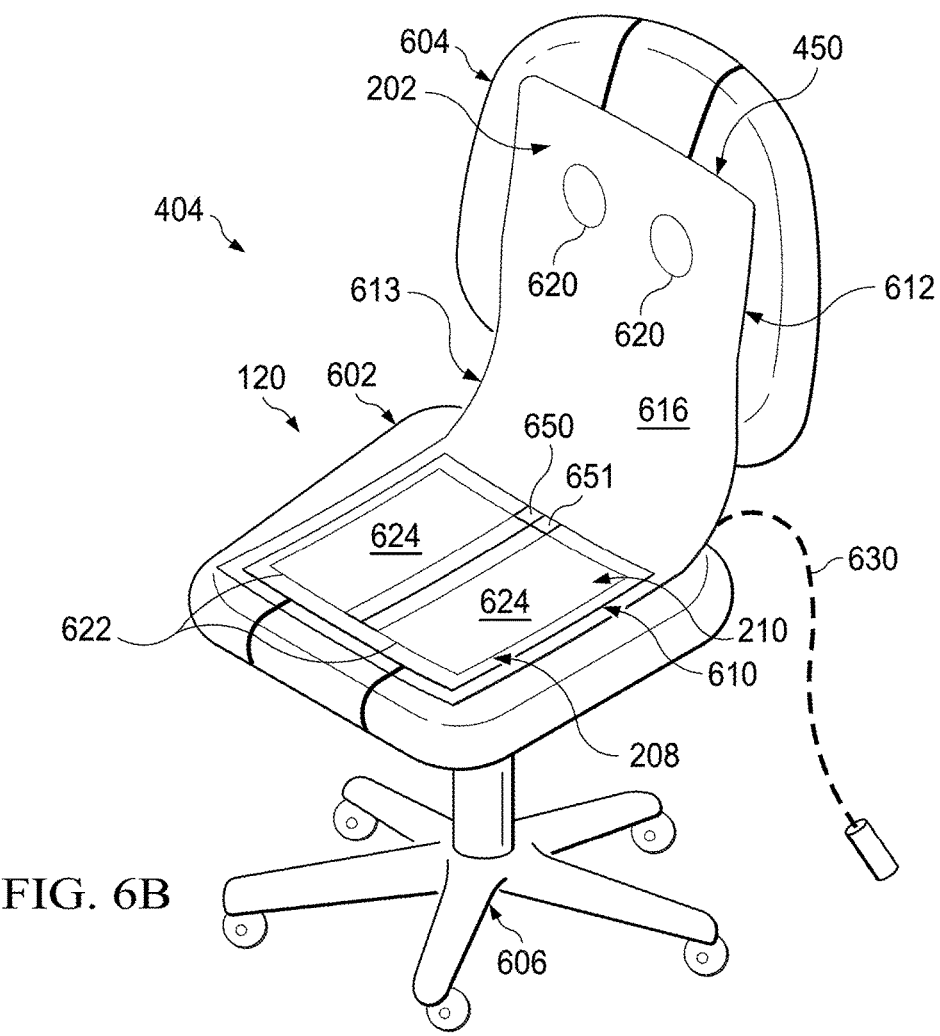
Figure 6C:
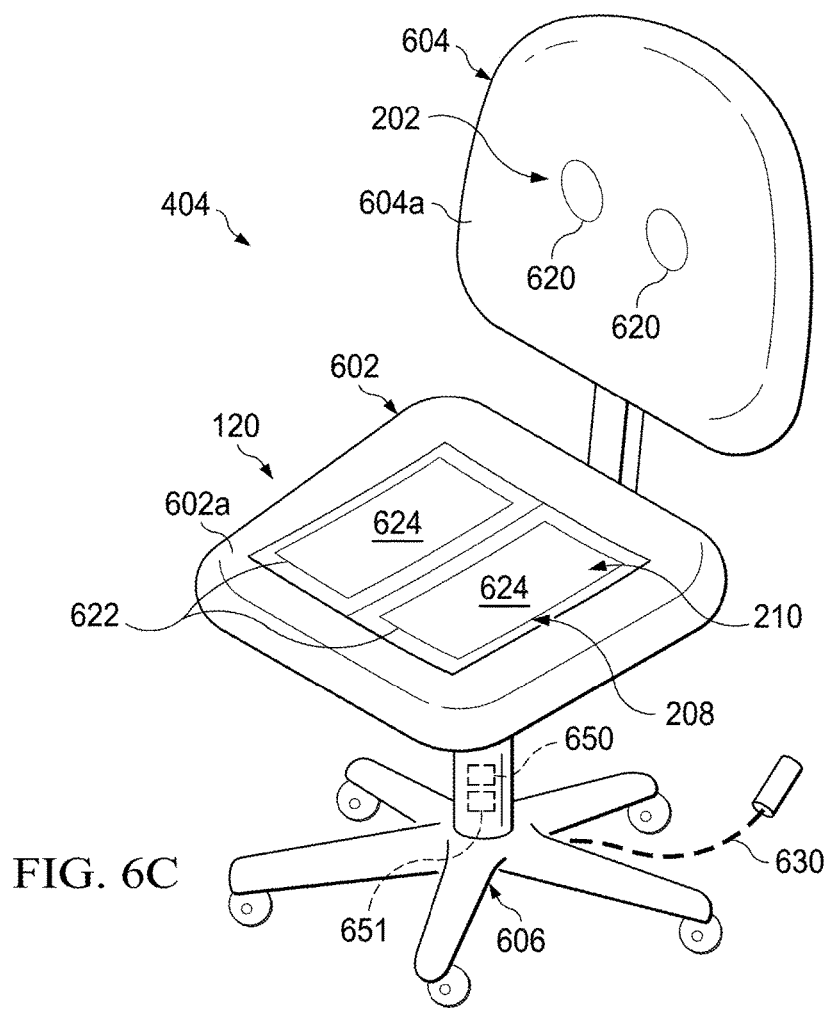

Chair Pad:

FIGS. 6A-6C are perspective views of the chair 404 and the chair pad 450 specially adapted to include sensors 120 for use in monitoring an employee's health in accordance with one or more embodiments of the present invention. As depicted, the chair 404 may include a seat 602, a back 604 and a pedestal 606. The seat 602 may include an upper/seating surface 602a, a right side 602b, a left side 602c, a front side 602d and a back side 602e. The back 604 may include a front surface 604a, a right side 604b, a left side 604c, a top side 604d and a bottom side 604e.

In some embodiments, the chair 404 includes the chair pad 450 disposed thereon and including various sensors 120 (e.g., see FIGS. 6A, 6B and 6C). In some embodiments, the chair pad 450 is disposed across one or more surfaces of the chair 404 such that the employee comes into contact with the sensors 120 of the chair pad 450 while seated in the chair 404. For example, the chair pad 450 may include a seat-pad 610 that is a disposed across upper/seating surface 602a of seat 602 and/or a back-pad 612 disposed across front surface 604a of back 604. Seat-pad 610 may support or otherwise contact the employee's upper-legs and/or buttocks while seated in chair 404. Back-pad 612 may support or otherwise contact the employee's back while seated in chair 404.

In some embodiments, the seat-pad 610 and the chair-pad 612 are communicatively coupled. For example, a wired connection may be provided between the seat-pad 610 and the back-pad 612 to facilitate the transmission of power to the various sensors 120 and/or a chair pad controller 650. A wired or wireless connection may be provided between the seat-pad 610 and the back-pad 612 to facilitate communication of control signals, the health data 200 sensed by the sensors 120, and/or the like between the various sensors 120 and/or a chair pad controller 650.

In some embodiments, the chair pad 450 includes two separate portions disposed on the seat 402 and back 404 of the chair 304. For example, as depicted in FIG. 6A, the chair pad 450 includes a seat-pad 610 coupled to the seat 602 of the chair 404 and a separate back-pad 612 coupled to the back 604 of the chair 404. Such an embodiment may be beneficial as it may reduce the weight/profile of the chair pad 450 as it does not include additional material that may increase the weight of the chair pad 450 or interfere with the employee's work duties while seated in the chair 404.

In some embodiments, the chair pad 450 includes a contiguous pad including two conjoined portions disposed on the seat 402 and the back 404 of the chair 304. For example, as depicted in FIG. 6B, the chair pad 450 may include a contiguous elongated pad having the seat-pad 610 coupled to the seat 602 of the chair 404, the back-pad 612 coupled to the back 604 of the chair 404 and an intermediate pad portion 613 spanning the distance between the seat-pad 610 and the back-pad 612. Such an embodiment may be beneficial as it provides a single unit that can be transported easily. Moreover, where a wired connection is provided between the seat-pad 610 and the chair-pad 612, the wires may be disposed with the intermediate pad portion 613, thereby reducing or eliminating exposed wiring that may otherwise interfere with the employee's work duties while seated in the chair 404. Where, as described herein, the chair pad 450 includes a wireless connection to external devices (e.g., the employee computer 130) and a battery 651 for powering the components of the chair pad 450, the contiguous pad may include a completely self-contained unit including the sensors 120, the chair pad controller 650, and the battery 651, wiring (e.g., between the sensors 120, the chair pad controller 650, and/or the battery 651) is housed within a shell/cover/casing 616 of the chair pad 450. Such an embodiment may be aesthetically pleasing as it appears to be a simple chair pad (e.g., with no external wiring or components) disposed on the chair 404. Moreover, such an embodiment may eliminate exposed wiring or components that may otherwise interfere with the employee's work duties while seated in the chair 404.

In some embodiments, the chair pad 450 includes various sensors 120 that can be used to collect heath data 200. For example, the chair pad 450 may include one or more temperature sensors 202, body fat sensors 210, position sensors 208, and/or the like. In some embodiments, the various sensors 120 of the chair pad 450 may sense/measure various aspects of the employees biometric and/or biomechanical health and may transmit corresponding health data 200 (e.g., temperature data 200a, position data 200d, body fat data 200e, and/or the like) to another device of system 100 (e.g., to a chair pad controller, to the employee computer 130 and/or the server 104) for use in monitoring the employee's health.

In some embodiments, the chair pad 450 includes one or more temperature sensors 202 disposed within the seat-pad 610 and/or the back-pad 612. For example, in the illustrated embodiment, the chair-pad 450 includes a temperature sensor 202, including two temperature transducers 620, disposed on a front surface of the back-pad 612. The temperature transducers 620 may include infrared sensors, thermocouples and/or the like adapted to sense the employee's body temperature and transmit corresponding temperature data 200a to the chair pad controller, the employee computer 130 and/or the server 104.

In some embodiments, the temperature transducers 620 are centered or approximately centered on back-pad 612 such that the temperature transducers 620 contact an employee's back while the employee is seated in the chair 404. For example, a pair of the temperature transducers 620 may be provided on the back-pad 612 approximately equidistant from the top-side 604d and the bottom-side 604e of the back 604 of the chair 404, with the two temperature transducers 620 approximately centered about a back-midline 626 that approximately bisects the back 604 of the chair 404 such that a first of the two temperature transducers 620 is disposed to the left of the back-midline 626 (e.g., closer to a left-side 604c of the back 604 of the chair 404) and a second of the two temperature transducers 620 is disposed to the right of the back-midline 626 (e.g., closer to a right-side 604b of the back 604 of the chair 404). A measurement from the temperature transducers 304 can be used for determining a temperature at the location of each the respective temperature transducers 620 using techniques that are known to those skilled in the art. For example, where the temperature transducers 620 include a thermocouple, a voltage (V) measurement from each of the temperature transducers 620 can be used to determine a temperature at the location of each of the respective temperature transducers 620 using techniques that are known to those skilled in the art.

Although the illustrated embodiment includes two temperature transducers 620 disposed on the back-pad 604, other embodiments may include any number of temperature transducers 620 located in any variety of suitable locations. In some embodiments, one or more temperature transducers 620 may be centered or approximately centered on the seat-pad 610 and/or the back-pad 612 such that the employee's body temperature at the respective locations can be determined. For example, an additional pair of temperature transducers 304 may be approximately centered in seat-pad 610 (e.g., in a location that is the same or similar to the illustrated locations of contact points 624). In such a configuration, the employee may contact some or all of the four temperature transducers 304 while seated in chair 104.

In some embodiments, the chair pad 450 includes one or more position sensors 208 disposed within the seat-pad 610 and/or the back-pad 612. For example, in the illustrated embodiment, the chair pad 450 includes a position sensor 208, including force transducers 622, disposed on an upper surface of the seat-pad 610 and the front surface of the back-pad 612. Force transducers 622 may include a load cell, a strain gauge, or the like adapted to sense force and transmit corresponding position data 200d (e.g., indicative of the forces sensed) to the chair pad controller, the employee computer 130 and/or the server 104. In some embodiments, such position data 200d may be used to determine the physical position of the employee within the chair 404, the employee's weight or the like using techniques that are known to those skilled in the art. For example, the position data 200d may be used to determine when the employee is seated in the chair 404 (e.g., when the force sensors 208 in the seat-pad 610 sense a force), when the employee is leaning against the back 604 of the chair 404 (e.g., when the force sensors 208 in the back-pad 612 sense a relatively high force indicative of the employee resting against the back 602), or the like. In addition to the position data 200d (e.g., from the force transducers 622), other data (e.g., temperature data 200a from the temperature transducers 620) may be used to determine how the employee is positioned in the chair 404 (e.g., whether the employee is reclining (e.g., by detecting an increase in the force and/or temperature sensed by the force transducers 622 and/or the temperature transducers 620 located in the back-pad 612).

Although the illustrated embodiment includes force transducers 622 disposed on the seat-pad 610 and the back-pad 612, other embodiments may include any number of force transducers 622 located in any variety of suitable locations. For example, a force transducer(s) 622 may be located on one of the seat-pad 610 or the back-pad 612. In some embodiments, multiple force transducers 622 are located in the seat-pad 610 and/or the back-pad 612. For example, force transducers 622 may be provided in locations similar to those described herein with regard to the temperature transducers 620 and/or the contact points 624. In an embodiment where multiple force transducers are provided, the system 100 may be able to more accurately determine how the employee is positioned within the chair. For example, where four force transducers 622 are provided on the left and right sides of the seat-pad 610 and the back-pad 612, the forces sensed by the transducers may be used to determine whether the employee is leaning to one side based on force transducers 622 on that side sensing a higher force than the force transducer 622 on the opposite side. In some embodiments, force transducers 622 are disposed on toward the front 602d and/or the back 602e of the seat-pad 610 to enable a determination of whether the employee is leaning backward or forward in their chair (e.g., sitting on the edge of their chair). For example, where force transducers 622 are provided on the front and back of the seat-pad 610, the forces sensed by the force transducers 622 may be used to determine whether the employee is leaning forward or backwards based on the front force transducer 622 sensing a higher force than the back force transducer 622 indicative of the employee leaning forward in the chair 404 and/or the rear force transducer 622 sensing a higher force than the front force transducer 622 indicative of the employee leaning back in the chair 404.

In some embodiments, the chair pad 450 includes one or more body fat sensors 210 disposed within seat-pad 610 and/or back-pad 612. For example, in the illustrated embodiment, the chair-pad 450 includes a body fat sensor 210, including two conductive (e.g., metallic) contact points 624, disposed on an upper surface of the seat pad 610. Body fat sensor 210 may sense resistivity between the contacts 624 and transmit corresponding body fat data 200e. For example, where the body fat sensor 210 is disposed on a seating surface of the chair 404 such that the two contact points 624 contact the employee's upper legs and/or buttocks region, a current may be induced between the metallic contact points 624 to sense/measure a resistivity between the contact points (e.g., through the employee's body tissue) and body fat data 200e indicative of the resistivity measurement may be forwarded to the chair pad controller, the employee computer 130 and/or the server 104.

In some embodiments, the contact points 624 are approximately centered on the seat-pad 610 such that they contact the backside of the employee's right and left legs and/or the right and left portions of the employee's buttocks while the employee is seated in the chair 404. For example, the contact points 624 may be centered on the seat-pad 610 such that they are approximately equidistant from the front side 602d and the back side 602e of the seat 404, with the two contact points 624 approximately centered about a seat-midline 628 that approximately bisects the seat 602 such that a first of the two contact points 624 is disposed to the right of the seat-midline 628 (e.g., closer to a right-side 602b of the seat 404) and a second of the two contact points 624 is disposed to the left of the seat midline 626 (e.g., closer to the left-side 602c of the seat 602 of the chair 404). In such a configuration, the employee may sit across both of the contact points 624 such that the first and second of the contact points 624 contact the backside of the employee's right and left legs/buttock, respectively, and a resistivity measurement between the contact points 624 can be sensed/measured for use in assessing the employee's body fat or related health information. For example, a current (I) may be induced between the two contact points 624, a voltage (V) between the two contact points 624 can be sensed/measured, the current (I) and voltage (V) can be used to determine a resistance/resistivity (R) through the portion of the employee's body spanning the contact points 624, e.g., using the equation Voltage (V)=Current (I)*Resistance (R), and the determined resistivity measurement can be used to determine the employee's body fat using techniques that are known to those skilled in the art.

Although the illustrated embodiment includes a body fat sensor 210 including two contact points 624 disposed on the seat 602 of the chair 404, other embodiments may include one or more body fat sensors 210 including any number of contact points 624 located in any variety of suitable locations. In some embodiments, one or more contact points 624 are provided on each of the seat-pad 610 and the back-pad 612 such that the employee's body fat can be determined using a resistivity measurement between the contact point(s) 624 positioned at the employee's back (e.g., contact point(s) on back-pad 612) and/or bottom (e.g., contact point(s) 624 on seat-pad 610). For example, a pair of contact points 624 may be provided on the back-pad 612 (e.g., in a location that is the same or similar to the illustrated locations of temperature transducers 620). In such a configuration, the employee may contact some or all four contact points 624 while seated in the chair 404. Thus, for example, resistivity measurements can be determined between the right and left contact points 624 of the back 604 of the chair 404, between the right contact points 624 of the seat 602 and the back 604 of the chair 404, and/or between the left contact points 624 of the seat 602 and the back 604 of the chair 404.

In some embodiments, the chair pad 450 includes a cable 630 that can be coupled to an external device (e.g., the employee computer 130) for communicating data and/or receiving power. For example, the cable 630 may include a USB cable that is plugged into a USB port of the I/O interface 304 of the employee computer 130. The chair pad 450 may receive power via the cable and/or may transmit health data 200 via the cable. In some embodiments, the chair pad 350 may have a wireless connection (e.g., Bluetooth connection, WLAN connection, or the like) with the employee computer 130 and/or the server 104. In such an embodiment, the chair pad 450 may also include the battery 651 for a power source such that the chair pad 450 is not physically tethered to the employee computer 130 or other components of system 100.

In some embodiments, the surface of the chair 404 includes sensors 120 integrated therein in a similar manner to the chair pad 450 such that health data 200 may be acquired without the need for a separate chair pad 350. For example, as depicted in FIG. 6C, the chair 404 may include sensors 120 (e.g., temperature sensors 202, positions sensors 208, and/or body fat sensors 210) disposed/integrated in the front surface 604a of the back 604 of the chair 404 and/or the top surface 602a of the seat 602 of the chair 404. Although embodiments are described herein with regard to components of the chair pad 450, it will be appreciated that similar components may be integrated into the chair 404 to provide the chair 404 with similar functionality described with regard to the chair pad 350. For example, the chair 404 may include a controller 650 (e.g., that is the same or similar to the chair-pad controller described herein) for communicating with the sensors 120 integrated within the chair 404 and/or external devices (e.g., the employee computer 130) and a battery 651 integrated therein for powering the controller 650 and/or the sensors 120.

Figure 6D:
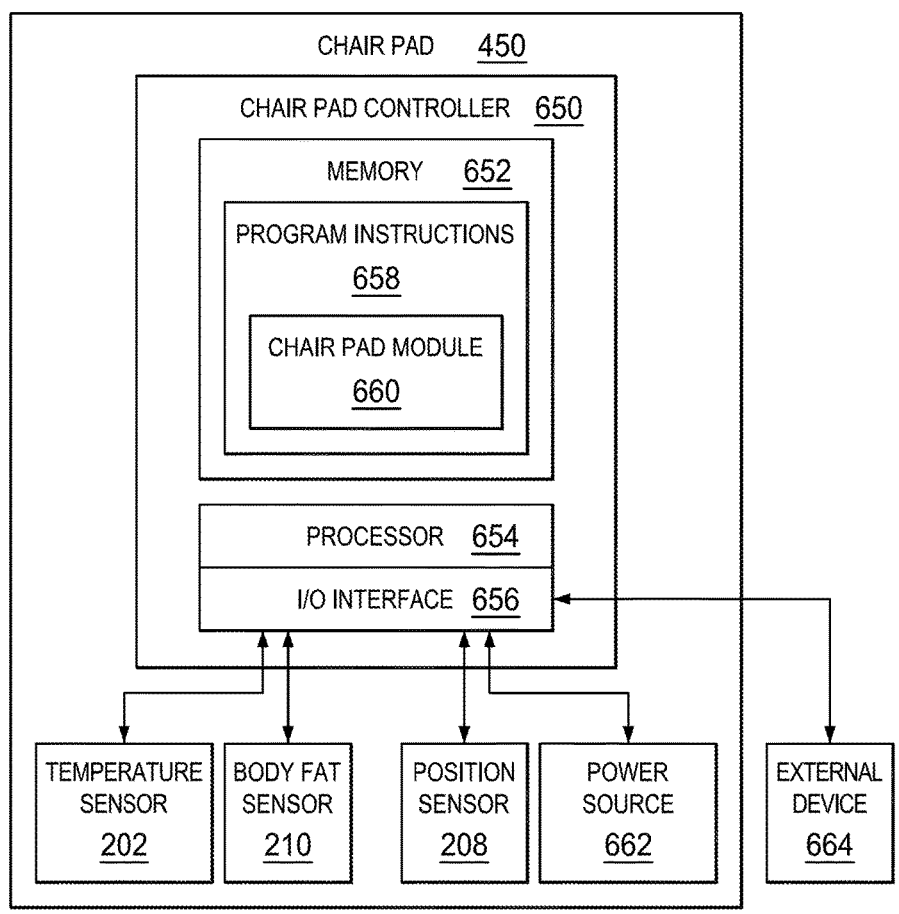
FIG. 6D is a block diagram that illustrates components of the chair pad in accordance with one or more embodiments of the present invention.

FIG. 6D is a block diagram that illustrates components of the chair pad 450 in accordance with one or more embodiments of the present invention. In some embodiments, the chair pad 450 includes a chair pad controller 650 for controlling the operational aspects of chair pad 450. For example, the chair pad controller 650 may provide for allocating power to the various sensors 120 of the chair pad 450, collecting the health data 200 from the various sensors 120 of the chair pad 450 and/or transmitting the collected health data 200 to the employee computer 130 and/or the server 104.

In some embodiments, the chair pad controller 650 includes a memory 652, a processor 654 and an input/output (I/O) interface 656. The chair pad controller 650 may be a microcontroller device such as STMicroelectronics, ST10 (16-bit) and STM32 (32-bit); Atmel, AVR32 (32-bit) and AT91SAM (32-bit); Freescale ColdFire (32-bit); Hitachi SuperH (32-bit); and the Hyperstone E1/E2 (32-bit, full integration of RISC and DSP on one processor core), which is adapted for use in the functions described herein.

The memory 652 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 652 may include a non-transitory computer readable storage medium having program instructions 658 stored thereon that are executable by a computer processor (e.g., the processor 654) to cause the functional operations described herein with regard to the chair pad 450. The program instructions 658 may include a chair pad module 660 including program instructions that are executable by the processor 654 to provide some or all of the functionality described herein with regard to the chair pad 450.

The processor 654 may be any suitable processor capable of executing/performing program instructions. The processor 654 may include a central processing unit (CPU) that carries out program instructions (e.g., of the chair pad module 660) to perform arithmetical, logical, input/output and other operations of chair pad 450, including those described herein.

The I/O interface 656 may provide an interface for connection of one or more I/O devices to the chair pad controller 650. I/O devices may include the sensors 120 (e.g., temperature sensors 202, position sensors 208, and/or body fat sensors 210), power source(s) 662 (e.g., a battery 651, AC/DC power delivered via cable 630, or the like), external device(s) 664 (e.g., the employee computer 130 and/or server 104), and/or the like. The I/O devices may be connected to I/O interface 656, via a wired or wireless connection.

Figure 6E:
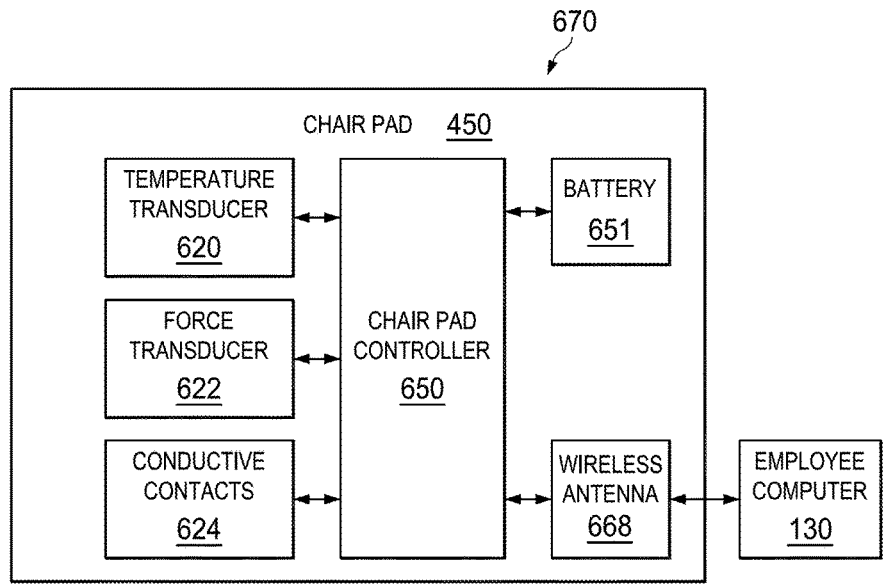
FIG. 6E is a block diagram that illustrates an exemplary chair pad system in accordance with one or more embodiments of the present invention.

FIG. 6E is a block diagram that illustrates an exemplary chair pad system 670 in accordance with one or more embodiments of the present invention. The chair pad system 670 includes the chair pad 450 having a chair pad controller 650 coupled to one or more temperature transducers 620, one or more force transducers 622, one or more conductive contacts 624, a battery 651, and a wireless antenna 668. In some embodiments, the chair pad controller 650 employs the temperature transducers 620, the force transducers 622, and/or the conductive contacts 624 to collect corresponding measurements. For example, where the temperature transducer 620 includes a thermocouple, to take a temperature measurement, the chair pad controller 650 may take a voltage measurement across two leads connected to the thermocouple of the temperature transducer 620, the measured voltage being indicative of the temperature sensed by the temperature transducer 620. Where, for example, the force transducers 622 includes a strain gauge, to take a force measurement, the chair pad controller 650 may induce a current (I) across two leads connected to the strain gauge and take a measurement of voltage (V) across the two leads to determine a resistance (R) across the two leads that is indicative of the force sensed by the force transducer 622. As a further example, to take a body fat measurement, the chair pad controller 650 may induce a current (I) across two conductive contacts 624 and take a measurement of voltage (V) across the two conductive contacts 624 to determine a resistance (R) across the contacts 624 that is indicative of the body fat for the employee. In some embodiments, the battery 651 provides power to operate the controller 650 and/or provides the power required to take a measurement from the temperature transducers 620, force transducers 622, and/or conductive contacts 624. In some embodiments, the wireless antenna includes a Bluetooth transceiver or other wireless transceiver for use in communicating with the employee computer 130 (e.g., via a complementary transceiver of computer 130).

Figure 6F:
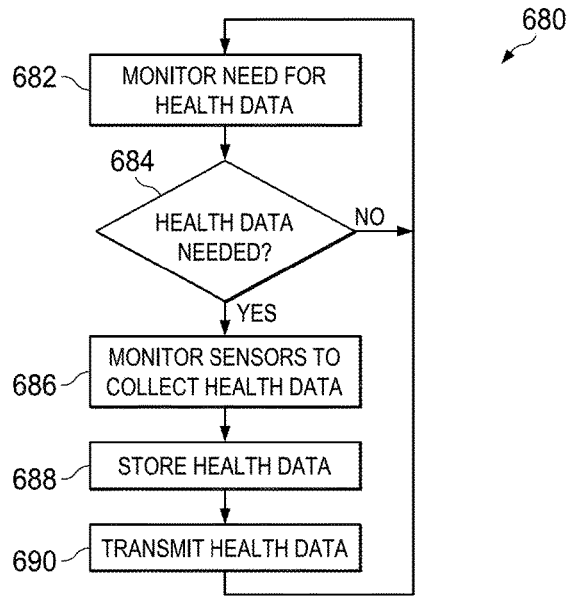
FIG. 6F is a flowchart that illustrates a method of operating the chair pad in accordance with one or more embodiments of the present invention.

FIG. 6F is a flowchart that illustrates a method 680 of operating the chair pad 450 in accordance with one or more embodiments of the present invention. Method 680 may include monitoring the need for health data 200, as depicted at block 682. In some embodiments, monitoring the need for health data includes determining whether or not there is a need to collect health data 200 (i.e., take a measurement) from one or more of the sensors 120 (e.g., the temperature transducers 620, the force transducers 622, and/or the conductive contacts 624) of the chair pad 450. In some embodiments, the need for health data 200 is identified based on a request from another component of system 100. For example, the chair pad controller 650 may determine that there is a need to collect health data 200 in response to a request for the health data 200 (e.g., a request to initiate a health test and/or a query for the health data 200) received from the computer 130, the server 104 and/or the employee 401.

Where it is determined that health data 200 is not needed, at block 684, method 680 may include returning to monitoring the need for health data 200, as depicted at block 682. Where it is determined that health data 200 is needed, at block 684, method 680 may include proceeding to monitoring of the sensors 120 (e.g., the temperature transducers 620, the force transducers 622, and/or the conductive contacts 624) to collect the health data 200, as depicted at block 686. In some embodiments, monitoring the sensors 120 to collect the health data 200 includes monitoring the particular sensors 120 that provide the particular health data 200 needed. Where the heath data 200 needed includes the employee's body temperature, body position and/or body fat, monitoring the sensors 120 to collect the health data 200 may include, for example, the chair pad controller 650 taking measurements from the temperature transducers 620, the force transducers 622, and/or the conductive contacts 624, respectively, to collect health data 200 including measured voltages indicative of body temperature, measured resistances indicative of forces, and/or measured resistances indicative of the employee's body fat.

Method 680 may include storing the health data 200, as depicted at block 688. In some embodiments, storing the health data 200 includes storing the collected health data 200 in local or remote memory. For example, the chair pad controller 650 may store the measured voltages indicative of body temperature, measured resistances indicative of forces, and/or measured resistances indicative of the employee's body fat in the memory 652. In some embodiments, storing the heath data 200 includes buffering/queuing the health data 200 for transmission at a later time.

Method 680 may include transmitting the health data 200, as depicted at block 690. In some embodiments, transmitting the health data 200 may include transmitting the health data 200 to another component/entity of system 100. For example, the chair pad controller 650 may transmit the health data 200 (e.g., collected via the sensors 120 of the chair pad 450 and stored in the memory 652), to the computer 130 and/or the server 104 for use in monitoring the health of the employee. In some embodiments, the health data 200 is transmitted via a wired or wireless communication. For example, where the chair pad 450 is connected to the computer 130 and/or the server 104 via data cables (e.g., via cable 630) the chair pad controller 650, may transmit some or all of the health data 200 to the computer 130 and/or the server 104 via the data cables. Where the chair pad 450 is in wireless communication with the computer 130 and/or the server 104 (e.g., via Bluetooth connection, WLAN connection, or the like), the chair pad controller 650 may transmit some or all of the health data 200 to the computer 130 and/or the server 104 via wireless communication. For example, the chair pad controller 650 may communicate the health data 200 to the computer 130 and/or the server 104 via wireless antenna 668.

In some embodiments, after transmitting the health data 200, method 680 may progress back to monitoring the need for health data 682. Where for example, the request for health data is still active and/or another request for health data is received, the chair pad controller 650 may execute another iteration of monitoring the sensors to collect health data, storing the health data and/or transmitting the health data.

It will be appreciated that the method 680 is an exemplary embodiment of a method that may be employed in accordance with techniques described herein. The method 680 may be may be modified to facilitate variations of its implementations and uses. The method 680 may be implemented in software, hardware, or a combination thereof. Some or all of the method 680 may be implemented by one or more of the modules/applications described herein, such as chair pad module 660. The order of the method 680 may be changed, and various elements may be added, reordered, combined, omitted, modified, etc.

Figure 7A:
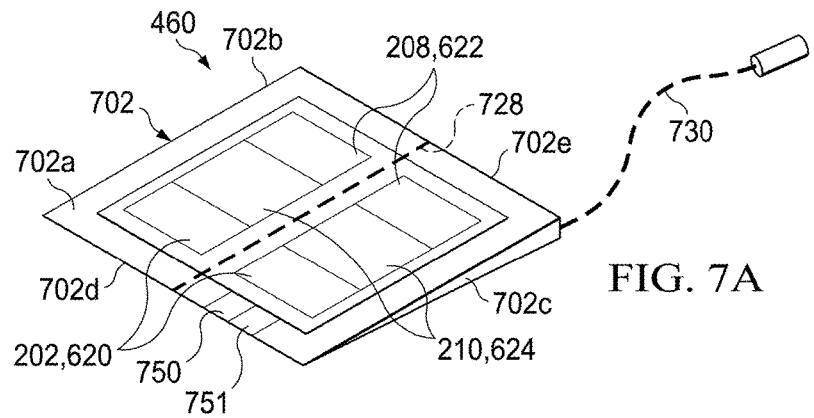
FIG. 7A is a perspective view of a floor mat specially adapted to include sensors for use in monitoring an employee's health in accordance with one or more embodiments of the present invention.

Floor Mat:

FIG. 7A is a perspective view of the floor mat 460 specially adapted to include sensors 120 for use in monitoring an employee's health in accordance with one or more embodiments of the present invention. During use, the floor mat 460 may be disposed on the floor within the workstation 102 and the employee may stand on the floor mat 460 or otherwise rest their feet (e.g., with or without their shoes on) on the floor mat 460. As depicted, the floor mat 460 may include a mat 702. The mat 702 may include an upper surface 702a, a left side 702b, a right side 702c, a front side 702d and a back side 702e.

In some embodiments, the floor mat 460 may include various sensors 120 that can be used to collect heath data 200. For example, the floor mat 460 may include one or more temperature sensors 202, body fat sensors 210, position sensors 208, and/or the like. In some embodiments, the various sensors 120 of the floor mat 460 may sense/measure various aspects of the employees biometric and/or biomechanical health and may transmit corresponding health data 200 (e.g., temperature data 200a, position data 200d, body fat data 200e, and/or the like) to another device of system 100 (e.g., to a floor mat controller, the employee computer 130 and/or the server 104) for use in monitoring the employee's health.

In some embodiments, the floor mat 460 includes one or more temperature sensors 202 disposed within the mat 702. For example, in the illustrated embodiment, the floor mat 460 includes a temperature sensor 202 including two temperature transducers 620 disposed on the upper surface 702a of the mat 702. Temperature transducers 620 may include infrared sensors, thermocouples and/or the like adapted to sense the employee's body temperature and transmit corresponding temperature data 200a to the floor mat controller, the employee computer 130 and/or the server 104.

In some embodiments, the floor mat 460 includes one or more position sensors 208 disposed within the mat 702. For example, in the illustrated embodiment, the floor mat 460 includes a position sensor 208 including force transducers 622, disposed on the upper surface 702a of mat 702. Force transducers 622 may include a load cell, a strain gauge, or the like adapted to sense force and transmit corresponding position data 200d to the floor mat controller, the employee computer 130 and/or the server 104. In some embodiments, such position data 200d may be used to determine the physical position of the employee (e.g., whether the employees feet are positioned on the mat 702, etc.), the employee's body weight and/or the like.

In some embodiments, the floor mat 460 includes one or more body fat sensors 210 disposed within the mat 702. For example, in the illustrated embodiment, the floor mat 460 includes a body fat sensor 210 including two conductive (e.g., metallic) contact points 624 disposed on the upper surface 702a of the mat 702. The body fat sensor 210 may sense resistivity between the contacts and transmit corresponding body fat data 200e to the floor mat controller, the employee computer 130 and/or the server 104. For example, where the body fat sensor 210 is disposed on the upper surface 702a of the mat 702, such the two contact points 624 contact the employee's feet (e.g., when the employee's shoes are removed), a current may be induced between the contact points 624 to sense/measure a resistivity there between (e.g., through the employee's lower body tissue) and body fat data 200e including the resistivity measurement may be forwarded to the floor mat controller, the employee computer 130 and/or the server 104.

In some embodiments, the temperature transducers 620, the force transducers 622 and/or the conductive contacts 624 may be centered or approximately centered on the upper surface 702a of the floor mat 460 such that the temperature transducers 620, the force transducers 622 and/or the conductive contacts 624 contact an employee's right and left feet/shoes while the employee is seated in the chair 404 or is standing on the floor mat 460. For example, a pair of the temperature transducers 620, the force transducers 622 and/ or the conductive contacts 624 may be provided on the upper surface 702a of the floor mat 460 approximately centered about a floor mat-midline 728 that approximately bisects the upper surface 702a of the floor mat 460 such that a first of the temperature transducers 620, the force transducers 622 and/or the conductive contacts 624 is disposed to the left of the mat-midline 728 (e.g., closer to the left-side 702b of the floor mat 460) and a second of the temperature transducers 620, the force transducers 622 and/or the conductive contacts 624 is disposed to the right of the mat-midline 728 (e.g., closer to the right-side 702c of the floor mat 460). Although the illustrated embodiment includes pairs of the temperature transducers 620, the force transducers 622 and/ or the conductive contacts 624 disposed in a symmetric arrangement, other embodiments may include any number of the temperature transducers 620, the force transducers 622 and/or the conductive contacts 624 provided in any variety of suitable locations.

In some embodiments, the floor mat 460 includes a cable 730 that may be coupled to an external device (e.g., the employee computer 130) for communicating and/or receiving power. For example, the cable 730 may include a USB cable that is plugged into a USB port of the I/O interface 304 of the employee computer 130. The floor mat 460 may receive power via the cable and/or may transmit health data 200 via the cable. In some embodiments, the floor mat 460 may communicate wirelessly (e.g., via Bluetooth, WLAN, or the like) with the employee computer 130 and/or the server 104. In such an embodiment, the floor mat 460 may also include a battery for a power source such that the floor mat 460 is not physically tethered to the employee computer 130 or other components of the system 100.

Although embodiments are described herein with regard to components of the floor mat 460, it will be appreciated that similar components may be integrated into the floor 403 underfoot of the employee. Such embodiments may not require the use of a separate floor mat for sensing health data.

Figure 7B:
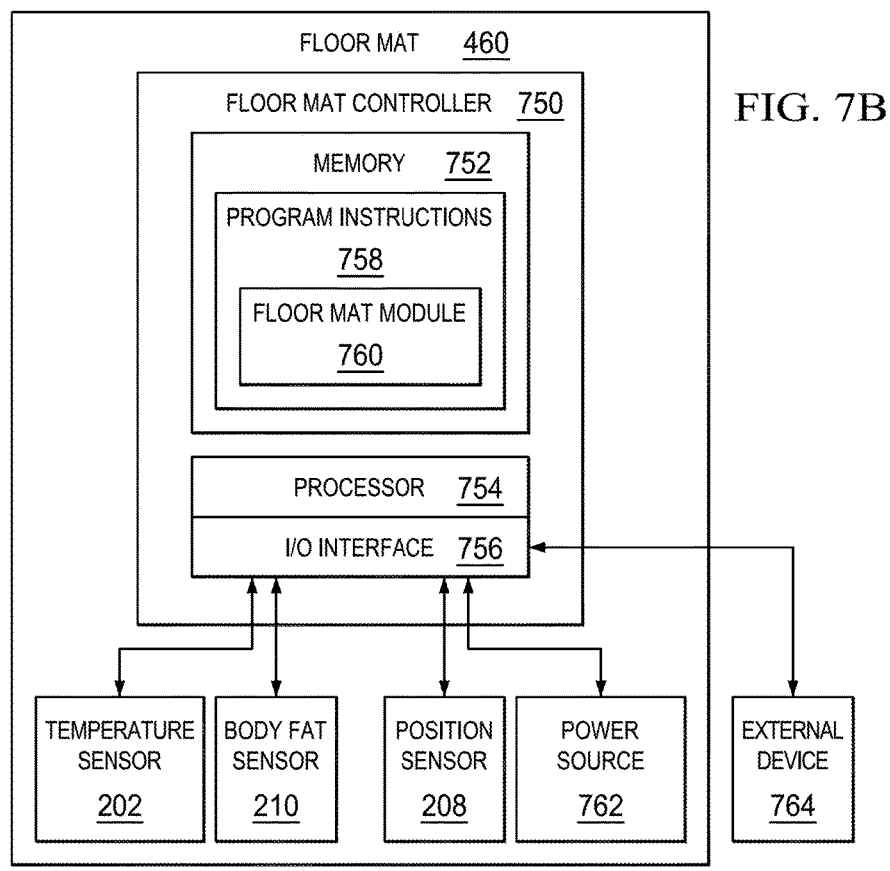
FIG. 7B is a block diagram that illustrates components of the floor mat in accordance with one or more embodiments of the present invention.

FIG. 7B is a block diagram that illustrates components of the floor mat 460 in accordance with one or more embodiments of the present invention. In some embodiments, the floor mat 460 may include a floor mat controller 750 for controlling the operational aspects of floor mat 460. For example, the floor mat controller 750 may provide for allocating power to various sensors 120 of the floor mat 460, collecting health data 200 from the various sensors 120 of the floor mat 460 and/or transmitting the collected health data 200 to the employee computer 130 and/or the server 104.

In some embodiments, the floor mat controller 750 includes a memory 752, a processor 754, and an input/output (I/O) interface 756. The floor mat controller 750 may be a microcontroller device such as STMicroelectronics, ST10 (16-bit) and STM32 (32-bit); Atmel, AVR32 (32-bit) and AT91SAM (32-bit); Freescale ColdFire (32-bit); Hitachi SuperH (32-bit); and the Hyperstone E1/E2 (32-bit, full integration of RISC and DSP on one processor core), which is adapted for use in the functions described herein.

The memory 752 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 752 may include a non-transitory computer readable storage medium having program instructions 758 stored thereon that are executable by a computer processor (e.g., the processor 754) to cause the functional operations described herein with regard to the floor mat 460. The program instructions 758 may include a floor mat module 760 including program instructions that are executable by the processor 754 to provide some or all of the functionality described herein with regard to the floor mat 460.

The processor 754 may be any suitable processor capable of executing/performing program instructions. The processor 754 may include a central processing unit (CPU) that carries out program instructions (e.g., program instruction of the floor mat module 760) to perform arithmetical, logical, input/output and other operations of the floor mat 460, including those described herein.

The I/O interface 756 may provide an interface for connection of one or more I/O devices to the floor mat controller 750. I/O devices may include sensors 120 (e.g., temperature sensors 202, position sensors 208, and/or body fat sensors 210), power source(s) 662 (e.g., a battery 751, AC/DC power delivered via cable 730, and/or the like), external device(s) 764 (e.g., the employee computer 130 and/or server 104), and/or the like. The I/O devices may be connected to I/O interface 756, via a wired or wireless connection.

Figure 7C:
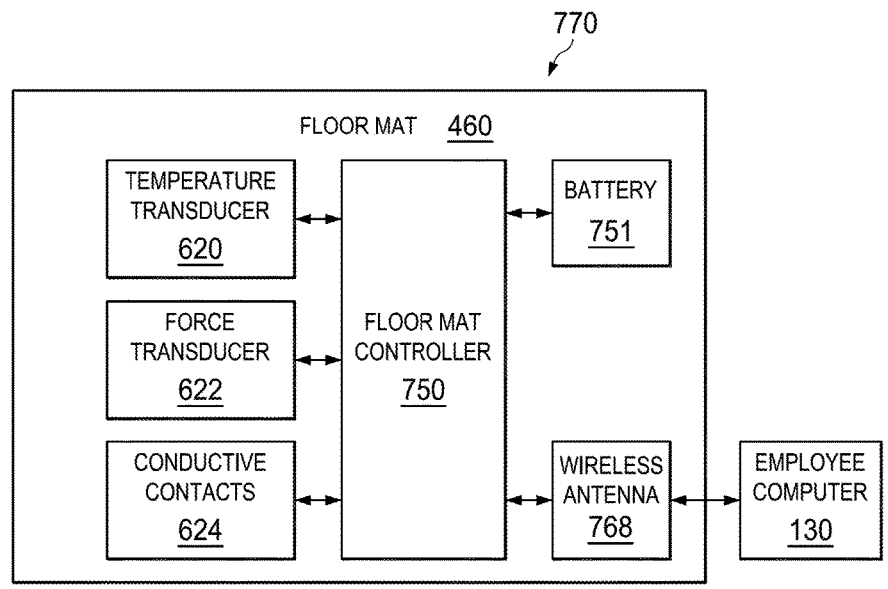
FIG. 7C is a block diagram that illustrates an exemplary floor mat system in accordance with one or more embodiments of the present invention.

FIG. 7C is a block diagram that illustrates an exemplary floor mat system 770 in accordance with one or more embodiments of the present invention. The floor mat system 770 includes a floor mat 460 having a floor mat controller 750 coupled to one or more temperature transducers 620, one or more force transducers 622, one or more conductive contacts 624, a battery 751, and a wireless antenna 768. In some embodiments, floor mat controller 750 may employ the temperature transducers 620, the force transducers 622, and/or the conductive contacts 624 to collect corresponding measurements. For example, where a temperature transducer 620 includes a thermocouple, to take a temperature measurement, the floor mat controller 750 may take a voltage measurement across two leads connected to the thermocouple of the temperature transducer 620, the measured voltage being indicative of the temperature sensed by the temperature transducer 620. Where, for example, a force transducers 622 includes a load cell including a strain gauge, to take a force measurement, the floor mat controller 750 may induce a current (I) across two leads connected to the strain gauge and take a measurement of voltage (V) across the two leads to determine a resistance (R) across the two leads that is indicative of the force sensed by the force transducer 622. As a further example, to take a body fat measurement, the floor mat controller 750 may induce a current (I) across two conductive contacts 624 and take a measurement of voltage (V) across the two conductive contacts 624 to determine a resistance (R) across the contacts 624 that is indicative of the body fat for the employee. In some embodiments, the battery 751 may provide power to operate the controller 750 and/or provide the power required to take a measurement from the temperature transducers 620, force transducers 622, and/or conductive contacts 624. In some embodiments, the wireless antenna 768 may include a Bluetooth transceiver for use in communicating with the employee computer 130 (e.g., e.g., via complementary transceiver of computer 130).

Figure 7D:
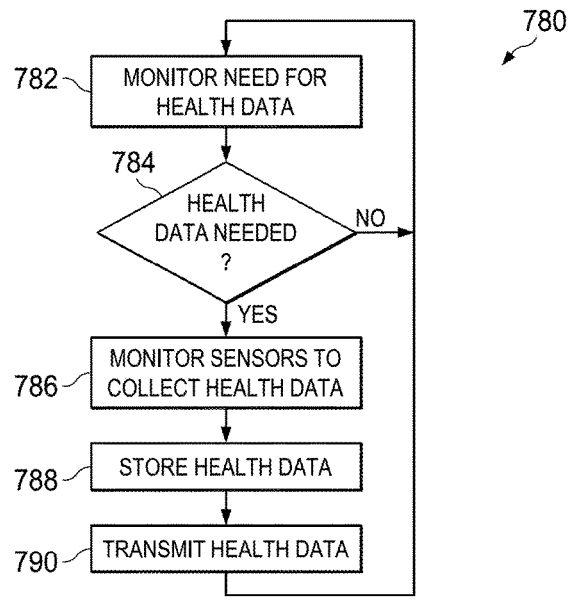
FIG. 7D is a flowchart that illustrates a method of operating the floor mat in accordance with one or more embodiments of the present invention.

FIG. 7D is a flowchart that illustrates a method 780 of operating the floor mat 460 in accordance with one or more embodiments of the present invention. Method 780 may include monitoring the need for health data 200, as depicted at block 782. In some embodiments, monitoring the need for health data may include determining whether or not there is a need to collect health data 200 (i.e., take a measurement) from one or more of the sensors 120 (e.g., the temperature transducers 620, the force transducers 622, and/or the conductive contacts 624) of the floor mat 460. In some embodiments, the need for health data 200 may be identified based on a request from another component of system 100. For example, the floor mat 460 may determine that there is a need to collect health data 200 in response to a request for the health data 200 (e.g., a request to initiate a health test and/or a query for the health data 200) received from the computer 130, the server 104, and/or the employee 401.

Where it is determined that health data 200 is not needed, at block 784, method 780 may include returning to monitoring the need for health data 200, as depicted at block 782. Where it is determined that health data 200 is needed, at block 784, method 780 may include proceeding to monitoring of the sensors 120 (e.g., the temperature transducers 620, the force transducers 622, and/or the conductive contacts 624) to collect the health data 200, as depicted at block 786. In some embodiments, monitoring the sensors 120 to collect the health data 200 includes monitoring the particular sensors 120 that provide the particular health data 200 needed. Where the heath data 200 needed includes the employee's body temperature, body position and/or body fat, monitoring the sensors 120 to collect the health data 200 may include, for example, the floor mat controller 750 taking measurements from the temperature transducers 620, the force transducers 622, and/or the conductive contacts 624, respectively, to collect health data 200 including measured voltages indicative of body temperature, measured resistances indicative of forces, and/or measured resistances indicative of the employee's body fat.

Method 780 may include storing the health data 200, as depicted at block 788. In some embodiments, storing the health data 200 includes storing the collected health data 200 in local or remote memory. For example, the floor mat controller 750 may store the measured voltages indicative of body temperature, measured resistances indicative of forces, and/or measured resistances indicative of the employee's body fat in memory 752. In some embodiments, storing the heath data 200 may include buffering/queuing the health data 200 for transmission at a later time.

Method 780 may include transmitting the health data 200, as depicted at block 790. In some embodiments, transmitting the health data 200 includes transmitting the health data 200 to another component/entity of system 100. For example, the floor mat controller 750 may transmit the health data 200 (e.g., collected via the sensors 120 of the floor mat 460 and stored in memory 752), to computer 130 and/or server 104 for use in monitoring the health of the employee. In some embodiments, the health data 200 is transmitted via a wired or wireless communication. For example, where the floor mat 460 is connected to the computer 130 and/or the server 104 via data cables (e.g., via cable 730) the floor mat controller 750 may transmit some or all of the health data 200 to the computer 130 and/or the server 104 via the data cables. Where the floor mat 460 is in wireless communication with the computer 130 and/or the server 104 (e.g., via Bluetooth connection, WLAN connection, or the like), the floor mat controller 750 may transmit some or all of the health data 200 to the computer 130 and/or the server 104 via wireless communication. For example, the floor mat controller 750 may communicate the health data to computer 130 and/or server 104 via wireless antenna 768.

In some embodiments, after transmitting the health data 200, method 780 may progress back to monitoring the need for health data 782. Where for example, the request for health data is still active and/or another request for health data is received, the floor mat controller 750 may execute another iteration of monitoring the sensors to collect health data, storing the health data and/or transmitting the health data.

It will be appreciated that the method 780 is an exemplary embodiment of a method that may be employed in accordance with techniques described herein. The method 780 may be may be modified to facilitate variations of its implementations and uses. The method 780 may be implemented in software, hardware, or a combination thereof. Some or all of the method 780 may be implemented by one or more of the modules/applications described herein, such as floor mat module 760. The order of the method 780 may be changed, and various elements may be added, reordered, combined, omitted, modified, etc.

Figure 8A:
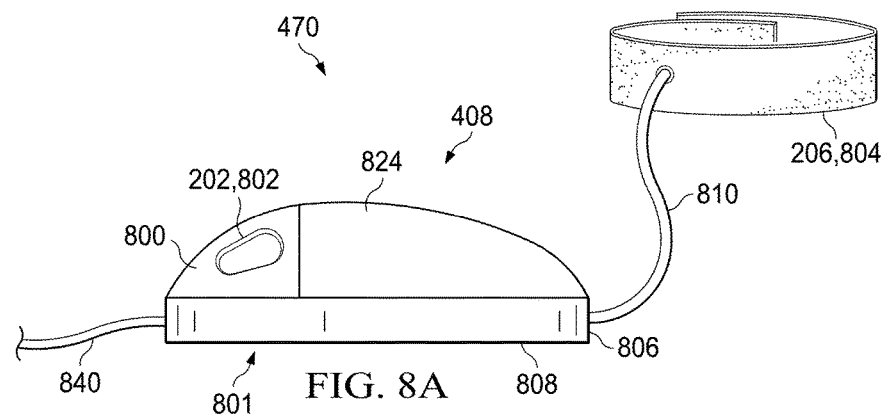
FIGS. 8A-8C are side and end elevation views of a mouse specially adapted to include sensors for use in monitoring an employee's health in accordance with one or more embodiments of the present invention.
Figure 8B:
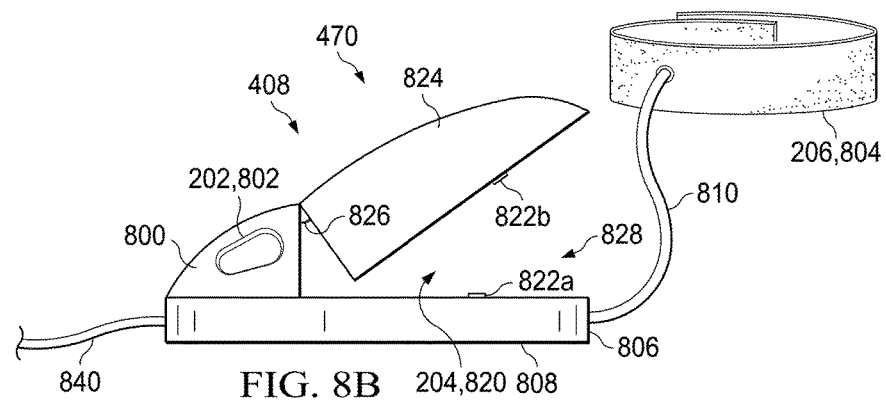
Figure 8C:
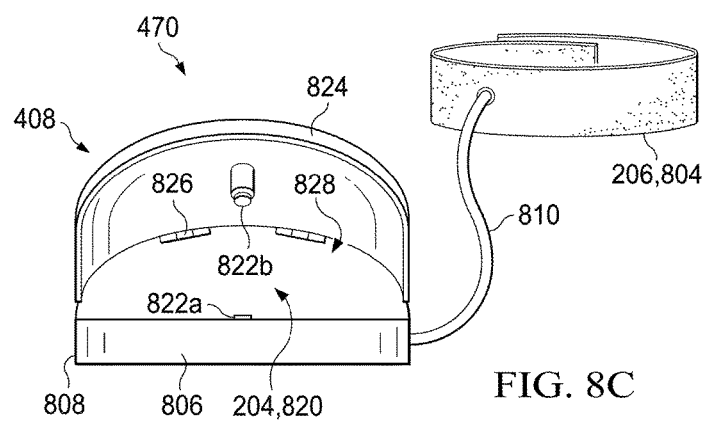

Mouse:

FIGS. 8A-8C are side and end elevation views of a computer mouse system 470 including the mouse 408 specially adapted to integrate with sensors 120 (e.g., temperature sensors, blood condition sensors, and blood pressure sensor) for use in monitoring an employee's health in accordance with one or more embodiments of the present invention.

In some embodiments, the mouse 408 includes a device that can be used in a traditional manner to manipulate a cursor in the employee's workstation display. For example, the employee can manipulate the mouse 408 (e.g., move the mouse on their desk 402) to cause a cursor on the computer display 412 to move in a similar fashion, and/or interact with content displayed on the computer display 412 via selection of the mouse buttons 800 (e.g., right-click, left click, etc.). In some embodiments, a location sensor 801 of the mouse (e.g., a laser, mouse ball, or the like) detects movement of the mouse relative to the surface on which it is being moved, the mouse 408 transmits corresponding location/movement data to the computer (e.g., computer 130) for use in determining the location of the mouse, the movement of the mouse and the like. The location/movement data can be used to determine how the user is interacting with displayed content and to update the display of a pointer on the display screen to mimic the movement of the mouse. In some embodiments, data reflecting movement of the mouse is used to determine the length of time the employee has been interacting with the mouse 408. For example, the total amount of time the employee has been moving the mouse 408 may be used to determine whether the employee is experiencing muscle tension or other biomechanical and/or biometric conditions (e.g., characteristics/conditions/risks).

In some embodiments, the mouse system 470 includes various sensors 120 that can be used to collect heath data 200. For example, mouse system 470 may include one or more temperature sensors 202, blood condition sensors 204, blood pressure sensors 206, and/or the like. In some embodiments, the various sensors 120 of the mouse system 470 are used to sense/measure various aspects of the employees biometric and/or biomechanical health and provide corresponding health data 200 (e.g., temperature data 200*a*, blood condition data 200*b*, and/or blood pressure data 200*c*) to another device of system 100 (e.g., to a mouse controller, the employee computer 130 and/or the server 104) for use in monitoring the employee's health.

In some embodiments, the mouse system 470 includes a temperature sensor 202 including an infrared ("IR") sensor 802 integrated with the mouse 408 as depicted in FIGS. 8A-8B. The IR sensor 802 may be used to sense a body temperature of the employee while the employee is using the mouse 408. For example, while the employee's hand is grasping the mouse 408, such that employee's palm, finger or other portion of the hand is disposed above the IR sensor 802, the IR sensor 802 may sense a temperature of the corresponding portion of the palm, finger or other portion of the hand and transmit corresponding temperature data 200*a* to a mouse controller, the employee computer 130 and/or the server 104. In some embodiments, the IR sensor 802 employs an emitter to emit thermal radiation that is focused by a lens onto the skin of the employee and a detector that senses the radiant power reflected back to the detector.

In some embodiments, the mouse system 470 includes a blood pressure sensor 206 including a blood pressure cuff 804 integrated with the mouse 408 as depicted in FIGS. 8A-8C. The blood pressure cuff 804 may be used to detect the employee's blood pressure and/or heart rate. For example, the employee may place the blood pressure cuff 804 about their wrist/arm, and the cuff 804 may be inflated to detect the variation in pressure as blood flows through the employee's wrist/arm. The detected variation in pressure may be used to determine the employee's blood pressure (i.e., the systolic and diastolic blood pressure numbers for the employee) and/or heart rate using known techniques. For example, the bladder of the cuff 804 may be inflated about the employee's wrist/arm, a pressure transducer may sense pressure oscillations in the cuff 804 that are indicative of the variation in pressure as blood flows through the employee's wrist/arm, the blood pressure cuff 804 may transmit corresponding blood pressure data 200*c* to the mouse controller, the employee computer 130 and/or the server 104, and the blood pressure data 200*c* (e.g., sensed pressure oscillations) may be processed to determine the employee's blood pressure and/or heart rate using known methods.

In some embodiments, the blood pressure cuff 804 may be fabricated to include at least one flexible, non-frangible-inflatable bladder disposed between two fabric cuff layers. The bladder may be fabricated from rubber or plastic and/or the fabric cuffs may be fabricated from nylon or polyester. In such an embodiment, only the fabric cuff layers, and not the surface of the bladder, may contact the employee's skin or clothing during use.

In some embodiments, the blood pressure cuff 804 is physically connected to the mouse 408. For example, the blood pressure cuff 804 can be connected to the bottom portion 806 of the body 808 of the mouse 408 via a connector 810. As discussed in more detail below, in some embodiments, connector 810 may include a hollow conduit (e.g., a pneumatic tube) that is physically coupled to the bladder of cuff 804. The conduit may be used to supply/draw air to inflate/deflate the bladder and/or physically communicate air pressure within the bladder of cuff 804. As discussed in more detail below, in some embodiments, connector 810 includes a wire (e.g., a coated wire or similar electrical conduit) for communicating electrical signals that can be used to operate cuff 804 and/or communicate blood pressure data 200*c* to the mouse controller, the employee computer 130 and/or the server 104.

In some embodiments, the pressure transducer used to sense pressure oscillations and/or the pump used to inflate the cuff 804 is located within the body 808 of the mouse 408 (e.g., see FIG. 8E discussed in more detail below). In such an embodiment, the connector 810 may include a pneumatic tube that is used supply air to inflate the bladder of the cuff 804 and/or physically communicate the pressure of the bladder to a pressure transducer used to sense the pressure in the bladder. For example, a pump located in the body of the mouse 408 may supply air to cuff 804 via the pneumatic tube 810 to inflate the cuff 804, the pressure in the cuff 804 may be physically communicated through the pneumatic tube 810 to the pressure transducer located within the body 808 of the mouse 408, the pressure transducer may sense the variations in pressure within the pneumatic tube 810, and the pressure transducer may transmit corresponding blood pressure data 200c to the mouse controller, the employee computer 130 and/or the server 104.

In some embodiments, a pressure transducer and/or a pump used to inflate the cuff 804 is integrated with the cuff 804 (e.g., located in or on the cuff 804) (e.g., see FIG. 8F discussed in more detail below). In such an embodiment, the connector 810 may include a wire for communicating, to the mouse 408, the pressure detected by the pressure transducer. For example, a pump located in mouse 408 and/or cuff 804 may supply are to inflate the cuff 804, the pressure transducer located within the cuff 804 may sense the variations in pressure within the bladder of the cuff 804, and the pressure transducer may transmit corresponding blood pressure data 200c to the mouse controller via the wire connector 810, the employee computer 130 and/or the server 104.

In some embodiments, the cuff 804 may communicate with the mouse 408 or other components of the system 100 via wireless communication. For example, blood pressure data 200c indicative of the sensed variation in pressure may be communicated from a pressure transducer of cuff 804 to a mouse controller, the employee computer 130 and/or the server 104 via a wireless communication (e.g., via Bluetooth communication, a WLAN connection and/or the like). Such an embodiment may eliminate the need for a connector 810 such that the cuff 804 is not physically tethered to mouse 408, thereby allowing the employee to have more physical freedom (e.g., the employee can leave the workstation 102 without having to physically remove the cuff 804 from their arm/wrist).

In some embodiments, the mouse 408 includes a blood condition sensor 204 including a pulse oximeter 820. The pulse oximeter 820 may be used to measure various aspects of the employee's blood that are indicative of the employee's blood oxygenation, heart rate, and/or the like and provide corresponding blood condition data 200b to the mouse controller, the employee computer 130 and/or the server 104.

In some embodiments, the pulse oximeter 820 includes a transmissive type pulse oximetry sensor having an emitter (e.g., an LED emitter) 822a for emitting light into and through the employee's fingertip pulp (or similar cross-section of an employee's body such as an earlobe) and a detector (e.g., an optical detector) 822b for detecting the emitted light that passes though the fingertip pulp. For example, the emitter 822a and the detector 822b may be placed on opposite sides (e.g., bottom and top) of the employee's fingertip, the pulse oximeter 820 may be activated such that emitter 822a emits light at multiple/different wavelengths such that at least some of the light is transmitted through the employee's fingertip pulp and is detected by the detector 822b, and corresponding blood condition data 200b indicative of the light transmitted through and/or absorbed by the employee's fingertip pulp is provided to the mouse controller, the employee computer 130 and/or the server 104. The blood condition data 200b indicative of the light transmitted through and/or absorbed by the employee's fingertip pulp may be used in accordance with known methods to determine measurements of the employee's blood oxygenation, heart rate and/or the like.

As depicted in FIGS. 8B and 8C a lid portion of 824 of the mouse 804 may be rotated into an "opened" position (see FIGS. 8B and 8C) to expose the pule oximeter 820 located inside of the mouse 804. As depicted, when the lid portion 824 of the mouse 804 is opened (e.g., rotated about hinge 826 upward and away from the body 808 of the mouse 408) the resulting opening 828 may provide access to the pulse oximeter 820 located within the mouse 408. During use, the employee may insert their fingertip into opening 828 and position the fingertip between an emitter 822a and an optical detector 822b of the pulse oximeter 820. The lid portion 824 may be adapted such that in a "closed position" (see FIG. 8A) the lid portion 824 is disposed on the computer mouse body 808 and the pulse oximeter 820 is enclosed within the shell of the mouse 408 (i.e., enclosed within the lid 824 and lower body 808 of the mouse 408). In such a configuration, the mouse 408 looks, feels and operates like a traditional computer mouse. In some embodiments, the lid 824 may be biased to the closed position and/or the opened position such the lid 824 stays closed while the mouse 408 is used in a traditional manner and/or the lid 824 stays open when the employee has opened lid 824 to access the pulse oximeter 820. In such a configuration, the employee can easily place their fingertip into opening 828 without the lid 824 inadvertently closing. In some embodiments, the lid 824 may be biased to a closed position such that the emitter 822a and the detector 822b squeezes about the employee's fingertip to provide an acceptable reading by the pulse oximeter 820. In some embodiments, the emitter 822a and the detector 822b may be aligned such when the emitter 822a and the detector 822b are disposed about the employee's fingertip, the light emitted by the emitter 822a is directed toward the detector 822b.

As described above, when the employee's fingertip is located between the emitter 822a and the detector 822b, the pulse-oximeter sensor 820 may be activated such that emitter 822a (e.g., an LED emitter) emits light at multiple different wavelengths and the optical detector 822b detects the emitted light that is transmitted through the employee's fingertip. Although the illustrated embodiment includes the emitter 822a disposed at a lower surface of the opening 828 (e.g., a top surface of body 808 of the mouse 408) and the optical detector 822b located on an underside of lid 824, other embodiments may include any suitable number and location of emitters and detectors. For example, the positions of the emitter 822a and the detector 822b may be swapped such that the detector 822b is disposed at a lower surface of opening 826 and the emitter 822a is located on an underside of lid 824.

In some embodiments, the pulse oximeter 820 includes a reflectance type pulse oximeter sensor (e.g., having an emitter 822a for emitting light into the employee's pulp and a detector 822b that is located proximate the emitter 822a for detecting the light that reflects back from the employee's pulp). In some embodiments, both of the emitter 822a and the detector 822b of the reflectance type pulse oximeter 820 may be provided in one of the locations where the emitter 822a or the detector 822b are illustrated in FIGS. 8B and 8C, or any other suitable location. In such an embodiment, the employee may simply need to dispose a portion of their skin onto the surface of the reflectance type pulse oximeter 820, and, thus, may not have to place a cross-section of their body (e.g., their fingertip) between two separate sensing devices. For example, where the pulse oximeter 820 includes a reflectance type pulse oximeter having an emitter and detector located in the same position where emitter 822a is illustrated the employee may simply have to place the bottom of their fingertip pulp onto the reflectance type pulse oximeter 820. In some embodiments, the pulse oximeter 820 may be located elsewhere on the mouse 408. For example, a reflectance type pulse oximeter 820 may be located at an exterior surface of the mouse 408 (e.g., in the same or similar location as the IR sensor 802) such that readings may be taken while the user is grasping the exterior of the mouse 408. A reflectance type pulse oximeter 820 is located at or near the location of temperature sensor 202 may take readings while the employee's palm, finger or other portion of the hand is disposed on the pulse oximeter (e.g., while the employee is grasping the mouse 408 during traditional use of the mouse 408).

In some embodiments, the IR sensor 802 may be adapted to detect the employee's pulse oxygenation. For example, the IR sensor 802 may be employed to conduct a passive pulse oximetry or photoplethysomography test while the employee's palm, finger or other portion of the hand is disposed above the IR sensor 802 (e.g., while the employee is grasping the mouse 408 during traditional use of the mouse 408). In some embodiments, the IR sensor 802 may use photonic glucose crystal sensing/photoplethysomography to detect blood pressure, body temperature, heart rate and blood glucose as is understood in the art. Accordingly, the IR sensor 802 may be used to collect blood condition data 200b and/or blood pressure data 200c.

In some embodiments, the mouse 408 includes a cable 840 that is coupled to an external device (e.g., the employee computer 130) for communicating and/or receiving power. For example, the cable 840 may include a USB cable that is plugged into a USB port of the I/O interface 304 of the employee computer 130. The mouse 408 may receive power via the cable 840, communicate with employee computer 130 regard to operations of the mouse 408 via the cable 840, and/or transmit health data 200 via the cable 840. In some embodiments, the mouse 408 may include a wireless mouse that communicates wirelessly with the employee computer 130 (e.g., via Bluetooth communication, WLAN connection, or the like). In such an embodiment, the mouse 408 may also include a battery for a power source such that the mouse is not physically tethered to the employee computer 130 or other components of system 100.

Figure 8D:
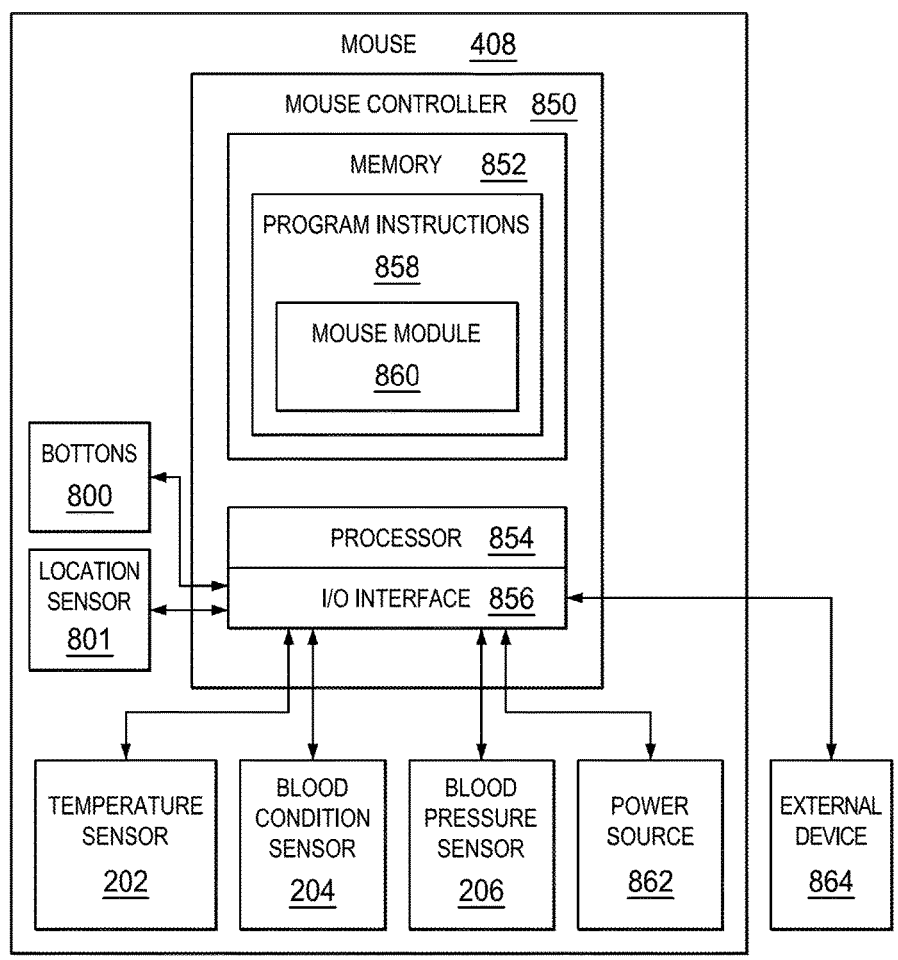
FIG. 8D is a block diagram that illustrates components of the mouse in accordance with one or more embodiments of the present invention.

FIG. 8D is a block diagram that illustrates components of the mouse 408 in accordance with one or more embodiments of the present invention. In some embodiments, the mouse 408 includes a mouse controller 850 for controlling the operational aspects of mouse 408. For example, the mouse controller 850 may provide for allocating power to the various sensors 120 of the mouse 408, collecting health data 200 from the various sensors 120 of the mouse 408 and/or transmitting the collected health data 200 to the employee computer 130 and/or the server 104. In some embodiments, the mouse controller 850 includes a memory 852, a processor 854 and an input/output (I/O) interface 856. The mouse controller 850 may be a microcontroller device such as STMicroelectronics, ST10 (16-bit) and STM32 (32-bit); Atmel, AVR32 (32-bit) and AT91SAM (32-bit); Freescale ColdFire (32-bit); Hitachi SuperH (32-bit); and the Hyperstone E1/E2 (32-bit, full integration of RISC and DSP on one processor core), which is adapted for use in the functions described herein.

The memory 852 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 852 may include a non-transitory computer readable storage medium having program instructions 858 stored thereon that are executable by a computer processor (e.g., the processor 854) to cause the functional operations described herein with regard to the mouse 408 and/or mouse system 470. The program instructions 858 may include a mouse module 860 including program instructions that are executable by the processor 854 to provide some or all of the functionality described herein with regard to the mouse 408.

The processor 854 may be any suitable processor capable of executing/performing program instructions. The processor 854 may include a central processing unit ("CPU") that carries out program instructions (e.g., program instructions of the mouse module 860) to perform arithmetical, logical, input/output and other operations of the mouse 408 and/or the mouse system 470, including those described herein.

The I/O interface 856 may provide an interface for connection of one or more I/O devices to mouse controller 850. The I/O devices may include mouse buttons 800, location sensor 801, sensors 120 (e.g., a temperature sensor 202, a blood condition sensor 204, a blood pressure sensor 206), power source(s) 862 (e.g., a battery, AC/DC power delivered via cable 840, and/or the like), external device(s) 864 (e.g., the computer 130 and/or the server 104), and/or the like. The I/O devices may be connected to I/O interface 856 via a wired or wireless connection.

Figure 8E:
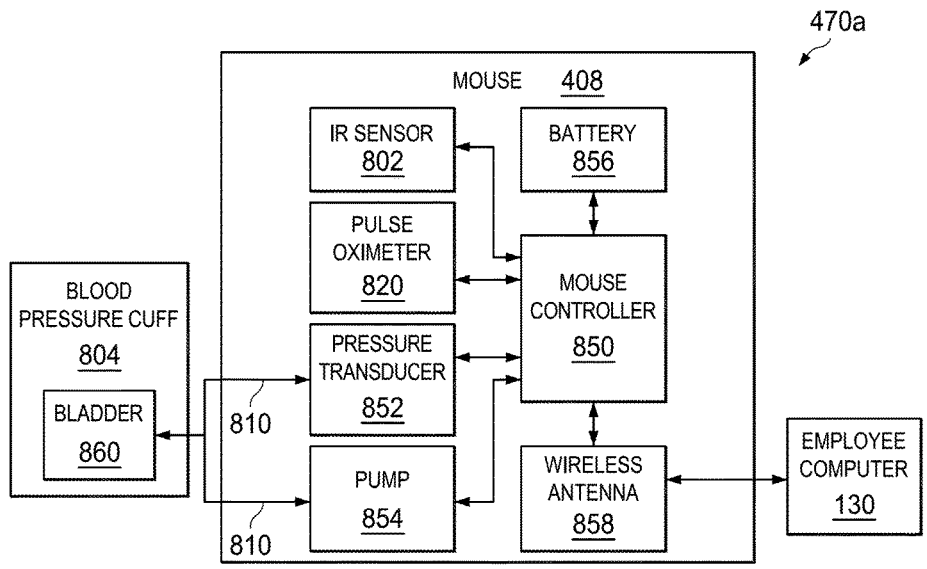
FIG. 8E is a block diagram that illustrates an exemplary mouse system including a blood pressure cuff physically connected to the mouse in accordance with one or more embodiments of the present invention.

FIG. 8E is a block diagram that illustrates an exemplary mouse system 470a including the blood pressure cuff 804 connected to the mouse 408 via a pneumatic tube 810 in accordance with one or more embodiments of the present invention. The mouse system 470 includes a mouse controller 850 coupled to one or more IR sensors 802, a pulse oximeter 820, a pressure transducer 852, a pump 854, a battery 856, and a wireless antenna 858. In some embodiments, the wireless antenna 858 includes a Bluetooth transceiver for use in communicating with the employee computer 130 (e.g., e.g., via a complementary transceiver of computer 130).

In some embodiments, the pump 854 and/or the pressure transducer 852 are connected to an air bladder 860 of the blood pressure cuff 804 via the pneumatic tube 810. During use, the pump 854 may supply/draw air to inflate/deflate the bladder 860 via the pneumatic tube 810 and/or the pressure transducer 852 may take pressure readings from the pneumatic tube 810 that are indicative of the air pressure within the bladder 860. For example, the cuff 804 may be disposed about the employee's wrist, the pump 854 may supply air to the bladder 860 via the pneumatic tube 810 to inflate the bladder 860 about the employee wrist, the pressure within the bladder 860 may be communicated to the air within in the pneumatic tube 810, the pressure transducer 852 may take pressure readings of the air within the pneumatic tube 810 that are indicative of the air pressure within the bladder 860 (e.g., including the pressure oscillations due to the oscillations of the employee's blood pressure), blood pressure data 200c including the readings may be communicated to the mouse controller 850, and the bladder 860 may be deflated.

In some embodiments, the mouse controller 850 may employ the IR sensors 802, the pulse oximeter 820, and the pressure transducer 852 to collect corresponding measurements. For example, where the IR sensor 802 outputs a voltage indicative temperature and the pressure transducer 852 outputs a voltage indicative pressure, the mouse controller 850 may take voltage measurements from the IR sensor 802 and the pressure transducer 852. Where, for example, the pulse oximeter 622 outputs a data value indicative of blood oxygenation, the mouse controller 850 may query or otherwise read the data value. In some embodiments, the mouse controller 850 may control operation of the pump 854. For example, the mouse controller 850 may activate the pump 854 to inflate/deflate the bladder 860 as required. In some embodiments, the battery 751 provides power to operate the controller 750, to operate the pump 854, and/or to provide the power required to take measurements from the IR sensor(s) 802, the pulse oximeter 820, and/or the pressure transducer 852.

Figure 8F:
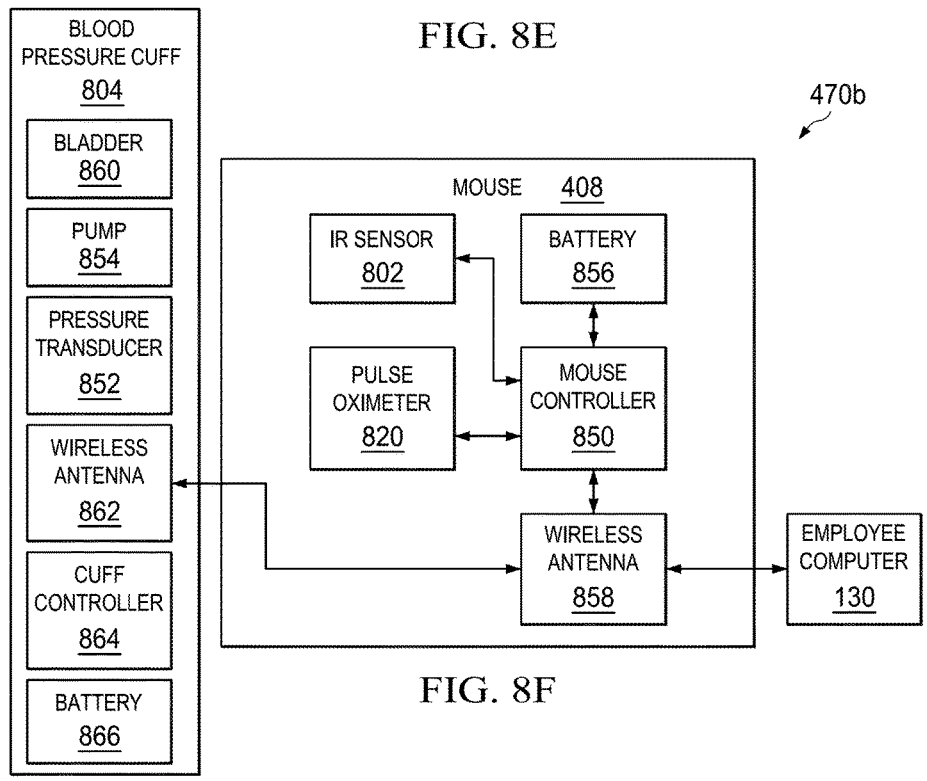
FIG. 8F is a block diagram that illustrates an exemplary mouse system including a blood pressure cuff wirelessly connected to the mouse in accordance with one or more embodiments of the present invention.

FIG. 8F is a block diagram that illustrates an exemplary mouse system 470b including the blood pressure cuff 804 wirelessly connected to the mouse 408 in accordance with one or more embodiments of the present invention. In some embodiments, the mouse controller 850 may employ the IR sensor 802 and/or the pulse oximeter 820 in a manner similar to that described with regard to FIG. 8E. As depicted, the blood pressure cuff 622 may include the pump 854, the pressure transducer 852, a wireless antenna 862, a cuff controller 864, and/or a battery 866 integrated therein In some embodiments, the battery 866 provides power to operate the cuff controller 864, to operate the pump 854, and/or provide the power required to take measurements from the pressure transducer 852. In some embodiments, the wireless antenna 862 includes a Bluetooth transceiver, or similar wireless communication device, for use in communicating with the mouse controller 850 (e.g., e.g., via the complementary antenna 858). In such an embodiment, the blood pressure cuff 622 may not be physically tethered to the mouse 408, thereby providing more physical freedom to the employee.

During use, the mouse controller 850 may query the blood pressure cuff 622 to provide various readings. For example, upon detecting the need for a blood pressure reading, the mouse controller 850 may send a request for a blood pressure reading to the cuff controller 864 (e.g., using wireless communication via antennas 858 and 862) and, in response to the request, the cuff controller 864 may operate the pump 854 to inflate the bladder 860, take a pressure reading indicative of the blood pressure from the pressure transducer 852, and transmit corresponding blood pressure data 200c, including the pressure reading, to the mouse controller 850 (e.g., using wireless communication via antennas 858 and 862).

Figure 8G:
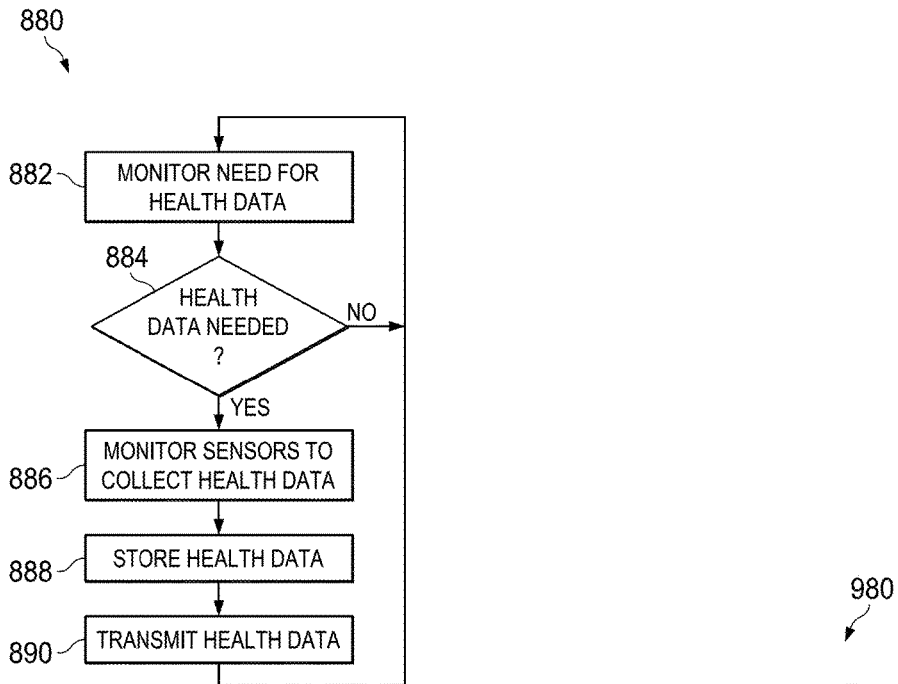
FIG. 8G is a flowchart that illustrates a method of operating the mouse system in accordance with one or more embodiments of the present invention.

FIG. 8G is a flowchart that illustrates a method 880 of operating the mouse system 870 in accordance with one or more embodiments of the present invention. Method 880 may include monitoring the need for health data 200, as depicted at block 882. In some embodiments, monitoring the need for health data includes determining whether or not there is a need to collect health data 200 (i.e., take a measurement) from one or more of the sensors 120 (e.g., the IR sensor 802, the pulse oximeter 820 and/or the blood pressure transducer 852). In some embodiments, the need for health data 200 is identified based on a request from another component of system 100. For example, the mouse controller 850 may determine that there is a need to collect health data 200 in response to a request for the health data 200 (e.g., a request to initiate a health test and/or a query for the health data 200) received from the computer 130, the server 104 and/or the employee 401.

Where it is determined that health data 200 is not needed, at block 884, method 880 may include returning to monitoring the need for health data 200, as depicted at block 882. Where it is determined that health data 200 is needed, at block 884, method 880 may include proceeding to monitoring of the sensors 120 of the mouse system 870 (e.g., the IR sensor 802, the pulse oximeter 820 and/or the blood pressure transducer 852) to collect the health data 200, as depicted at block 886. In some embodiments, monitoring the sensors 120 to collect the health data 200 includes monitoring the particular sensors 120 that provide the particular health data 200 needed. Where the heath data 200 needed includes the employee's body temperature, blood oxygenation level and/or blood pressure, monitoring the sensors 120 to collect the health data 200 may include, for example, the mouse controller 850 taking measurements from the IR sensor 802, the pulse oximeter 820 and/or the blood pressure transducer 852, respectively, to collect the need health data 200 including measured voltages indicative of body temperature, values from the pulse oximeter that are indicative of the blood oxygenation level, and/or voltages/values indicative of the employee's blood pressure.

Method 880 may include storing the health data 200, as depicted at block 888. In some embodiments, storing the health data 200 may include storing the collected health data 200 in local or remote memory. For example, the mouse controller 850 may store the values for corresponding to the measured body temperature, the blood oxygenation level, and/or blood pressure in memory 852. In some embodiments, storing the heath data 200 may include buffering/queuing the health data 200 for transmission at a later time.

Method 880 may include transmitting the health data 200, as depicted at block 890. In some embodiments, transmitting the health data 200 includes transmitting the health data 200 to another component/entity of system 100. For example, the mouse controller 850 may transmit the health data 200 (e.g., collected via the sensors 120 of the mouse system 470 and stored in memory 852), to computer 130 and/or server 104 for use in monitoring the health of the employee. In some embodiments, the health data 200 is transmitted via a wired or wireless communication. For example, where the mouse 408 is connected to computer 130 and/or server 104 via a data cable (e.g., via cable 840) the mouse controller 850 may transmit some or all of the health data 200 to the computer 130 and/or the server 104 via the data cable. Where the mouse 408 is in wireless communication with the computer 130 and/or the server 104 (e.g., via Bluetooth connection, WLAN connection, or the like), the mouse controller 850 may transmit some or all of the health data 200 to the computer 130 and/or the server 104 via wireless communication. For example, the mouse controller 850 may communicate the health data 200 to the computer 130 and/or the server 104 via wireless antenna 858.

In some embodiments, after transmitting the health data 200, method 880 may progress back to monitoring the need for health data. Where the request for health data is still active and/or another request for health data is received, for example, the mouse controller 850 may execute another iteration of monitoring the sensors to collect health data, storing the health data and/or transmitting the health data.

It will be appreciated that the method 880 is an exemplary embodiment of a method that may be employed in accordance with techniques described herein. The method 880 may be may be modified to facilitate variations of its implementations and uses. The method 880 may be implemented in software, hardware, or a combination thereof. Some or all of the method 880 may be implemented by one or more of the modules/applications described herein, such as mouse module 860. The order of the method 880 may be changed, and various elements may be added, reordered, combined, omitted, modified, etc.

Figure 9C:
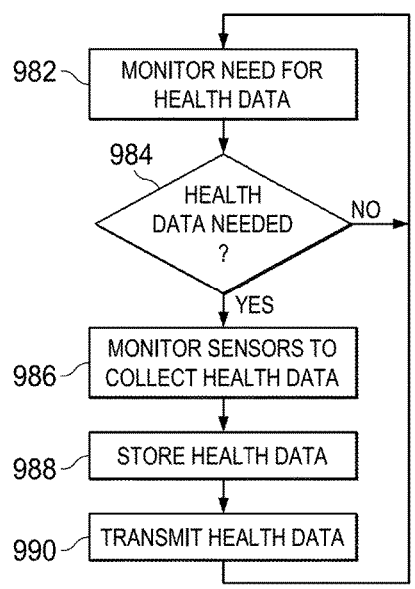
FIG. 9C is a flowchart that illustrates a method of operating the 3D position sensor in accordance with one or more embodiments of the present invention.
Figure 9A:
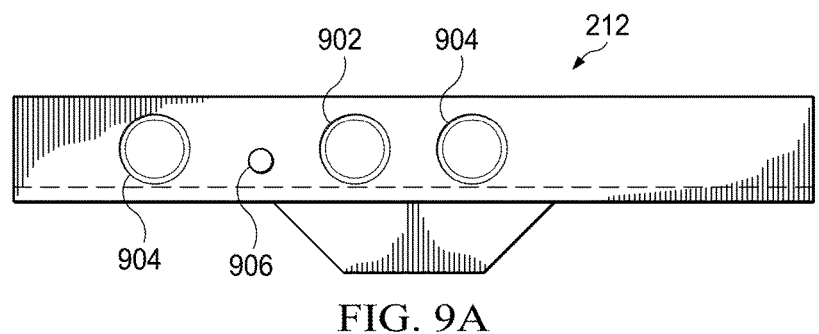
FIG. 9A is a front view of a three-dimensional ("3D") position sensor for use in monitoring an employee's health in accordance with one or more embodiments of the present invention.

3D Position Sensor:

FIG. 9A is a front view of the 3D position sensor 212 for use in monitoring an employee's health in accordance with one or more embodiments of the present invention. As depicted, the 3D position sensor 212 may include a one or more image sensors (e.g., red-green-blue ("RGB") video camera) 902, one or more 3D depth sensors 904, and/or audio sensors (e.g., a multi-array microphone) 906. In some embodiments, 3D position data 200f may include video, depth and audio data corresponding to events/actions that occur in the zone 420 acquired by the camera 902, 3D depth sensor 904 and/or microphone 906. The 3D position data 200f may be extrapolated to assess body position (e.g. the position of the employee's head, arms/hands, torso, legs, feet and so forth), the employee's posture, the employee's level of muscle tension, the employee's eye location/movements, the employee's level of eye fatigue and/or the like. For example, the 3D position data 200f acquired by the 3D position sensor 212 may be used to determine relative position measurements of the employee and associated peripherals. In some embodiments, 3D position sensor 212 includes a device such as the Kinect™ manufactured by Microsoft. Such a 3D position sensor 212 may include a software development kit that provides for employing the 3D position sensor 212 as a biomechanical sensor. As one skilled in the art will appreciate, though a specific 3D video camera device is described herein, other such cameras may be manufactured that can be adapted for use in the instant system. For example, any camera may be employed that is capable of capturing 3D body images such that movements may be "sensed" and corresponding data extrapolated for use in monitoring the health of the employee (e.g., via a posture analysis, eye fatigue analysis, etc.). In some embodiments, the audio sensor 906 may be used for acquiring audio data 200g that may be transmitted to other devices of the system 100, such as the computer 130 and/or the server 104 for use in monitoring the employee's health.

In some embodiments, health data 200 provided from the mouse 408 and/or 3D position sensor 212 may be used to determine various biomechanical characteristics of the employee. For example, position information from the computer mouse 408 and the 3D position sensor 212 may also be used to locate the employee's hand position in the test zone relative to the computer screen, chair pad, and floor mat. In such embodiments, electronics in the computer mouse 408 used to locate a cursor position could be used in combination with the video data to extrapolate the relative position of the computer mouse 408 within the test zone 420, and the position of the computer mouse could be used to locate the employee's chair and/or the employee's heard, arms/hands, torso, legs and feet.

Figure 9B:
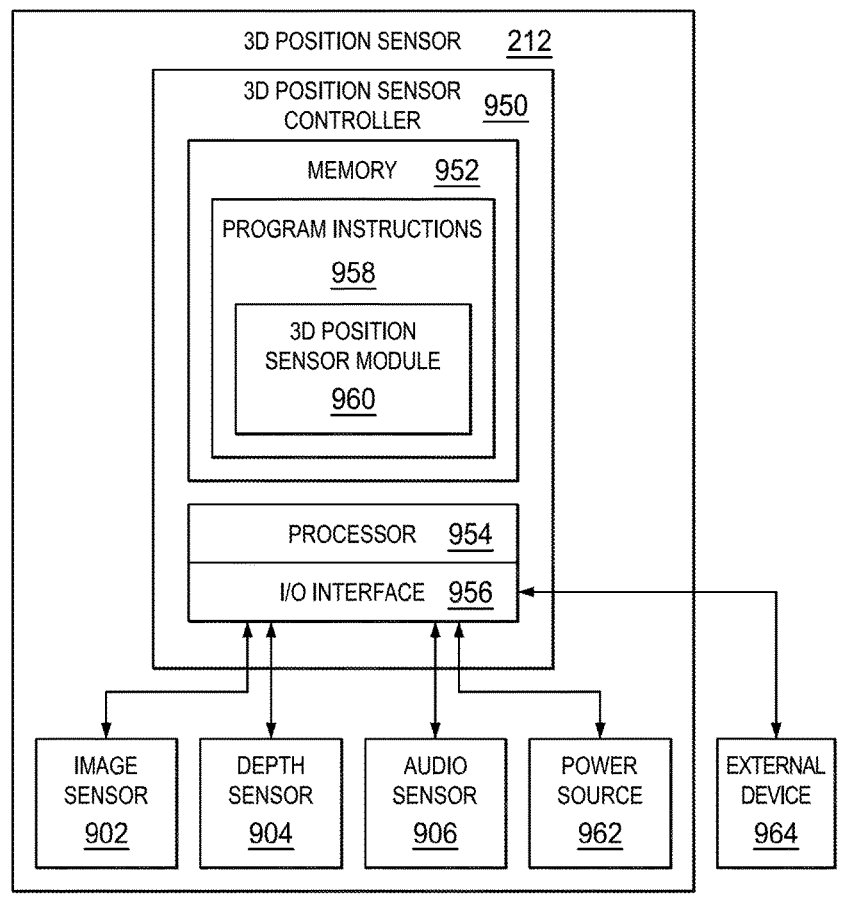
FIG. 9B is a block diagram of components of the 3D position sensor in accordance with one or more embodiments of the present invention.

FIG. 9B is a block diagram of components of the 3D position sensor 212 in accordance with one or more embodiments of the present invention. In some embodiments, the 3D position sensor 212 may include a 3D position sensor controller 950 for controlling the operational aspects of 3D position sensor 212. For example, 3D position sensor controller 950 may provide for allocating power to various sensors (e.g., image, depth and/or audio sensors) of the 3D position sensor 212, collecting health data 200 from the various sensors of the 3D position sensor 212 and/or transmitting the collected health data 200 to the employee computer 130 and/or the server 104. In some embodiments, the 3D position sensor controller 950 includes a memory 952, a processor 954 and an input/output (I/O) interface 956. The 3D position sensor controller 950 may be a microcontroller device such as STMicroelectronics, ST10 (16-bit) and STM32 (32-bit); Atmel, AVR32 (32-bit) and AT91SAM (32-bit); Freescale ColdFire (32-bit); Hitachi SuperH (32-bit); and the Hyperstone E1/E2 (32-bit, full integration of RISC and DSP on one processor core), which is adapted for use in the functions described herein.

The memory 952 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 952 may include a non-transitory computer readable storage medium having program instructions 958 stored thereon that are executable by a computer processor (e.g., the processor 954) to cause the functional operations described herein with regard to the 3D position sensor 212. The program instructions 958 may include a 3D position sensor module 960 including program instructions that are executable by the processor 954 to provide some or all of the functionality described herein with regard to 3D position sensor 212.

The processor 954 may be any suitable processor capable of executing/performing program instructions. The processor 954 may include a central processing unit (CPU) that carries out program instructions (e.g., program instructions of the 3D position sensor module 960) to perform arithmetical, logical, input/output and other operations of the 3D position sensor 212, including those described herein.

The I/O interface 956 may provide an interface for connection of one or more I/O devices to 3D position sensor controller 950. The I/O devices may include sensors (e.g., image, depth and/or audio sensors), power source(s) 962 (e.g., a battery, AC power, etc.), external device(s) 964 (e.g., the computer 130 and/or the server 104), etc. The I/O devices may be connected to the I/O interface 956, the computer 130 and/or the server 104 via a wired or wireless connection.

FIG. 9C is a flowchart that illustrates a method 980 of operating the 3D position sensor 980 in accordance with one or more embodiments of the present invention. Method 980 may include monitoring the need for health data 200, as depicted at block 982. In some embodiments, monitoring the need for health data includes determining whether or not there is a need to collect health data 200 (i.e., take a measurement) from one or more of the sensors 120 (e.g., the image sensor 902, the depth sensor 904, and/or the audio sensor 906). In some embodiments, the need for health data 200 may be identified based on a request from another component of system 100. For example, the 3D position sensor controller 950 may determine that there is a need to collect health data 200 in response to a request for the health data 200 (e.g., a request to initiate a health test and/or a query for the health data 200) received from the computer 130, the server 104 and/or the employee 401.

Where it is determined that health data 200 is not needed, at block 984, method 980 may include returning to monitoring the need for health data 200, as depicted at block 982. Where it is determined that health data 200 is needed, at block 984, method 980 may include proceeding to monitoring of the sensors 120 (e.g., the image sensor 902, the depth sensor 904, and/or the audio sensor 906) to collect the health data 200, as depicted at block 986. In some embodiments, monitoring the sensors 120 to collect the health data 200 includes monitoring the particular sensors 120 that provide the particular health data 200 needed. Where the heath data 200 needed includes the employee's body position and/or eye movement, monitoring the sensors 120 to collect the health data 200 may include, for example, the 3D position sensor controller 950 taking measurements from the image sensor 902 and/or the depth sensor 904, to collect the need health data 200 including 2D and/or 3D image data indicative of the employee's body position and/or eye position/movements. Where the heath data 200 needed includes the employee's speech, monitoring the sensors 120 to collect the health data 200 may include, for example, the 3D position sensor controller 950 taking measurements from the audio sensor 906, to collect the need health data 200 including, for example, audio data indicative of words spoken by the employee.

Method 980 may include storing the health data 200, as depicted at block 988. In some embodiments, storing the health data 200 may include storing the collected health data 200 in local or remote memory. For example, the 3D position sensor controller 950 may store the 2D image data, 3D image data and/or the audio data in the memory 952. In some embodiments, storing the heath data 200 may include buffering/queuing the health data 200 for transmission at a later time.

Method 980 may include transmitting the health data 200, as depicted at block 990. In some embodiments, transmitting the health data 200 may include transmitting the health data 200 to another component/entity of the system 100. For example, the 3D position sensor controller 950 may transmit the health data 200 (e.g., collected via the sensors 120 of the 3D position sensor 212 and stored in memory 952), to the computer 130 and/or the server 104 for use in monitoring the health of the employee. In some embodiments, the health data 200 may be transmitted via a wired or wireless communication. For example, where the 3D position sensor 212 is connected to the computer 130 and/or the server 104 via a data cable the 3D position sensor controller 950 may transmit some or all of the health data 200 to the computer 130 and/or the server 104 via the data cable. Where the 3D position sensor 212 is in wireless communication with the computer 130 and/or the server 104 (e.g., via Bluetooth connection, WLAN connection, or the like), the 3D position sensor controller 950 may transmit some or all of the health data 200 to the computer 130 and/or the server 104 via wireless communication. For example, the 3D position sensor controller 950 may communicate the health data to the computer 130 and/or the server 104 via a wireless antenna.

In some embodiments, after transmitting the health data 200, method 980 may progress back to monitoring the need for health data. Where the request for health data is still active and/or another request for health data is received, for example, the mouse controller 950 may execute another iteration of monitoring the sensors to collect health data, storing the health data and/or transmitting the health data.

It will be appreciated that the method 980 is an exemplary embodiment of a method that may be employed in accordance with techniques described herein. The method 980 may be may be modified to facilitate variations of its implementations and uses. The method 980 may be implemented in software, hardware, or a combination thereof. Some or all of the method 980 may be implemented by one or more of the modules/applications described herein, such as 3D position sensor module 960. The order of the method 980 may be changed, and various elements may be added, reordered, combined, omitted, modified, etc.

In some embodiments, health data 200 provided from the mouse 408 and/or the 3D position sensor 212 is used to determine various biomechanical characteristics of the employee. For example, position information from the computer mouse 408 and the 3D position sensor 212 may also be used to locate the employee's hand position in the test zone relative to the computer screen, chair pad, and floor mat. In such embodiments, electronics in the computer mouse 408 used to locate a cursor position could be used in combination with the video data to extrapolate the relative position of the computer mouse 408 within the test zone 420, and the position of the computer mouse could be used to locate the employee's chair and/or the employee's heard, arms/hands, torso, legs and feet.

Figure 10A:
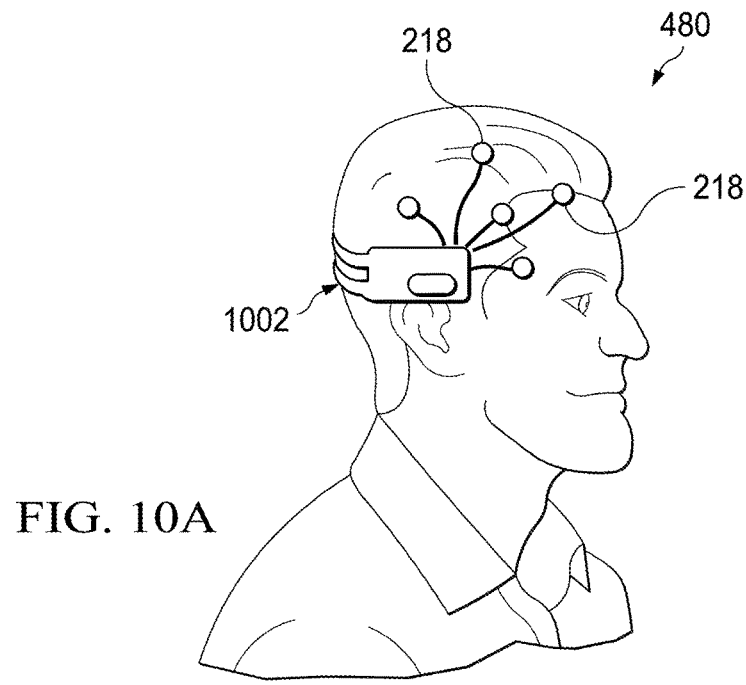
FIG. 10A is a perspective view of a neuro-headset for use in monitoring an employee's health in accordance with one or more embodiments of the present invention.
Figure 10B:
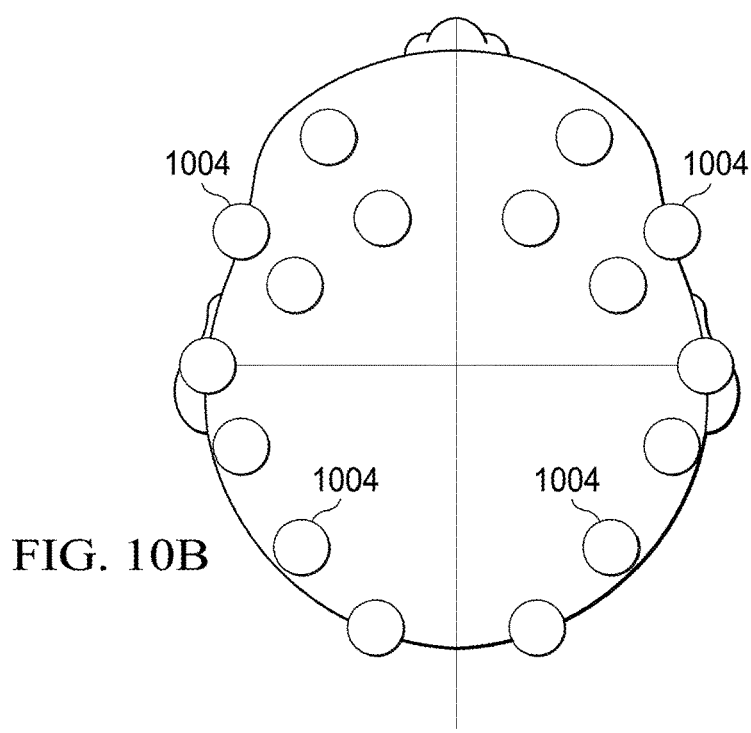
FIG. 10B is a top-view of an employee's head that illustrates exemplary neural sensor locations about the employee's head in accordance with one or more embodiments of the present invention.

Neural Sensors:

FIG. 10A is a perspective view of the neuro-headset 480 for use in monitoring an employee's health in accordance with one or more embodiments of the present invention. In some embodiments, the neuro-headset 480 includes a neuro-headset frame 1002 having a plurality of neural sensors 218 (e.g., sixteen neural sensors 218) coupled thereto. The neuro-headset frame 1002 may provide for positioning of the neural sensors 218 in discrete neural sensor locations about the employee's head while the neuro-headset 418 is being worn by the employee. FIG. 10B is a top-view of an employee's head that illustrates sixteen exemplary neural sensor locations 1004 about the employee's head/scalp in accordance with one or more embodiments of the present invention. As discussed above, the neural-headset 480 may be used to sense brain activity of the employee that can be used to detect neuro-signals (e.g., including alpha, beta, gamma, and delta waves) that can be used to determine the employee's emotional state, thoughts (e.g., cognitive thoughts, subconscious thoughts, intent), facial movements (e.g., facial expressions), motor functions and/or the like. In some embodiments, the neuro-headset 480 may be employed to sense brain activity and provide corresponding neural data 200i that is indicative of the sensed brain activity. For example, the neuro-headset 480 may transmit neural data 200i corresponding to brain activity sensed by the neural sensors 218 to or other device within the system 100 (e.g., to the computer 130 and/or the server 104).

FIG. 10C is a block diagram that illustrates components of the neuro-headset 480 in accordance with one or more embodiments of the present invention. In some embodiments, the neuro-headset 480 may include a neuro-headset controller 1050 for controlling the operational aspects of the neuro-headset 480. For example, the neuro-headset controller 1050 may provide for allocating power to the neural sensors 418 of the neuro-headset 480, collecting neural data 200i from the neural sensors 418 of the neuro-headset 480, and/or transmitting the collected neural data 200i to the employee computer 130 and/or the server 104.

In some embodiments, the neuro-headset controller 1050 includes a memory 1052, a processor 1054 and an input/output (I/O) interface 1056. The neuro-headset controller 1050 may be a microcontroller device such as STMicroelectronics, ST10 (16-bit) and STM32 (32-bit); Atmel, AVR32 (32-bit) and AT91SAM (32-bit); Freescale ColdFire (32-bit); Hitachi SuperH (32-bit); and the Hyperstone E1/E2 (32-bit, full integration of RISC and DSP on one processor core), which is adapted for use in the functions described herein.

The memory 1052 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 1052 may include a non-transitory computer readable storage medium having program instructions 1058 stored thereon that are executable by a computer processor (e.g., the processor 1054) to cause the functional operations described herein with regard to the neuro-headset 480. The program instructions 1058 may include a neuro-headset module 1060 including program instructions that are executable by the processor 1054 to provide some or all of the functionality described herein with regard to the neuro-headset 480.

The processor 1054 may be any suitable processor capable of executing/performing program instructions. The processor 1054 may include a central processing unit (CPU) that carries out program instructions (e.g., of the neuro-headset module 1060) to perform arithmetical, logical, input/output and other operations of the neuro-headset 480, including those described herein.

The I/O interface 1056 may provide an interface for connection of one or more I/O devices to neuro-headset controller 1050. I/O devices may include neural sensors 218, power source(s) 1062 (e.g., a battery, AC/DC power delivered via a cable, and/or the like), external device(s) 1064 (e.g., the employee computer 130 and/or the server 104), and/or the like. The I/O devices may be connected to the I/O interface 1056, via a wired or wireless connection.

FIG. 10D is a flowchart that illustrates a method 1080 of operating the neuro-headset 480 in accordance with one or more embodiments of the present invention. Method 1080 may include monitoring the need for neural data 200i, as depicted at block 1082. In some embodiments, monitoring the need for neural data includes determining whether or not there is a need to collect neural data 200i (i.e., take a measurement) from one or more of the neural sensors 218. In some embodiments, the need for the neural data 200i may be identified based on a request from another component of system 100. For example, the neuro-headset controller 1050 may determine that there is a need to collect neural data 200i in response to a request for the neural data 200i (e.g., a request to initiate a health test and/or a query for the neural data 200i) received from the computer 130, the server 104 and/or the employee 401.

Where it is determined that neural data 200i is not needed, at block 1084, method 1080 may include returning to monitoring the need for neural data 200i, as depicted at block 1082. Where it is determined that neural data 200i is needed, at block 1084, method 1080 may include proceeding to monitoring of the neural sensors 218 of the neuro-headset 480 to collect the neural data 200i, as depicted at block 1086. For example, the neural data 200i collected may include a log of brain activity detected by each of the neural sensors 218.

Method 1080 may include storing the neural data 200i, as depicted at block 1088. In some embodiments, storing the neural data 200i includes storing the collected neural data 200i in local or remote memory. For example, the neuro-headset controller 1050 may store a log of the neural data 200i in memory 1052. In some embodiments, storing the neural data 200i may include buffering/queuing the neural data 200i for transmission at a later time.

Method 1080 may include transmitting the neural data 200i, as depicted at block 1090. In some embodiments, transmitting the neural data 200i includes transmitting the neural data 200i to another component/entity of the system 100. For example, the neuro-headset controller 1050 may transmit the neural data 200i (e.g., stored in the memory 1052), to the computer 130 and/or the server 104 for use in monitoring the health of the employee. In some embodiments, the neural data 200i may be transmitted via a wired or wireless communication. For example, where the neuro-headset 4780 is connected to the computer 130 and/or the server 104 via a data cable, the neuro-headset controller 1050 may transmit some or all of the neural data 200i to the computer 130 and/or the server 104 via the data cable. Where the neuro-headset 480 is in wireless communication with the computer 130 and/or the server 104 (e.g., via Bluetooth connection, WLAN connection, or the like), the neuro-headset controller 1050 may transmit some or all of the neural data 200i to the computer 130 and/or the server 104 via wireless communication.

In some embodiments, after transmitting the neural data 200i, method 1080 may progress back to monitoring the need for neural data. Where the request for neural data is still active and/or another request for neuro data is received, for example, the neuro-headset controller 1050 may execute another iteration of monitoring the neural sensors 218 to collect neural data 200i, storing the neural data 200i and/or transmitting the neural data 200i.

It will be appreciated that the method 1080 is an exemplary embodiment of a method that may be employed in accordance with techniques described herein. The method 1080 may be may be modified to facilitate variations of its implementations and uses. The method 1080 may be implemented in software, hardware, or a combination thereof. Some or all of the method 1080 may be implemented by one or more of the modules/applications described herein, such as the neuro-headset module 1060. The order of the method 1080 may be changed, and various elements may be added, reordered, combined, omitted, modified, etc.

In some embodiments, neural sensors 218 are disposed in a surface that contacts and/or supports the employee's head. For example, neural sensors 218 may be disposed in the headrest of a chair. In some embodiments, such neural sensors 218 disposed in a surface that contacts and/or supports the employee's head may be used in place of or in conjunction with the neural sensors 218 of neuro headset 480. For example, where an employee's chair includes neural sensors 218 implanted in a front surface of a headrest of the chair, the employee may not need to wear the neuro headset 480. Neural data 200i may be acquired via the neural sensors 218 implanted in the headrest that contact the back of the employee's head/scalp. In some embodiments, the employee may still wear neuro480 headset such that neural data 200i can be acquired via the neural sensors 218 of the neuro headset 480, as well as the neural sensors 218 implanted in the headrest.

Figure 10E:
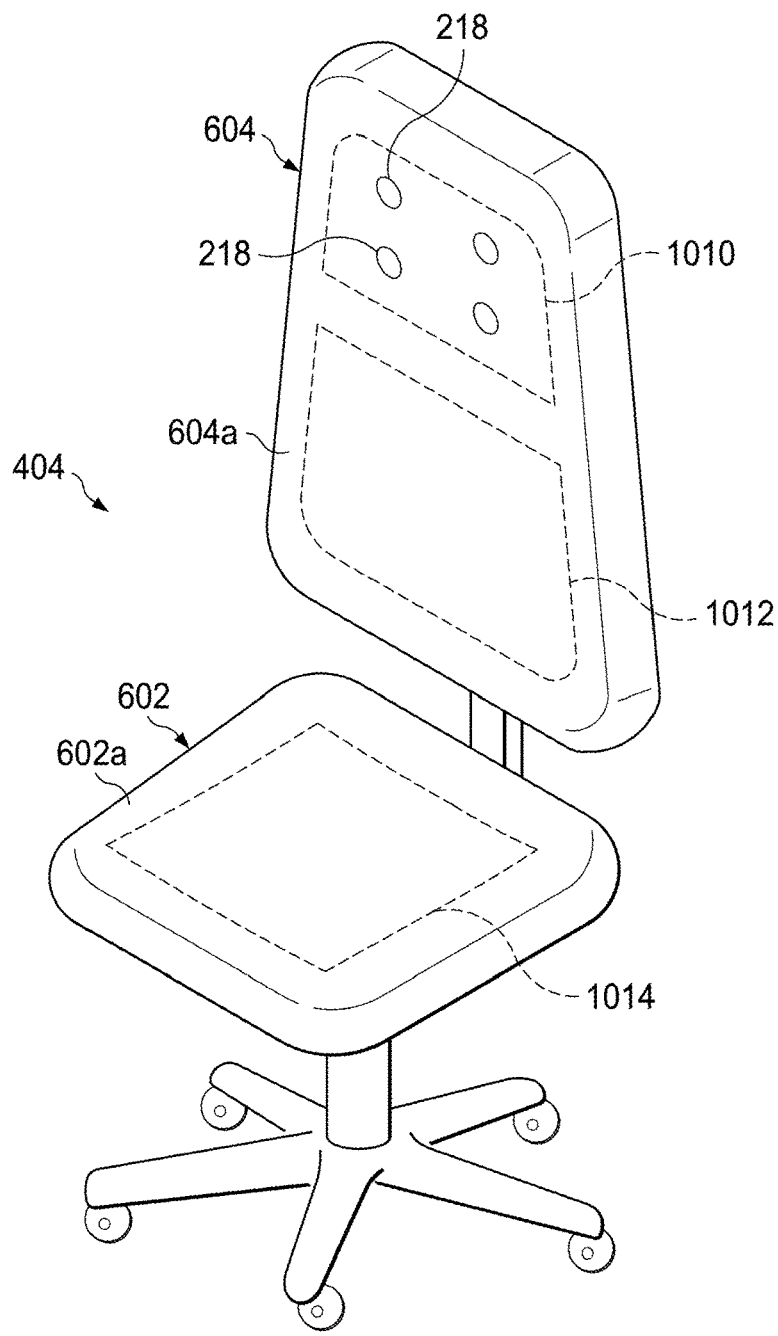
FIG. 10E is a perspective view of a chair specially adapted to include neural sensors for use in monitoring an employee's health in accordance with one or more embodiments of the present invention.

FIG. 10E is a perspective view of the chair 404 specially adapted to include neural sensors 218 for use in monitoring an employee's health in accordance with one or more embodiments of the present invention. As depicted, in some embodiments, the chair 404 includes a high-back chair having one or more neural sensors 218 disposed in a surface of headrest 1010 (e.g., an upper portion of seat back 604). Headrest 1010 may contact and/or support the back of the employee's head while the employee is seated in the chair 404. The neural sensors 218 of the headrest 1010 may include dry electrodes that can be used to sense neuro signals. Such dry electrodes may require minimal or no skin preparation for engaging the neural sensors 218 on the employee's scalp for sensing the employee's brain activity. Accordingly, neural data 200i for the employee may be acquired via the neural sensors 218 of the headrest 1010 when the employee's scalp contacts one or more of the neural sensors 218 of the headrest 1010. Such a configuration may not require the employee to wear a neuro headset to acquire neural data 200i.

In some embodiments, the chair 404 includes other sensors 120. For example, a back support area 1012 on the front surface 604a of seat back 604 may include temperature sensors 102, position sensors 208, and/or body fat sensors and/or a seat support area 1014 of the top surface 602a may include temperature sensors 102, position sensors 208, and/ or body fat sensors disposed therein (e.g., see FIG. 6C). Neural data 200*i* may be acquired from neural sensors 218 provided at headrest 1010 in a manner that is the same or similar to that described with regard to method 1080.

In some embodiments, neural sensors 218 provided at the headrest 1010 of the chair 404 can be provided via a chair pad (see FIGS. 6A and 6B). For example, the chair pad 450 may include neural sensors 218 disposed at or near a top of back-pad 612. Such a chair pad 450 can be provided on the chair 404 such that the back of the employee's head/scalp contacts that the neural sensors 218 of the chair pad 450 when the employee is seated in chair 404. In such an embodiment, neural data 200*i* may be acquired from neural sensors 218 provided at the headrest 1010 in a manner that is the same or similar to that of method 680.

Accordingly, the system 100 may provide for collecting employee health data via multiple points of contact with the employee. For example health data 200 may be collected via a first point of contact with the employee's head/eyes (e.g., via the 3D position sensor 212), a second point of contact with the employee's arms/hands (e.g., via the 3D position sensor 212, and/or the temperature sensor 202, the blood condition sensor 204 and/or blood pressure sensor 206 of the mouse 408), a third point of contact with the employee's torso/back/legs (e.g., via the 3D position sensor 212, and/or the temperature sensor 202, the position sensor 208 and/or the body fat sensor 210 of the chair pad 450), a fourth point of contact with the employee's feet (e.g., via the 3D position sensor 212, and/or the temperature sensor 202, the position sensor 208 and/or the body fat sensor 210 of the floor mat 460), and a fifth point of contact via the employee's head/brain (e.g., via the neural sensors 218 of the neuro-headset 480).

Figure 11:
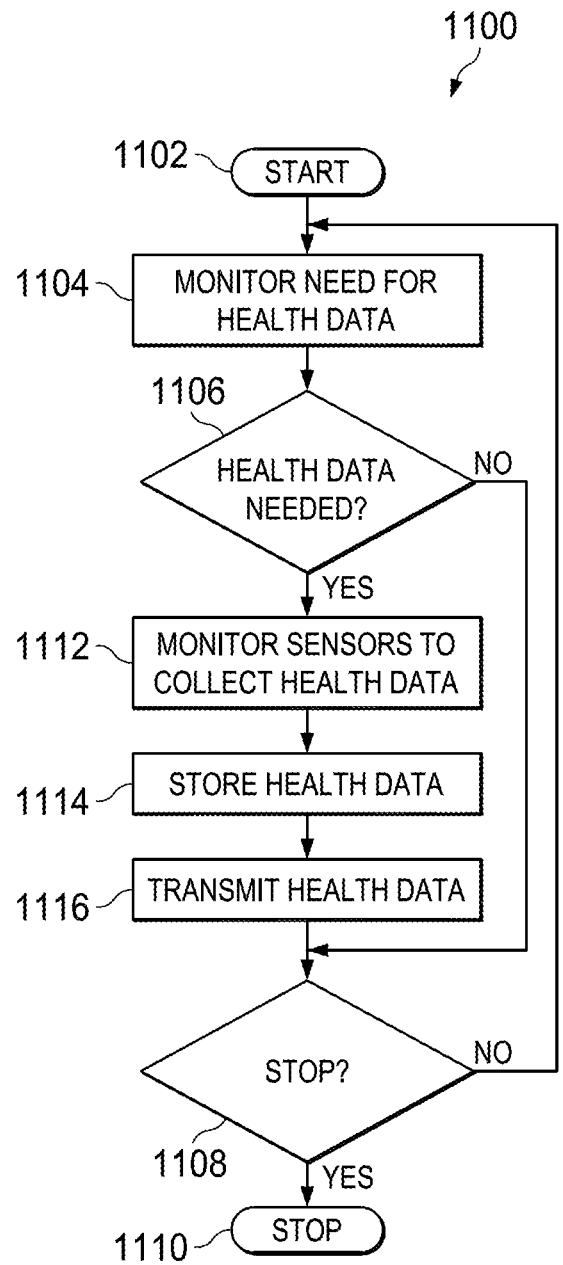
FIG. 11 is a flowchart that illustrates a method of acquiring health data in accordance with one or more embodiments of the present invention.

FIG. 11 is a flowchart that illustrates a method 1100 of collecting health data 200 in accordance with one or more embodiments of the present invention. Method 1100 may start at block 1102. In some embodiments, such a method of collecting health data 200 (e.g., temperature data 200*a*, blood condition data 200*b*, blood pressure data 200*c*, position data 200*d*, body fat data 200*e*, 3D position data 200*f*, audio data 200*g*, respiration data 200*h*, and/or neural data 200*i*) may be provided by the computer processor 302 executing program instructions of the employee computer module 308 to provide for collection of health data 200 from the various sensors 120 and/or transmission of the corresponding health data 200 to the server 104 for use in monitoring the health of the employee. Start of method 1100 at block 1102 may include initiating execution of a corresponding module (e.g., the computer module 308) to provide for collecting needed health data 200 by the computer 130. For example, the computer module 308 may be launched upon the employee successfully logging in to their workstation and/or the employee selecting to launch an employee health monitoring application as discussed in more detail below with regard to at least method 1500 of FIG. 15).

Method 1100 may include monitoring the need for health data 200, as depicted at block 1104. In some embodiments, monitoring the need for health data may include determining whether or not there is a need to collect health data 200 from one or more of the sensors 120 of the system 100. In some embodiments, the need for health data 200 is identified based on a request from another component of system 100. For example, the computer 130 may determine that there is a need to collect health data 200 in response to a request for the health data 200 (e.g., a request to initiate a health test and/or a query for the health data 200) received from the server 104 and/or the employee 401.

In some embodiments, the need for health data 200 is identified based on corresponding schedule (e.g., a health monitoring test schedule). For example, where a health test routine requires collection of health data 200 at 12:00 pm, it may be determined that health data 200 is needed if the current time is 12:00 pm or shortly thereafter. As another example, where a health test routine requires the continuous collection of a batch of health data 200 from 8:00 am-6:00 pm, it may be determined that health data 200 is needed if the current time is in the range of 8:00 am-6:00 pm. As yet another example, where a health test routine requires the repeated collection of health data 200 at an hourly interval from 8:00 am-6:00 pm, it may be determined that health data 200 is needed if the current time is 8:00 am, 9:00 am, and so forth. It will be appreciated that these test schedules are exemplary, and other embodiments may include any suitable test schedule.

Where it is determined that health data 200 is not needed, at block 1106, method 1100 may include proceeding to determining whether or not the test routine should be stopped, as depicted at block 1108. In some embodiments, it may be determined that the test routine should stop based on an instruction to stop from another device of system 100. For example, the computer 130 may determine that it should stop execution of the health monitoring test routine in response to an instruction from the server 104 and/or the employee 401 to stop the health test routine (e.g., a request to terminate the health test). Where it is determined that the health test routine should be stopped, the health test routine may be stopped, as depicted at block 1110.

Where it is determined that health data 200 is needed, at block 1106, method 1100 may include proceeding to monitoring of the sensors 120 to collect the health data 200, as depicted at block 1112. In some embodiments, monitoring the sensors 120 to collect the health data 200 includes monitoring the particular sensors 120 that provide the particular health data 200 needed. Where the heath data 200 needed includes the employee's body temperature, for example, monitoring the sensors 120 to collect the health data 200 may include monitoring one or more of the standalone temperature sensor 202 located on desk 402, the temperature sensor 202 of the chair pad 450, the temperature sensor 202 of the floor mat 460, the temperature sensor 202 of the mouse 408 and/or the like to sense/acquire temperature data 200*a*. Other embodiments may include similar monitoring of any of the standalone or integrated sensors 120 to collect the needed health data 200.

In some embodiments, the collected health data 200 may be transmitted between the various devices in route to the server 104. Where the heath data 200 needed includes the employee's body temperature, for example, the computer 130 may collect temperature data 200*a* directly from the standalone temperature sensor 202. As a further example, the chair pad 450, the floor mat 460, the mouse 408 may collect temperature data 200*a* directly from the respective temperature sensors 202 integrated therein and forward the collected temperature data 200*a* to the computer 130. Similar techniques may be employed for collecting other forms of health data 200 from the various sensors 120 of the system 100. For example, temperature data 200*a*, blood condition data 200*b*, blood pressure data 200*c*, position data 200*d*, body fat data 200*e*, 3D position data 200*f*, audio data 200*g*, respiration data 200*h*, neural data 200*i* and/or the like, may be collected from the corresponding temperature sensors 202, blood condition sensors 204, blood pressure sensors 206, position sensors 208, body fat sensors 210, 3D position sensors 212, audio sensors 214, respiration sensors 216, neural sensors 218, and/or the like, in a similar manner.

Method 1100 may include storing the health data 200, as depicted at block 1114. In some embodiments, storing the health data 200 includes storing the collected health data 200 in local or remote memory. For example, the employee computer 130 may store the health data 200 collected from the sensors 120 in local memory 300. In some embodiments, storing the heath data 200 includes buffering/queuing the health data 200 for transmission at a later time.

Method 1100 may include transmitting the health data 200, as depicted at block 1116. In some embodiments, transmitting the health data 200 may include transmitting the health data 200 to another component/entity of the system 100. For example, the computer 130 may transmit the health data 200 (e.g., the health data 200 stored in memory 300) to the server 104 for use in monitoring the health of the employee 401. In some embodiments, the health data 200 may be transmitted from the computer 130 to the server 104 via network 118.

In some embodiments, the transmission of the health data 200 may be regulated based on a corresponding schedule for sending/transmitting the health data. For example, where a health test routine requires collection of health data 200 at 12:00 pm, the health data 200 may be collected and transmitted at or about 12:00 pm. As further example, where a health test routine requires the continuous collection and transmission of health data 200 from 8:00 am-6:00 pm, the health data 200 may be collected and transmitted from 8:00 am-6:00 pm such that a substantially continuous stream of health care data 200 is transmitted (e.g., from the sensors 120 to the computer 130 and/or from the computer 130 to the server 104) for use in monitoring the employee's health. As a further example, where a health test routine requires the continuous collection of health data 200 from 8:00 am-6:00 pm and the transmission of the health data 200 in batches hourly, the health data 200 may be collected and stored over the period with the batches being transmitted at 9:00 am, 10:00 am and so forth).

In some embodiments, after transmitting the health data collected, method 1100 may progress to block 1108 to determine whether or not the acquisition of health data should continue. Accordingly, health data 200 may be collected from the various sensors 120 as required for monitoring the health of employees.

It will be appreciated that the method 1100 is an exemplary embodiment of methods that may be employed in accordance with techniques described herein. The method 1100 may be may be modified to facilitate variations of its implementations and uses. The method 1100 may be implemented in software, hardware, or a combination thereof. Some or all of the method 1100 may be implemented by one or more of the modules/applications described herein, such as employee computer module 308. The order of the method 1100 may be changed, and various elements may be added, reordered, combined, omitted, modified, etc.

Server:

The server 104 (see FIG. 1) may include a network entity that serves requests by other network entities. For example, the sever 104 may serve request by client entities, such as the employee computer 130, the employer computer 103 and/or the like. The server 104 may host a content site, such as a website, a file transfer protocol (FTP) site, an Internet search website or other source of network content. In some embodiments, the server 104 may host one or more applications, such an employee health monitoring application. Some or all of the application may be executed locally on the server 104 and/or remotely by various other network entities, such as the employee computer 130 and/or the employer computer 103. For example, the server 104 may cause the execution of remote applications/processes (e.g., an application executing the method 1100) on the employee computers 130 to collect the health data 200 from each respective employees and execute a local applications (e.g., a health monitoring application) to conduct processing of the collected health data 200 for use in monitoring an employee's health.

In some embodiments, the server 104, is connected to one or more of the employee computer workstations 130 (e.g., for interfacing with the employees in their work environment), one or more file servers 106 and associated databases 108 for accessing and storing employee health information 109, one or more employer computers 103 (e.g., for allowing the employer to review the health information of employees), one or more web servers 110 for connecting the computer server 104 to remote computers 112 (e.g., to provide communication with emergency response entities (e.g., a police, fire, ambulance station), health care entities (e.g., a doctor's office), an offsite workstation 102, or the like that may allow emergency response personnel, health care providers and/or employees to be alerted by the health monitoring system, to remotely access the health monitoring system (e.g., access health information 109 stored in database 108), and/or the like.

As shown, at least one file server 106 may be employed by the system to manage the employee health information 109 and/or to allow the computer server 104, the employee computer 130, the employer computer 103 and/or the remote workstation 112 to upload/download data (e.g., the employee health information 109) via the file server 106. The files server 106 may include or otherwise have access to the database 108. The database 108 may include an employee health database for storing the employee health information 109 and/or an employee access database that stores credential data and permissions data for verifying user's right to access the system 100 based on the credentials and/or restricting access to the system 100 based on corresponding permissions. The file server 106 and/or the database 109 may include network attached storage ("NAS"), storage area networks ("SAN"), or direct access storage ("DAS"), or any combination thereof, including, e.g., multiple hard disk drives. The file server 106 may have stored thereon a database management system, e.g. a set of software programs that controls the organization, storage, management, and retrieval of the data in the database(s) 108, such as the health information 109.

The database 108, and any other databases or files stored in the file server 106, may be a database separate from other employee databases or the same database as other employee databases, e.g., commingled in a database containing, for example, employee benefit or pay information. The employee health information 109 can also be stored in a plurality of databases (e.g., distributed databases, tables, or fields in separate portions of the file server memory). As one skilled in the art will appreciate, the file server 106 may provide the computer server 104, and the computer workstations 130 access to the database 108 through, e.g., database management software or other application. A database server may be used to store the database 108 instead of or in addition to the file server 106. An exemplary structure of the database 108 is discussed in more detail below with regard to FIG. 14 below.

The computers 130, 103 and/or 112 may include personal computers (PC) as is known in the art. The computers 130, 103 and/or 112 may run UNIX, Linux, Windows®, or some other operating system compatible with the networked systems discussed herein. In some embodiments, the computers 130, 103 and/or 112 may include remote terminals that enable a user to interact with various processes being controlled by the server 104. For example, the operations described herein with regard to the employee computer 130 may be executed by the server 104 and the employee computer 130 may include a network terminal that provides for user interaction with the operations provided by the server 104. Moreover, the computers 130, 103 and/or 112 may provide access computer program instructions stored on the server 104. For example, an application for providing employee data running on the server 104 may be accessible via the employee computer 130 such that the employee may provide access credentials to login to their account, the server may verify their credentials/permissions, and the employee may be able to enter, via the employee computer 130, their health profile information (e.g., their personal health profile data (e.g., age, sex, ethnicity, etc.), health goals (e.g., "lose 10 pounds" or "lower blood pressure") and/or the like). Thus, health information provided via the computer workstations 130 can be forwarded via the server 104 to the file server 106 for use in updating the employee's health information 109 stored in the database 108. In some embodiments, the computer workstations 130 can interface with different servers (e.g., the web or network servers 104, 106 or 110) for accessing the health information 109 via the communications network 118.

The employer computer 103 may provide an employer (e.g., the employee's manager, the employee's human resources manager, or the like) access to the employee health information 109 and/or corresponding reports for reviewing the health of one or more employees. For example, an employer may be provided regular reports and/or alerts regarding the health of some or all of their employees via the employer computers 103 and/or the employer may proactively initiate review of the employee health information 109 (e.g., via an interactive dashboard discussed in more detail below). Thus, for example, an employer may determine whether a health condition is affecting a given employee, determine whether or not an employee is following their health plan, determine whether some or all employees at a certain facility have are experiencing similar symptoms indicative of a facility wide health concern (e.g., a high percentage of employees at a given facility have developed asthma, chronic obstructive pulmonary disease ("COPD"), or other chronic condition).

Figures 12A, 12B:
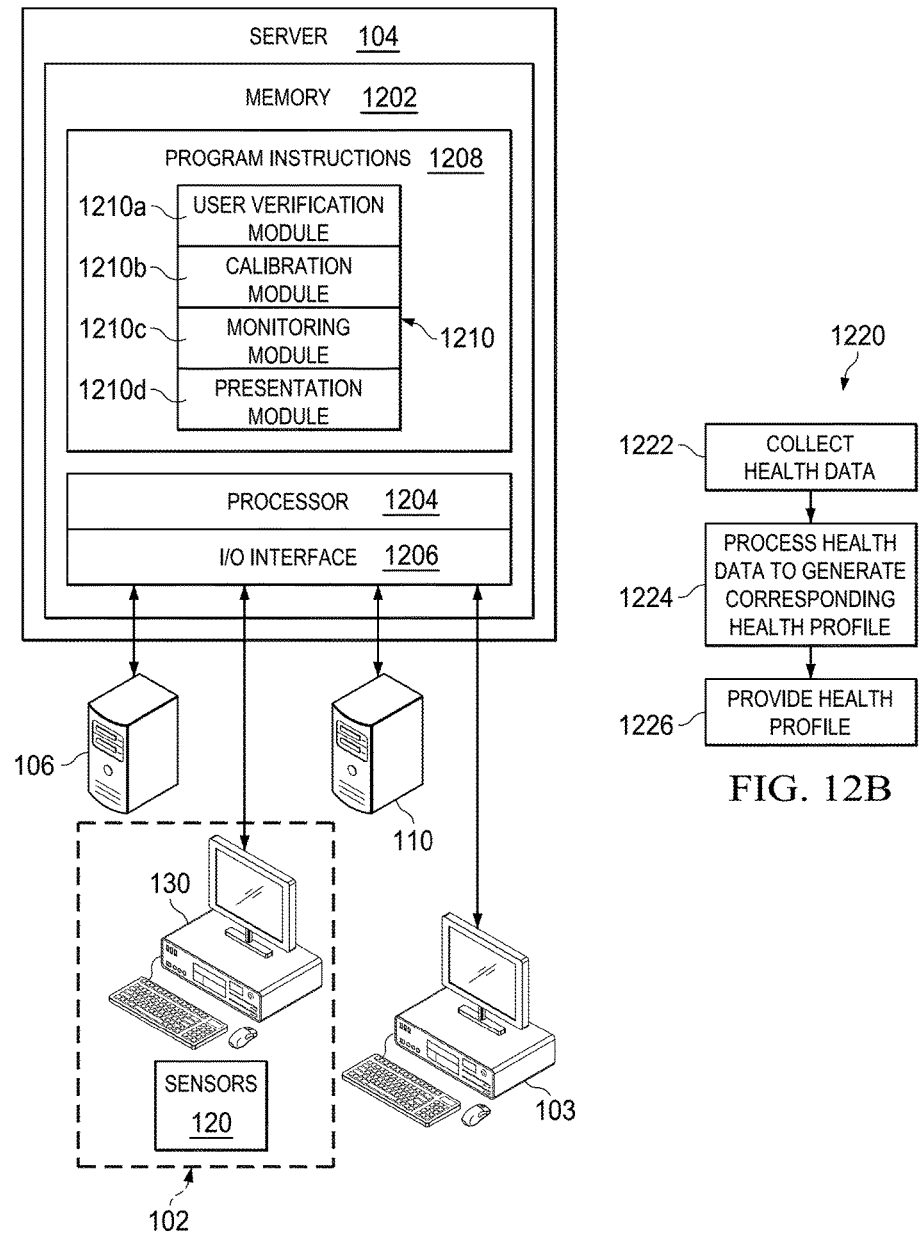
FIG. 12A is a block diagram illustrating components of a server in accordance with one or more embodiments of the present invention.
FIG. 12B is a flowchart that illustrates a method of monitoring the employee's health in accordance with one or more embodiments of the present invention.

FIG. 12A is a block diagram illustrating components of the server 104 in accordance with one or more embodiments of the present invention. In some embodiments, the server 1100 includes a memory 1202, a processor 1204 and an input/output (I/O) interface 1206.

The memory 1202 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. The memory 1202 may include a non-transitory computer readable storage medium having program instructions 1208 stored thereon that are executable by a computer processor (e.g., the processor 1204) to cause the functional operations described herein with regard to the server 104. The program instructions 1208 may include server modules 1210 (e.g., user verification module 1210a, calibration module 1210b, monitoring module 1210c, and/or display module 1210d) including program instructions that are executable by the processor 1204 to provide some or all of the functionality described herein with regard to the server 104.

The user verification module 1210a may be employed by the server 104 to verify a user's login information and/or provide corresponding access to other portions of the system 100, as discussed in more detail herein. For example, upon an employee, employer or other user attempting to login to the system 100, the user verification module 1210a may be executed to verify login credentials (e.g., a user ID and password) provided by an employee, employer or other user, and, upon verification of the credentials, grant access to the health information 109 of the database 108 in accordance with permissions associated with the credentials.

The calibration module may be executed by the server 104 to provide for calibrating the sensors 120 of the system 100, as discussed in more detail herein. For example, at start-up of monitoring of the employee's health or based on a request by the employee, the calibration module 1210b may be executed to provide for collecting a baseline set of data (e.g., initial measurement of temperature, weight, body fat heart rate, blood pressure, blood condition, body position, eye movement, and/or the like). Such data may be used to verify operation of the sensors 120 and/or to provide a baseline for comparing the health data collected during subsequent testing.

The monitoring module 1210c may be executed by the server 104 to provide for monitoring of the employee's health, as discussed in more detail herein. For example, the monitoring module 1210c may provide for collecting health data 200 from the various sensors 120 located about an employee's workstation (e.g., via conducting one or more health test) and processing the health data 200 to generate a health report including, for example determined health characteristics, health conditions, health risks and/or health plans for the employee. In some embodiments, the monitoring module 1210c may provide for conducting discrete health test at certain/limited times (e.g., "low productivity" times in which the employee is not as productive, such as the early morning, mid-afternoon, or the like). As one skilled in the art will appreciate, monitoring an employee at limited times may minimize any risk of over exposure of IR test measurements when photoplethysomography is used to monitor a health condition, e.g., to meet or exceed current government and safety protocols in relation to the frequency, intensity and duration of such test on the employee. In some embodiments, the monitoring module may provide for interpreting the incoming health data 200. For example, where the collected health data 200 includes raw electronic signals from the sensors 120, raw measurement values (e.g., datasets) or the like, the monitoring module 1210c may provide for converting the electronic signals and/or values to health characteristic data indicative of the actual health characteristics.

As discussed in more detail herein, the presentation module 1210d may be executed by the server 104 to provide for presenting employee health information (e.g., the employee's profile, heath report, health plan, and/or the like) to the employee, the employer, and/or another user. For example, the presentation module 1210d may provide for displaying (e.g., via a heath monitoring widget and/or an interactive health dashboard) or otherwise communicating the employee's health information and/or corresponding health alerts to the employee, an employer, emergency response personnel, the employee's physician, and/or the like. In some embodiments, the presentation module 1210d may provide for displaying a preventative plan for health maintenance, the employee's health statistics over time, the employee's progress relative to a predetermined health regime, display the employee's progress relative to a preventative plan calculated by the system and/or the like.

The processor 1204 may be any suitable processor capable of executing/performing program instructions. The processor 1204 may include a central processing unit (CPU) that carries out program instructions (e.g., of the server module(s) 1210) to perform arithmetical, logical, input/output and other operations of the server 104. The processor 1204 can be any commercially available processor, or plurality of processors, adapted for use in the computer server 104, such as Intel® Xeon® multicore processors manufactured by Intel Corporation, Intel® micro-architecture Nehalem manufactured by Intel Corporation, AMD Opteron™ multicore processors manufactured by AMD Corporation, or the like. As one skilled in the art will appreciate, the processor 1204 may also include components that allow the server 104 to be connected to peripherals (e.g., a display and keyboard that would allow direct access to the processor and memory 1202, and/or application executing via server 104).

The I/O interface 1206 may provide an interface for connection of one or more I/O devices to the server 104. The I/O devices may include other network devices, such as the file server 106, the web server 110, the employee computers 130, the employer computers 103, the sensors 120, and/or the like. The I/O devices may be connected to the I/O interface 1206 via a wired or wireless connection.

In some embodiments, the server 104 uses the health data 200 collected by the sensors 120 to monitor the employee's health. FIG. 12B is a flowchart that illustrates a method 1220 of monitoring the employee's health in accordance with one or more embodiments of the present invention.

Figure 13A:
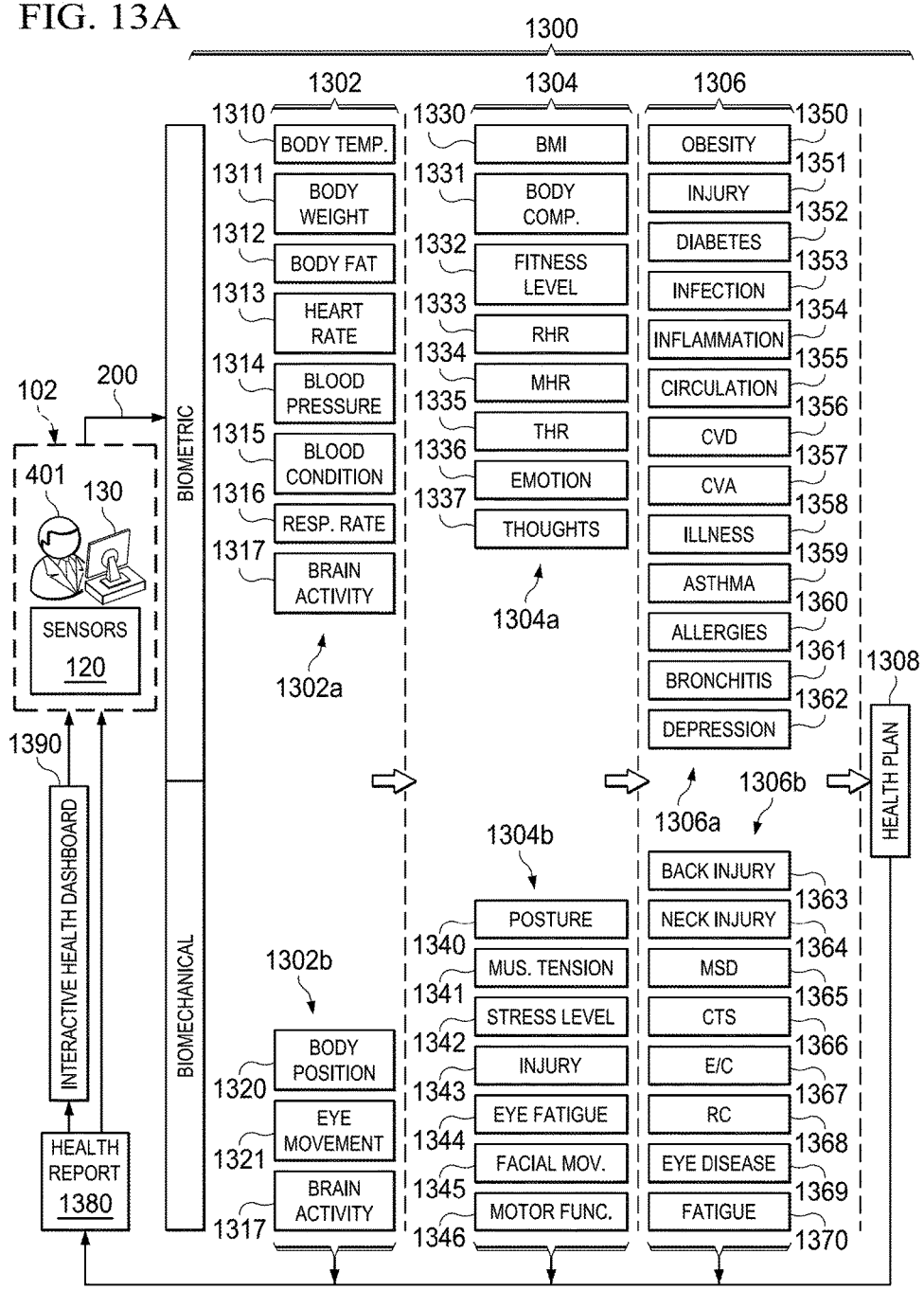
FIG. 13A is a block diagram illustrating dataflow within the health monitoring system in accordance with one or more embodiments of the present invention.

Method 1220 may include collecting health data, as depicted at block 1222. In some embodiments, collecting health data includes collecting health data 200 from other entities of the system 100. For example, as depicted in FIG. 13 (including a block diagram illustrating an exemplary dataflow within system 100 in accordance with one or more embodiments of the present invention), the server 104 may collect health data 200 (e.g., including temperature data 200*a*, blood condition data 200*b*, blood pressure data 200*c*, position data 200*d*, body fat data 200*e*, 3D position data 200*f*, audio data 200*g*, respiration data 200*h*, neural data 200*i*, and/or the like) via the various sensors 120 and/or the computer 130 of the employee's workstation 102. Accordingly, the server 104 may collect health data 200 via multiple points of contact with the employee (e.g., a first point of contact with the employee's head/eyes, a second point of contact with the employee's arms/hands, a third point of contact with the employee's torso/back/legs, a fourth point of contact with the employee's feet, and a fifth point of contact with the employee's head/brain).

In some embodiments, collecting health data includes executing a single measurement by some or all of the sensors 120. For example, some or all of the sensors 120 may be employed to record a single measurement in sequence (e.g., one after the other) or in parallel (e.g., at the same time) and transmit corresponding health data 200 to the computer 130. The computer 130 may collect the single measurement from each of the sensors 120 and transmit corresponding health data 200 to the server 104 for use in monitoring the employee's health.

In some embodiments, collecting health data includes executing multiple measurements by some or all of the sensors 120. For example, some or all of the sensors 120 may be employed to record a set of measurements (e.g., one per minute) over a given period of time (e.g., 5 minutes, 1 hour, 8 hours, or the like) and transmit corresponding health data 200 to the computer 130. The computer 130 may collect the measurements from each of the sensors 120 and transmit corresponding health data 200, as it is received, to the server 104 for use in monitoring the employee's health.

In some embodiments, the health data 200 is collected via health test that are initiated by the server 104. For example, the server 104 may execute a health monitoring routine that requires health data 200 to be sensed/collected according to a given test schedule/routine (e.g., sensed/collected from 8 am-6 pm, sensed/collected hourly from 8am to 6 pm, and/or the like), the server 104 may determine that health data is required based on the schedule, and, in response to determining that health data is required, the server 104 may transmit, to the computer 130 and/or the sensors 120 corresponding requests to sense, collect and forward, to the sever 104, the health data 200 according to the schedule. For example, where a test schedule/routine requires collection of health data from 8am to 6 pm, the server 104 may send, to the computer 130 at 8 am, a first request to initiate collection and forwarding of health data 200 to the server 104, and send, to the computer 130 at 6 pm, a second request to terminate collection and forwarding of the health data 200 to server 104. In such an embodiment, the computer 130 may continually acquire (and forward to server 104), health data 200 from 8am to 6 pm. The server 104 may transmit similar requests in accordance with any suitable test routine/schedule. For example, where a test schedule/routine requires collection of health data hourly from 8am to 6 pm, the server 104 may send, to computer 130 at each of 8 am, 9 am, 10 am, and so forth, a request to collect and forward health data 200 to the server 104. In such an embodiment, the computer 130 may collect (and forward to server 104) a set of health data 200 each hour from 8am to 6 pm (e.g. at 8 am, 9 am, 10 am, and so forth). In some embodiments, the health data 200 for one or more employees may be logged over time. The logged data may be used to generate health profiles and/or reports that are based on current and/or historical health data 200.

In some embodiments, the server 104 may initiate a health test based on an external request/event, such as a request initiated by a user. For example, where an employee or an employer is interacting with an interactive health dashboard for a given employee (as discussed in more detail below) and the user requests to run a health test, the server 104 may determine that health data is required based on the request, and, in response to determining that health data is required, the server 104 may transmit a corresponding request to collect and forward health data 200 to the computer 130. In such an embodiment, the computer 130 may collect a set of health data 200 at or near the time of the user's request to conduct a health test and forward the set of health data 200 to the server 104. Thus, the server 104 may initiate health test automatically (e.g., based on a test schedule/routine) and/or in response to external request (e.g., from an employee, an employer, or other user).

Method 1220 may include processing the collected health data to generate a corresponding health profile, as depicted at block 1224. In some embodiments, a health profile 1300 is generated based on processing of the collected health data 200. The health profile 1300 may include health characteristics 1302, health conditions 1304, health risks 1306, and/or health plans 1308 for the employee.

In some embodiments, the health characteristics 1302 may include a first level of health profile data that is derived from the collected health data 200. For example, the server 104 may process the collected health data 200 to identify various biometric health characteristics 1302a and/or biomechanical health characteristics 1302b for the employee. Biometric health characteristics 1302a may include, for example, the employee's sensed body temperature 1310, body weight 1311, body fat 1312, heart rate 1313, blood pressure 1314, blood condition (e.g., blood oxygenation, blood glucose level, etc.) 1315, respiration rate 1316, neural/brain activity 1317, and/or the like. Biomechanical health characteristics 1302b may include, for example, the employee's sensed body position 1320 (e.g., the employee's physical positioning and/or movement of the employee's head, torso, arms, hands, legs, feet, and/or the like), eye movement (e.g., focal point, blink rate, pupil dilation of the eye, and/or the like) 1321, neural/brain activity 1317, and/or the like.

In some embodiments, some or all of the health characteristics 1302 are provided directly via the health data 200. For example, the health data 200 may include a value for heart rate (e.g., 80 beats per minute ("BPM"). In some embodiments, some or all of the health characteristics 1302 are extrapolated from the health data 200. For example, the health data 200 may include a set of measurements indicative of the number of employee's heart beats over a period of time (e.g., 20 heart beats over fifteen seconds) and the server 104 may process the set of data to determine the corresponding hear rate value (e.g., 80 BPM). The health data 200 may be received and/or processed in a similar manner to determine values for the other health characteristics 1302 based on received values and/or data sets.

In some embodiments, the body weight 1311 is based on forces measured by one or more sensors. For example, where only the force transducers 622 of the floor mat 460 sense a force, it may be determined that the employee is standing, and the force sensed by the force transducers 622 of the floor mat 460 may be used to determine the employee's weight. As a further example, where the force transducers 622 of the chair pad 450 and/or the force transducers 622 of the floor pad 460 sense a force, it may be determined that the employee is seated in the chair 404, and the force sensed by the force transducers 622 of the seat pad 610 of the chair pad 450 and the floor may 460 may be added together to determine the employee's weight.

In some embodiments, the body fat 1312 is based on body fat data 200e collected via one or more of the body fat sensors 210. For example, the body fat 1012 may be determined using bioelectrical impedance analysis (BIA) of the impedance/resistance sensed by the body fat sensor 210. Ideally, male employees will have a body fat measurement of about 8-17% and female employees will have a measurement between about 10-21%. The body fat 1012 may include a body fat percentage which is determined as the total weight of the person's fat divided by the person's weight.

In some embodiments, the heart rate 1013 is based on blood pressure data 200c collected via one or more of the blood pressure sensors 206. For example, the heart rate 1013 may be determined using the rate of pulsations of blood pressure which may correspond to the heart rate. In some embodiments, the heart rate 1313 is determined as the number of heart beats over a given period of time, typically sixty seconds. The heart rate may be determined from the blood pressure data 200c which is indicative of the rate of pulsations of blood flow that correspond to the heart rate.

In some embodiments, the blood pressure 1314 is based on blood pressure data 200c collected via one or more of the blood pressure sensors 206. The blood pressure 1014 may be determined from the blood pressure data 200c which is indicative of pressure pulsations due to blood flow. For example, the blood pressure 1014 may be determined based on a maximum blood pressure detected (e.g., the "systolic" blood pressure) and the minimum blood pressure detected (e.g., the "diastolic" blood pressure). The blood pressure 1314 may be recorded as the systolic blood pressure over the diastolic blood pressure (e.g., 90/60 mmHg).

In some embodiments, the blood condition 1315 is based on blood condition data 200b collected via one or more of the blood condition sensors 204. For example, the blood oxygenation, blood glucose level, and/or the like may be determined from blood condition data 200b provided by a pulse oximeter or similar blood conditions sensor.

In some embodiments, the respiratory rate 1316 is based on respiration data 200h collected via one or more of the respiration sensors 216. For example, the respiration rate may be determined based on a number of breaths sensed by the respiration sensor 216 over a given period of time. For example, where the respiration data 200h indicates that the employee has taken four breaths in fifteen seconds, the employees respiration rate 1316 may be determined as sixteen breaths per minute (Vf).

In some embodiments, the brain activity 1317 is based on neural data 200i collected via one or more of the neural sensors 218. In some embodiments, the brain activity 1317 includes a log of neuro-signals (e.g., including alpha, beta, gamma, and delta waves) that are indicative of the employee's brain state, including the employee's emotional state, thoughts (e.g., cognitive thoughts, subconscious thoughts, and intent), facial movements (e.g., facial expressions), motor functions and/or the like. The brain activity 1317 may include or otherwise be extrapolated from the neural data 200i. The brain activity 1317 may be both of a biometric and biomechanical characteristic based at least on its use in determining various biometric and biomechanical health profile data (e.g., various biometric and biomechanical conditions and identified/predicted health risks).

In some embodiments, the body position 1320 is based on body position data 200f collected via one or more of the body position sensors 212. In some embodiments, the body position 1320 is indicative of the position of the employee's head, torso, arms, hands, legs, feet or the like. The employee's body position 1320 may be provided by 3D position sensor 212. In some embodiments, the employee's body position may be determined based on the forces sensed by various ones of the positions sensors 208. For example, it may be determined that the employee is leaning back in their chair where a high force is sensed by a force transducer 622 located in the back-pad 612 of the chair pad 450 relative to a force sensed by a force transducer 622 located in the seat pad 610 of the chair pad 450.

In some embodiments, one or more of the health characteristics 1302 may be used to determine one or more of the health conditions 1304. The health conditions 1304 may include a second level of health profile data that is derived from the one or more of the health characteristics 1302 and/or the collected health data 200. For example, the server 104 may process the health characteristics 1302 and/or the collected health data 200 to extrapolate various biometric health conditions 1304a and/or biomechanical health conditions 1304b for the employee. Biometric health conditions 1304a may include, for example, a body mass index ("BMI") 1330, a body composition 1331, a fitness level 1332, a resting heart rate ("RHR") 1333, a maximum heart rate ("MHR") 1334, a target heart rate ("THR") 1335, and/or the like for the employee. Biomechanical health conditions 1304b may include, for example, posture ("posture analysis") 1340, muscle tension 1341, a stress level 1342, an injury 1343, an eye fatigue level 1344, facial movements 1345, motor functions (e.g., gestures) 1346, and/or the like for the employee.

In some embodiments a health condition 1304 may be determined based on one or more health characteristics 1302 and/or other data (e.g., the employee's personal profile). For example, BMI 1330 and/or body composition 1331 may be extrapolated from body weight 1311 and body fat 1312. Fitness level 1332 may be based on weight 1311, heart rate 1313, and/or blood pressure 1314. Resting heart rate 1333, maximum heart rate 1334, and/or target heart rate 1335 may be based on the heart rate 1313 and/or the employee's age. Emotions 1336 and/or thoughts 1337 may be based on the employee's brain activity 1317. Posture 1340 and muscle tension 1341 may be based on the observed body position 1320 of the employee (e.g., physical positioning and movement of the head, torso, arms, hands, legs, feet, and/or the like). Stress level 1341 and injury 1343 may be based on the observed body position 1320 and/or eye movement 1321 of the employee. Eye fatigue 1344 may be based on the observed eye movement 1321 of the employee. Facial movements 1345 and/or motor functions 1346 may be determined based on the brain activity 1317.

The BMI 1330 may be the individual's body mass (m) divided by the square of their height (h). In some embodiments, BMI 1330 is determined using the following equation:

$$\text{BMI} = m*703/h^2 \quad (1)$$

Where "m" is the employee's mass (in kg. or lbs.) and "h" is the employee's height (in meters or inches). Using this relationship, the server 104 can determine whether the employee is of average weight (e.g., having a BMI in the range of about 18.5-25), overweight (e.g., having a BMI in the range of about 25-30), or obese (e.g., having a BMI over about 30).

The body composition 1331 may indicate a percentage of bone, fat and/or muscle in the employee's body. In some embodiments, the body composition is determined based at least on the body fat percentage and the body weight 1311.

In some embodiments, the fitness level 1332 is indicative of the employee's body's ability to withstand a physical workload and/or recover in a timely manner. The fitness level 1332 may be based on the employee's heart rate. For example, an employee may be determined to have a good fitness level if their heart rate 1313 includes a resting heart rate (e.g., RHR 1334) under about 100 BPM.

In some embodiments, the respiratory rate 1316 is indicative of the number of breaths taken within a set amount of time (e.g., 60 seconds). In some embodiments, the resting heart rate (RHR) 1333 is the measured heart rate (HR) 1313 taken at a period of low activity by the employee (e.g., while seated in the chair 404 and not engaging in any work activities). The maximum heart rate (MHR) 1334 may be determined using the following equation:

$$\text{MHR} = 205.8 - (0.685 \times \text{age}) \quad (2)$$

Where "age" is the age of the employee in years. The target heart rate (THR) 1335 may be calculated using the following formula (e.g., the "Karvonen method"):

$$\text{THR} = ((\text{MHR} - \text{RHR}) \times \% \text{ intensity}) + \text{RHR}. \quad (3)$$

Where intensity is a percentage, typically about 65%-85%. The target heart rate 1335, resting heart rate 1333 and maximum heart rate 1334 may be provided to the employee to aid the employee in safe exercise regimens, the formulation of a health plan, and the determination of whether the employee has met its health plan goals for the day, e.g., whether the employee has reached their target heart rate 1335 by the distance and length of time the employee has indicated to the program it has exercised. Also, if the employee's resting heart rate 1333 is above 100 beats per minute, for example, the system may provide the employee with an alert/warning regarding a risk of cardiovascular disease, stroke, or obesity via a health dashboard 1390 and/or a health report.

In some embodiments, the employee's emotions 1336, thoughts 1337, facial movements 1345 and/or motor functions 1346 are based on the sensed neuro signals (e.g., brain activity 1317). For example, a plurality of predetermined brain wave patterns may be associated with corresponding emotions, thoughts, facial movements and/or motor functions. During processing of the brain activity 1317, the sensed/observed neuro signals may be compared to the plurality of predetermined neural signal patterns to identify a match there between. Upon matching the observed neuro signals to one or more of the predetermined neural signal patterns, it may be determined that the employee is engaged in corresponding emotions (e.g., happy, sad, excited, depressed, etc.) 1336, thoughts (e.g., intent to take an action, etc.) 1337, facial movements (e.g., facial gestures such as smiling) 1345 and/or motor functions (e.g., a sequence of movements) 1346. In some embodiments, as described herein, an animated avatar may be used to mimic the employee's current emotional state and/or facial gesture. For example, when it is determined that the employee is happy and/or smiling, the avatar can be animated to include a smile, providing the employee or other persons reviewing the employee's health (e.g., the employer) with an indication of the employee's current emotional state and/or facial expression. In some embodiments, the ability to determine the employee's thoughts may be employed to assist the employee with completing their work duties. For example, where the system 100 is able to determine that the employee intends to open a word processing application, the system 100 may launch the word processing application based on the determined intent to act, without any physical interaction by the employee.

In some embodiments, a determination of the employee's posture 1340 may be based on body position 1320. For example, the employee may be determined to have good posture that where one or more of the employee's hands, wrists, and forearms are straight, in-line and roughly parallel to the floor; the employee's head is level, or bent slightly forward, forward facing, and balanced, and generally in-line with the torso; the employee's shoulders are relaxed and its upper arms hang normally at the side of the body; the employee's elbows stay in close to the body and are bent at angles between about 90 and 120 degrees; the employee's feet are fully supported by the floor or a footrest (if the employee's desk height is not adjustable); the employee's back is fully supported when sitting vertical or leaning back slightly; the employee's thighs and hips are generally parallel to the floor; and/or the employee's knees are about the same height as the hips with the feet slightly forward. The posture 1340 may include a determined proper alignment of the head, torso, arms, and feet when the employee is sitting in the chair and the employee's deviation from the proper alignment based on the observed body position 1320. In some embodiments, the actual body position of the employee, relative to the ideal body position may be determined and the posture 1340 may indicate, a percentage deviation of the actual body position to the ideal body position and/or may include suggestions for improving the employee's posture (e.g., sit up in chair with lower back firmly contacting chair lumbar support).

In some embodiments, the level of muscle tension 1341 may be determined based on the employee's body position 1320, including, for example the employee's arm position and shoulder height (e.g., whether the employee's shoulders are raised and the arm is bent in a sub-optimum way), the employee's respiratory rate 1316, and the length of time the employee's arm has been extended to operate the mouse 408. For example, it may be determined that the employee is experiencing a high level of muscle tension where the employee's arm is extended to use the mouse 408 and/or shoulder is raised for over twenty minutes. Using these measurements, the system can determine an estimate of the employee's muscle tension 1341 using known techniques.

In some embodiments, a level of eye fatigue 1344 may be determined based on the employee's eye movement 1321. For example, it may be determined that the employee is experiencing a high level of eye fatigue 1344 where their blink rate has slowed to less than fifteen blinks per minute and/or the employee has been staring at substantially the same position (e.g., the monitor) for an extended period (e.g., over twenty minutes).

Although the illustrated embodiment includes sets of health characteristics 1302 and corresponding health conditions 1304 extrapolated therefrom, it will be appreciated that embodiments may include one or more of the listed health conditions 1304 being provided as health characteristics 1302 or vice versa. For example, where a sensor 120 provides a resting heart rate value, the resting heart rate may be provided as a health characteristic 1302 as opposed to a health condition 1304 extrapolated from the health characteristics 1302. Similar characteristics may be provided for any of the health conditions 1304.

The biometric and/or biomechanical health characteristics 1302, health conditions 1304 and/or other data (e.g., personal profile information) may be used to identify/predict corresponding health risks 1306. The health risks 1306 may include a third level of health profile data that is derived from one or more of the health conditions 1304, the health characteristics 1302 and/or the collected health data 200. For example, the server 104 may process the health conditions 1304, the health characteristics 1302 and/or the collected health data 200 using predictive analytics to extrapolate various biometric health risks 1306a and/or biomechanical health risks 1306b for the employee (i.e., risks for developing the associated health condition). Risk 1306 may include a prediction of a health condition that may occur. For example, where the recent health data for an employee indicates a trend of increasing body weight for an employee, it may be predicted that the employee is at risk for becoming obese within a given time period. Biometric health risks 1306a may include, for example, risk of obesity 1350, risk of injury 1351, risk of diabetes 1352, risk of infection 1353, risk of inflammation 1354, risk of circulation problems 1355, risk of cardiovascular disease 1356, risk of a cardiovascular accidents (e.g., stroke) 1357, risk of illness (e.g., the flu) 1358, risk of developing asthma 1359, risk of developing allergies 1360, risk of developing bronchitis 1361, risk of experiencing depression 1362, and/or the like. Biomechanical health risks 1306b may include, for example, risk of back injury 1363 (e.g., upper/lower back pain), risk of neck injury 1364, risk of musculoskeletal syndrome ("MSD") 1365, risk of carpal tunnel syndrome ("CTS") 1366, risk of epicondylitis (i.e., tennis/golfer's elbow) 1367, risk of a rotator cuff injury 1368, risk of eye disease 1369, risk of physical fatigue, and/or the like. The prediction of health issues and the identification of associated health risks may provide a proactive environment for predicting and responding to health risks before they escalate into actual health conditions.

Risks of obesity 1350, injury 1351, diabetes 1352, and cardiovascular disease may be based on BMI 1330 and/or body comp 1331. Risk of infection 1353, inflammation 1354, and circulation problems 1355 may be based on body temperature 1310. Risk for cardio vascular disease 1356, cardiovascular accidents 1357, and obesity 1350 may be based on fitness level 1332, blood pressure 1314, and heart rate 1313. Risk for illness 1358, asthma 1359, allergies 1360 and bronchitis 1351 may be based on respiratory rate 1316. Risk of depression 1362 may be based on the employee's emotions 1336 and thoughts 1337. Risk of physical fatigue 1370 may be based on the employee's motor functions 1346.

In some embodiments, an employee that is obese (e.g., having a BMI over about 30) is determined to have a high risk of diabetes 1352 (e.g., a risk that is 7.37 time greater than normal), a high risk of cardiovascular disease 1356 (e.g., a risk that is 2.5 time greater than normal), a high risk of circulation problems 1355 (e.g., a risk that is 6.38 times greater than normal risk for high blood pressure), a high risk of asthma 1359 (e.g., a risk that is 2.72 time greater than normal) and other conditions, such as a risk for high cholesterol that is 1.88 times greater than normal, for high arthritis that is 4.41 times greater than normal, and so forth.

In some embodiments, it is determined that the employee is at risk or already has the flu or other illness if the employee has one or more of a body temperature 1310 over 101 degrees Fahrenheit, a respiratory rate 1333 greater than 20 respirations per minute, and a heart rate 1313 greater than 100 BPM.

In some embodiments, it is determined that the employee is at risk for inflammation where, for example, the employee's blood pressure 1314 is elevated, the employee's heart rate 1313 is irregular and/or the body temperature 1310 is elevated above normal (e.g., above 98.6 degrees Fahrenheit).

In some embodiments, it is determined that the employee is at risk for circulation problems where, for example, the employee has a low body temperature 1310 (e.g., less than 35° C. (96° F.) measured at the extremities) or a high respiratory rate 1333) (e.g., greater than 20 respirations per minute).

In some embodiments, it is determined that an employee is at risk for depression where, for example, the employee's emotions 1336 and/or thoughts 1337 demonstrate a negative pattern. For example, the employee may be determined to be at risk for depression where they have been determined to have an emotion of "unhappy" for greater than 50% of an observed period of at least one week.

In some embodiments, it is determined that an employee is at risk for fatigue where, for example, the employee's motor functions 1346 are below their normal level. For example, the employee may be determined to be at risk for physical fatigue where their motor function 1346 is less than 75% of its normal level for greater than one hour.

In some embodiments, some or all of the health characteristics 1302, health conditions 1304, and/or health risks 1306 may be determined/identified using known techniques for extrapolating data. Although the illustrated embodiment includes an exemplary listing of health risks, it will be appreciated by those skilled in the art that other embodiments may include assessing any variety of health risks that may be of interest to the employee, the employer and/or other users.

In some embodiments, a health plan 1308 may be generated based on the health characteristics 1302, the health conditions 1304 and/or the health risks 1306. Accordingly, the health plan 1308 may be based on biometric and/or biomechanical health information for the employee. The health plan 1308 may provide a listing of health goals (e.g., lose ten pounds, reduce calorie intake to two-thousand calories per day, etc.), suggested actions for the employee to take to reach the health goals (e.g., an exercise plan, a diet regime, regular breaks from using the computer, etc.) and/or the like. In some embodiments, the health plan 1308 includes a preventative health plan to help maintain and improve the employee's health over time. In some embodiments, the health plan 1308 may include an interactive health plan that can be modified by the employee and/or the employer and/or used to track the employee's progress relative to the plan goals, and/or the like.

In some embodiments, the health plan 1308 may be determined using a discrete health test, or formulated from a plurality of health tests (e.g., current and historical health profile data) to determine the plan based upon a health test trend (e.g., the employee's blood pressure is rising, the employee has gained weight, the employee's BMI is higher, the employee is underweight, the employee's resting heart rate is low or high based upon activity level, etc.). In some embodiments, the health plan is generated by calculating the employee's ideal health characteristics/conditions based on the current health characteristics/conditions/risks. In some embodiments, the difference between the current and ideal health characteristics/conditions/risks is used to identify or generate a corresponding health plan 1308.

Figure 13B:
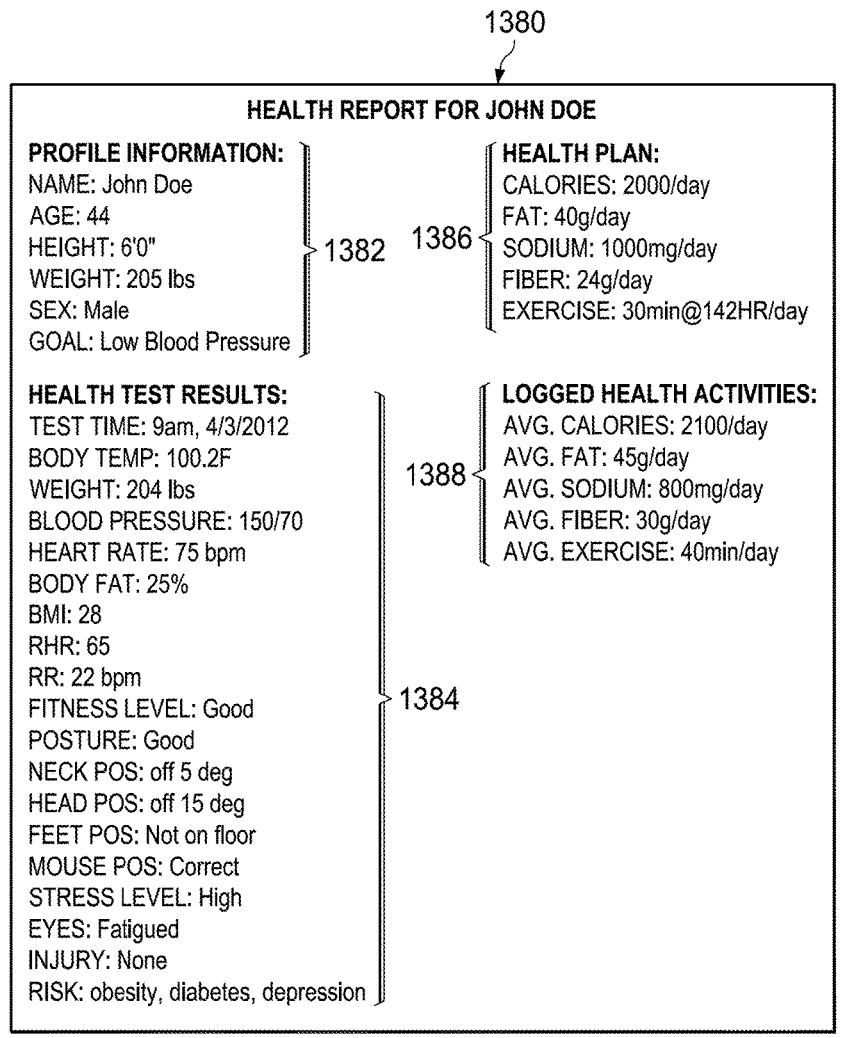
FIG. 13B illustrates an exemplary health report in accordance with one or more embodiments of the present invention.

FIG. 13B illustrates an exemplary health report 1380 in accordance with one or more embodiments of the present invention. Health report 1380 may be generated based on health profile 1300 and/or other profile information (e.g., personal profile data) for the employee. For example, in the illustrated embodiment, the health report 1380 includes personal profile information 1382, health test result data 1384 (e.g., corresponding to health characteristics 1302, health conditions 1304, and health risk 1306 of the health profile 1300), health plan data 1386 (e.g., corresponding to the health plan 1308 of the health profile 1300), and logged health activities 1388 (e.g., corresponding to activity entries by the employee, as discussed in more detail below).

Method 1220 may include providing a health profile, as depicted at block 1226. Providing a health profile may include providing some or all of the content of the health profile 1300 for display to the employee, the employer, a medical practitioner, an emergency responder, or the like. In some embodiments, the health profile 1300 may be provided via a health report document. For example, the server 104 may serve, to the employee's computer 130 and/or the employer's computer 103 a heath report document that is the same or similar to the health report 1380.

In some embodiments, the health profile 1300 may be communicated via an interactive interface. For example, the server 104 may serve, to the employee's computer 130 and/or the employer's computer 103, an interactive health dashboard 1390 for communicating/displaying information of the health profile 1300 to the employee (e.g., via computer 130) and/or the employer (e.g., via computer 103). In some embodiments, the interactive health dashboard 1390 may enable a user (e.g., the employee) to selectively view/edit health profile information 109 (e.g., including the health profile 1300, the personal profile data 1382, activity data 1388 and/or the like) for the employee. For example, an employee may login to the health dashboard 1390 via an application (e.g., a web browser or other network access application) of the computer 130 and interact with the dashboard 1390 to update their personal profile data 1382 (e.g., name, age, etc.), enter health activity information (e.g., food they have eaten, exercises they have competed, etc.), review the health profile data 1300, initiate a health test and so forth.

Providing the health report (including the health characteristics 1302 and conditions 1304) may help to "inform" the employee regarding their health status. Providing the health report (including the health risks 1306) may help to "protect" the employee by alerting them to potential problems that may need to be addressed. Providing the health report (including the health plans 1308) may help to "reinforce" the employee by providing a course of action that suggests actions that the employee should take to reduce their risk of developing health problems.

In some embodiments, an interactive health dashboard 1390 may enable the employer to selectively view data of the health profile 1300 (e.g., including health characteristics 1302, health conditions 1304, health risks 1306 and/or health plans 1308) for some or all of their employees. For example, an employer may login to the health dashboard 1390 via an application (e.g., a web browser) of the computer 103 and use the dashboard 1390 view/edit employees' personal profile 1382, the health profile 1300, the health activities 1388, and so forth.

In some embodiments, where the heath profile 1300 is indicative of the employee incurring a health crisis (e.g., a stroke, heart attack, etc.), the server 104 may generate an alert to emergency personnel, the employer or others. For example, upon detecting that the employee is currently having a heart attack, the server 104 may send an automated the alert to the employer (e.g., via computer 103) and make an automated emergency call to the fire department, the police department, a hospital, onsite medical response personnel located at the work facility, and/or other emergency response personnel (e.g., via the network server 110).

An alert may be generated where it is determined that the employee is experiencing a serious medical condition based on a health characteristic/condition falling outside of a normal range (e.g., falling below a minimum threshold value and/or exceeding a maximum threshold value) such as a respiration rate 1316 outside of the normal range of 12-120 breaths per minute, blood pressure 1314 outside of the normal range of 90/60-180/120, blood oxygenation level above 90%, a posture 1338 indicative of the employee being slumped over or on the floor and/or the like. In some embodiments, an abnormal characteristic or condition may be compared to other characteristics or conditions to confirm that they are, as a whole, consistent with an emergency actually occurring before alerting the corresponding response personnel, thereby reducing the likelihood of a false alert based on an inaccurate measurement (e.g., due to a faulty sensor 120). For example, an alert may not be provided where the heart rate 1313 exceeds an upper threshold limit but the other characteristics and conditions remain relatively unchanged (i.e., they are not elevated or low compared to their baseline).

In some embodiments, where the heath profile 1300 is indicative of the employee incurring a serious health risks (e.g., high potential for one of the health risk 1306 or the like), the server 104 may provide a notification to the employer and/or medical practitioners. For example, upon detecting that the employee is at risk of developing diabetes, the server 104 may transmit an automated notification to the employer (e.g., via the computer 103) and/or the employee's physician (e.g., via the network server 110).

In some embodiments, the employee health information 109 for the employee includes a record/log of the employee's health information. For example, the employee health profile data 109 may include, for each employee, employee personal profile data (e.g., name, age, etc.) 1312, the current/historical employee health profile 1300, the current/historical employee activity data 1318, and so forth.

Figure 14:
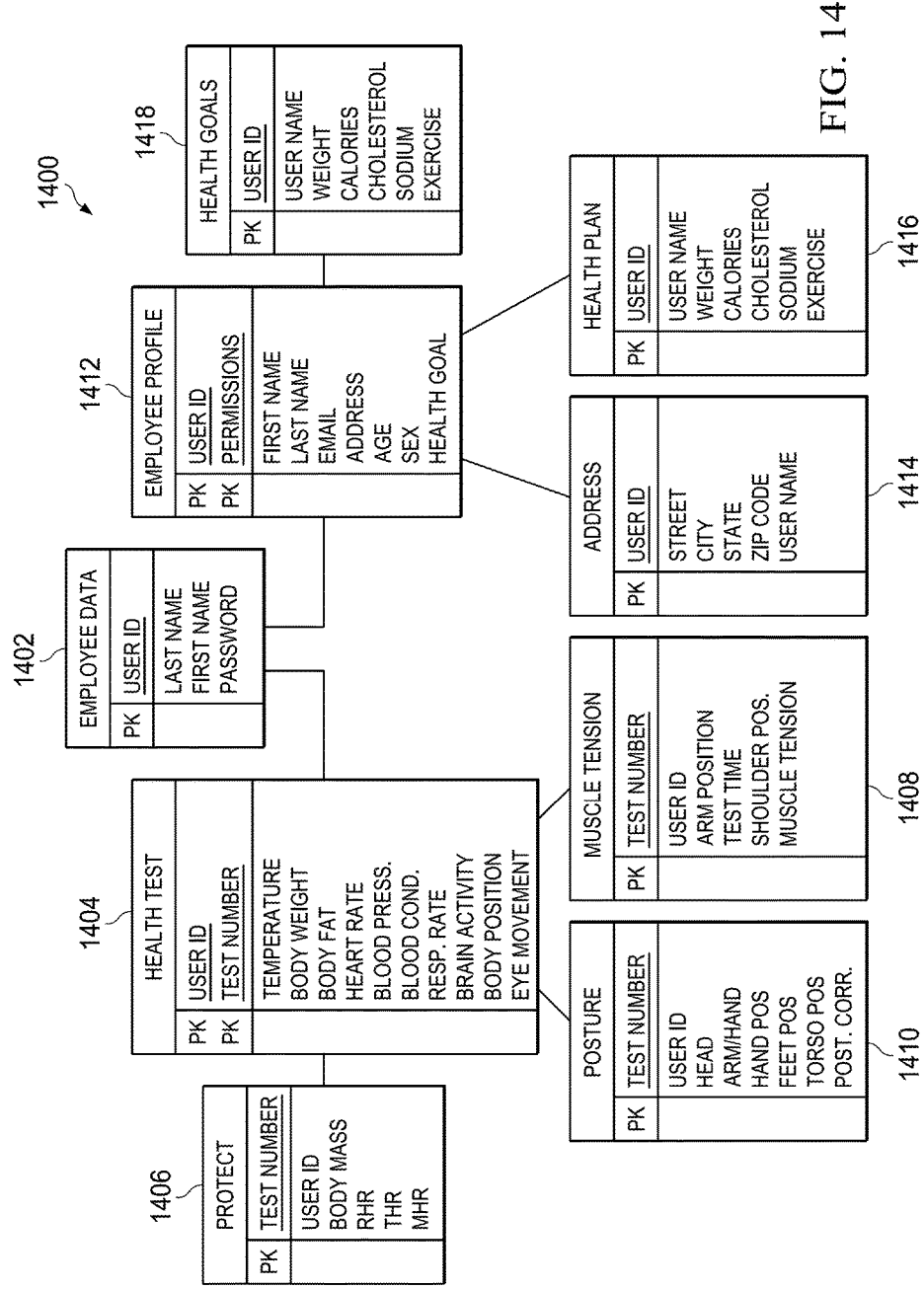
FIG. 14 is an exemplary database structure of health information in accordance with one or more embodiments of the present invention.

FIG. 14 is an exemplary database structure 1400 of health information 109 stored in the database 108 in accordance with one or more embodiments of the present invention. In some embodiments, the exemplary health information 109 is structured to include the following tables: employee data 1402, health test 1404, protect 1406, muscle tension 1408, posture 1410, employee profile 1412, address 1414, health plan 1416, and health goals 1418. Each of the tables for a given user (e.g., employee) may include the same primary key ("PK") that is unique with respect to other users, and, thus, may be used to identify tables/records for the given user. For example, all of the tables having health information for the employee "John Doe" (having an employee ID of "1234") may include the primary key of "1234".

The employee data table 1402 may include the employee's general user information. For example the employee data table 1402 may include entries for the employee's last name, first name, password, social security number, a remote login code, e.g., RSA code, user identification number and/or the like.

The health test table 1404 may include entries that reflect results of one more health tests of the employee (e.g., health test conducted using sensors 120 of workstation 102). The health test table 1404 may be dependent on employee data table 1402. In some embodiments, health test table 1404 may include a unique test number, as well as measured data for the respective test. For example, the health test table 1404 may include data relating to measured health characteristics 1302 such as body temperature, body weight, body fat, heart rate, respiratory rate, blood pressure, blood condition, body position, eye movement, and/or the like.

The protect table 1406, the posture table 1410 and/or the muscle tension table 1408 may include entries that reflect one or more health conditions 1304 for the employee associated with the given test number of health test table 1404. The protect table 1406, the posture table 1410 and/or the muscle tension table 1408 may be dependent on health test table 1404. In some embodiments, each of the protect table 1406, the posture table 1410 and/or the muscle tension table 1408 may include a unique test number, as well as measured/determined data for the respective condition. For example, the protect table 1406 may include entries for the employee's user ID, body mass, resting heart rate, target heart rate and maximum heart rate. The muscle tension table 1408 may include entries for related to the employee's muscle tension. In some embodiments, the muscle tension table 1408 includes data used to assess muscle tension, such as arm position, test time, shoulder position, and/or the like. In some embodiments, the muscle tension table 1408 includes a muscle tension value indicative of the determined level of the employee's muscle tension. The posture table 1410 may include entries for related to the employee's posture. In some embodiments, the posture table 1410 includes data used to assess posture, such as head, arm, hand, feet, torso position and/or the like. In some embodiments, posture table 1410 includes a posture correction indicative of whether the employee's posture is acceptable and/or suggestions for correcting/improving the employee's posture. In some embodiments, similar tables may be generated for some or all of the other health conditions 1304 and/or health risks 1306.

In some embodiments, tables (e.g., a health test table 1404, protect table 1406, posture table 1410, muscle tension table 1408 and/or similar tables may be generated for other health conditions 1304 and or health risks 1306 may be generated for each iteration of testing. For example, a set of tables may be generated for a first iteration of testing having test number "0001", a second set of tables may be generated for a second iteration of testing having test number "0002", and so forth. In some embodiments, the test number may represent the test iteration for the employee, such as a test number of "0001" is the first test taken by the employee, and a test number of "0010" is the tenth test taken by the employee. In alternative embodiments, the test number may indicate a date and time of a test so that multiple tests in run in a day can be identified by date, time, and/or test iteration.

The employee profile table 1412 may be dependent from the employee data table 1402. In some embodiments, the employee profile table 1412 may include primary keys of the employee's user ID and permissions that are indicative of which portion of the database the employee can access. For example, in some embodiments, administrators of the employee health program may have permission to download employee health profiles for a plurality of employees. In other embodiments, the permissions may grant some employees permission to access tables aggregating employee profile data, while other employees can only access their own profiles. In other embodiments, the permissions may be set by the employee to restrict the employer's access to health profile data (e.g., may allow no access, access for data aggregation only, or full access by restricted personnel). As one skilled in the art will appreciate, there are multiple different permission types that can be used to grant employees access to the data in the database, and all are included within the scope of this disclosure. The employee profile table 1412 may include entries for the employee's first name, last name, email address, physical address, age, sex, health goal and/or the like.

The address table 1412, the health plan table 1416, and the health goals table 1418 may be dependent from the employee profile table 1412. The address table 1414 may include a primary key of the employee's user ID, and entries for the employee's street address, city, state, zip code, user/employee name and/or the like. The health plan table 1416 may include a primary key of the employee's user ID, and entries for the employee's employee name, weight, calorie intake, cholesterol level, sodium intake, exercise regimen, blood glucose level, and/or the like. Health plan table 146 may reflect aspect of health plan(s) 1308 for the employee. The health goals table 1418 may include a primary key of the employee's user ID, and entries for target weight, calorie intake, cholesterol level, sodium intake, exercise regimen, blood glucose level, and/or the like. As one skilled in the art will appreciate, some embodiments of the invention may include one, both or none of the health plan and health goals tables depending upon the implementation of the system. As one skilled in the art will also appreciate, the health plan table 1416 and health goals table 1418 can be compared to one another to determine a deviation between the two that is indicative of the employee meeting, exceeding or falling short of their health goals. In some embodiments, a notification indicative of the employee meeting, exceeding or falling short of their health goals may be provided to the employee and/or the employer (e.g., via the interactive health dashboard 1390).

It will be appreciated that the method 1220 is an exemplary embodiment of methods that may be employed in accordance with techniques described herein. The method 1220 may be may be modified to facilitate variations of its implementations and uses. The method 1220 may be implemented in software, hardware, or a combination thereof. Some or all of the method 1220 may be implemented by one or more of the modules/applications described herein, such as server modules 1210. The order of the method 1220 may be changed, and various elements may be added, reordered, combined, omitted, modified, etc.

Collecting and Displaying Health Information:

In some embodiments, a health monitoring application (e.g., executed by server 104) provides various user interfaces for interacting with the employee health information, including health profile data, health reports, and the like. For example, a user may be able to login to the application to view or edit health information for themselves or employees. In some embodiments, health information may be communicated via a health monitoring widget and/or an interactive health dashboard (e.g., dashboard 1390). For example, upon a user (e.g., an employee) logging in to the health monitoring application, the user's desktop may be populated with a widget that displays a summary of the most recent health profile data for the employee and/or the user may be able to launch an interactive health dashboard that allows the user to view/edit their health information and/or control the execution of health test for the employee.

Figure 15:
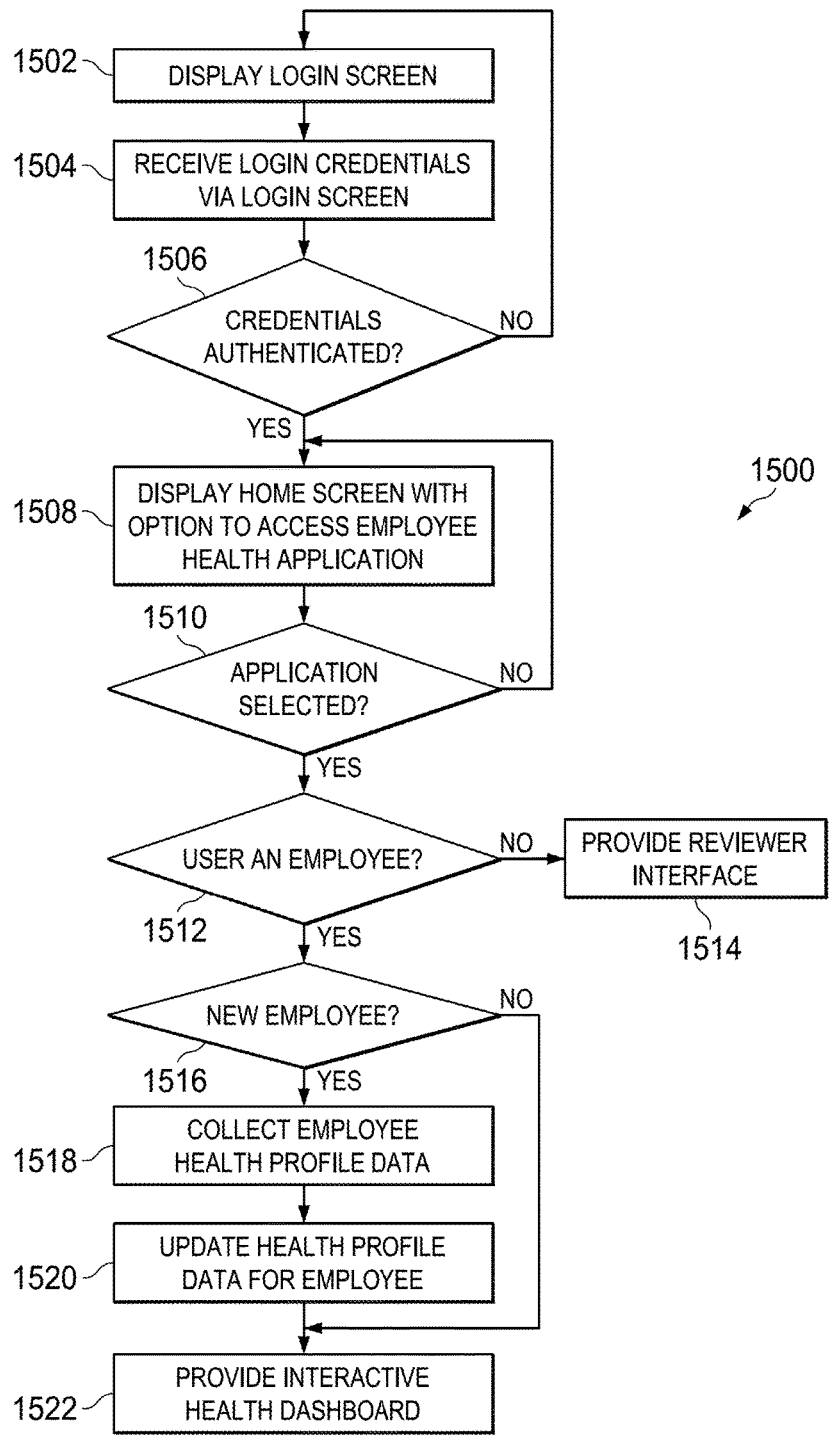
FIG. 15 is a flowchart that illustrates an interactive health monitoring method in accordance with one or more embodiments of the present invention.

FIG. 15 is a flowchart that illustrates an interactive health monitoring method 1500 in accordance with one or more embodiments of the present invention. Method 1500 may include displaying a login screen, as depicted at block 1502. In some embodiments, the login screen includes fields for entering user login credentials such as user ID, name, employee number, social security number, password, RSA code, and/or the like. For example, FIG. 16 illustrates an exemplary login screen 1600 that may be displayed to a user via a computer display in accordance with one or more embodiments of the present invention. The login screen 1600 includes a login dialog 1602 having name field 1604 for the entry of a user name, a password field 1606 for the entry of a user's password, and a login button 1608 that may be selected to submit the credentials for validation. In some embodiments, the login screen 1600 may be displayed to an employee, employer, or other personnel via a graphical user interface of the employee computer 130, the employer computer 103, a remote computer 112 and/or the like. Upon selection of the login button 1608, the login credentials that have been entered by the user may be received as depicted at block 1504. For example, the login credential submitted may be received by the server 104 for use in authenticating the user login credentials.

In some embodiments, method 1500 may include authenticating the login credentials as depicted at block 1506. In some embodiments, authenticating the login credentials may be provided by execution of user verification module 1210*a*. In some embodiments, authenticating the login credentials may include comparing the received credentials to user credentials stored in database 108 to determine whether or not the user has permissions to access the employee health monitoring application. Where the credentials are not authenticated, the user may be denied access, and returned to the display of the login screen as described with regard to block 1502. Where the login credentials are authenticated, the method 1500 may proceed to displaying a home screen with an option to access the employee health monitoring application, as depicted at block 1508. For example, if the login credentials are authenticated, a home page screen 1700 (e.g., a user desktop screen) including a user selectable employee health monitoring application icon 1702 may be displayed, as depicted in FIG. 17.

In some embodiments, the home page screen 1700 may include an employee health status widget 1704. The employee health status widget 1704 may be displayed on the user's home screen in response to the user successfully logging into the health monitoring application such that the employee can view at least some of their health information and/or corresponding health alerts while working with other applications (e.g., word processing applications, spreadsheet applications, etc.) on their computer 130. The employee health status widget 1704 may provide the employee with feedback regarding their health condition based on their most recent health tests and health reports. For example, the health status widget 1704 may include a health status avatar 1703, a health summary 1706, a performance indicator 1708, an emotion avatar 1710, and/or the like. The health status avatar 1703 may include a graphical depiction of the employee's current health. For example, the health status avatar 1703 may include a graphical depiction of a human body that provides a graphical depiction of areas of the employee's body that may require attention. For example, in the illustrated embodiment, the health status avatar 1703 includes a graphic alert including the message "You are experiencing high blood pressure" and a heart graphic that may be displayed in response to determining that the employee has high blood pressure. Similar graphic alerts may be provided for other characteristics, conditions and/or risks. For example, a graphic alert including the message "Your eyes are fatigued" and a corresponding graphic at the eyes of the health status avatar 1703 may be provided in response to a determination that the employee's eye are fatigued.

In some embodiments, the health status avatar 1703 may include a coaching avatar that provides instructions, suggestions, and/or demonstrations that are intended to help coach the employee in improving their health and accomplishing one or more of their health goals. For example, as described herein, the health status avatar 1703 may provide an animated demonstration of an exercise that can be performed to help the employee alleviate a health alert condition, accomplish one or more of their health goals, or the like. In some embodiments, the health status avatar 1703 may provide the information audibly (e.g., via speakers of the user computer), with the avatar being animated such that it appears the avatar is speaking to the user.

In some embodiments, the health summary 1706 displays of some or all of the current health characteristics, conditions and/or risks for the employee. For example, in the illustrated embodiment, the health summary 1706 includes a listing of various health characteristics/conditions each accompanied by a check indicative of the characteristic/condition being acceptable or a flag indicative of the characteristic/condition needing attention. Thus, the health summary 1706 may provide a listing of current health characteristics, conditions, and/or risks for the employee and corresponding alerts for health characteristics, conditions, and/or risks that may require attention.

In some embodiments, the performance indicator 1708 includes an indication of how the employee is performing. For example, the illustrated embodiment, the performance indicator includes a graphical scale indicating the current determined level of stress for the employee.

In some embodiments, the emotion avatar 1710 includes a graphical depiction of the employee's current emotional state, facial expression, gestures, and/or the like. For example, in response to determining that the employee is smiling and/or happy (e.g., via the determined emotion 1336 and/or the determined facial movement 1345), the avatar 1710 may be dynamically updated to include a graphic illustration of a smile, as depicted, to mimic the current emotion and/or facial expression of the employee. Thus, the avatar 1710 may reflect the employee's current emotional state, current facial expressions, gestures, and/or the like In some embodiments, the health status information provided via the health widget 1704 is based on the most recent health report 1300 for the employee. For example, where the employee undergoes a health test once per hour, the health widget 1704 may be updated once per hour to display information corresponding to the most recent health test. As a further example, where the employee undergoes continuous health testing (e.g., once per second, once per minute, etc.), the health widget 1704 may be updated continuously (e.g., once per second, once per minute, etc.) to display information corresponding to the most recent health test. Such an embodiment may provide the employee with real-time feedback regarding their current health status/profile.

In response to the user selecting the employee health monitoring application icon 1702 (and/or the health status widget 1704), method 1500 may include proceeding to determining whether the user is an employee to be monitored or other type of user (e.g., an employer that has access to review employee health information 109) as depicted at block 1512. In some embodiments, the determination of the type of user is based on a "user type" associated with their user profile. For example, a first set of login credentials may be associated with an employee profile and a second set of login credentials may be associated with an employer profile. Where the user is determined to not be an employee, the method 1500 may proceed to providing a reviewer interface, as depicted at block 1514. The reviewer interface is discussed in more detail below with regard to FIG. 27.

Where the user is determined to be an employee, the method 1500 may proceed to determining whether the employee is a new employee or existing employee, as depicted at block 1516. The user may be determined to be a "new employee" where, for example, the user has not previously logged into the system and/or has not yet provided basic employee personal profile information (e.g., sex, age, e-mail address, etc.). The user may be determined to be an "existing user" where, for example, the user has previously logged into the system and/or has already provided basic employee personal profile information. In some embodiments, upon determining that the user is a "new user", method 1500 may proceed to collecting user personal profile information, as depicted at block 1518. For example, an edit profile dialog 1800, as depicted in FIG. 18, may be displayed, thereby prompting the user to enter employee personal profile information (e.g., the employee's height, age, gender, health goal, etc.). In some embodiment, the edit profile dialog 1800 may be pre-populated with any information that is already known (e.g., stored in database 108). For example, where the user's name is known based on the login-credentials, the "name" field may be populated with the user's name. The user may enter/edit the personal profile information via the various user profile information fields 1802 and may submit the updated user profile information via section of the submit button 1804. Method 1500 may include updating the employee's health information to reflect the updated employee personal profile information, as depicted at block 1520. For example, upon the user entering/editing the various user profile information fields 1802 and selecting the submit button 1804, the employee health information 109 stored in database 108 may be updated to reflect the updated personal profile data of the fields 1802. Such profile data may be stored as separate records, tables or fields in the database (e.g., such as those discussed with regard to the data structure of FIG. 14).

In some embodiments, upon the user having submitted their personal profile information (e.g., via edit profile screen 1800) and/or determining that the user is not a "new user" (i.e., the user is an "existing user"), method 1500 may proceed to providing an interactive health dashboard (e.g., interactive health dashboard 1390) as depicted at block 1522. In some embodiments, the interactive health dashboard may include user selectable options to review/edit their health information, review/edit their health profile data, and/or initiate one or more employee health tests.

Figure 19:
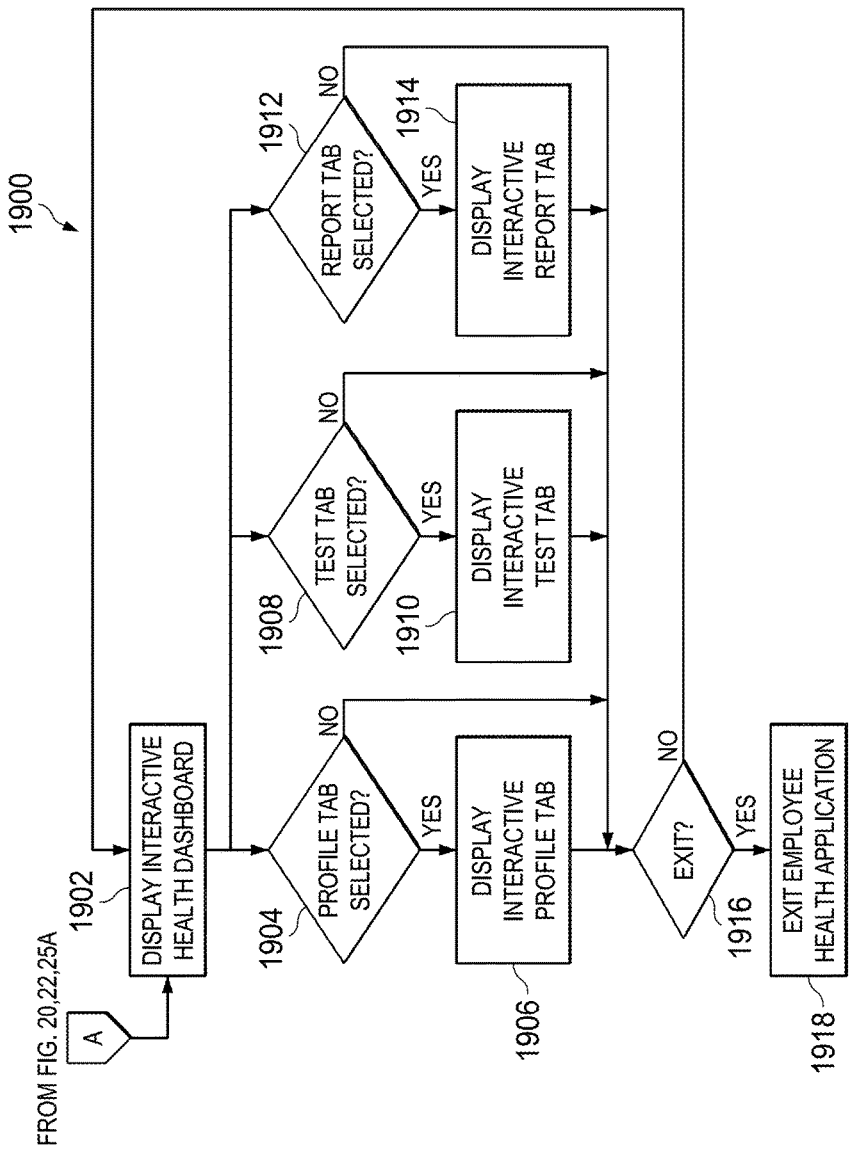
FIG. 19 is a flowchart that illustrates a method for providing an interactive health dashboard in accordance with one or more embodiments of the present invention.

FIG. 19 is a flowchart that illustrates a method 1900 for providing an interactive health dashboard in accordance with one or more embodiments of the present invention. Method 1900 may include displaying the interactive health dashboard, as depicted at block 1902. In some embodiments, displaying the interactive health dashboard includes displaying a default view of the interactive health dashboard. For example, displaying a default view of the interactive dashboard may include display of a health dashboard 1390 similar to that described with regard to FIG. 21. As discussed in more detail herein, the health dashboard 1390 may include a profile tab 2102 that is user selectable to access employee personal profile data, a report tab 2104 that is user selectable to access employee health profile data, and a test tab 2106 that is user selectable to access employee health test functions. In some embodiments, the profile tab 2102 is displayed by default.

Figure 20:
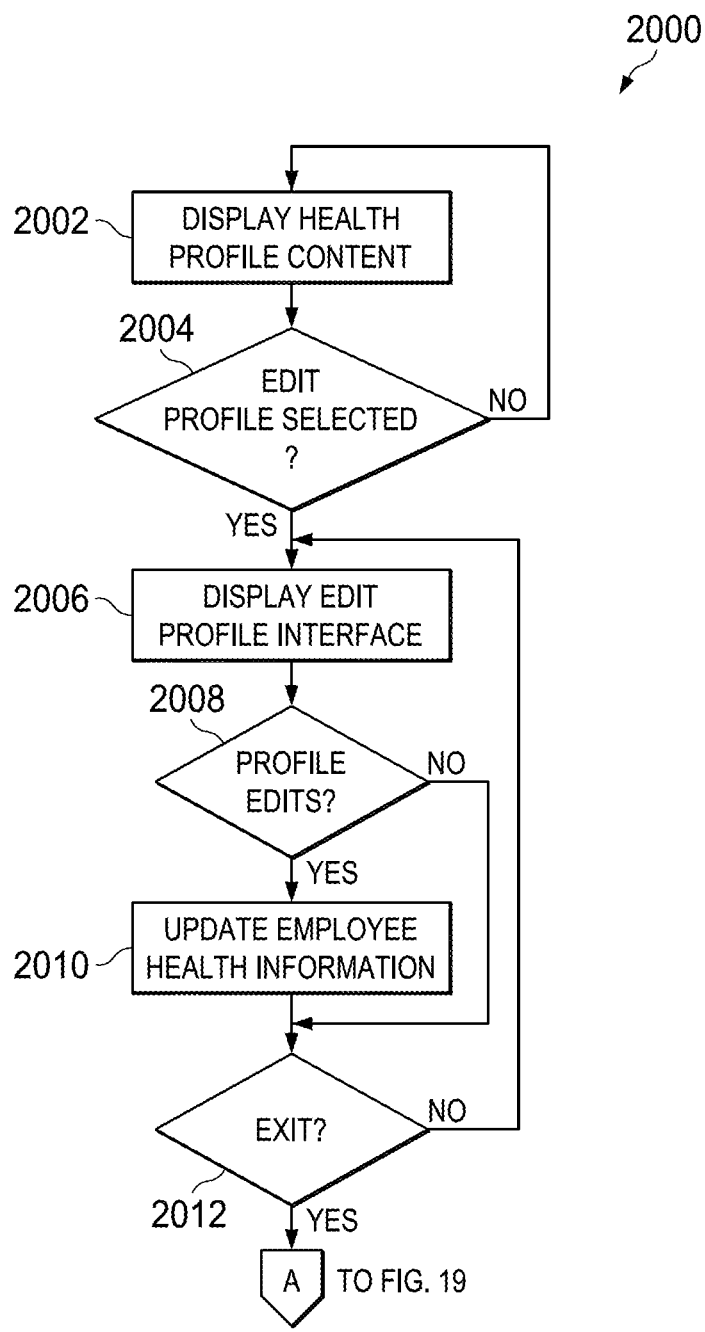
FIG. 20 is a flowchart that illustrates a method for displaying a profile tab in accordance with one or more embodiments of the present invention.
Figure 21:
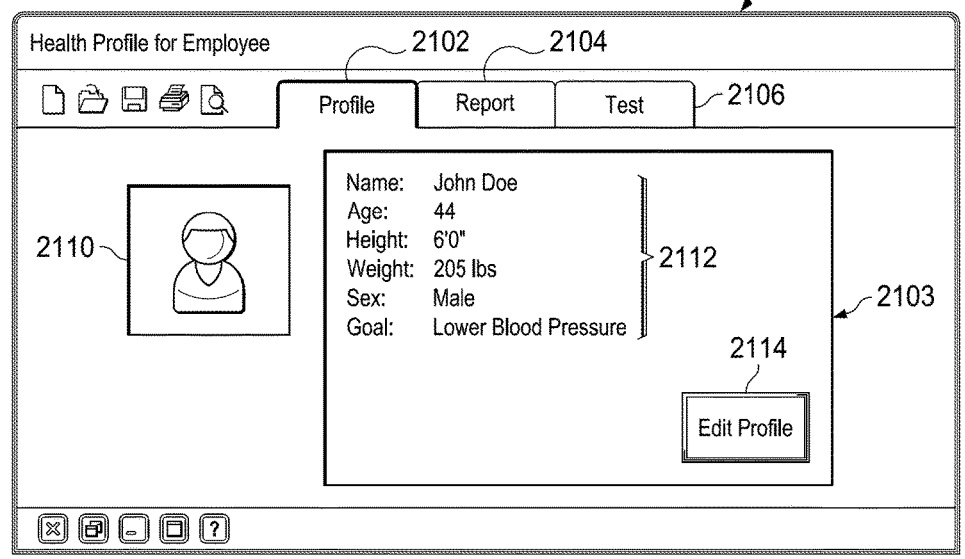
FIG. 21 is a screen-shot that illustrates an exemplary display of a profile tab in accordance with one or more embodiments of the present invention.

In some embodiments, upon the user selecting the profile tab 2102, as depicted at block 1904, method 1900 may include displaying the interactive profile tab 2102, as depicted at block 1906. FIG. 20 is a flowchart that illustrates a method 2000 for displaying the profile tab in accordance with one or more embodiments of the present invention. Method 2000 may include displaying profile content, as depicted at block 2002. FIG. 21 illustrates an exemplary display of the profile tab 210 including profile content 2103 in accordance with one or more embodiments of the present invention. In some embodiments, the health profile content 2103 of the profile tab 2102 includes an interactive avatar 2110, health profile information 2112 and an edit profile button 2114. In some embodiments, the server 104 may serve the profile content 2103 to the employee computer 130 for display.

In some embodiments, the avatar 2110 may provide for communicating health information to the user. For example, the avatar 2110 may include an animated character that "speaks" to the user (e.g., via speakers of computer 130 and/or an audio headset) to communicate the profile information. For example, the avatar may ask audibly, "Would you like to update your user profile information? If so, select the 'edit profile' button." Such communication may help to encourage the employee to interact with the employee health monitoring application and/or provide valuable instructions for how to use the application. In some embodiments, upon initially opening the employee health monitoring application, the avatar 2110 may direct the employee to certain data that may be of interest and/or task that should be completed. For example, at the initial display of the profile tab 2102, the avatar 2110 may state audibly, "You have not conducted a health test today, would you like to do so? If so, select the 'test' tab." As a further example, at the initial display of the profile tab 2102, the avatar 2110 may state audibly, "You test results indicate that you are at risk for eye fatigue and your posture is poor. Please select the report tab to receive suggestions on how to reduce eye fatigue and improve your posture." In some embodiments, the avatar 2110 may include a "coaching avatar" that provides instructions, suggestions, and/or demonstrations that are intended to help coach the employee in improving their health and accomplishing one or more of their health goals of their health plan. For example, as described herein, the avatar 2110 may provide an animated demonstration of an exercise (e.g., how to perform sit-ups, stretching, or the like) that can be performed by the employee to accomplish on more goals of their health plan (e.g., complete a daily exercise goal) or otherwise improve their health (e.g., reduce an identified health risk).

As discussed herein, a similar avatar may be provided in each of the tab displays to help communicate the corresponding health information to the user and assist them with using the employee health monitoring application. Thus, an employee may be more likely to use the application and follow the health plan for the employee.

In some embodiments, the profile information 2112 reflects the current health information 109 stored in database 108. The profile information 2112, thus, may be based on personal profile information entered by the employee (e.g., the employee's name) and/or health profile information obtained as a result of test (e.g., the employee's weight). In some embodiments, upon user selection of the "Edit Profile" button 2114, as depicted at block 2004, an interface for editing the user's personal profile information may be displayed, as depicted at block 2006. For example, the edit profile screen 1800 of FIG. 18 may be displayed, thereby prompting the user to enter/edit the employee personal profile information. Where the user edits their personal profile information (e.g., via entry of edits and selection of the "Submit" button 1804), as depicted at block 2008, the health information 109 stored in database 108 may be updated to reflect the updated personal profile information, as depicted at block 2010. Upon selecting the option to "Exit" (e.g., selecting the "Exit" button 1806), as depicted at block 2012, the method 2000 may return to displaying the interactive health dashboard as discussed with regard to block 1902.

Figure 22:
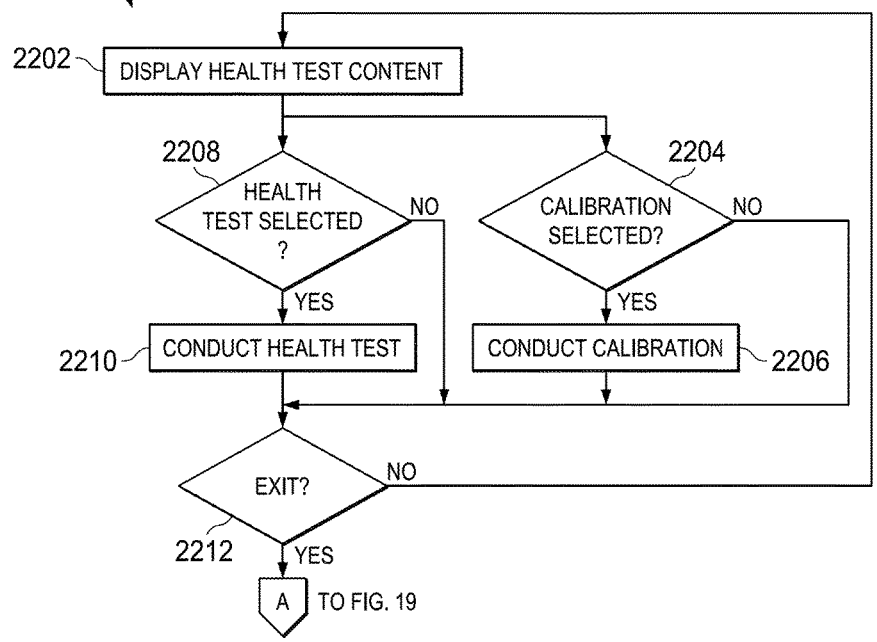
FIG. 22 is a flowchart that illustrates a method for displaying a test tab in accordance with one or more embodiments of the present invention.
Figure 23A:
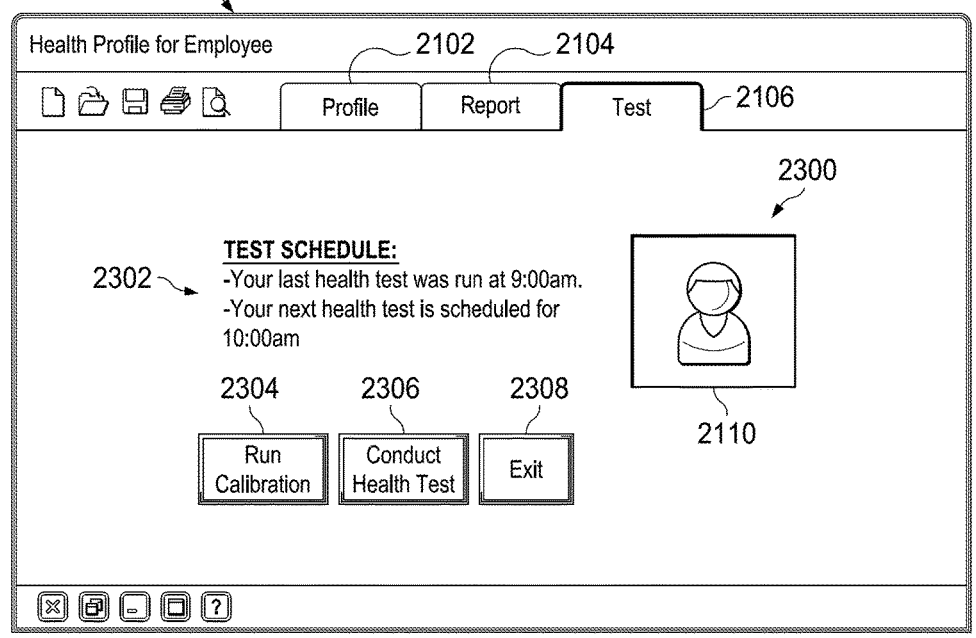
FIGS. 23A and 23B are screen-shots that illustrate exemplary displays of a test tab in accordance with one or more embodiments of the present invention.
Figure 23B:
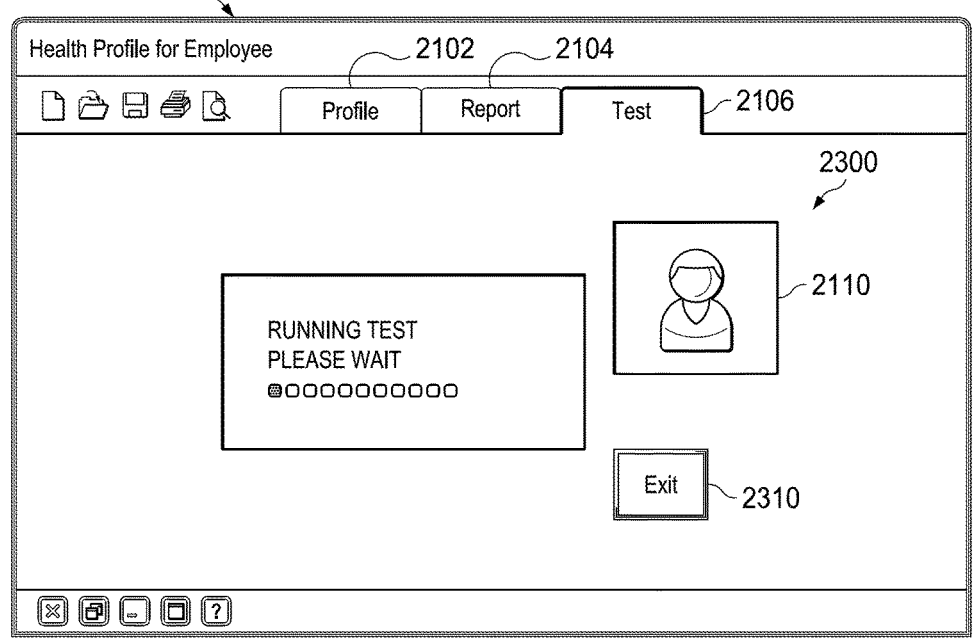

In some embodiments, upon the user selecting the test tab 2106, as depicted at block 1908 of FIG. 19, method 1900 may include displaying the interactive test tab 2106, as depicted at block 1910. FIG. 22 is a flowchart that illustrates a method 2200 for displaying the interactive test tab in accordance with one or more embodiments of the present invention. Method 2200 may include displaying heath test content, as depicted at block 2202. FIGS. 23A and 23B illustrate exemplary displays of the test tab 2106 including heath test content 2300 in accordance with one or more embodiments of the present invention. In some embodiments, heath test content 2300 includes the avatar 2110, test schedule information 2302, a "Run Calibration" button 2304, a "Conduct Health Test" button 2306, and an "Exit" button 2308. In some embodiments, the server 104 may serve the health test content 2300 to computer 130 for display.

In some embodiments, upon initially displaying the test tab 2106, the avatar 2110 may direct the employee to certain data that may be of interest and/or task that should be completed relating to health test. For example, at the initial display of the test tab 2106, the avatar 2110 may state audibly, "A health test was conducted at 9 am and another one is schedule for 10 am. Would you like to conduct a test now? If so, select the 'Conduct Health Test' button." In some embodiments, the health test schedule information 2302 reflects when prior tests were conducted and/or when future test are scheduled.

In some embodiments, upon user selection of the "Run Calibration" button 2304, as depicted at block 2204, a calibration routine (e.g., calibration module 1210b) may be conducted, as depicted at block 2206. For example, a scan of the sensors 120 may be conducted to collect a set of baseline measurements for some or all of the health characteristics 1302 and/or conditions 1304. The baseline measurements may be used to confirm the operation of the sensors 120 and/or stored in health data 109 for use in comparisons to other health data collected. In some embodiments, the calibration collects normative data regarding the employee that can be used to properly interpret relative aspects of the health data. In some embodiments, the baseline measurements may not be added to the content of a health profile data and/or health report 1380 for the employee. In some embodiments, during execution of a calibration routine, a display similar to that of FIG. 23B may be displayed, stating "Calibrating, Please Wait" such that the user is aware of the current state of system 100.

In some embodiments, upon user selection of the "Conduct Health Test" button 2306, as depicted at block 2208, a health test routine (e.g., monitoring module 1210c) may be executed, as depicted at block 2210. For example, the sensors 120 may be monitored to collect health data 200 and/or a corresponding health profile data 1300 and/or a corresponding report 1380 may be generated. In some embodiments, during execution of the health test, a display similar to that of FIG. 23B may be displayed, stating "Running Test, Please Wait" such that the user is aware of the current state of system 100.

Figure 24:
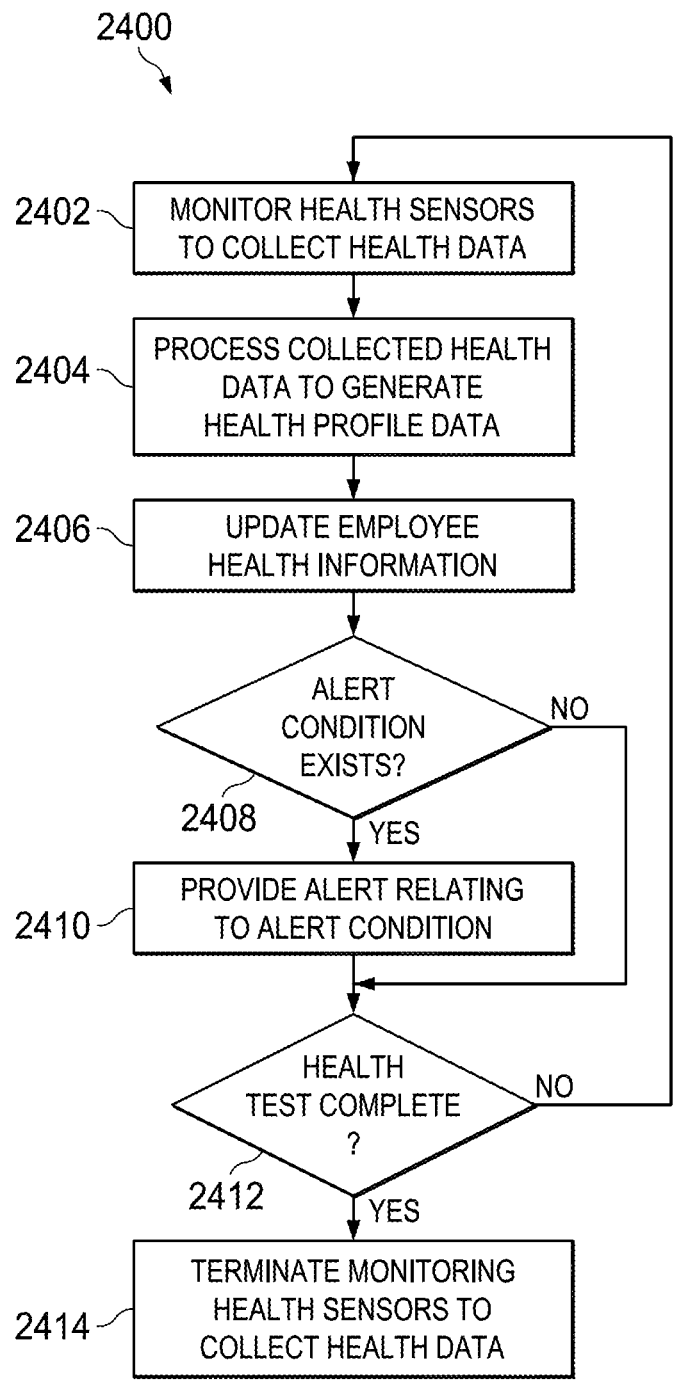
FIG. 24 is a flowchart that illustrates a method for conducting a health test in accordance with one or more embodiment of the present invention.

FIG. 24 is a flowchart that illustrates a method 2400 for conducting a health test in accordance with one or more embodiment of the present invention. Method 2400 may include monitoring health sensors to collect health data, as depicted at block 2402. In some embodiments, monitoring health sensors to collect health data includes monitoring health sensors 120 (e.g., one or more temperature sensors (e.g., thermocouples, IR sensors, etc.) 202, one or more blood condition sensors (e.g., pulse oximeters) 204, one or more blood pressure sensors (e.g., blood pressure cuff) 206, one or more position sensors (e.g., force transducers) 208, one or more body fat sensors (e.g., metallic contacts) 210, one or more 3D position sensors (e.g., video sensors) 212, one or more audio sensors (e.g., microphone) 214, respiration sensors 216, neural sensors 218, and/or the like) to collect health data 200 (e.g., temperature data 200a, blood condition data 200b, blood pressure data 200c, position data 200d, body fat data 200e, 3D position data 200f, audio data 200g, respiration date 200h, neural data 200i, and/or the like). In some embodiments, the health data is received by the server 104 as discussed herein.

In some embodiments, method 2400 may include processing the collected health data to generate health profile data, as depicted at block 2404. For example, the health data 200 collected may be processed by the server 104 to generate a health profile 1300 as described herein with regard to FIG. 13, including health characteristics 1302, health conditions 1304, health risks 1306, and/or health plans 1308.

In some embodiments, method 2400 may include updating employee health information, as depicted at block 2406. For example, the employee's user health information 109 stored in database 108 (e.g., the tables of data structure 1400) may be updated to include the data of the health profile 1300 (e.g., including health characteristics 1302, health conditions 1304, health risk 1306 and one or more health plans 1308).

In some embodiments, method 2400 may include determining whether an alert condition exists, as depicted at block 2408, and, if an alert condition does exists, providing an alert relating to the alert condition, as depicted at block 2410. Such a determination maybe made in the course of the health test such that an immediate alert may be provided to the necessary personnel. As discussed above, in some embodiments, determining whether an alert condition exists may include determining whether the health data 200 and/or the health profile 1300 is indicative of the employee incurring a health crisis (e.g., a stroke, heart attack, etc.), and, if it determined that the employee is experiencing a health crisis, providing a corresponding alert to emergency personnel and/or the employer. For example, upon detecting that the employee is currently having a heart attack, the server 104 may generate an automated the alert to the employer (e.g., via computer 103) and/or an automated emergency request call to the fire department, the police department, a hospital, onsite medical response personnel located at the work facility, and/or other emergency response personnel (e.g., via network server 110 and a remote computer 112). In some embodiments, determining whether an alert condition exists may include determining whether the heath report 1300 is indicative of the employee incurring a serious health risk (e.g., high potential for one of the health risk 1306 or the like), and, if it determined that the employee is experiencing a serious health risk, the server 104 generating a notification to the employer and/or medical practitioners. For example, upon detecting that the employee is at risk of developing diabetes, the server 104 may generate an automated notification indicative of the risk to the employer (e.g., via computer 103) and/or the employee's physician (e.g., via network server 110 and a remote computer 112).

In some embodiments, the determination of whether an employee is experiencing an alert condition may be based on comparison of the health data 200 and/or the health profile 1300 to predetermined threshold limits. For example, as discussed above, it may be determined that the employee is experiencing a serious medical condition where a health characteristic 1302 or condition 1304 falls outside of a predetermined normal/threshold range (e.g., falling below a minimum threshold value and/or exceeding a maximum threshold value) such as a respiration rate 1316 outside of the normal range of 12-120 breaths per minute, blood pressure 1314 outside of the normal range of 90/60-180/120, blood oxygenation level above 90%, a posture 1338 indicative of the employee being slumped over or on the floor. In some embodiments, an abnormal characteristic or condition is be compared to other characteristics or conditions to confirm that they are, as a whole, consistent with an emergency actually occurring before alerting the corresponding response personnel, thereby reducing the likelihood of a false alert based on an inaccurate measurement (e.g., due to a faulty sensor 120). For example, an alert may not be provided where the heart rate 1313 exceeds an upper threshold limit but the other related characteristics and conditions (e.g., blood pressure and blood oxygenation) remain relatively unchanged (i.e., they are not abnormally elevated or low compared to their baseline). In some embodiments, the employee may be displayed an option to override the alert prior to it being sent. Such an option may enable the employee to inhibit false alerts from being transmitted.

In some embodiments, method 2400 may include determining whether the health test is complete, as depicted at block 2412, and terminating monitoring the health sensors where the heath test is determined to be complete, as depicted at block 2414. In some embodiments, the health test is determined to be complete when the required amount of health data has been collected and processed. For example, where the health test requires only a single set of measurements from the sensors 120 (e.g., a single measurement from each of the sensors 120), the health test may be complete after a single iteration of monitoring, processing, updating, and checking for alert conditions. As a further example, where the health test requires a set of measurements from the sensors 120 be collected over a given period of time (e.g., one minute, five minutes, one hour, eight hours), the health test may not be complete until the expiration of the given time period. Thus, for example, iterations of health testing may continue for one minute, five minutes, one hour, eight hours, or the like.

Although the illustrated embodiment refers to the method 2400 for conducting a health test being executed in response to a user request via selection of the "Conduct Heath Test" button, it will be appreciated that such a test routine may be executed in response to any variety of requests. In some embodiments, the method 2400 is executed automatically in accordance with a corresponding test schedule as discussed above. For example, where a health test schedule requires collection of health data 200 at a given time (e.g., 12:00 pm), method 2400 may be automatically executed at 12:00 pm. As another example, where a health test schedule requires the continuous collection of a batch of health data 200 from 8:00 am-6:00 pm, method 2400 may be automatically executed at 8:00 am, and the health test may not be completed until 6:00 pm. As yet another example, where a health test schedule requires the repeated collection of health data 200 hourly from 8:00 am-6:00 pm, method 2400 may be automatically executed at 8:00 am, 9:00 am, and so forth. In some embodiments, the method may be executed in response to an employer's request to execute a health test of the employee (e.g., via selection of the 'Conduct Health Test" button 2306).

Upon user selection of the option to "Exit" (e.g., selecting the "Exit" button 2308 or 2310 of FIG. 23A or 23B), as depicted at block 2212 of FIG. 22, the method may return to displaying the interactive health dashboard as discussed with regard to block 1902. In some embodiments, the user may abort a health test, using the exit button 2310, regardless of whether the health test was initiated by the employee or initiated automatically by the system 100 (e.g., based on a test schedule).

Figure 25A:
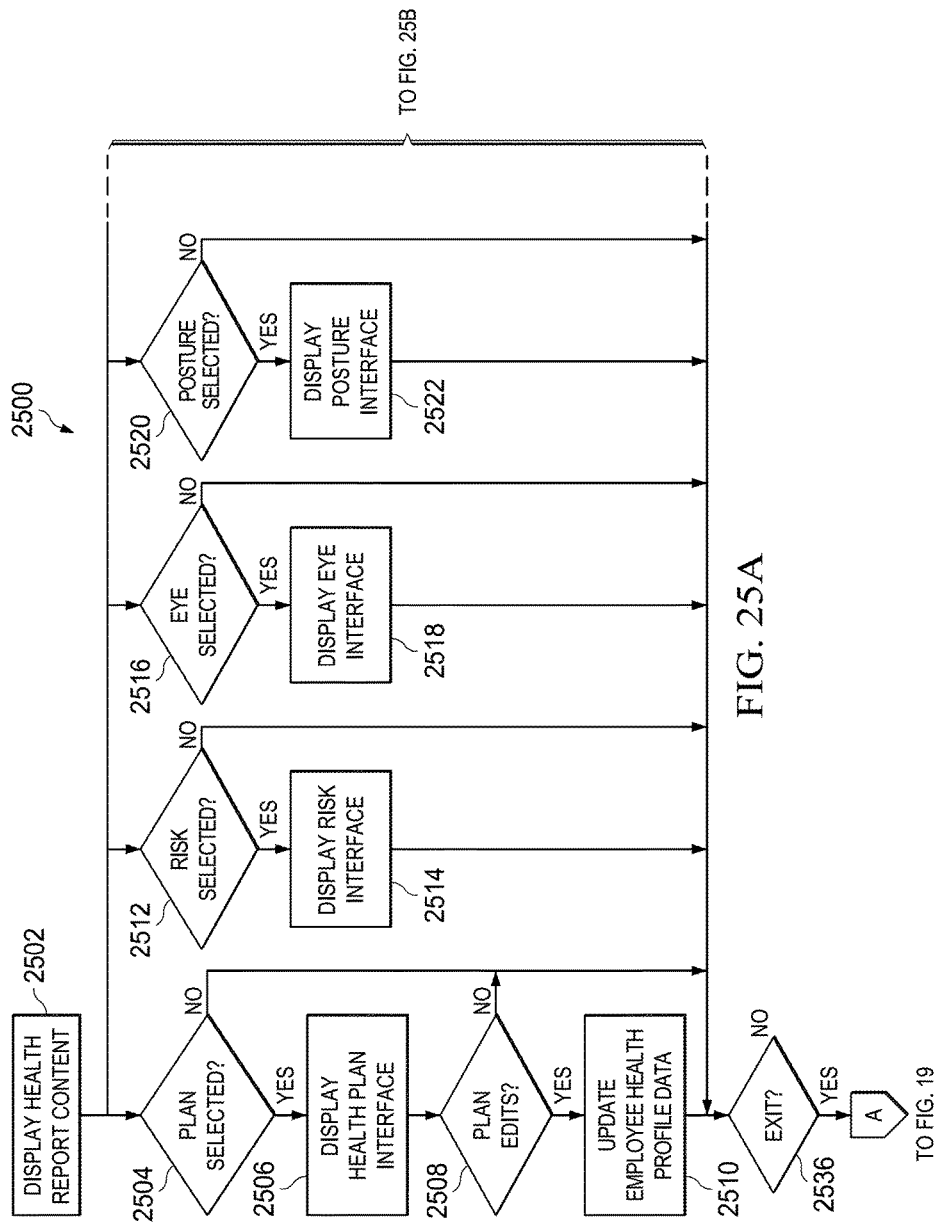
FIGS. 25A and 25B include a flowchart that illustrates a method for displaying an interactive report tab in accordance with one or more embodiments of the present invention.
Figure 25B:
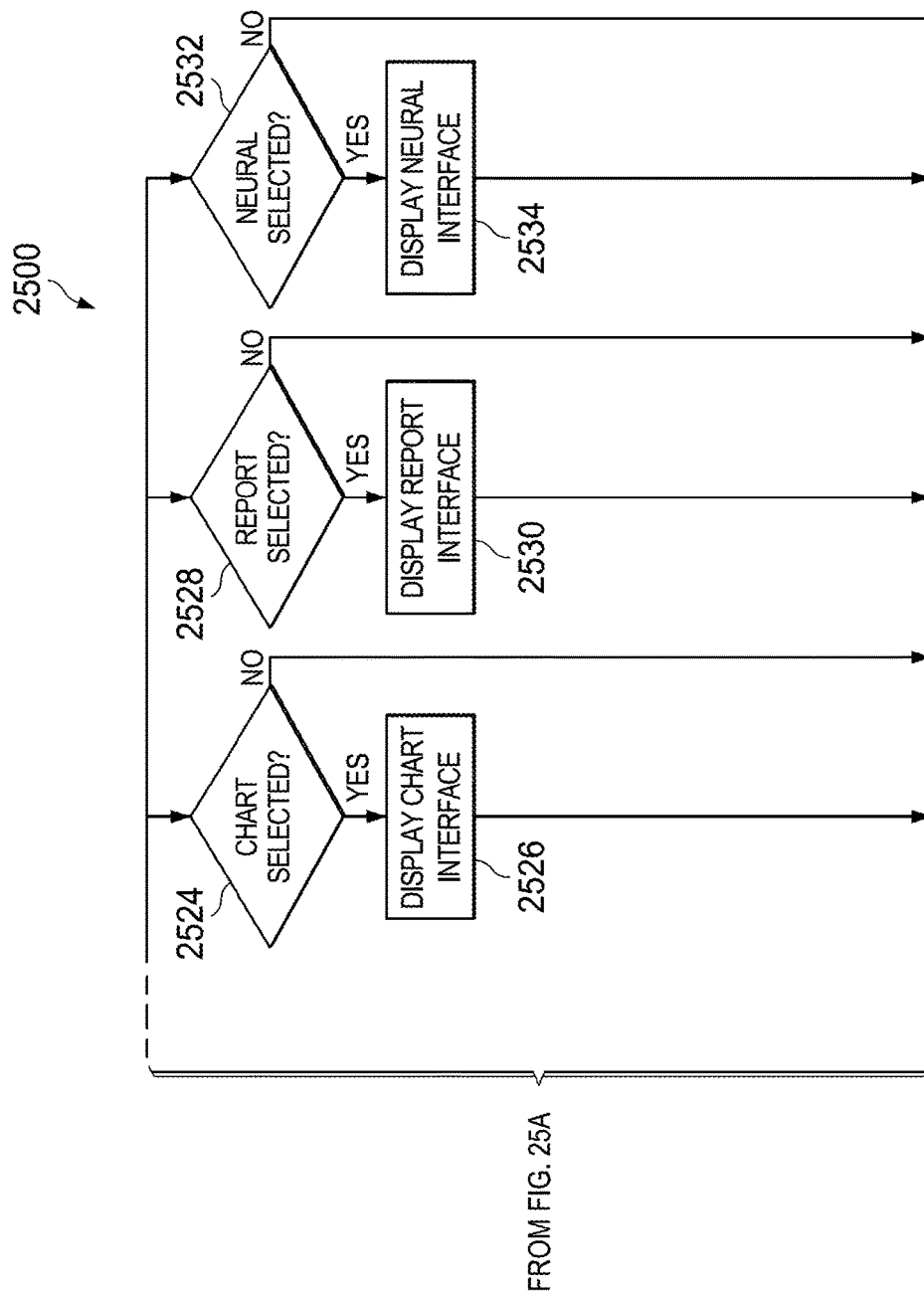

In some embodiments, upon the user selecting the report tab 2104, as depicted at block 1912 of FIG. 19, method 1900 may include displaying the interactive report tab 2104, as depicted at block 1914. FIGS. 25A and 25B include a flowchart that illustrates a method 2500 for displaying the interactive report tab in accordance with one or more embodiments of the present invention. Method 2500 may include displaying health report content, as depicted at block 2502. FIG. 26A-26G illustrate an exemplary displays of the health report tab 2100 including health report content 2600 in accordance with one or more embodiments of the present invention. In some embodiments, the server 104 may serve the health report content 2600 to computer 130 for display.

Figure 26A:
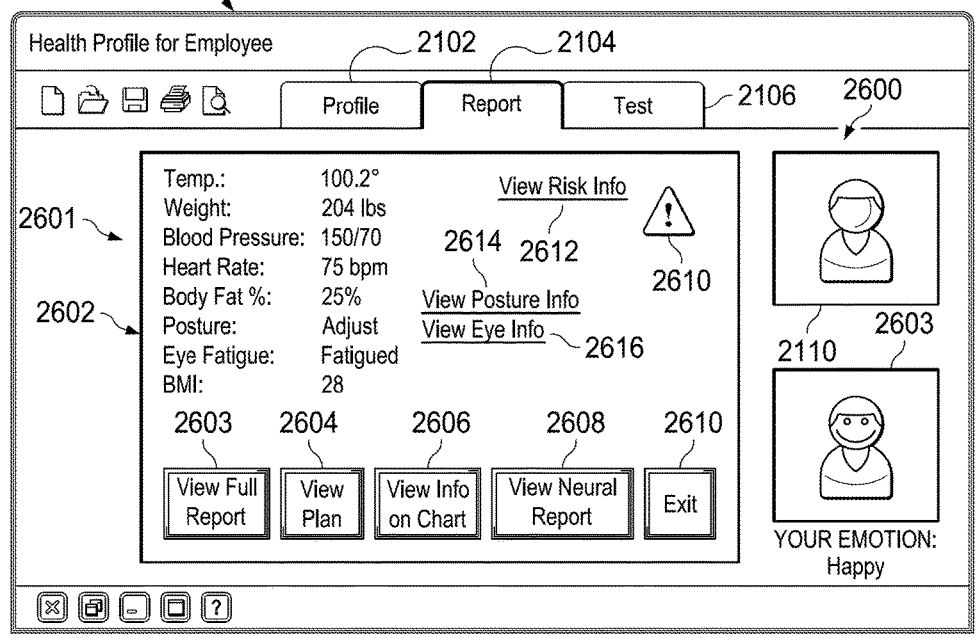
FIG. 26A to 26K are screen-shots that illustrate exemplary displays of a report tab in accordance with one or more embodiments of the present invention.

In some embodiments, an initial/summary view 2601 of the health report tab 2102 includes the interactive avatar 2110, an emotion avatar 2603, an overview/summary of the heath profile data 2602, a "View Full Report" button 2603, a "View Plan" button 2604, a "View Info on Chart" button 2606, a "View Neural Report" button 2608, and an "Exit" button 2610 (See FIG. 26A). The emotion avatar 2603 may be similar to the emotion avatar 1710 described with regard to FIG. 17. For example, the emotion avatar 2603 may include a graphical depiction of the employee's current emotional state, current facial expressions, gestures, and/or the like. In response to determining that the employee is smiling and/or happy (e.g., via the determined emotion 1336 and/or the determined facial movement 1345), the avatar 2603 may be dynamically updated to include graphic illustration of a smile, as depicted, to mimic the current facial emotion and/or expression of the employee. Thus, the avatar 2603 may reflect the employee's current emotional state, facial expressions, gestures, and/or the like The overview of the heath profile data 2602 may include the determined values for some or all of the health characteristics and/or health conditions of the most recent health profile data 1300 for the employee.

In some embodiments, where the health profile data 1300 identifies one or more health risk for the employee, a warning icon may be displayed in association to a user selectable link "View Risk Info". For example, where the health profile data 1300 indicates the user is at risk for obesity and diabetes and/or heart disease, warning icon 2610 and the link to "View Risk Info" 2612 may be displayed in the summary view of the report tab 2104. In some embodiments, where a condition is determined to be serious (e.g., where an alert condition exists), the warning icon 2610 may be replaced with an "alert icon" that is intended to communicate the importance of the alert condition. For example, the warning icon 2610 may include a yellow triangle, where as the "alert icon" may include a flashing red "X" intended to catch the employee's attention. In some embodiments, upon selecting the alert icon, the employee may be prompted to override a corresponding alert or allow the alert to be transmitted. If the employee selects to override the alert, the alert may not be sent. Thus, a user may be able to control the sending of alerts, including those generated during execution of the health test of method 2000. If the employee does not override the alert in a given period of time (e.g., 10 seconds) the alert may be transmitted. In some embodiments, a similar warning icon and/or interactive alert icon is displayed via the health status widget 1704.

In some embodiments, where the health profile data 1300 identifies one or more health characteristics/conditions that may require attention/correction, a user selectable link for navigating to a corresponding set of information is displayed. For example, where the health profile data 1300 indicates the employee's posture is incorrect or otherwise needs to be adjusted, a user selectable link to "View Posture Info" 2614 may be provided. As a further example, where the health profile data 1300 indicates the employee's eyes may be fatigued, a user selectable link to "View Eye Info" 2616 may be provided.

Figure 26B:
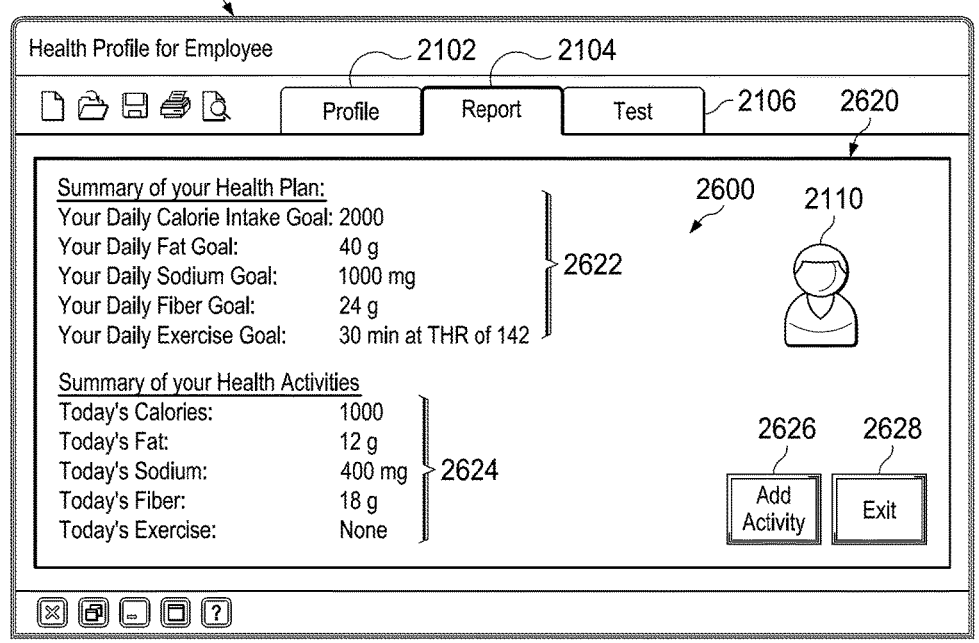

Upon selection of the "View Plan" button 2604, as depicted at block 2504, method 2500 may proceed to displaying health plan interface view, as depicted at block 2506. FIG. 26B illustrates an exemplary health plan interface view 2620 in accordance with one or more embodiments of the present invention. In some embodiments, the health plan interface view 2620 may include a health plan summary 2622. The health plan summary 2622 may provide a summary of some or all of the current health plan 1308 for the employee. For example, the health plan summary 2622 may include a listing of health goals specified by health plan 1308. In some embodiments, the employee can edit the plan 1308 by selecting and modifying a particular goal via the health plan interface view.

Figure 26C:
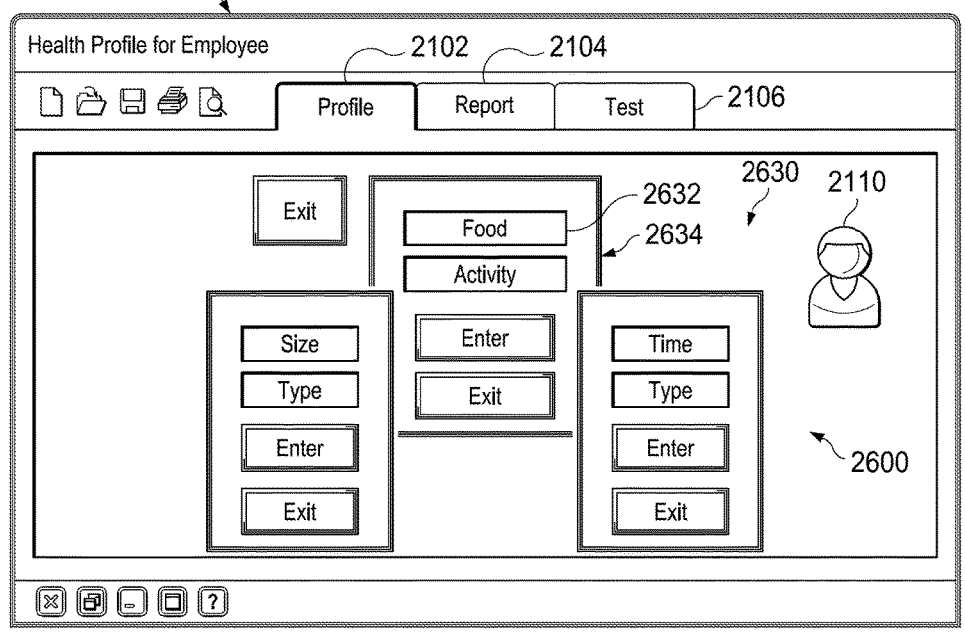

In some embodiments, the health plan interface view 2620 may include a health activity summary 2624 that reflects activities undertaken by the employee in an attempt to follow the health plan 1308. For example, the health activity summary 2624 may include a listing of information related to what the employee has eaten that day (e.g., calorie, fat, sodium, and fiber intake) and/or exercises undertaken by the employee. In some embodiments, upon selection of an "Add Activity" button 2626, an activity entry view 2630 may be displayed, as depicted in FIG. 26C. The employee may select the "Food" button 2632 to enter a size/type of food consumed (one serving of oatmeal), and or select the "Activity" button 2634 to enter a time/type of activity (e.g., running for 1 hour).

In response to receiving any edits to the plan (e.g., edit of the health plan and/or entry of activities), as depicted at block 2508, the employee's health information is updated to reflect the changes, as depicted at block 2510. For example, the employee's user health information 109 may be updated to include the modified health plan data and/or the activities entered. Upon selection of the "Exit" button 2628, the method may return to displaying the initial/summary plan view of FIG. 26A.

Figure 26D:
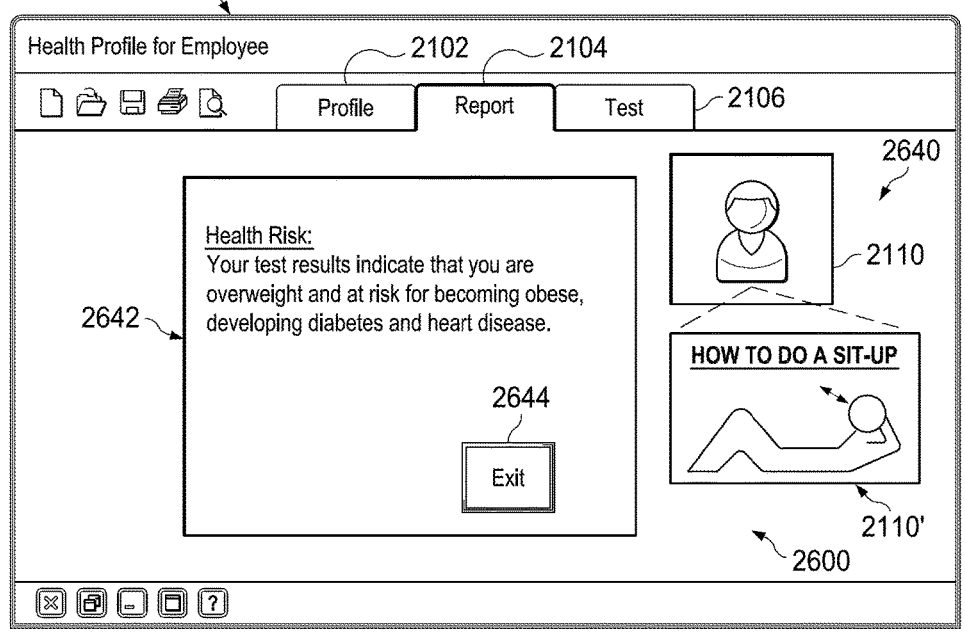

Upon selection of the risk icon/link 2610/2612, as depicted at block 2512, method 2500 may proceed to displaying a risk interface view, as depicted at block 2514. FIG. 26D illustrates an exemplary risk interface view 2640 in accordance with one or more embodiments of the present invention. The risk interface view 2640 may include a health risk dialog 2642 that alerts the user to health risk 1306 identified in their current health profile data 1300. For example, where the current health profile data 1300 indicates the user is at risk for obesity and diabetes and/or heart disease, the dialog may inform them of the risk. In some embodiments, the avatar 2110 may read the content of the dialog aloud to ensure the employee is aware of the risk. Alerting the employee to predicted health issues and/or associated health risks may enable the employee to proactively respond to predicted health issues and/or associated health risks before they escalate into actual health conditions.

In some embodiments, the avatar 2110 may include a coaching avatar that provides instructions, suggestions, and/or demonstrations that are intended to help coach the employee in improving their health and accomplishing one or more of their health goals. For example, as described herein, the avatar 2110 may provide an animated demonstration of an exercise (e.g., how to perform sit-ups, stretching, or the like) that can be performed by the employee to accomplish on more goals of their health plan (e.g., complete a daily exercise goal) or otherwise improve their health (e.g., reduce an identified health risk). In some embodiments, the coaching avatar 2110 may include an animated character that talks to the employee to help communicate coaching and suggestions. For example, the avatar 2110 may provide suggestions, such as "Your blood pressure is high, try walking twenty minutes per day to reduce your blood pressure". The avatar 2110 may provide the information audibly (e.g., via speakers of the user computer), with the avatar 2110 being animated such that it appears the avatar is speaking to the user. As a further example, the coaching avatar 2110 may provide coaching regarding the suggested actions. For example, where the health plan includes performing sit-up exercises, the coaching avatar 2110 may tell the user audibly, "This is how to do a sit-up properly" followed by the avatar 2110 being animated to provide a visual demonstration of how to do a sit-up (See avatar 2110'). Such an interface may provide an aspect of interaction that encourages the employee to listen to, comprehend and act on the provided information. Moreover, such coaching may help to reduce the employee's level of anxiety about engaging in the suggested activities of the health plan by providing guidance that walks the employee through the steps for completing the suggested activities. Coaching avatars may be provided throughout the interactive health dashboard or similar interfaces (e.g., the health status avatar 1703 of the health status widget 1704) for communicating health information and coaching the employee in improving their health and/or accomplishing their health goals.

Upon selection of the "Exit" button 2644, the method 2500 may return to displaying the initial/summary plan view of FIG. 26A.

Figure 26E:
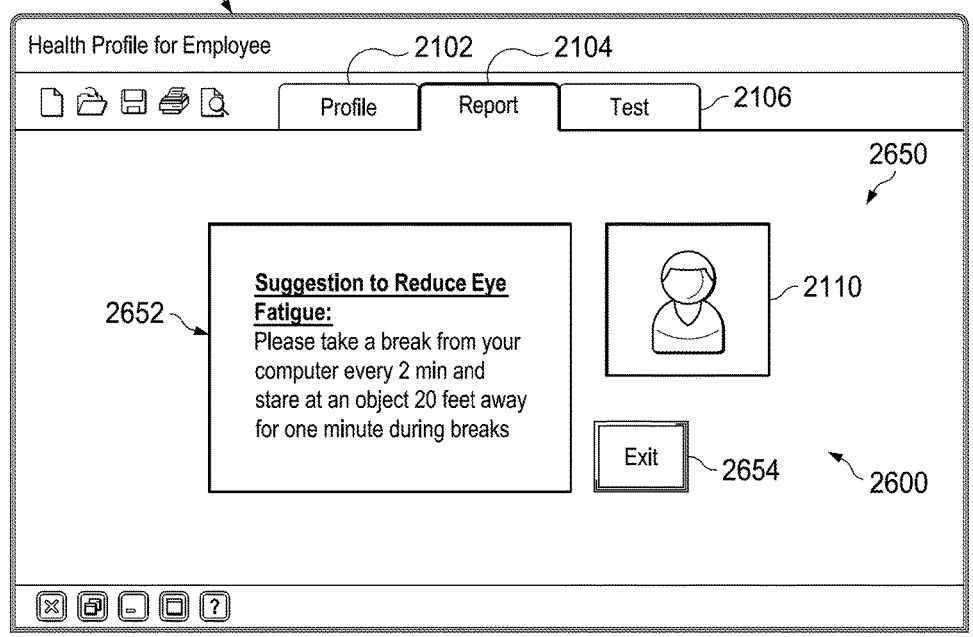

Upon selection of the "View Eye Info" link 2616, as depicted at block 2516, method 2500 may proceed to displaying an eye interface view, as depicted at block 2518. FIG. 26E illustrates an exemplary eye interface view 2650 in accordance with one or more embodiments of the present invention. The eye interface view 2650 may include an eye information dialog 2652 that provides suggestions to the employee for reducing eye fatigue. For example, the dialog may suggest that the employee take a break from the computer every twenty minutes, and stare at an object twenty feet away for one minute during the breaks. In some embodiments, the avatar 2110 may read the content of the dialog aloud to ensure the employee is aware of the exercise. In some embodiments, the avatar 2110 may include a coaching avatar to help communicate the suggestions for reducing eye fatigue. For example, the avatar 2646 may include an animated demonstration of a user looking away from their monitor to another object located nearby. Upon selection of the "Exit" button 2654, the method may return to displaying the initial/summary plan view of FIG. 26A.

Figure 26F:
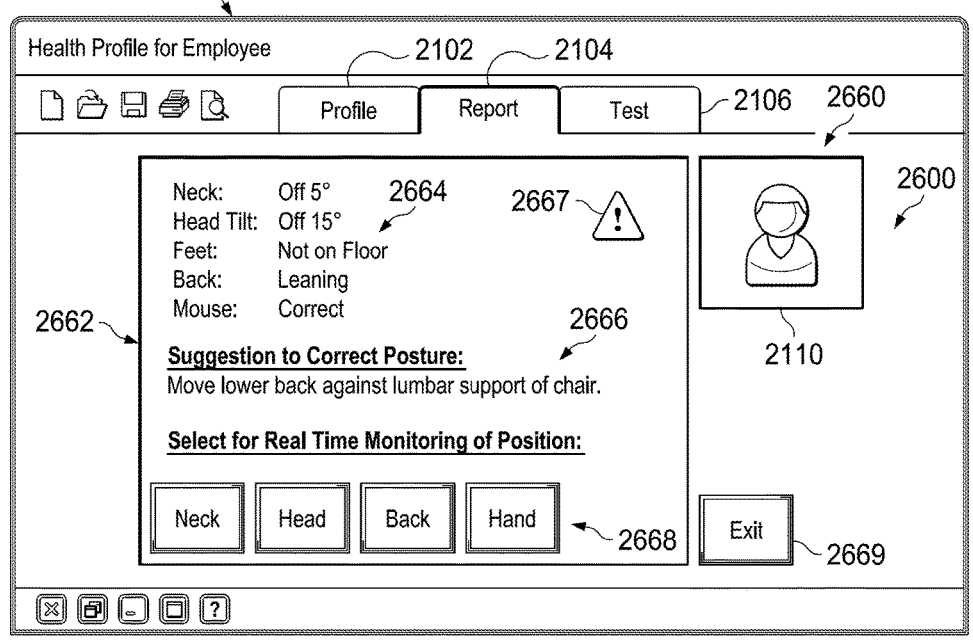
Figure 26G:
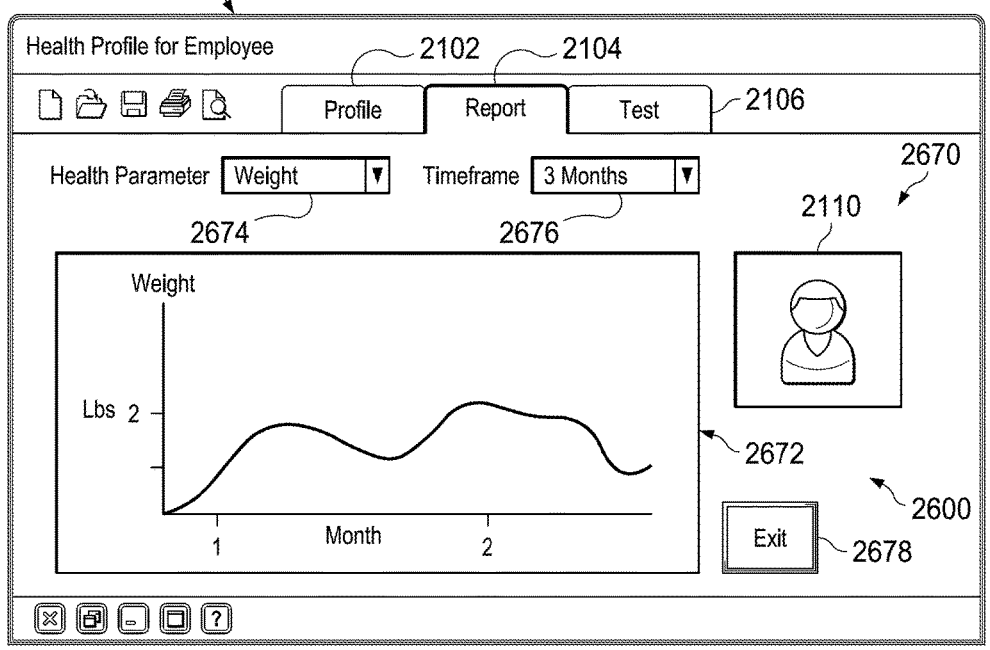

Upon selection of the "View Posture Info" link 2614, as depicted at block 2520, method 2500 may proceed to displaying a posture interface view, as depicted at block 2522. FIG. 26F illustrates an exemplary posture interface view 2660 in accordance with one or more embodiments of the present invention. The posture interface view 2660 may include a posture information dialog 2662 that includes a summary of the employee's body position 2664 (e.g., according to the most recent health test) and provides suggestions 2666 to the employee for improving their posture. For example, the suggestion 2666 may suggest that the employee move their lower back against the lumbar support of their chair. In some embodiments, the avatar 2110 may read the content of the dialog aloud to ensure the employee is aware of their posture and the suggestions to correct/improve their posture. In some embodiments, the avatar 2110 may include a coaching avatar to help communicate the suggestions for improving the employee's posture. For example, the avatar 2110 may include an animated demonstration of how to sit in a chair properly. In some embodiments, the dialogue may include buttons to initiate testing of a particular aspect of their posture. For example, upon user selection of one of the "Neck", "Head", "Back" or "Hand" buttons 2668, the server 104 may employ corresponding sensors 104 and/or the computer 130 to acquire health data 200 corresponding thereto, process the health data 200 to determine the current position of the employee's neck, head, back or hand, and update the summary of their body position 2664 in the dialogue 2662 to reflect their current body position. Such an interactive feature may enable the employee to make incremental adjustments to their body position, initiate a test for one or more parts of the body, and receive instant feedback to ensure they are correcting their body position/posture. In some embodiments, a posture status icon 2667 may provide an indication of the employee's posture. The icon 2667 may be a warning icon (e.g., yellow triangle) when the employee's posture needs to be adjusted and may be a positive icon (e.g., a green check) when the employee's posture is good and, thus, does not need to be adjusted. Upon selection of the "Exit" button 2669, the method may return to displaying the initial/summary view of FIG. 26A.

Upon selection of the "View Info on Chart" button 2606, as depicted at block 2524, method 2500 may proceed to displaying a chart interface view, as depicted at block 2526. FIG. 26F illustrates an exemplary chart interface view 2670 in accordance with one or more embodiments of the present invention. The chart interface view 2670 may include a chart 2672 displaying a plot of selected parameters. For example, the chart may display a graph of the employee's weight over a selected period of time (e.g., the last 3 months). In some embodiments, the employee may select one or more parameters (e.g., health characteristics 1302 and/or health conditions 1304) to be graphed and/or a timeframe over which they are to be graphed, via a "Health Parameter" selection drop-down box 2674 and a "Timeframe" selection drop-down box 2676, respectively. In some embodiments, the avatar 2110 may instruct the employee to select a parameter and a timeframe to be displayed via the drop-down selections. Upon selection of the "Exit" button 2678, the method may return to displaying the initial/summary plan view of FIG. 26A.

Upon selection of the "View Report" button 2603, as depicted at block 2528, method 2500 may proceed to displaying a health report interface, as depicted at block 2530. The health report interface may include display of some or all of the information of the health profile 1300 for the employee. For example, the health report interface may include display of a health report similar to that of health report 1380 of FIG. 13B. Upon completion of viewing the health report, the method may return to displaying the initial/summary view of FIG. 26A.

Figure 26H:
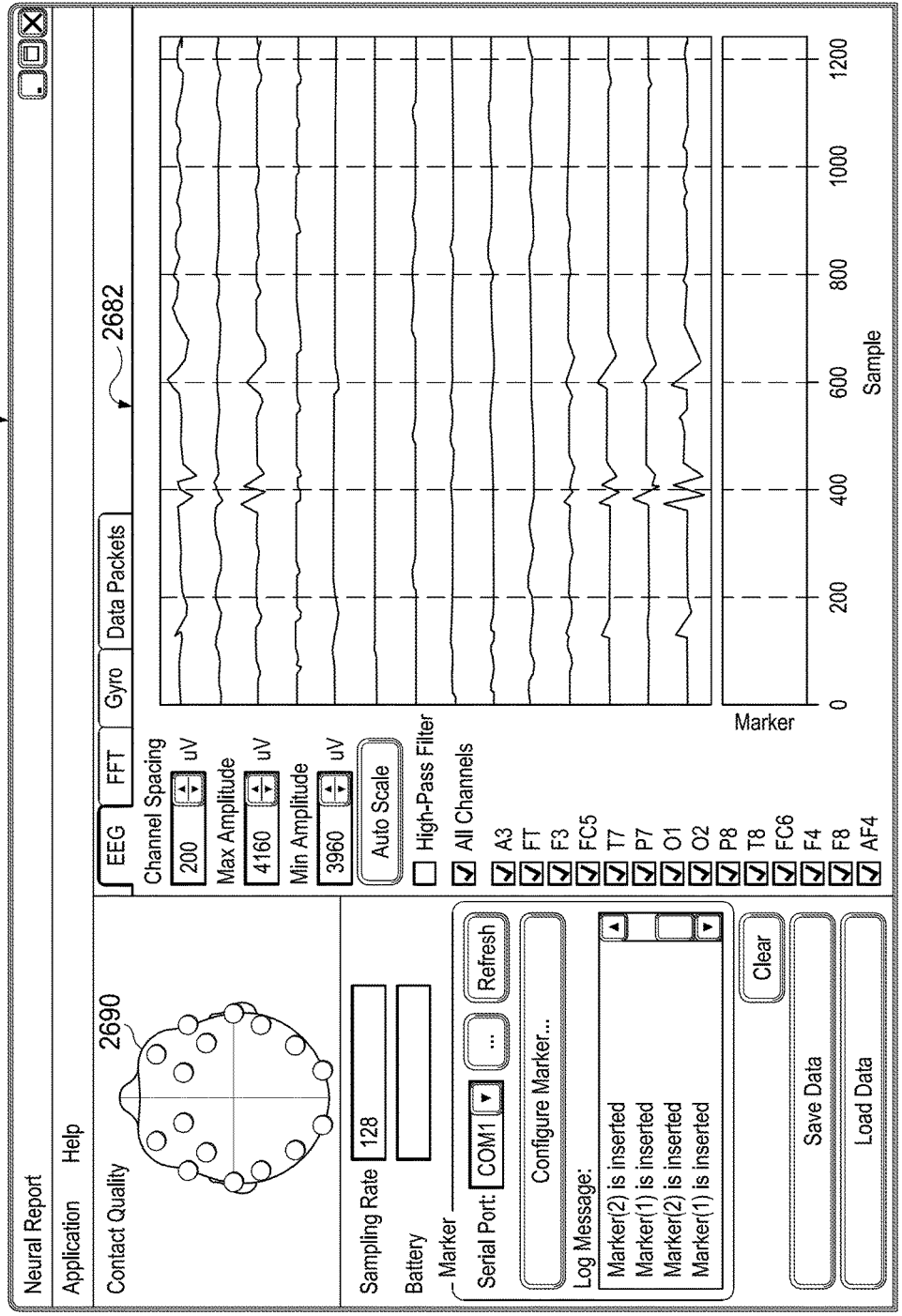
Figure 26I:
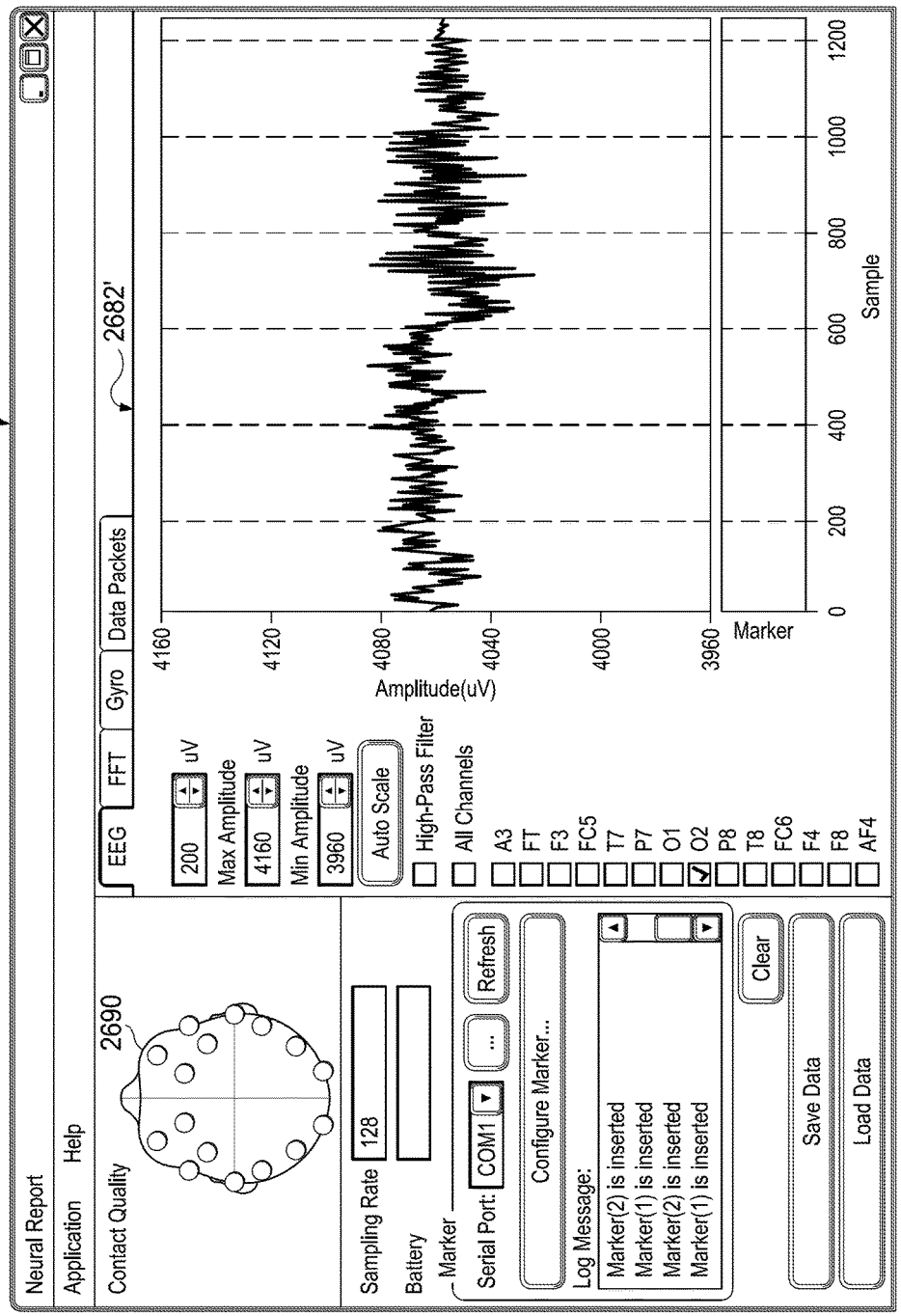
Figure 26J:
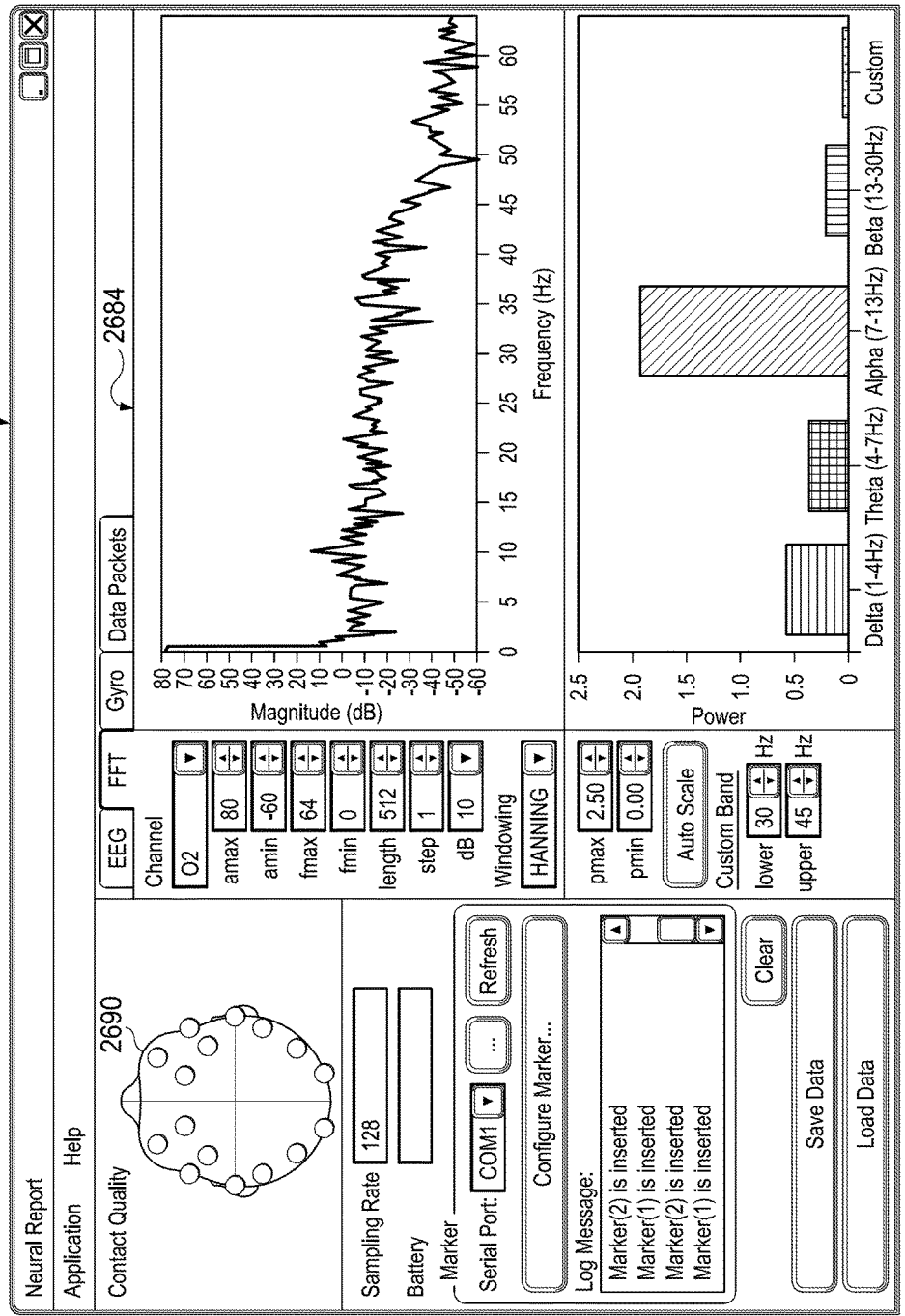
Figure 26K:
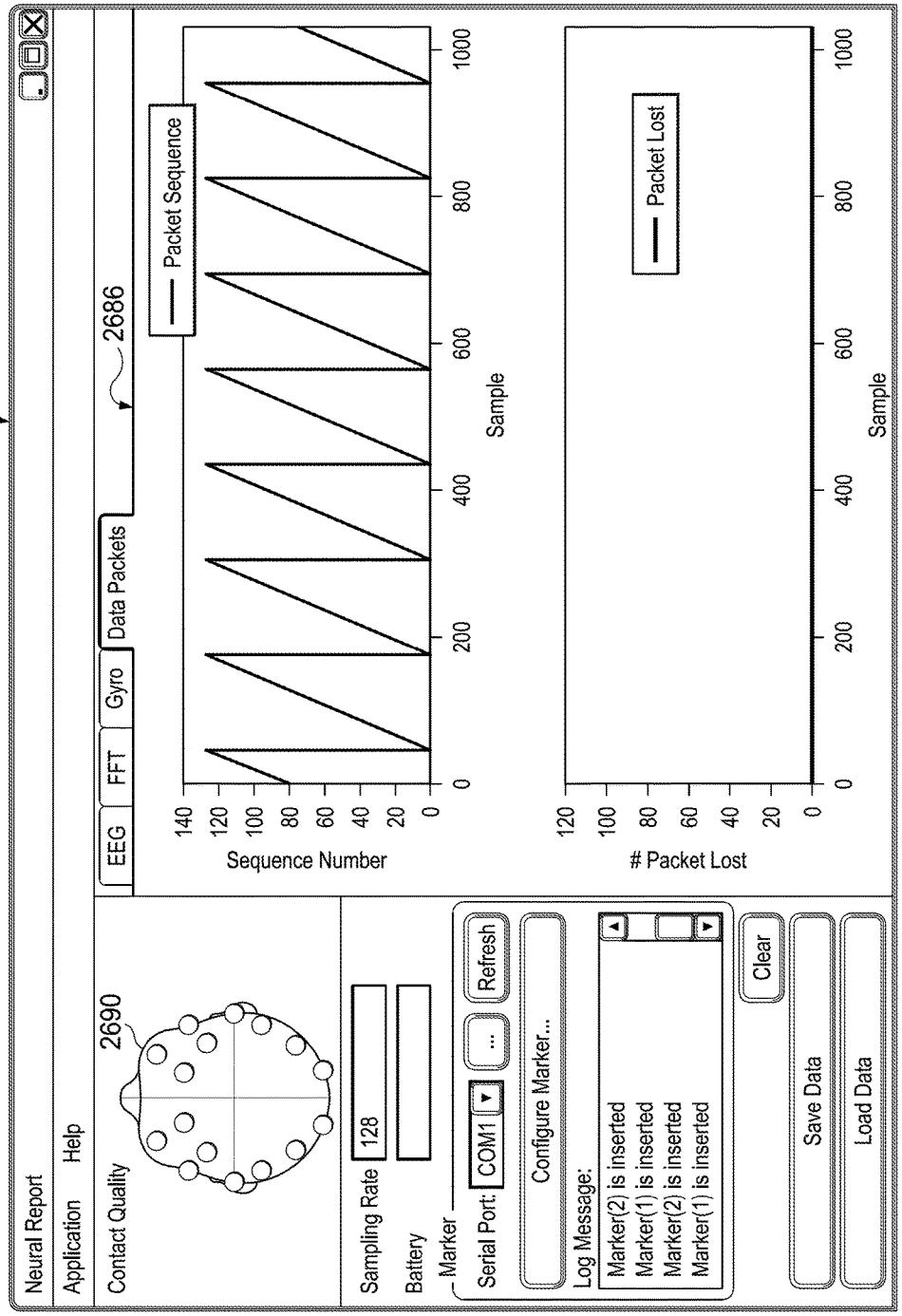

Upon selection of the "View Neural Report" button 2608, as depicted at block 2532, the method 2500 may proceed to displaying a neural report interface, as depicted at block 2534. The neural report interface may include display of the health profile data relating to the neural/brain activity for the employee. For example, the neural report interface may include display of a neural report 2680 as depicted in FIGS. 26H-26K, including an EEG report 2682, an FFT report 2684, and a data packets report 2686. The neural report 2680 may include a neural sensor graphic 2690 indicative of the status of various contacts points with the employee's scalp. FIG. 26H illustrates an exemplary EEG report 2682 for multiple sensor channels. FIG. 26I illustrates an exemplary EEG report 2682' for a single selected sensor channel. The EEG report 2682 may include a real time data stream and/or log of the neuro signals received from the neural sensors 218. FIG. 26J illustrates an exemplary FFT report 2684 for a single selected sensor channel. The FFT report 2684 may include a real time data stream and/or log of the neuro signals received from the neural sensors 218 and an FFT histogram display of the various signal types (e.g., delta, theta, alpha, beta, and/or custom bands). FIG. 26K illustrates an exemplary data packets report 2686. The data packets report 2686 may include a log of data packets transmitted from the neural sensors 218 (e.g., from the neuro-headset 480), including a log of any data packets that have been lost. Such a data packets report 2686 may help verify data integrity by enabling confirmation of the transmission of neural data 200i to server 104.

Upon completion of viewing the health report, the method may return to displaying the initial/summary plan view of FIG. 26A.

Upon selection of the "Exit" button 2610 illustrated in FIG. 26B, as depicted at block 2536, the method 2500 may return to displaying the interactive health dashboard as discussed with regard to block 1902.

Figure 27:
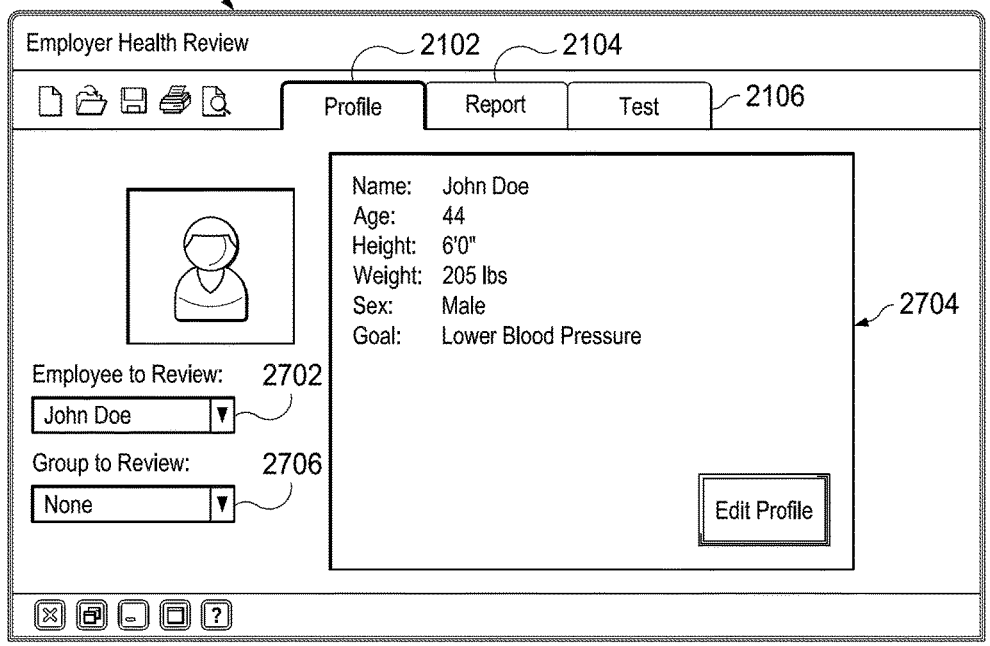
FIG. 27 is a screen-shot that illustrates an exemplary display of a reviewer interface in accordance with one or more embodiments of the present invention.

Upon determining that the user is not an employee (see block 1514 of FIG. 15), but is instead, for example, an employer having permissions to review employee health profile, the method 1500 may proceed to providing a reviewer interface, as depicted at block 1514. FIG. 27 depicts an exemplary reviewer interface 2700 in accordance with one or more embodiments of the present invention. In some embodiments, where the user has permission to review a set of employee's health information, the drop-down selection box 2702 is populated with the names of the set of employees. Upon selection of an employee (e.g., John Doe), the reviewer interface 2700 may provide an interactive reviewer health dashboard 2704 that is the same or similar to the interactive dashboard that would be displayed to the employee (i.e., the same or similar to the interactive dashboard described above). Thus, for example, the reviewer may review and/or edit the selected employee's health profile and health report, and even initiate a health test for the employee. Such review may enable the employer to identify health conditions that may need to be addressed, to track employees' progress with regard to health plans, to ensure employees are engaging with the health monitoring system/application, and/or the like.

In some embodiments, a reviewer interface may enable a reviewer to select a plurality of employee's to review. For example, a group drop-down box 2706 may enable a reviewer to select a particular facility, region, division, team, or the like. Upon selection of a group (e.g., a particular facility, region, division, team, or the like) the reviewer interface may display health data/reports corresponding the employees that work in the particular facility, region, division, team, or the like. For example, the reviewer may be presented with a report similar to that of report 1380 of FIG. 13B, for the selected group. Such a group report may include the average values of the health characteristics, conditions, risk, plans and/or the like for the group, and/or corresponding statistics that can be used to assess the health of the group (e.g., standard deviations, etc.). Such an embodiment may enable an employer to determine whether or not a particular group of employees (e.g., employees of a facility, region, division, team, or the like) is experiencing normal or abnormal health conditions. For example, where a report for a facility indicates that an abnormally high percentage of the employees at the facility have symptoms of allergies, the reviewer may determine that steps need to be taken at the facility to reduce airborne contaminants that may be causing the allergy symptoms. As a further example, where a report for a team indicates that an abnormally high percentage of the employee team members have symptoms of high stress or depression, the reviewer may determine that steps need to be taken to reduce the stress level and/or depression for the team. Thus, the review of employee health may enable the employer to take steps to improve employee health, which may, in turn, increase the employee's productivity.

In some embodiments, system 100 may identify whether or not a plurality of employees appears to be experiencing similar conditions, characteristics, risks or the like, and may provide a corresponding alert to the employer. For example, where a report for a facility indicates that an abnormally high percentage of the employees at the facility have symptoms of allergies, the system 100 may generate an alert to the employer regarding the condition.

Figure 28:
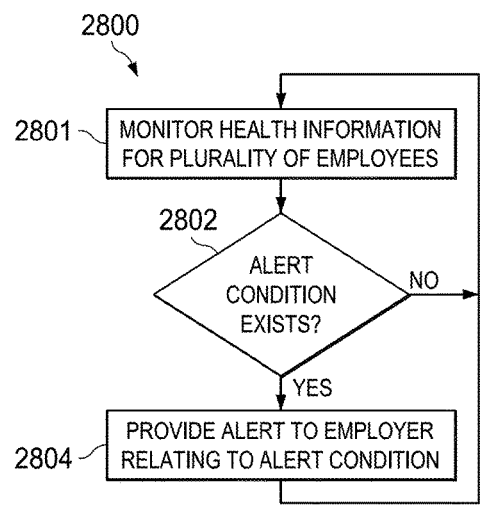
FIG. 28 is a flowchart that illustrates a method of assessing health information for a plurality of employees in accordance with one or more embodiments of the present invention.

FIG. 28 is a flowchart that illustrates a method 2800 of assessing health information for a plurality of employees to determine whether an alert condition exists in accordance with one or more embodiments of the present invention. Method 2800 may include monitoring health information for a plurality of employees, as depicted at block 2801. In some embodiments, monitoring health information for a plurality of employees may include reviewing the health profile data for a discrete group of employees. For example, monitoring health information for a plurality of employees may include reviewing health profile data for all of the employees that work in a particular facility, region, division, team, or the like. In some embodiments, monitoring health information for a plurality of employees includes determining the number/percentage of the plurality of employees that are experiencing a given characteristic, condition or risk. For example, monitoring health information for a plurality of employees may include determining the percentage of the employee's that have a body weight is above 113 kg (250 lbs.). In some embodiments, monitoring health information for a plurality of employees includes determining a single value for a given characteristic, condition or risk. For example, monitoring health information for a plurality of employees may include determining the average weight for the plurality of employees. Other embodiments may include similar determinations for various other characteristics 1302, conditions 1304 and risks 1306.

Method 2800 may include determining whether an alert condition exists based on the review of the health profile data for the plurality of employees, as depicted at block 2802. In some embodiments, it may be determined that an alert condition exists based on comparison of results of the monitoring to predetermined threshold values. For example, where a threshold percentage for a group of employees over 113 kg (250 lbs.) is 50%, it may be determined that an alert condition exists if greater than 50% of the group of employees has a body weight above 113 kg (250 lbs.). As a further example, where a threshold average weight for a group of employees is 113 kg (250 lbs.), it may be determined that an alert condition exists if the average weight for the group of employees is above 113 kg (250 lbs.). Other embodiments may include similar determinations for various other characteristics 1302, conditions 1304 and risks 1306.

In response to determining that an alert condition exists, method 2800 may proceed to providing an alert to the employer relating to the alert condition, as depicted at block 2804. In some embodiments, providing an alert to the employer relating to the alert condition may include providing the employer with an alert indicating that a plurality of the employees each have health profiles that are of concern. For example, upon logging into the health monitoring application, the employer may be provided with a homepage screen that includes an alert to the condition. Alerting the employer to predicted health issues and/or associated health risks may enable the employer to proactively respond to predicted health issues and/or associated health risks before they escalate into actual health issues. For example, where an alert indicates that a high percentage of employees at a facility are at risk for becoming obese, the employer may be able to implement a dietary program and/or an exercise program for the employees at the facility to help prevent the employees from becoming obese.

Figure 29:
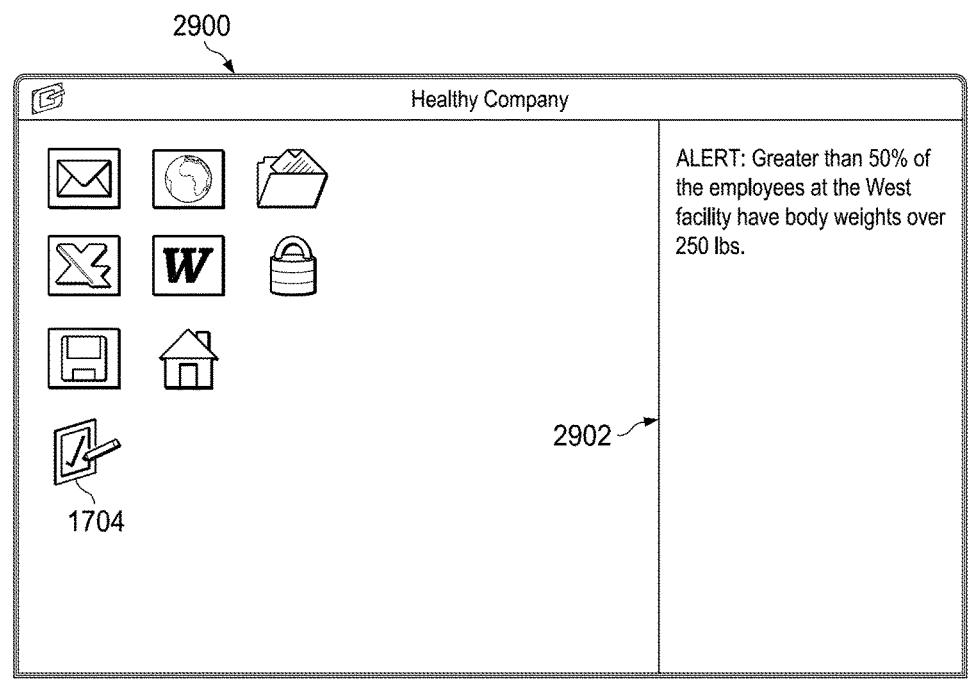
FIG. 29 is a screen-shot that illustrates an exemplary display of a reviewer homepage screen in accordance with one or more embodiments of the present invention.

FIG. 29 illustrates reviewer homepage screen 2900 including an alert 2902 that may be displayed upon the reviewer logging into the health monitoring application in accordance with one or more embodiments of the present technique. Alert 2902 may include an icon, text, or other information that is indicative of a plurality of employees experiencing health characteristics, conditions, or risk that may be of concern. For example, in the illustrated embodiment, the alert 2902 is provided in a widget on the employer's desktop and states, "Greater than 50% of the employees at the West facility have body weights over 250 lbs.". In some embodiments, a similar alert may be provided within the interactive health dashboard displayed to the employer. For example, referring to FIG. 27, where the employer selects the "West Facility" in the "Group to review" drop-down box 2706, the resulting display may include a similar alert stating "Greater than 50% of the employees at the West facility have body weights over 250 lbs." Such embodiments may provide employers with the ability to identify and remedy health issues that may be affecting a group of employees.

It will be appreciated that the methods 1500, 1900, 2000, 2200, 2400, 2500 and 2800 are exemplary embodiments of methods that may be employed in accordance with techniques described herein. The methods 1500, 1900, 2000, 2200, 2400, 2500 and 2800 may be may be modified to facilitate variations of its implementations and uses. The methods 1500, 1900, 2000, 2200, 2400, 2500 and 2800 may be implemented in software, hardware, or a combination thereof. Some or all of the methods 1500, 1900, 2000, 2200, 2400, 2500 and 2800 may be implemented by one or more of the modules/applications described herein, such as server modules 1210 and/or computer module 308. The order of the method 1500, 1900, 2000, 2200, 2400, 2500 and 2800 may be changed, and various elements may be added, reordered, combined, omitted, modified, etc.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification.

As used throughout this application, the word "may" is used in a permissive sense (i.e., meaning having the potential to), rather than the mandatory sense (i.e., meaning must). The words "include", "including", and "includes" mean including, but not limited to. As used throughout this application, the singular forms "a", "an" and "the" include plural referents unless the content clearly indicates otherwise. Thus, for example, reference to "an element" may include a combination of two or more elements. Unless specifically stated otherwise, as apparent from the discussion, it is appreciated that throughout this specification discussions utilizing terms such as "processing", "computing", "calculating", "determining" or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical electronic or magnetic quantities within memories, registers, or other information storage devices, transmission devices, or display devices of the special purpose computer or similar special purpose electronic processing/computing device.

The techniques described herein may include or otherwise be used in conjunction with techniques described in U.S. Provisional Patent Application No. 61/504,638 filed on Jul. 5, 2011 and titled "SYSTEM, COMPUTER PROGRAM PRODUCT AND COMPUTER-IMPLEMENTED METHOD FOR IMPROVING AND MONITORING THE HEALTH AND PRODUCTIVITY OF EMPLOYEES", U.S. Provisional Patent Application No. 61/659,831 filed on Jun. 14, 2012 and titled "SYSTEMS, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,790 filed on Jun. 14, 2012 and titled "SYSTEMS, COMPUTER MEDIUM AND COMPUTER-IMPLEMENTED METHODS FOR MONITORING AND IMPROVING COGNITIVE AND EMOTIVE HEALTH OF EMPLOYEES", U.S. Provisional Patent Application No. 61/659,796 filed on Jun. 14, 2012 and titled "COMPUTER MOUSE SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,800 filed on Jun. 14, 2012 and titled "CHAIR PAD SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,807 filed on Jun. 14, 2012 and titled "FLOOR MAT SYSTEM AND ASSOCIATED, COMPUTER MEDIUM AND COMPUTER-IMPLEMENTED METHODS FOR MONITORING AND IMPROVING HEALTH AND PRODUCTIVITY OF EMPLOYEES", U.S. Provisional Patent Application No. 61/659,810 filed on Jun. 14, 2012 and titled "SYSTEMS, COMPUTER MEDIUM AND COMPUTER-IMPLEMENTED METHODS FOR MONITORING AND IMPROVING BIOMETRIC HEALTH OF EMPLOYEES", U.S. Provisional Patent Application No. 61/659,818 filed on Jun. 14, 2012 and titled "SYSTEMS, COMPUTER MEDIUM AND COMPUTER-IMPLEMENTED METHODS FOR MONITORING AND IMPROVING BIOMECHANICAL HEALTH OF EMPLOYEES", and U.S. Provisional Patent Application No. 61/659,824 filed on Jun. 14, 2012 and titled "SYSTEMS, COMPUTER MEDIUM AND COMPUTER-IMPLEMENTED METHODS FOR COACHING EMPLOYEES BASED UPON MONITORED HEALTH CONDITIONS USING AN AVATAR", the disclosures of which are each hereby incorporated by reference in their entireties.

In this patent, certain U.S. patents, U.S. patent applications, or other materials (e.g., articles) have been incorporated by reference. The text of such U.S. patents, U.S. patent applications, and other materials is, however, only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference in this patent.

What is claimed is:

1. A system for monitoring employee health, comprising:
an employee workstation comprising:
- a computer display;
- a computer mouse sensing system;
- a chair sensing system;
- a floor mat sensing system; and
- a neural sensing system, the computer mouse sensing system comprising a computer mouse and a set of computer mouse sensors, the set of computer mouse sensors comprising:
- a computer mouse temperature sensor disposed in a body of the computer mouse and configured to sense a body temperature of an employee seated in a chair;
- a computer mouse blood condition sensor disposed in the body of the computer mouse and configured to sense blood condition of the employee seated in the chair; and
- a computer mouse blood pressure sensor comprising a wireless blood pressure cuff configured to sense a blood pressure of the employee, the chair sensing system comprising the chair and a set of chair pad sensors disposed in a seating surface of the chair, the set of chair pad sensors comprising:
- a chair pad temperature sensor configured to sense the body temperature of the employee seated in the chair; and
- a chair pad force sensor configured to sense force of the employee seated in the chair, the floor mat sensing system comprising a floor mat with a set of floor mat sensors disposed in the floor mat, the set of floor mat sensors comprising:
- a floor mat temperature sensor configured to sense the body temperature of the employee seated in the chair; and
- a floor mat force sensor configured to sense force of the employee seated in the chair, and the neural sensing system comprising a set of neural sensors configured to be disposed about a scalp of the employee seated in the chair and to sense brain activity of the employee, a health monitoring server configured to:
collect health data comprising:
- the body temperature of the employee sensed by the computer mouse temperature sensor;
- the blood condition of the employee sensed by the computer mouse blood condition sensor;
- the blood pressure of the employee sensed by the computer mouse blood pressure sensor;
- the body temperature of the employee sensed by the chair pad temperature sensor;
- the force of the employee sensed by the chair pad force sensor;
- the body temperature of the employee sensed by the floor mat temperature sensor;
- the force of the employee sensed by the floor mat force sensor; and
- the brain activity of the employee sensed by the neural sensors;

determine a body temperature of the employee based on the body temperature of the employee sensed by the computer mouse temperature sensor, the body temperature of the employee sensed by the chair pad temperature sensor and the body temperature of the employee sensed by the floor mat temperature sensor;

determine a blood condition of the employee based on the blood condition of the employee sensed by the computer mouse blood condition sensor;

determine a blood pressure of the employee based on the blood pressure of the employee sensed by the computer mouse blood pressure sensor;

determine a weight of the employee based on the force of the employee sensed by the chair pad force sensor and the force of the employee sensed by the floor mat force sensor;

determine a brain activity of the employee based on the brain activity of the employee sensed by the neural sensors;

determine, based on the brain activity of the employee, a sequence of motor functions and a risk of physical fatigue corresponding to the sequence of motor functions; and provide, to the employee workstation for display by way of the computer display, a health profile for the employee comprising the body temperature of the employee determined, the blood condition of the employee determined, the blood pressure of the employee determined, the weight of the employee determined, the brain activity of the employee determined, and the risk of physical fatigue determined, the computer display configured to display the health profile for the employee.

2. The system of claim 1, wherein the neural sensing system comprises a neural headset comprising the set of neural sensors configured to be disposed about a scalp of the employee.

3. The system of claim 1, wherein the neural sensing system comprises the set of neural sensors disposed in a headrest of the chair and configured to be disposed about the scalp of the employee seated in the chair.

4. The system of claim 1, wherein the set of neural sensors comprise dry electrodes.

5. The system of claim 1, wherein the health monitoring server is further configured to:
- compare a neural signal pattern of the brain activity of the employee sensed to a plurality of predetermined neural signal patterns to determine a matching neural signal pattern comprising neural signal pattern of the plurality of predetermined neural signal patterns that matches the neural signal pattern of the brain activity of the employee sensed; and
- determine a characteristic of the employee corresponding to the matching neural signal pattern, wherein the health profile for the employee comprises the characteristic of the employee corresponding to the matching neural signal pattern.

6. The system of claim 5, wherein the characteristic of the employee corresponding to the matched the neural signal pattern comprises risk of fatigue of the employee.

7. The system of claim 6, wherein the health monitoring server is further configured to:
- determine a level of motor function corresponding to the matching neural signal pattern;
- determine that the level of motor function is below a threshold value; and
- determining, in response to determining that that the level of motor function is below the threshold value, the risk of fatigue for the employee.

8. A method for monitoring employee health, comprising:
collecting, by a health monitoring server, health data for an employee located in an employee workstation, the employee workstation comprising:
- a computer display;
- a computer mouse sensing system;
- a chair sensing system;
- a floor mat sensing system; and
- a neural sensing system,
- the computer mouse sensing system comprising a computer mouse and a set of computer mouse sensors, the set of computer mouse sensors comprising:
  - a computer mouse temperature sensor disposed in a body of the computer mouse and configured to sense a body temperature of an employee seated in a chair;
  - a computer mouse blood condition sensor disposed in the body of the computer mouse and configured to sense blood condition of the employee seated in the chair; and
  - a computer mouse blood pressure sensor comprising a wireless blood pressure cuff configured to sense a blood pressure of the employee,
- the chair sensing system comprising the chair and a set of chair pad sensors disposed in a seating surface of the chair, the set of chair pad sensors comprising:
  - a chair pad temperature sensor configured to sense the body temperature of the employee seated in the chair; and
  - a chair pad force sensor configured to sense force of the employee seated in the chair,
- the floor mat sensing system comprising a floor mat with a set of floor mat sensors disposed in the floor mat, the set of floor mat sensors comprising:
  - a floor mat temperature sensor configured to sense the body temperature of the employee seated in the chair; and
  - a floor mat force sensor configured to sense force of the employee seated in the chair, and
- the neural sensing system comprising a set of neural sensors configured to be disposed about a scalp of the employee seated in the chair and to sense brain activity of the employee,
- the health data collected comprising:
  - the body temperature of the employee sensed by the computer mouse temperature sensor;
  - the blood condition of the employee sensed by the computer mouse blood condition sensor;
  - the blood pressure of the employee sensed by the computer mouse blood pressure sensor;
  - the body temperature of the employee sensed by the chair pad temperature sensor;
  - the force of the employee sensed by the chair pad force sensor;
  - the body temperature of the employee sensed by the floor mat temperature sensor;
  - the force of the employee sensed by the floor mat force sensor; and
  - the brain activity of the employee sensed by the neural sensors;
- determining, by the health monitoring server, a body temperature of the employee based on the body temperature of the employee sensed by the computer mouse temperature sensor, the body temperature of the employee sensed by the chair pad temperature sensor and the body temperature of the employee sensed by the floor mat temperature sensor;
- determining, by the health monitoring server, a blood condition of the employee based on the blood condition of the employee sensed by the computer mouse blood condition sensor;
- determining, by the health monitoring server, a blood pressure of the employee based on the blood pressure of the employee sensed by the computer mouse blood pressure sensor;
- determining, by the health monitoring server, a weight of the employee based on the force of the employee sensed by the chair pad force sensor and the force of the employee sensed by the floor mat force sensor;
- determining, by the health monitoring server, a brain activity of the employee based on the brain activity of the employee sensed by the neural sensors;
- determining, by the health monitoring server based on the brain activity of the employee, a sequence of motor functions and a risk of physical fatigue corresponding to the sequence of motor functions; and
- displaying, by the computer display, a health profile for the employee comprising the body temperature of the employee determined, the blood condition of the employee determined, the blood pressure of the employee determined, the weight employee determined, the brain activity of the employee determined, and the risk of physical fatigue determined.

9. The method of claim 8, wherein the neural sensing system comprises a neural headset comprising the set of neural sensors configured to be disposed about a scalp of the employee.

10. The method of claim 8, wherein the neural sensing system comprises the set of neural sensors disposed in a headrest of the chair and configured to be disposed about the scalp of the employee seated in the chair.

11. The method of claim 8, wherein the health monitoring server is further configured to:
- compare a neural signal pattern of the brain activity of the employee sensed to a plurality of predetermined neural signal patterns to determine a matching neural signal pattern comprising neural signal pattern of the plurality of predetermined neural signal patterns that matches the neural signal pattern of the brain activity of the employee sensed; and
- determine a characteristic of the employee corresponding to the matching neural signal pattern, wherein the health profile for the employee comprises the characteristic of the employee corresponding to the matching neural signal pattern.

12. The method of claim 11, wherein the characteristic of the employee corresponding to the matched the neural signal pattern comprises risk of fatigue of the employee.

13. The method of claim 12, wherein the health monitoring system is further configured to:
- determine a level of motor function corresponding to the matching neural signal pattern;
- determine that the level of motor function is below a threshold value; and
- determining, in response to determining that that the level of motor function is below the threshold value, the risk of fatigue for the employee.

14. Non-transitory computer readable storage medium comprising program instructions for monitoring employee health stored thereon that are executable by a processor to cause the following operations:
- collecting, by a health monitoring server, health data for an employee located in an employee workstation, the employee workstation comprising:
- a computer display;
- a computer mouse sensing system;
- a chair sensing system;
- a floor mat sensing system; and
- a neural sensing system, the computer mouse sensing system comprising a computer mouse and a set of computer mouse sensors, the set of computer mouse sensors comprising:
- a computer mouse temperature sensor disposed in a body of the computer mouse and configured to sense a body temperature of an employee seated in a chair;
- a computer mouse blood condition sensor disposed in the body of the computer mouse and configured to sense blood condition of the employee seated in the chair; and
- a computer mouse blood pressure sensor comprising a wireless blood pressure cuff configured to sense a blood pressure of the employee, the chair sensing system comprising the chair and a set of chair pad sensors disposed in a seating surface of the chair, the set of chair pad sensors comprising:
- a chair pad temperature sensor configured to sense the body temperature of the employee seated in the chair; and
- a chair pad force sensor configured to sense force of the employee seated in the chair, the floor mat sensing system comprising a floor mat with a set of floor mat sensors disposed in the floor mat, the set of floor mat sensors comprising:
- a floor mat temperature sensor configured to sense the body temperature of the employee seated in the chair; and
- a floor mat force sensor configured to sense force of the employee seated in the chair, and the neural sensing system comprising a set of neural sensors configured to be disposed about a scalp of the employee seated in the chair and to sense brain activity of the employee, the health data collected comprising:
- the body temperature of the employee sensed by the computer mouse temperature sensor;
- the blood condition of the employee sensed by the computer mouse blood condition sensor;
- the blood pressure of the employee sensed by the computer mouse blood pressure sensor;
- the body temperature of the employee sensed by the chair pad temperature sensor;
- the force of the employee sensed by the chair pad force sensor;
- the body temperature of the employee sensed by the floor mat temperature sensor;
- the force of the employee sensed by the floor mat force sensor; and
- the brain activity of the employee sensed by the neural sensors;

determining, by the health monitoring server, a body temperature of the employee based on the body temperature of the employee sensed by the computer mouse temperature sensor, the body temperature of the employee sensed by the chair pad temperature sensor and the body temperature of the employee sensed by the floor mat temperature sensor;

determining, by the health monitoring server, a blood condition of the employee based on the blood condition of the employee sensed by the computer mouse blood condition sensor;

determining, by the health monitoring server, a blood pressure of the employee based on the blood pressure of the employee sensed by the computer mouse blood pressure sensor;

determining, by the health monitoring server, a weight of the employee based on the force of the employee sensed by the chair pad force sensor and the force of the employee sensed by the floor mat force sensor;

determining, by the health monitoring server, a brain activity of the employee based on the brain activity of the employee sensed by the neural sensors;

determining, by the health monitoring server based on the brain activity of the employee, a sequence of motor functions and a risk of physical fatigue corresponding to the sequence of motor functions; and displaying, by the computer display, a health profile for the employee comprising the body temperature of the employee determined, the blood condition of the employee determined, the blood pressure of the employee determined, the weight of the employee determined, the brain activity of the employee determined, and the risk of physical fatigue determined.

15. The medium of claim 14, wherein the neural sensing system comprises a neural headset comprising the set of neural sensors configured to be disposed about a scalp of the employee.

16. The medium of claim 14, wherein the neural sensing system comprises the set of neural sensors disposed in a headrest of the chair and configured to be disposed about the scalp of the employee seated in the chair.

17. The medium of claim 14, wherein the health monitoring server is further configured to:
- compare a neural signal pattern of the brain activity of the employee sensed to a plurality of predetermined neural signal patterns to determine a matching neural signal pattern comprising neural signal pattern of the plurality of predetermined neural signal patterns that matches the neural signal pattern of the brain activity of the employee sensed; and
- determine a characteristic of the employee corresponding to the matching neural signal pattern, wherein the health profile for the employee comprises the characteristic of the employee corresponding to the matching neural signal pattern.

18. The medium of claim 17, wherein the characteristic of the employee corresponding to the matched the neural signal pattern comprises risk of fatigue of the employee.

19. The medium of claim 18, wherein the health monitoring system is further configured to:
- determine a level of motor function corresponding to the matching neural signal pattern;
- determine that the level of motor function is below a threshold value; and
- determining, in response to determining that that the level of motor function is below the threshold value, the risk of fatigue for the employee.

* * * * *